(12) United States Patent
Friedman et al.

(10) Patent No.: US 6,350,730 B1
(45) Date of Patent: *Feb. 26, 2002

(54) OB POLYPEPTIDES AND MODIFIED FORMS AS MODULATORS OF BODY WEIGHT

(75) Inventors: Jeffrey M. Friedman; Yiying Zhang, both of New York; Ricardo Proenca, Astoria, all of NY (US)

(73) Assignee: The Rockefeller University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/488,223

(22) Filed: Jun. 7, 1995

Related U.S. Application Data

(63) Continuation-in-part of application No. 08/438,431, filed on May 10, 1995, which is a continuation-in-part of application No. 08/347,563, filed on Nov. 30, 1994, now Pat. No. 5,935,810, which is a continuation-in-part of application No. 08/292,345, filed on Aug. 17, 1994, now Pat. No. 6,001,968.

(51) Int. Cl.⁷ .......................... C07K 14/47; A61K 38/17
(52) U.S. Cl. .............................. 514/12; 514/2; 514/8; 514/909; 530/350; 530/421
(58) Field of Search .................. 424/851; 512/2, 512/8, 12, 844, 866, 909, 350; 530/421

(56) References Cited

U.S. PATENT DOCUMENTS

| | | |
|---|---|---|
| 3,650,090 A | 3/1972 | Temple et al. |
| 3,654,090 A | 4/1972 | Wilhemus et al. |
| 3,850,752 A | 11/1974 | Schuurs et al. |
| 4,016,043 A | 4/1977 | Schuurs et al. |
| 4,179,337 A | 12/1979 | Davis et al. |
| 4,341,761 A | 7/1982 | Ganfield et al. |
| RE31,006 E | 8/1982 | Schuurs et al. |
| 4,342,566 A | 8/1982 | Theofilopoulos et al. |
| 4,399,121 A | 8/1983 | Albarella et al. |
| 4,427,783 A | 1/1984 | Newman et al. |
| 4,444,887 A | 4/1984 | Hoffmann |
| 4,451,570 A | 5/1984 | Royston et al. |
| 4,466,917 A | 8/1984 | Nussenzweig et al. |
| 4,472,500 A | 9/1984 | Milstein et al. |
| 4,491,632 A | 1/1985 | Wands et al. |

(List continued on next page.)

FOREIGN PATENT DOCUMENTS

| | | |
|---|---|---|
| AU | B-51978/96 | 3/1998 |
| CA | 2012311 | 9/1990 |
| EP | 0 401 384 | 12/1990 |
| EP | 0566410 | 10/1993 |
| EP | 401384 B1 | 3/1996 |
| EP | 725078 A1 | 8/1996 |
| EP | 725079 A1 | 8/1996 |
| EP | 736599 A2 | 10/1996 |
| EP | 741187 A2 | 11/1996 |
| EP | 743321 A2 | 11/1996 |
| EP | 744408 A2 | 11/1996 |
| EP | 745610 A2 | 12/1996 |
| EP | 759441 A2 | 2/1997 |
| EP | 764722 A2 | 3/1997 |
| EP | 784979 A2 | 7/1997 |
| EP | 784981 A2 | 7/1997 |
| EP | 784982 A2 | 7/1997 |

(List continued on next page.)

OTHER PUBLICATIONS

Genbank Accession No. U18812, Mus musculus obese precursor (ob) mRNA, complete cds., deposited by Zhang, Y. et al., Dec. 21, 1994.

Altman, S.W. et al., "Expression and Purification of a Synthetic Human Obese Gene Product," *Protein Expression and Purification*, 6:722–726 (1995).

Angier, N., "Researchers Link Obesity In Humans To Flaw In A Gene," *The New York Times* reported on Dec. 1, 1994.

Barinaga, "'Obese' Protein Slims Mice", *Science*, 269:475–476 (Jul., 1995).

Baron, M.H. et al., "Antibodies against the Chemically Synthesized Genome–Linked Protein of Poliovirus React with Native Virus–Specific Proteins," *Cell*, 28:395–404 (Feb., 1982).

(List continued on next page.)

*Primary Examiner*—Christine J. Saoud
(74) *Attorney, Agent, or Firm*—Klauber & Jackson

(57) ABSTRACT

The present invention relates generally to the control of body weight of animals including mammals and humans, and more particularly to materials identified herein as modulators of body weight, and to diagnostic and therapeutic uses of such modulators. In one of its broadest aspects, the present invention relates to nucleotide sequences corresponding to the murine and human OB gene, and two isoforms thereof, and proteins expressed by such nucleotides or degenerate variations thereof, that demonstrate the ability to participate in the control of mammalian body weight and that have been postulated to play a critical role in the regulation of body weight and adiposity. The present invention further provides nucleic acid molecules for use as molecular probes or as primers for polymerase chain reaction (PCR) amplification. In further aspects, the present invention provides cloning vectors and mammalian expression vectors comprising the nucleic acid molecules of the invention. The invention further relates to host cells transfected or transformed with an appropriate expression vector and to their use in the preparation of the modulators of the invention. Also provided are antibodies to the OB polypeptide. Moreover, a method for modulating body weight of a mammal is provided.

27 Claims, 61 Drawing Sheets

U.S. PATENT DOCUMENTS

| | | | |
|---|---|---|---|
| 4,493,890 A | 1/1985 | Morris | |
| 4,631,211 A | 12/1986 | Houghten | |
| 4,650,764 A | 3/1987 | Temin et al. | |
| 4,816,567 A | 3/1989 | Cabilly et al. | |
| 4,925,673 A | 5/1990 | Steiner et al. | |
| 4,946,778 A | 8/1990 | Ladner et al. | |
| 4,980,289 A | 12/1990 | Temin et al. | |
| 4,981,784 A | 1/1991 | Evans et al. | |
| 5,010,175 A | 4/1991 | Rutter et al. | |
| 5,013,556 A | 5/1991 | Woodle et al. | |
| 5,073,627 A | 12/1991 | Curtis et al. | |
| 5,098,833 A | 3/1992 | Lasky et al. | |
| 5,116,964 A | 5/1992 | Capon et al. | |
| 5,124,263 A | 6/1992 | Temin et al. | |
| 5,225,538 A | 7/1993 | Capon et al. | |
| 5,284,656 A | 2/1994 | Platz et al. | |
| 5,359,034 A | 10/1994 | Skelly et al. | |
| 5,399,346 A | 3/1995 | Anderson et al. | |
| 5,428,130 A | 6/1995 | Capon et al. | |
| 5,447,851 A | 9/1995 | Beutler et al. | |
| 5,455,165 A | 10/1995 | Capon et al. | |
| 5,480,981 A | 1/1996 | Goodwin et al. | |
| 5,512,457 A | 4/1996 | Lyman et al. | |
| 5,514,582 A | 5/1996 | Capon et al. | |
| 5,521,283 A * | 5/1996 | DiMarchi et al. | 530/324 |
| 5,525,705 A * | 6/1996 | DiMarchi et al. | 530/324 |
| 5,532,336 A * | 7/1996 | DiMarchi et al. | 530/324 |
| 5,552,522 A | 9/1996 | DiMarchi et al. | 530/324 |
| 5,552,523 A | 9/1996 | Basinski et al. | 530/324 |
| 5,552,524 A | 9/1996 | Basinski et al. | 530/324 |
| 5,554,727 A | 9/1996 | Basinski et al. | 530/324 |
| 5,559,208 A | 9/1996 | Basinski et al. | 530/317 |
| 5,563,243 A | 10/1996 | DiMarchi et al. | 530/324 |
| 5,563,244 A * | 10/1996 | DiMarchi et al. | 530/324 |
| 5,563,245 A * | 10/1996 | DiMarchi et al. | 530/4 |
| 5,567,678 A * | 10/1996 | DiMarchi et al. | 530/324 |
| 5,567,803 A | 10/1996 | Basinski et al. | 530/324 |
| 5,569,743 A * | 10/1996 | DiMarchi et al. | 530/324 |
| 5,569,744 A | 10/1996 | Basinski et al. | 530/324 |
| 5,574,018 A | 11/1996 | Habberfield et al. | |
| 5,574,133 A * | 11/1996 | DiMarchi et al. | |
| 5,580,954 A * | 12/1996 | DiMarchi et al. | 530/324 |
| 5,594,101 A | 1/1997 | Becker et al. | 530/317 |
| 5,594,104 A | 1/1997 | Basinski et al. | 530/324 |
| 5,605,886 A | 2/1997 | Basinski et al. | 514/12 |
| 5,614,379 A | 3/1997 | MacKellar et al. | 435/68.1 |
| 5,643,748 A | 7/1997 | Snodgrass et al. | 435/69.1 |
| 5,670,625 A | 9/1997 | Lyman et al. | |
| 5,691,309 A | 11/1997 | Basinski et al. | 514/12 |
| 5,698,389 A | 12/1997 | de la Brousse | 435/4 |
| 5,714,147 A | 2/1998 | Capon et al. | |
| 5,719,266 A | 2/1998 | DiMarchi et al. | |
| 5,739,277 A | 4/1998 | Presta et al. | |
| 5,756,461 A | 5/1998 | Stephens | |
| 5,827,734 A | 10/1998 | Weigle et al. | |

FOREIGN PATENT DOCUMENTS

| | | |
|---|---|---|
| EP | 786256 A2 | 7/1997 |
| EP | 797999 A2 | 10/1997 |
| JP | 8-333394 | 12/1996 |
| JP | 9-3098 | 1/1997 |
| WO | WO 83/04053 | 11/1983 |
| WO | WO 88/03168 | 5/1988 |
| WO | WO 89/10932 | 11/1989 |
| WO | WO 90/03431 | 4/1990 |
| WO | WO 90/10697 | 9/1990 |
| WO | WO 90/14092 | 11/1990 |
| WO | WO 91/06666 | 5/1991 |
| WO | WO 91/09955 | 7/1991 |
| WO | WO 92/00252 | 1/1992 |
| WO | WO 94/00558 | 1/1994 |
| WO | WO 94/20069 | 9/1994 |
| WO | WO 95/07358 | 3/1995 |
| WO | WO 95/21629 | 8/1995 |
| WO | WO 96/03141 | 2/1996 |
| WO | WO 96/04388 | 2/1996 |
| WO | WO 96/05309 | 2/1996 |
| WO | WO 96/05861 | 2/1996 |
| WO | WO 96/11953 | 4/1996 |
| WO | WO 96/18412 | 6/1996 |
| WO | WO 96/22308 | 7/1996 |
| WO | WO 96/23513 | 8/1996 |
| WO | WO 96/23514 | 8/1996 |
| WO | WO 96/23515 | 8/1996 |
| WO | WO 96/23516 | 8/1996 |
| WO | WO 96/23517 | 8/1996 |
| WO | WO 96/23518 | 8/1996 |
| WO | WO 96/23519 | 8/1996 |
| WO | WO 96/23520 | 8/1996 |
| WO | WO 96/23815 | 8/1996 |
| WO | WO 96/24670 | 8/1996 |
| WO | WO 96/27385 | 9/1996 |
| WO | WO 96/29405 | 9/1996 |
| WO | WO 96/29989 | 10/1996 |
| WO | WO 96/31526 | 10/1996 |
| WO | WO 96/34111 | 10/1996 |
| WO | WO 96/34885 | 10/1996 |
| WO | WO 96/35787 | 11/1996 |
| WO | WO 96/36641 | 11/1996 |
| WO | WO 96/36644 | 11/1996 |
| WO | WO 96/37517 | 11/1996 |
| WO | WO 96/38152 | 12/1996 |
| WO | WO 96/38586 | 12/1996 |
| WO | WO 96/40912 | 12/1996 |
| WO | WO 97/00319 | 1/1997 |
| WO | WO 97/00866 | 1/1997 |
| WO | WO 97/02004 | 1/1997 |
| WO | WO 97/06816 | 2/1997 |
| WO | WO 97/11192 | 3/1997 |
| WO | WO 97/12037 | 4/1997 |
| WO | WO 97/13500 | 4/1997 |
| WO | WO 97/15322 | 5/1997 |
| WO | WO 97/16189 | 5/1997 |
| WO | WO 97/16550 | 5/1997 |
| WO | WO 97/18228 | 5/1997 |
| WO | WO 97/18806 | 5/1997 |
| WO | WO 97/18833 | 5/1997 |
| WO | WO 97/19952 | 6/1997 |
| WO | WO 97/20933 | 6/1997 |
| WO | WO 97/24137 | 7/1997 |
| WO | WO 97/24440 | 7/1997 |
| WO | WO 97/25424 | 7/1997 |
| WO | WO 97/25425 | 7/1997 |
| WO | WO 97/26004 | 7/1997 |
| WO | WO 97/26011 | 7/1997 |
| WO | WO 97/26012 | 7/1997 |
| WO | WO 97/26013 | 7/1997 |
| WO | WO 97/26335 | 7/1997 |
| WO | WO 97/26523 | 7/1997 |
| WO | WO 97/26916 | 7/1997 |
| WO | WO 97/27286 | 7/1997 |
| WO | WO 97/28824 | 8/1997 |
| WO | WO 97/31015 | 8/1997 |
| WO | WO 97/32022 | 9/1997 |
| WO | WO 97/35620 | 10/1997 |
| WO | WO 97/38014 | 10/1997 |
| WO | WO 97/40380 | 10/1997 |
| WO | WO 97/41217 | 11/1997 |
| WO | WO 97/41263 | 11/1997 |
| WO | WO 97/42340 | 11/1997 |

| | | |
|---|---|---|
| WO | WO 97/46585 | 12/1997 |
| WO | WO 97/46587 | 12/1997 |

OTHER PUBLICATIONS

Bennett, B.D. et al., "A role for leptin and its cognate receptor in hematopoiesis," *Current Biology*, 6(9):1170–1180 (Sep. 1, 1996).

Bishop, J.E., "Newfound Gene May Control Fat Storage," *The Wall Street Journal, Health and Science*, reported on Dec. 1, 1994.

Bishop, J.E., "Rockefeller Study Supports Theory That Body Has Fat–Maintenance System," *Wall Street Journal*, reported on Mar. 9, 1995.

Campfield, L.A. et al., "Strategies and Potential Molecular Targets for Obesity Treatment," *Science*, 280:1383–1387 (May, 1998).

Capon, D.J. et al., "Designing CD4 immunoadhesins for AIDS therapy," *Nature*, 337:525–531 (Feb., 1989).

Chen, H. et al., "Evidence That the Diabetes Gene Encodes the Leptin Receptor: Identification of a Mutation in the Leptin Receptor Gene in db/db Mice," *Cell*, 84:491–495 (Feb., 1996).

Cioffi, J.A. et al., "Novel B219/OB receptor isoforms: Possible role of leptin in hematopoiesis and reproduction," *Nature Medicine*, 2(5):585–589 (May, 1996).

Coleman, D.L. et al., "The Influence of Genetic Background on the Expression of the Obese (Ob) Gene in the Mouse," *Diabetologia*, 9:287–293 (1973).

Comuzzie, A.G. et al., "The Search for Human Obesity Genes," *Science*, 280:1374–1377 (May, 1998).

Considine, R.V. et al., "Ob Gene Expression Is Increased in Adipocytes from Obese Humans," Diabetes, 44:202A (May, 1995) (Abstract 739).

Cusin I. et al., "The ob Gene and Insulin A Relationship Leading to Clues to the Understanding of Obesity," *Diabetes*, 44:1467–1470 (Dec., 1995).

Detjen, J. (Philadelphia Inquirer), "Obesity gene find may help millions someday," The Durham Herald Co., *The Herald–Sun* (Durham, NC), p. A1, reported on Dec. 1, 1994.

Dressman, G.R. et al., "Antibody to hepatitis B surface antigen after a single inoculation of uncoupled synthetic HbsAg peptides," *Nature*, 295:158–160 (Jan., 1982).

Ellison, J.W. et al., "The nucleotide sequence of a human immunoglobulin $C\gamma_1$ gene," *Nucleic Acids Research*, 10(13):4071–4079 (1982).

Enerbäck, S. et al., "Mice lacking mitochondrial uncoupling protein are cold–sensitive but not obese," *Nature*, 387:90–93 (May, 1997).

Evans, D.J. et al., "Relationship of Body Fat Topography to Insulin Sensitivity and Metabolic Profiles in Premenopausal Women," *Metabolism*, 33(1):68–75 (Jan., 1984).

Ferré, P, "Obésité. Produit de Gène ob Et Contrôle De La Masse Adipeuse [Obesity, The ob Gene Product and Control of Adipose Mass]," *Diabete & Metabolisme (Paris)*, 21:217–218 (1995).

Fisher, C.J. et al., "Treatment of Septic Shock with the Tumor Necrosis Factor Receptor:Fc Fusion Protein," *N. Engl. J. Med.*, 334:1697–1702 (1996).

Flam, "Obesity Gene Discovery May Help Solve Weighty Problem," *Science*, 266:1477–1478 (Dec., 1994).

Ford, C.F. et al., "Fusion Tails for the Recovery and Purification of Recombinant Proteins," *Protein Expression and Purification*, 2:95–107 (1991).

Frederich, R. et al., "Nutritional Regulation of ob Gene mRNA in White Adipose Tissue," *The Endocrine Society*, Programs & Abstracts, 77th Meeting, Jun. 14–17, 1995, Washington, D.C., p. 173 (Abstract OR25–3).

Frederich R.C. et al., "Leptin levels reflect body lipid content in mice: Evidence for diet–induced resistance to leptin action," *Nature Medicine*, 1(12):1311–1314 (Dec., 1995).

GenBank Accession No. 603288, ob, Deposited by Zhang et al., Mar. 30, 1995.

GenBank Accession No. 623332, ob, Deposited by Zhang et al., Jan. 13, 1995.

GenBank Accession No. 726297, obesity protein, Deposited by Chehab et al., Mar. 21, 1995.

GenBank Accession No. U18812, Mus musculus obese precursor (ob) mRNA, complete cds., deposited by Zhang, Y. et al., Mar. 30, 1995.

GenBank Accession No. U18915, Human obese (ob) mRNA, complete cds., deposited by Zhang, Y. et al., Jan. 13, 1995.

GenBank Accession No. U22421, Mus musculus obesity protein (ob) gene, complete cds., Deposited by Chehab et al., Mar. 23, 1995.

Grundy and Barnett, "Metabolic and Health Complications of Obesity," *Disease– a– Month (DM)*, 36:645–696 (Dec., 1990).

Gura, T., "Uncoupling Proteins Provide New Clue to Obesity's Causes," *Science*, 280:1369–1370 (May, 1998).

Hamilton, B.S. et al., "Increased obese mRNA expression in omental fat cells from massively obese humans," *Nature Medicine*, 1(9):953–956 (Sep., 1995).

Harvill, E.T. et al., "An IgG3–IL2 fusion protein activates complement, binds FcγRI, generates LAK activity and shows enhanced binding to the high affinity IL–2R," *Immunotechnology*, 1:95–105 (1995).

Hawkes, N. "Obesity of Mice and Men," Times Newspaper Limited, *The Times*, reported on Dec. 5, 1994.

He, Y. et al., "The Mouse obese Gene," *Journal of Biological Chemistry*, 270(48):28887–28891 (Dec., 1995).

Helm, L. (Times Staff Writer), "Gene Found That May Lead To Obesity," *The Times Mirror Company, Los Angeles Times*, part A, page 1, col. 3 (Dec. 1, 1994).

Henry R.R. et al., "Effects of Weight Loss on Mechanisms of Hyperglycemia in Obese Non–Insulin–Dependent Diabetes Mellitus," *Diabetes*, 35:990–998 (Sep., 1986).

Highfield, R. (Science Editor), "Scientists find cause of fat mice and men Gene discovery from overweight rodents may help to produce drugs for people with a hereditary risk of obesity," *Telegraph Group Limited, The Daily Telegraph*, p. 7 (Dec. 1, 1994).

Hill, J.O. et al., "Environmental Contributions to the Obesity Epidemic," *Science*, 280:1371–1374 (May, 1998).

Hirsch, J., "Some heat but not enough light," *Nature*, 387:27–28 (May, 1997).

Hodgson, "'Obesity' Where Less is More," *Bio/Technology*, 13:1060–1063 (Oct., 1995).

Hulsey, M.G. et al., "An Anorectic Agent From Adipose Tissue of Overfed Rats: Effects of Feeding Behavior," *Physiol. & Behav.*, 52:1141–1149 (1992).

Hummel, K.P. et al., "Diabetes, a New Mutation in the Mouse," *Science*, 153:1127–1128 (1966).

Huse, W.D. et al., "Generation of a Large Combinatorial Library of the Immunoglobulin Repertoire in Phage Lambda," *Science*, 246:1275–1281 (Dec., 1989).

IBI Flag Biosystem, "High Yield Expression, Detection, and Purification of Recombinant Proteins in E. coli," Integrated Sciences Pty Ltd, Sydney, Australia.

IBI Flag Epitope, A Technical Bulletin for Users of Flag Technology, International Biotechnologies Inc., Flag Product Development Group, IBI, A Kodak Company, New Havem, CT, vol. 1, No. 1, pp. 1–24, (Sep., 1992).

Iida, M. et al., "Substitution at Codon 269 (Glutamine→Proline) of the Leptin Receptor (OB–R) cDNA Is the Only Mutation Found in the Zucker Fatty (fa/fa) Rat," Biochemical and Biophysical Research Communications, 224:597–604 (Jul. 16, 1996).

Köhler, G. et al., "Derivation of specific antibody–producing tissue culture and tumor lines by cell fusion," Eur. J. Immunol., 6:511–519 (1976).

Lerner, R.A. et al., "Antibodies to Chemically Synthesized Peptides Predicted from DNA Sequences as Probes of Gene Expression," Cell, 23:309–310 (Feb., 1981).

Lerner, R.A. et al., "Chemically synthesized peptides predicted from the nucleotide sequence of the hepatitis B virus genome elicit antibodies reactive with the native envelope protein of Dane particles," Proc. Natl. Acad. Sci., USA, 78(6):3403–3407 (Jun., 1981).

Lerner, R.A., "Synthetic Vaccines," Scientific American, 248:66–74 (1983).

Levin, N. et al., "Decreased food intake does not completely account for adiposity reduction after ob protein infusion," Proc. Natl. Acad. Sci., 93:1726–1730 (Feb., 1996).

LindPaintner, K., "Clinical Implications of Basic Research: Finding an Obesity Gene–A Tale of Mice and Man," New England Journal of Medicine, 332(10):679–680 (Mar., 1995).

Marx, J., "Obesity Gene Discovery May Help Solve Weighty Problem," Surg. Neurol., 43:351–352 (1995).

Marx, J., "Obesity Gene Discovery May Help Solve Weighty Problem," Science, 266:1477–1478 (Dec., 1994).

Masuda, K. et al., "Effects of Troglitazone (CS–045) on insulin secretion in isolated rat pancreatic islets and HIT cells: an insulinotropic mechanism distinct from glibenclamide," Diabetologia, 38:24–30 (1995).

Masuzaki et al., "Molecular Cloning of a Rat Obese (ob) Complement DNA—Augmented Gene Expression in Obese–Hyperglycemic Wistar Fatty Rats," The Endocrine Society, Programs & Abstracts, 77th Annual Meeting, Jun. 14–17, 1995, Washington, D.C., p. 175 (Abstract P1–250).

Masuzaki, H. et al., "Adipose Tissue–specific Expression of the Obese (ob) Gene in Rats and Its Marked Augmentation in Genetically Obese–hyperglycemic Wistar Fatty Rats," Proceedings of the Japan Academy Series B Physical and Biological Sciences, 71(5):148–152 (1995).

McGarry, J.D., "Does leptin lighten the problem of obesity?" Current Biology, 5(12):1342–1344 (1995).

Mini–Symposium on Flag Technology, ASCB 1992, "Purification and Characterization of Cellular Proteins with the Flag Epitope," Colorado Convention Center, Denver, Colorado, 8 pages (Nov. 18, 1992).

Mizuno, T. et al., "Elevated Expression of Obese (ob/ob) Gene Product in Adipose Tissue, and Impaired Induction by Insulin of Jun–B MRNA in Liver, in Genetically Obese Yellow Mice," The Endocrine Society, Programs & Abstracts, 77th Annual Meeting, Jun. 14–17, 1995, Washington, D.C., p. 174 (Abstract P1–248).

Moinat, M. et al., "Modulation of obese gene expression in rat brown and white adipose tissues," FEBS Letters, 373:131–134 (1995).

Murakami, N. et al., "Amelioration of insulin resistance in genetically obese rodents by M16209, a new antidiabetic agent," European Journal of Pharmacology, 304:129–134 (1996).

Murakami, T. et al., "Cloning of Rat Obese cDNA and its Expression in Obese Rats," Biochemical and Biophysical Research Communications, 209(3):944–952 (Apr., 1995).

Nakamura, M.T., "Another Obese Gene Function," Nature, 374:124 (Mar., 1995).

Ogawa, et al., "Region–Specificities of the Obese (ob) Gene Expression in Adipose Tissue in Mice and Altered Gene Expression in C57BL/6J ob/ob Mice," The Endocrine Society, Programs and Abstracts, 77th Annual Meeting, Jun. 14–17, 1995, Washington, D.C., p. 175 (Abstract P1–249).

Olefsky, J.M., "Weighing in on the Lean Genes," Journal of Clinical Investigations, 95:2427–2428 (Jun., 1995).

Palmiter, R.D. et al., "Metallothionein–Human GH Fusion Genes Stimulate Growth of Mice," Science, 222:809–814 (Nov., 1983).

Peiris, A.N. et al., "Glucose Metabolism in Obesity: Influence of Body Fat Distribution," J. Clinical Endocrinology Metabolism, 67(4):760–767 (1988).

Peiris, A.N. et al., "Relationship of Body Fat Distribution to the Metabolic Clearance of Insulin in Premenopausal Women," International J. Obesity, 11:581–589 (1987).

Peiris, A.N. et al., "Splanchinic Insulin Metabolism in Obesity Influence of Body Fat Distribution," J. Clin. Invest, 78:1648–1657 (Dec., 1986).

Polonsky, K.S. et al., "Use of Biosynthetic Human C–peptide in the Measurement of Insulin Secretion Rates in Normal Volunteers and Type I Diabetic Patients," J. Clin. Invest, 77:98–105 (Jan., 1986).

Reddy, R. et al., "Equivalent Levels of OB Gene Expression in Adipose Tissues of Morbidly Obese and Lean Patients," The Endocrine Society, Programs & Abstracts, 77th Annual Meeting, Jun. 14–17, 1995, Washington, D.C., (Abstract P3–266).

Rink, "In Search of a Satiety Factor," Nature, 372(1):406–407 (Dec., 1994).

Schwartz, M.W. et al., "Specificity of Leptin Action on Elevated Blood Glucose Levels and Hypothalamic Neuropeptide Y Gene Expression in ob/ob Mice," Diabetes, 45:531–535 (Apr., 1996).

Shafrir, E., "Animal Models of Non–Insulin–Dependent Diabetes," Diabetes/Metabolism Reviews, 8(3):179–208 (1992).

Shigemoto, M. et al., "Tissue Distribution of the Obese (ob) Gene Expression in Mice and Augmented Gene Expression in the ob/ob Mice," Diabetes, 44:204A (May, 1995) (Abstract 748).

Sohda, T. et al., "Studies on Antidiabetic Agents. XII. [1]) Synthesis and Activity of the Metabolites of (±)–5–[p–[2–(5–Ethyl–2–pyridyl)ethoxy]benzyl]–2,4–thiazolidinedione (Pioglitazone)," Chem. Pharm. Bull., 43(12):2168–2172 (1995).

Stephens et al., "The Role of Neuropeptide Y in the Antiobesity Action of the Obese Gene Product," Nature, 377:530–532 (Oct., 1995).

Stirling B. et al., "Identification of Microsatellite Markers Near the Human ob Gene and Linkage Studies in NIDDM–Affected Sib Pairs," *Diabetes*, 44: 999–1001 (Aug., 1995).

Sugiyama, Y. et al, "Effects of Pioglitazone on Glucose and Lipid Metabolism in Wistar Fatty Rats," *Arzneim.–Forsch./Drug Res.40(I)*, Nr.3:263–267 (1990).

Sugiyama, Y. et al., "Effects of Pioglitazone on Hepatic and Peripheral Insulin Resistance in Wistar Fatty Rats," *Arzneim.–Forsch./Drug Res. 40(I)*, Nr.4:436–440 (1990).

Swanson, M.L. et al., "Antidiabetic Agent Pioglitazone Increases Insulin Receptors on 3T3–L1 Adipocytes," *Drug Development Research*, 35: 69–82 (1995).

Tartaglia, L.A. et al., "Identification and Expression Cloning of a Leptin Receptor, OB–R," *Cell*, 83:1263–1271 (Dec., 1995).

Taubes, G., "As Obesity Rates Rise, Experts Struggle to Explain Why," *Science*, 280:1367–1368 (May, 1998).

Thomas, S.A. et al., "Thermoregulatory and metabolic phenotypes of mice lacking noradrenaline and adrenaline,"*Nature*, 387:94–97 (May, 1997).

Van Zee, K. et al., "Protection Against Lethal *Escherichia coli* Bacteremia in Baboons (*Papio anubis*) by Pretreatment with a 55–kDa TNF Receptor (CD120a)–Ig Fusion Protein, Ro 45–2081[1] ," *The Journal of Immunology*, 156:2221–2230 (1996).

Vydelingum S. et al., "Overexpression of the Obese Gene in the Genetically Obese JCR:LA–Corpulent Rat," *Biochemical and Biophysical Research Communications*, 216(1):148–153 (Nov., 1995).

Walsh, B.T. et al., "Eating Disorders: Progress and Problems," *Science*, 280:1387–1390 (May, 1998).

Watson, T., "What really plumps you up," *U.S. News and World Report*, vol. 117, No. 23, p. 80, reported on Dec. 12, 1994.

Weigle, D.S., "Appetite and the regulation of body composition," *FASEB*, 8:302–310 (1994).

Weigle et al., "Recombinant ob Protein Reduces Feeding and Body Weight in the ob/ob Mouse," *J. Clin. Invest.*, 96:2065–2070 (Oct., 1995).

West, D.B. et al., "Genetics of Dietary Obesity in AKR/J X SWR/J Mice—Segretation of the Trait and Identification of a Linked Locus on Chromosome–4," *Mammalian Genome*, 5(9):546–552 (Sep., 1994).

Wickelgren, I., "Obesity: How Big a Problem?" *Science*, 280:1364–1367 (May, 1998).

Willson, T.M. et al., "The Structure–Activity Relationship between Peroxisome Proliferator–Activated Receptor γ Agonism and the Antihyperglycemic Activity of Thiazolidinediones," *J. Med. Chem.*, 39:665–668 (1996).

Wilson, B.E. et al., "Identification of an overfeeding–induced adipocyte 5kb mRNA Lacking Sequence Homology to Known Adipocyte Genes," *The Adipose Cell: A Model for Integration of Hormone Signalling in the Regulation of Cellular Function*, p. 34 (Abstract CA 318).

Woods, S.C. et al., "Signals That Regulate Food Intake and Energy Homeostasis," *Science*, 280:1378–1383 (May, 1998).

Yamakawa, T. et al., "Augmented Production of Tumor Necrosis Factor–α in Obese Mice," *Clinical Immunol. Immunopathol.*, 75(1):51–56 (Apr., 1995).

Zarjevski et al., "Chronic Intracerebroventricular Neuropeptide–Y Administration to Normal Rats Mimics Hormonal and Metabolic Changes of Obesity," *Endocrinology*, 133(4):1753–1758 (1993).

Zhang, B. et al., "Down–regulation of the Expression of the Obese Gene by an Antidiabetic Thiazolidinedione in Zucker Diabetic Fatty Rats and db/db Mice," *J. Biological Chemistry*, 271(16): 9455–9459 (Apr., 1996).

Zheng, X. et al., "Administration of Noncytolytic IL–10/Fc in Murine Models of Lipopolysaccharide–Induced Septic Shock and Allogeneic Islet Transplantation," *The Journal of Immunology*, 154:5590–5600 (1995).

Zucker, L.M. et al., "Fatty, A New Mutation in the Rat," *J. Heredity*, 52:275–278 (1961).

Frommel etal, *J. Mol Evol* 21, 1985, p 233–57.*

The Protein Folding Problem, ed Merz, 1994, Ngo etal, p 492–494.*

Bowie etal, *Serene* 247, 1990, p1306–10.*

Considine et al., 1995, J. Clin. Invest. 95:2986–8.

Froguel et al., 1995, Trends in Biotech. 13:52–5.

Funahashi et al., 1995, Biochem, Res. Communica. 211:469–75.

Rentsch et al., 1995, Biochem. Biophy. Res. Communica. 214:131–6.

Zhang et al., 1994, Nature 372:425–32.

Bahary et al., 1993, Genomics 16:113–22.

Bahary et al., 1993, Mammalian Genome 4: 511–5.

Leibel et al., 1993, Crit. Rev. Food Sci. Nutr. 33:351–8.

Bahary et al., 1992, Genomics 13:761–9.

Friedman and Leibel, 1992, Cell 69:217–20.

Weigle et al., 1992, Pennington Cent. Nutr. Ser. 2:22–36.

Friedman et al., 1991, Ann. NY Acad. Sci. 630:100–15.

Friedman et al., 1991, Mammalian Genome 1:130–44.

Friedman et al., 1991, Genomics 11:1054–62.

Moll et al., 1991, Am. J. Hum. Genet. 49:1243–55.

Truett et al., 1991, Proc. Natl. Acad. Sci. USA 88:7806–9.

Walther et al., 1991, Genomics 11:424–34.

Bahary, 1990, Proc. Natl. Acad. Sci. USA 87:8642–6.

Harris, 1990, FASEB J. 4:3310–8.

Leibel et al., 1990, *World Review of Nutrition and Dietetics*, vol. 63 (Simopoulos, A.P. and Childs, B., eds.), pp. 90–101.

Bray, 1989, Am. J. Clin. Nutr. 50:891–902.

Harris et al., 1987, Diabetes 36:523–34.

Bogardus et al., 1986, N. Engl. J. Med. 315:96–100.

Keesey and Powley, 1986, Ann. Rev. Psychol. 37:109–33.

Coleman, 1978, Diabetologia 14:141–8.

Coleman, 1973, Diabetologia 9:294–8.

Hervey, 1959, J. Physiol. 145:336–52.

Dickie and Lane, 1957, Mouse News Lett. 17:52.

Ingalls et al., 1950, J. Hered. 41:317–8.

Adjei and Garren *Pharm. Res.*, 7(6):565–569 (1990).

Adjei et al. *Int. J. Pharm.*, 63:135–144 (1990).

Albertsen et al. *Proc. Natl. Acad. Sci. USA*, 87:4256–4260 (Jun. 1990).

Anand et al. *Nucl. Acids Res.*, 18(8):1951–1956 (1990).

Anand et al. *Nucl. Acids Res.*, 17(9):3425–3433 (1989).

Ashwell et al. *Proc. R. Soc. Lond.*, 195:343–353 (1977).

Bachmann et al. *Bacteriol. Rev.*, 40:116–167 (1976).

Bahary et al. *Genomics*, 11:33–47 (1991).

Bahary et al. *Proc. Nat. Acad. Sci. USA*, 87:8642–8646 (Nov. 1990).

Baura et al. *J. Clin. Invest.*, 92:1824–1830 (Oct. 1993).

Bax and Davis, *J. Magn. Reson.*, 65:355–360 (1985).

Beavis and Chait, *Proc. Natl. Acad. Sci. USA*, 87:6873–6877 (1990).
Becker et al. (1995) FEBS lett. 371:324–8.
Benton and Davis, *Science*, 196:180 (1977).
Blank et al., *Mammalian Genome*, 1:S51–S78 (1991).
Bogardus et al., *Diabetes*, 35:1–5 (Jan. 1986).
Braquet et al., *Journal of Cardiovascular Pharmacology*, 13(suppl. 5):S143–S146 (1989).
Bray and Campfield, *Metabolism*, 24(1):99–117 (Jan. 1975).
Buchwald et al., *Surgery*, 88:507–516 (Oct. 1980).
Cech, *J. Am. Med. Assoc.*, 260(20):3030–3034 (Nov. 25, 1988).
Chirgwin et al., *Biochem.*, 18:5294–5299 (1979).
Chou and Fasman, *Biochem.*, 13(2):222–245 (1974).
Cohen et al., *Protein Science*, 4:1088 (1995).
Cole et al., in *Monoclonal Antibodies and Cancer Therapy*, pp. 77–96, Alan R. Liss, Inc., (1985).
Considine et al., *N. Engl. J. Med.*, 334:292–295 (Feb. 1, 1996).
Cote et al., *Proc. Natl. Acad. Sci. USA*, 80:2026–2030 (Apr. 1983).
Cwirla et al., *Proc. Natl. Acad. Sci. USA*, 87:6378–6382 (Aug. 1990).
Dani et al., *J. Biol. Chem.*, 264(17):10119–10125 (Jun. 15, 1989).
Dani et al., in *Obesity in Europe* vol. 88, pp. 371–376, Bjorntorp and Rossner, Eds., John Libbey Company Ltd., London, England (1989).
Dani et al., *Mol. Cell. Endocrinol.*, 63:199–208 (1989).
Dausset et al., *Behring Inst. Mitt.*, 91:13–20 (1992).
De Vos et al., *J. Biol. Chem.*, 270(27):15958–15961 (Jul. 7, 1995).
Debons et al., *Fed. Proc.*, 36:143–147 (1977).
Debs et al., *J. Immunol.*, 140(10):3482–3488 (May 15, 1988).
During et al., *Ann. Neurol.*, 25:351 (1989).
Edge, *Nature*, 292:756 (Aug. 20, 1981).
Ellman, *Arch. Biochem. Biophys.*, 82:70–77 (1959).
Engstom, *Biochem. Exp. Biol.*, 11:7–13 (1974).
Faust et al., *Am. J. Physiol.*, 235:E279–E286 (1978).
Faust et al., *Science*, 197:393–396 (Jul. 22, 1977).
Felgner et al., *Proc. Natl. Acad. Sci. USA*, 84:7413–7417 (1987).
Francis, *Focus on Growth Factors*, 3:4–10 (1992).
Frederich et al., *J. Clin. Invest.*, 96:1658–1663 (Sep. 1995).
Furka, *Int. J. Peptide Protein Res.*, 37:487–493 (1991).
Geffroy et al., *Genomics*, 28:603–604 (1995).
Geysen et al., *Molecular Immunology*, 23(7):709–715 (1986).
Geysen et al., *J. Immunologic Method*, 102:259–274 (1987).
Goodson, in *Med. Applica. of Controlled Release*, vol. 2, pp. 115–138 (1984).
Green, in *Methods in Molecular Genetics* vol. 1, Gene & Chromosome Anal. (Part A), pp. 192–210, Adolph ed., Academic Press, Inc., San Diego (1993).
Green and Green, *PCR Methods Applic.*, 1:77–90 (1991).
Green and Olson, *Proc. Natl. Acad. Sci. USA*, 87:1213–7 (Feb. 1990).
Green et al., *Genomics*, 25:170–183 (1995).
Green et al., *Hum. Mol. Genet.*, 3(3):489–501 (1994).
Green et al., *Genomics*, 11:548–564 (1991).
Green et al., *Genome Research*, 5:5–12 (1995).
Green et al., *Annu. Rev. Biochem.*, 55:569–597 (1986).

Grunstein and Hogness, *Proc. Natl. Acad. Sci. USA*, 72(10):3961 (1975).
Hambor et al., *J. Exp. Med.*, 168:1237–1245 (Oct. 1988).
Harris, *Diabetes Care*, 14(7):639–648 (Jul. 1991).
Harris et al., *Int. J. Obes.*, 11:275–283 (1987).
Heng et al., *Cytogenet Cell Genet.*, 62:108–109 (1993).
Hood et al., in *Immunology*, p. 384, Second Ed., Benjamin/Cummings, Menlo Park, California (1984).
Hopp and Woods, *Proc. Natl. Acad. Sci. USA*, 78(6):3824–3828 (Jun. 1981).
Howard et al., *J. Neurosurg.*, 71:105–112 (1989).
Hubbard et al., *Annals of Internal Medicine*, 3(3):206–212 (1989).
Izant and Weintraub *Cell*, 36:1007–1015 (Apr. 1984).
Jacobsson et al., *J. Biol. Chem.*, 260(30):16250–16254 (1985).
Jay et al., *J. Biol. Chem.*, 259(10):6311–6317 (May 25, 1984).
Johnson and Gross, *FASEB J.*, 7:678–686 (1983).
Johnson and Hirsch, *J. Lipid Res.*, 13:2–11 (1972).
Kaplitt et al., *Molec. Cell. Neurosci.*, 2:320–330 (1991).
Keesey, in *Association for Research in Nervous and Mental Disease*, pp. 87–96, Stunkard and Stellar, eds., Raven Press, New York (1984).
Kimura et al., *Proc. Natl. Acad. Sci. USA*, 77(3):1681–1685 (1980).
Kohler and Milstein, *Nature*, 256:495–497 (Aug. 7, 1975).
Kozbor and Roder, *Immunology Today*, 4(3):72–79 (1983).
Kuo et al., *Blood*, 82(3):845–852 (Aug. 1, 1993).
Langer et al., *J. Macromol. Sci. Rev. Macromol. Chem.*, 23:61–126 (1983).
Leibel et al., *N. Engl. J. Med.*, 332(10):621–628 (Mar. 9, 1995).
Leiter et al., *Endocrinology*, 124(2):912–922 (1989).
Lonnqvist et al., *Nature Med.*, 1(9):950–952 (Sep. 1995).
MacDougald et al., *Proc. Natl. Acad. Sci USA*, 92:9034–9037 (1995).
Machy et al., *Proc. Natl. Acad. Sci. USA*, 85:8027–8031 (1988).
Madej et al., *FEBS Lett.*, 373:13–18 (1995).
Maffei et al., *Proc. Natl. Acad. Sci. USA*, 92:6957–6960 (Jul. 1995).
Maffei et al., *Nature Med.*, 1(11):1155–1161 (Nov. 1995).
Malik et al., *Exp. Hematol.*, 20:1028–1035 (1992).
Mann et al., *Cell*, 33:153–159 (May 1983).
Marcus–Sekura, *Anal. Biochem.*, 172:289–295 (1988).
Marion et al. *Biochem. Biophys. Res. Commun.*, 113(3):967–974 (1983).
Markowitz et al., *J. Virol.*, 62(4):1120–1124 (Apr. 1988).
Marshall, in *Modern Pharmaceutics*, Chapter 10, Banker et al. ed., (1979).
Masuzaki et al., *Diabetes*, 44:855–858 (Jul. 1995).
Murakami et al., *Biochem. Biophys. Res. Comm.*, 214(3):1260–7 (1995).
Needels et al., *Proc. Natl. Acad. Sci. USA*, 90:10700–10704 (1993).
Neuberger et al., *Nature*, 312:604–608 (Dec. 1984).
Newmark et al., *J. Appl. Biochem.*, 4:185–189 (1982).
Ogawa et al., *J. Clin. Invest.*, 96:1647–1652 (Sep. 1995).
Pardridge, *Endocrine Reviews*, 7(3):314–330 (1986).
Pearson and Lipman, *Proc. Natl. Acad. Sci. USA*, 85:2444–2448 (1988).
Richardson et al., *Growth, Development & Aging*, 56:149–157 (1992).

Samulski et al., *J. Virol.*, 61(10):3096–3101 (Oct. 1987).
Samulski et al., *J. Virol.*, 63(9):3822–3828 (Sep. 1989).
Saudek et al., *N. Engl. J. Med.*, 321:574 (1989).
Schaeren–Wiemers et al., *Histochemistry*, 100:431–440 (1993).
Sefton, *CRC Crit. Ref. Biomed. Eng.*, 14(3):201–240 (1987).
Smith and Johnson, *Gene*, 67:31–40 (1988).
Smith et al., *J. Clin. Invest.*, 84:1145–1146 (Oct. 1989).
Stratford–Perricaudet et al., *J. Clin. Invest.*, 90:626–630 (Aug. 1992).
Studier et al., *Meth. Enzymology*, 185:80–89 (1990).
Stunkard et al., *N. Engl. J. Med.*, 322(21):1483–1487 (1990).
Takeda et al., *Nature*, 314:452–454 (1985).
Tamura et al., *Cytogenet. Cell Genet.*, 66:132–134 (1994).
Trayhurn et al., *Biochem. J.*, 311:729–733 (1995).
Trayhurn et al., *FEBS Lett.*, 368:488–490 (1995).
Treat et al., in *Liposomes in the Therapy of Infectious Disease and Cancer*, pp. 353–365, Lopez–Berestein and Fidler eds., Liss, New York (1989).
von Heijne, *Nucl. Acids Res.*, 14(11):4683–4690 (1986).
Wasserman, "The Concept of the 'Fat Organ'" in *Rodahl, Issekutz, fat as a tissue*, pp. 22–92, McGraw Hill, New York (1964).
Weigle, *Int. J. Obesity*, 12:567–578 (1988).
Wilson et al., *J. Biol. Chem.*, 267(2):963–967 (Jan. 15, 1992).
Wu and Wu, *J. Biol. Chem.*, 263(29):14621–14624 (Oct. 15, 1988).
Campfield et al., *Science*, 279:546–549 (Jul. 28, 1995).
Halaas et al., *Science*, 269:543–546 (Jul. 28, 1995).
Pelleymounter et al., *Science*, 269:540–543 (Jul. 28, 1995).

* cited by examiner

FIG. 1

```
GGATCCCTGCTCCAGCAGCTGCAAGGTGCAAGAAGAAGAAGATCCCAGGGAGGAAAATGTG    120
                                                         M  C      2
CTGGAGACCCCTGTGTCGGTTCCTGTGGCTTTGGTCCTATCTGTCTTATGTTCAAGCAGT    180
 W  R  P  L  C  R  F  L  W  S  Y  L  S  Y  V  Q  A  V           22
GCCTATCCAGAAAGTCCAGGATGACACCAAAACCCTCATCAAGACCATTGTCACCAGGAT    240
 P  I  Q  K  V  Q  D  D  T  K  T  L  I  K  T  I  V  T  R  I     42
CAATGACATTTCACACACGCAGTCGGTATCCGCCAAGCAGAGGGTCACTGGCTTGGACTT    300
 N  D  I  S  H  T  Q  S  V  S  A  K  Q  R  V  T  G  L  D  F     62
CATTCCTGGGCTTCACCCCATTCTGAGTTTGTCCAAGATGGACCAGACTCTGGCAGTCTA    360
 I  P  G  L  H  P  I  L  S  L  S  K  M  D  Q  T  L  A  V  Y     82
TCAACAGGTCCTCACCAGCCTGCCTTCCCAAAATGTGCTGCAGATAGCCAATGACCTGGA    420
 Q  Q  V  L  T  S  L  P  S  Q  N  V  L  Q  I  A  N  D  L  E    102
GAATCTCCGAGACCTCCTCCATCTGCTGGCCTTCTCCAAGAGCTGCTCCCTGCCTCAGAC    480
 N  L  R  D  L  L  H  L  L  A  F  S  K  S  C  S  L  P  Q  T    122
CAGTGGCCTGCAGAAGCCAGAGAGCCTGGATGGCGTCCTGGAAGCCTCACTCTACTCCAC    540
 S  G  L  Q  K  P  E  S  L  D  G  V  L  E  A  S  L  Y  S  T    142
AGAGGTGGTGGCTTTGAGCAGGCTGCAGGGCTCTCTGCAGGACATTCTTCAACAGTTGGA    600
 E  V  V  A  L  S  R  L  Q  G  S  L  Q  D  I  L  Q  Q  L  D    162
TGTTAGCCCTGAATGCTGAAGTTTCAAAGGCCACCAGGCTCCCAAGAATCATGTAGAGGG    660
 V  S  P  E  C  *                                              167
AAGAAACCTTGGCTTCCAGGGGTCTTCAGGAGAAGAGAGCCATGTGCACACATCCATCAT    720
TCATTTCTCTCCCTCCTGTAGACCACCCATCCAAAGGCATGACTCCACAATGCTTGACTC    780
AAGTTATCCACACAACTTCATGAGCACAAGGAGGGGCCAGCCTGCAGAGGGGACTCTCAC    840
CTAGTTCTTCAGCAAGTAGAGATAAGAGCCATCCCATCCCTCCATGTCCCACCTGCTCC    900
GGGTACATGTTCCTCCGTGGGTACACGCTTCGCTGCGGCCCAGGAGAGGTGAGGTAGGGA    960
TGGGTAGAGCCTTTGGGCTGTCTCAGAGTCTTTGGGAGCACCGTGAAGGCTGCATCCACA   1020
CACAGCTGGAAACTCCCAAGCAGCACACGATGGAAGCACTTATTTATTTATTCTGCATTC   1080
TATTTTGGATGGATCTGAAGCAAGGCATCAGCTTTTTCAGGCTTTGGGGGTCAGCCAGGA   1140
TGAGGAAGGCTCCTGGGGTGCTGCTTTCAATCCTATTGATGGGTCTGCCCGAGGCAAACC   1200
TAATTTTTGAGTGACTGGAAGGAAGGTTGGGATCTTCCAAACAAGAGTCTATGCAGGTAG   1260
CGCTCAAGATTGACCTCTGGTGACTGGTTTTGTTTCTATTGTGACTGACTCTATCCAAAC   1320
ACGTTTGCAGCGGCATTGCCGGGAGCATAGGCTAGGTTATTATCAAAAGCAGATGAATTT   1380
TGTCAAGTGTAATATGTATCTATGTGCACCTGAGGGTAGAGGATGTGTTAGAGGGAGGGT   1440
GAAGGATCCGGAAGTGTTCTCTGAATTACATATGTGTGGTAGGCTTTTCTGAAAGGGTGA   1500
GGCATTTTCTTACCTCTGTGGCCACATAGTGTGGCTTTGTGAAAAGGACAAAGGAGTTGA   1560
CTCTTTCCGGAACATTTGGAGTGTACCAGGCACCCTTGGAGGGGCTAAAGCTACAGGCCT   1620
TTTGTTGGCATATTGCTGAGCTCAGGGAGTGAGGGCCCCACATTTGAGACAGTGAGCCCC   1680
AAGAAAGGGTCCCTGGTGTAGATCTCCAAGGTTGTCCAGGGTTGATCTCACAATGCGTT   1740
TCTTAAGCAGGTAGACGTTTGCATGCCAATATGTGGTTCTCATCTGATTGGTTCATCCAA   1800
AGTAGAACCCTGTCTCCCACCCATTCTGTGGGAGTTTTGTTCCAGTGGGAATGAGAAAT   1860
CACTTAGCAGATGGTCCTGAGCCCTGGGCCAGCACTGCTGAGGAAGTGCCAGGGCCCCAG   1920
GCCAGGCTGCCAGAATTGCCCTTCGGGCTGGAGGATGAACAAAGGGGCTTGGGTTTTTCC   1980
ATCACCCCTGCACCCTATGTCACCATCAAACTGGGGGGCAGATCAGTGAGAGGACACTTG   2040
ATGGAAAGCAATACACTTTAAGACTGAGCACAGTTTCGTGCTCAGCTCTGTCTGGTGCTG   2100
TGAGCTAGAGAAGCTCACCACATACATATAAAAATCAGAGGCTCATGTCCCTGTGGTTAG   2160
ACCCTACTCGCGGCGGTGTACTCCACCACAGCAGCACCGCACCGCTGGAAGTACAGTGCT   2220
GTCTTCAACAGGTGTGAAAGAACCTGAGCTGAGGGTGACAGTGCCCAGGGGAACCCTGCT   2280
TGCAGTCTATTGCATTTACATACCGCATTTCAGGGCACATTAGCATCCACTCCTATGGTA   2340
GCACACTGTTGACAATAGGACAAGGGATAGGGGTTGACTATCCCTTATCCAAAATGCTTG   2400
GGACTAGAAGAGTTTTGGATTTTAGAGTCTTTTCAGGCATAGGTATATTTGAGTATATAT   2460
AAAATGAGATATCTTGGGGATGGGGCCCAAGTATAAACATGAAGTTCATTTATATTTCAT   2520
AATACCGTATAGACACTGCTTGAAGTGTAGTTTTATACAGTGTTTTAAATAACGTTGTAT   2580
GCATGAAAGACGTTTTTACAGCATGAACCTGTCTACTCATGCCAGCACTCAAAAACCTTG   2640
GGGTTTTGGAGCAGTTTGGATCTTGGGTTTTCTGTTAAGAGATGGTTAGCTTATACCTAA   2700
AACCATAATGGCAAACAGGCTGCAGGACCAGACTGGATCCTCAGCCCTGAAGTGTGCCCT   2760
TCCAGCCAGGTCATACCCTGTGGAGGTGAGCGGGATCAGGTTTTGTGGTGCTAAGAGAGG   2820
AGTTGGAGGTAGATTTTGGAGGATCTGAGGGC                               2852
```

| | | | | |
|---|---|---|---|---|
| ---G--GTTG | CAAGGCCCAA | GAAGCCCA-- | -TCCTGGGAA | GGAAAATGCA | 50
| TTGGGGAACC | CTGTG-CGGA | TTCTTGTGGC | TTTGGCCCTA | TCTTTTCTAT | 100
| GTCCAAGCTG | TGCCCATCCA | AAAAGTCCAA | GATGACACCA | AAACCCTCAT | 150
| CAAGACAATT | GTCACCAGGA | TCAATGACAT | TTCACACACG | CAGTCAGTCT | 200
| CCTCCAAACA | GAAAGTCACC | GGTTTGGACT | TCATTCCTGG | GCTCCACCCC | 250
| ATCCTGACCT | TATCCAAGAT | GGACCAGACA | CTGGCAGTCT | ACCAACAGAT | 300
| CCTCACCAGT | ATGCCTTCCA | GAAACGTGAT | CCAAATATCC | AACGACCTGG | 350
| AGAACCTCCG | GGATCTTCTT | CACGTGCTGG | CCTTCTCTAA | GAGCTGCCAC | 400
| TTGCCCTGGG | CCAGTGGCCT | GGAGACCTTG | ACAGCCTGG | GGGGTGTCCT | 450
| GGAAGCTTCA | GGCTACTCCA | CAGAGGTGGT | GGCCCTGAGC | AGGCTGCAGG | 500
| GGTCTCTGCA | GGACATGCTG | TGGCAGCTGG | ACCTCAGCCC | TGGGTGCTGA | 550
| GGCCTTGAAG | GTCACTCTTC | CTGCAAGGAC | T-ACGTTAAG | GGAAGGAACT | 600
| CTGGTTTCCA | GGTATCTCCA | GGATTGAAGA | GCATTGCATG | GACACCCCTT | 650
| ATCCAGGACT | CTGTCAATTT | CCCTGACTCC | TCTAAGCCAC | TCTTCCAAAG | 700
| G | | | | | 701

FIG.2

| | | | | | | | | | | | | | | | |
|---|---|---|---|---|---|---|---|---|---|---|---|---|---|---|---|
| 1 | Met | His | Trp | Gly | Thr | Leu | Cys | Gly | Phe | Leu | Trp | Leu | Trp | Pro | Tyr |
| 16 | Leu | Phe | Tyr | Val | Gln | Ala | Val | Pro | Ile | Gln | Lys | Val | Gln | Asp | Asp |
| 31 | Thr | Lys | Thr | Leu | Ile | Lys | Thr | Ile | Val | Thr | Arg | Ile | Asn | Asp | Ile |
| 46 | Ser | His | Thr | Gln | Ser | Val | Ser | Ser | Lys | Gln | Lys | Val | Thr | Gly | Leu |
| 61 | Asp | Phe | Ile | Pro | Gly | Leu | His | Pro | Ile | Leu | Thr | Leu | Ser | Lys | Met |
| 76 | Asp | Gln | Thr | Leu | Ala | Val | Tyr | Gln | Gln | Ile | Leu | Thr | Ser | Met | Pro |
| 91 | Ser | Arg | Asn | Val | Ile | Gln | Ile | Ser | Asn | Asp | Leu | Glu | Asn | Leu | Arg |
| 106 | Asp | Leu | Leu | His | Val | Leu | Ala | Phe | Ser | Lys | Ser | Cys | His | Leu | Pro |
| 121 | Trp | Ala | Ser | Gly | Leu | Glu | Thr | Leu | Asp | Ser | Leu | Gly | Gly | Val | Leu |
| 136 | Glu | Ala | Ser | Gly | Tyr | Ser | Thr | Glu | Val | Val | Ala | Leu | Ser | Arg | Leu |
| 151 | Gln | Gly | Ser | Leu | Gln | Asp | Met | Leu | Trp | Gln | Leu | Asp | Leu | Ser | Pro |
| 166 | Gly | Cys | End | | | | | | | | | | | | |

FIG. 3

```
Mouse   MCWRPLCRFL WLWSYLSYVQ AVPIQKVQDD TKTLIKTIVT RINDISHTQS
        * *** *    * *                                           50
Human   MHWGTLCGFL WLWPYLFYVQ AVPIQKVQDD TKTLIKTIVT RINDISHTQS Mouse   VSAKQRVTGL DFIPGLHPIL SLSKMDQTLA VYQQVLTSLP SQNVLQIAND
        *                     -                  *              100
Human   VSSKQKVTGL DFIPGLHPIL TLSKMDQTLA VYQQILTSMP SRNVIQISND Mouse   LENLRDLLHL LAFSKSCSLP QTSGLQKPES LDGVLEASLY STEVVALSRL
                        *     *-    *      *                150
Human   LENLRDLLHV LAFSKSCHLP WASGLETLDS LGGVLEASGY STEVVALSRL Mouse   QGSLQDILQQ LDVSPEC
         *    -     *                                           167
Human   QGSLQDMLWQ LDLSPGC
```

FIG.4

| | | | | | | | | | | | | | | | |
|---|---|---|---|---|---|---|---|---|---|---|---|---|---|---|---|
| 1 | Met | Cys | Trp | Arg | Pro | Leu | Cys | Arg | Phe | Leu | Trp | Ser | Tyr |
| 16 | Leu | Ser | Tyr | Val | Gln | Ala | Val | Pro | Ile | Gln | Lys | Val | Gln | Asp | Asp |
| 31 | Thr | Lys | Thr | Leu | Ile | Lys | Thr | Ile | Val | Thr | Arg | Ile | Asn | Asp | Ile |
| 46 | Ser | His | Thr | Ser | Val | Ser | Ala | Lys | Gln | Arg | Val | Thr | Gly | Leu | Asp |
| 61 | Phe | Ile | Pro | Gly | Leu | His | Pro | Ile | Leu | Ser | Leu | Ser | Lys | Met | Asp |
| 76 | Gln | Thr | Leu | Ala | Val | Tyr | Gln | Gln | Val | Leu | Thr | Ser | Leu | Pro | Ser |
| 91 | Gln | Asn | Val | Leu | Gln | Ile | Ala | Asn | Asp | Leu | Glu | Asn | Leu | Arg | Asp |
| 106 | Leu | Leu | His | Leu | Leu | Ala | Phe | Ser | Lys | Ser | Cys | Ser | Leu | Pro | Gln |
| 121 | Thr | Ser | Gly | Leu | Gln | Lys | Pro | Glu | Ser | Leu | Asp | Gly | Val | Leu | Glu |
| 136 | Ala | Ser | Leu | Tyr | Ser | Thr | Glu | Val | Val | Ala | Leu | Ser | Arg | Leu | Gln |
| 151 | Gly | Ser | Leu | Gln | Asp | Ile | Leu | Gln | Gln | Leu | Asp | Val | Ser | Pro | Glu |
| 166 | Cys | End | | | | | | | | | | | | | |

FIG.5

| | | | | | | | | | | | | | | | |
|---|---|---|---|---|---|---|---|---|---|---|---|---|---|---|---|
| 1 | Met | His | Trp | Gly | Thr | Leu | Cys | Gly | Phe | Leu | Trp | Leu | Trp | Pro | Tyr |
| 16 | Leu | Phe | Tyr | Val | Gln | Ala | Val | Pro | Ile | Gln | Lys | Val | Gln | Asp | Asp |
| 31 | Thr | Lys | Thr | Leu | Ile | Lys | Thr | Ile | Val | Thr | Arg | Ile | Asn | Asp | Ile |
| 46 | Ser | His | Thr | Ser | Val | Ser | Ser | Lys | Gln | Lys | Val | Thr | Gly | Leu | Asp |
| 61 | Phe | Ile | Pro | Gly | Leu | His | Pro | Ile | Leu | Thr | Leu | Ser | Lys | Met | Asp |
| 76 | Gln | Thr | Leu | Ala | Val | Tyr | Gln | Gln | Ile | Leu | Thr | Ser | Met | Pro | Ser |
| 91 | Arg | Asn | Val | Ile | Gln | Ile | Ser | Asn | Asp | Leu | Glu | Asn | Leu | Arg | Asp |
| 106 | Leu | Leu | His | Val | Leu | Ala | Phe | Ser | Lys | Ser | Cys | His | Leu | Pro | Trp |
| 121 | Ala | Ser | Gly | Leu | Glu | Thr | Leu | Asp | Ser | Leu | Gly | Gly | Val | Leu | Glu |
| 136 | Ala | Ser | Gly | Tyr | Ser | Thr | Glu | Val | Val | Ala | Leu | Ser | Arg | Leu | Gln |
| 151 | Gly | Ser | Leu | Gln | Asp | Met | Leu | Trp | Gln | Leu | Asp | Leu | Ser | Pro | Gly |
| 166 | Cys | End | | | | | | | | | | | | | |

FIG. 6

```
        +10            +20            +30            +40
    GTGCAAGAAG AAGAAGATCC CAGGGCAGGA AAATGTGCTG GAGACCCCTG
 1  ---------- ---------- ---------- ---------- ----------
    CACGTTCTTC TTCTTCTAGG GTCCCGTCCT TTTACACGAC CTCTGGGGAC

+10            +20            +30            +40
    TGTCGGGTCC NGTGGNTTTG GTCCTATCTG TCTTATGTNC AAGCAGTGCC
 51 ---?------ ---?------ ---------- ------?--- ----------
    ACAGCCCAGG NCACCNAAAC CAGGATAGAC AGAATACANG TTCGTCACGG

+10            +20            +30            +40
    TATCCAGAAA GTCCAGGATG ACACCAAAAG CCTCATCAAG ACCATTGTCA
101 ---------- ---------- ---------- ---------- ----------
    ATAGGTCTTT CAGGTCCTAC TGTGGTTTTC GGAGTAGTTC TGGTAACAGT

+10            +20            +30            +40
    NCAGGATCAC TGANATTTCA CACACG
151 ?--------- ---?------ ------
    NGTCCTAGTG ACTNTAAAGT GTGTGC
```

FIG. 10

2G7
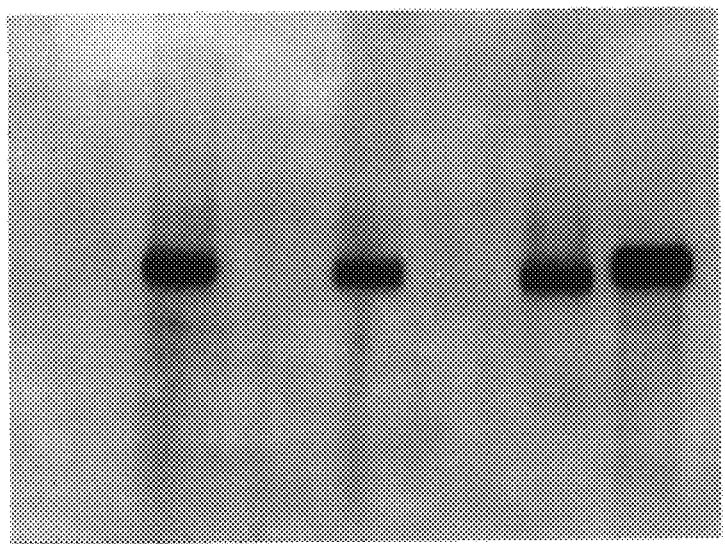
ap2
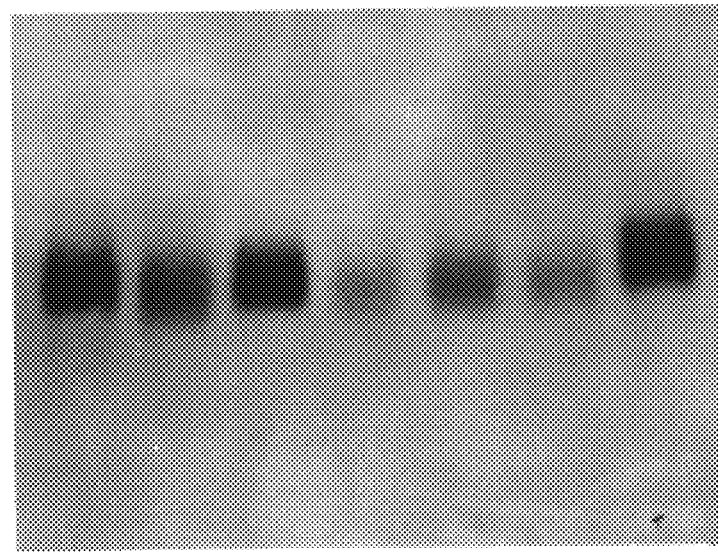
FIG.13

```
                T7 PROMOTER PRIMER 69348-1
                ------------------------->
                       T7 PROMOTER
                -------------------------->
  BglII                                                LAC OPERATOR                XbaI
AGATCTCGATCCCGCGAAATTAATACGACTCACTATAGGGGAATTGTGAGCGGATAACAATTCCCCTCTACA

His•Tag
                     RBS             NcoI
AATAATTTTGTTAACTTTAAGAAGGAGATATACCATGGGCAGCAGCCATCATCATCATCATCACAGCAGCGGC
                                     MetGlySerSerHisHisHisHisHisHisSerSerGly

NdeI     XhoI BamHI
CTGGTGCCGCGCGGCAGCCAGATATGCTCGAGGATCCCGCTGTAACAAAGCCCGAAAGGAAGCTGAGTTGGCT
LeuValProArgGlySerHisMetLeuGluAspProAlaAlaAlaAsnLysAlaArgLysGluAlaGluLeuAla
         THROMBIN

BpuI102I                                       T7 TERMINATOR
GCTGCCACCGCTGAGCAATAAACTAGCATAACCCCCTTGGGGCCTCTAAACGGGTCTTGAGGGGTTTTTG
AlaAlaAlaThrAlaGluGluGln End
       <---------------------------
         T7 TERMINATOR PRIMER #69337-1
```

FIG. 17

```
         260        270        280        290        300
          |          |          |          |          |
CCAGATAGTC CAAGAAACAT TTATTGAACG CCTCCTGAAT GCCAGGCACC 310        320        330        340        350
          |          |          |          |          |
TACTGGAAGC TGAGAAGGAT TTTGGATAGC ACAGGGCTCC ACTCTTTCTG 360        370        380        390        400
          |          |          |          |          |
GTTGTTTCTT NTGGCCCCCT CTGCCCTGCTG AGATNCCAGG GGTTAGNGGT 410        420        430        440        450
          |          |          |          |          |
TCTTAATTCC TAAA------ ---------- ---------- -------CT
                        GAP OF SEQUENCE (~1.4 KB)

460        470        480        490        500
          |          |          |          |          |
GGTTCTTTCA GGAAGAGGCC ATGTAAGAGA AAGGAATTGA CCTAGGGAAA
```

FIG.20A - 2

```
510                520                530                540                550
ATTGGCCTGG  GAAGTGGAGG  GAACGGATGG  TGTGGGAAAA  GCAGGAATCT 560                570                580                590                600
CGGAGACCAG  CTTAGAGGCT  TGGCAGTCAC  CTGGGTGCAG  GANACAAGGG 610                620                630                640                650
CCTGAGCCAA  AGTGGTGAGG  GAGGGTGGAA  GGAGACAGCC  CAGAGAATGA 660                670                680                690                700
CCCTCCATGC  CCACGGGGAA  GGCAGAGGGC  TCTGAGAGCG  ATTCCTCCCA
                                    3' OF 1ST INTRON→

710                720                730                740                750
CATGCTGAGC  ACTTGTTCTC  CCTCTTCCTC  CTNCATAGCA  GTCAGTCTCC
HOB 2G F →
```

FIG. 20A-3

```
760         770         780         790         800
TCCAAACAGA  AAGTCACCGG  TTTGGACTTC  ATTCCTGGGC  TCCACCCCAT 810         820         830         840         850
CCTGACCTTA  TCCAAGATGG  ACCAGACACT  GGCAGTCTAC  CAACAGATCC 860         870         880         890         900
TCACCAGTAT  GCCTTCCAGA  AACGTGATCC  AAATATCCAA  CGACCTGGAG 910         920         930         940         950
AACCTCCGGG  ATCTTCTTCA  CGTGCTGGCC  TTCTCTAAGA  GCTGCCACTT 960         970         980         990         1000
GCCCTGGGCC  AGTGGCCTGG  AGACCTTGGA  CAGCCTGGGG  GGTGTCCTGG
```

FIG.20A-4

```
       1010       1020       1030       1040       1050
        |          |          |          |          |
AAGCTTCAGG CTACTCCACA GAGGTGGTGG CCCTGAGCAG GCTGCAGGGG 1060       1070       1080       1090       1100
        |          |          |          |          |
TCTCTGCAGG ACATGCTGTG GCAGCTGGAC CTCAGCCCTG GGTGCTGAGG
                                                  STOP
       1110       1120       1130       1140       1150
        |          |          |          |          |
CCTTGAAGGT CACTCTTCCT GCAAGGACTA CGTTAAGGGA AGGAACTCTG 1160       1170       1180       1190       1200
        |          |          |          |          |
GCTTCCAGGT ATCTCCAGGA TTGAAGAGCA TTGCATGGAC ACCCCTTATC
           ◄────────
              HOB 2G R
       1210       1220       1230       1240       1250
        |          |          |          |          |
CAGGACTCTG TCAATTTCCC TGACTCCCTCT AAGCCACTCT TCCAAAGG
```

FIG. 20A-5

MOUSE OB STRUCTURE

HUMAN OB STRUCTURE

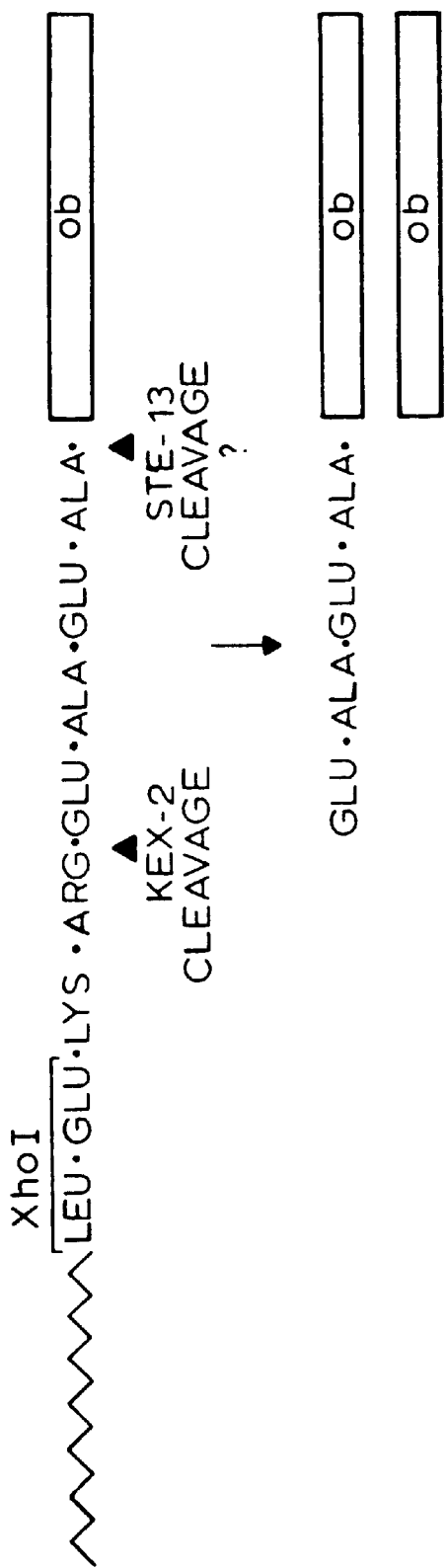
FIG.21B
FIG.21C

Human ob

| Peptide | Mass (Da) | |
|---|---|---|
| | Expected | Observed |
| 22-167 | 16,024 | 16,024 ± 3 |
| 22-75 | 5936.9 | 5936.6 ± 1 |
| 76-89 | 1562.7 | N.D. |
| 90-167 | 8434.5 | 8435.6 ± 1 |
| 158-167 | 1131.9 | N.D. |

OB POLYPEPTIDES AND MODIFIED FORMS AS MODULATORS OF BODY WEIGHT

RELATED APPLICATIONS

The present application is a continuation-in-part of application Ser. No. 08/438,431, filed May 10, 1995, which in turn is a continuation-in-part of application Ser. No. 08/347,563, filed Nov. 30, 1994 now U.S. Pat. No. 5,935,810, which in turn is a continuation-in-part of application Ser. No. 08/292,345, filed Aug. 17, 1994 now U.S. Pat. No. 6,001,968, to each of which the instant application claims the benefit of the filing date pursuant to 35 U.S.C. § 120, and each of which is incorporated herein by reference in its entirety.

The research leading to the present inventions was funded in part by Grant No. DK 41096 from the National Institutes of Health. The government may have certain rights in the invention.

TECHNICAL FIELD OF THE INVENTION

The present invention relates generally to the control of body weight of mammals including animals and humans, and more particularly to materials identified herein as modulators of weight, and to the diagnostic and therapeutic uses to which such modulators may be put.

BACKGROUND OF THE INVENTION

Obesity, defined as an excess of body fat relative to lean body mass, is associated with important psychological and medical morbidities, the latter including hypertension, elevated blood lipids, and Type II or non-insulin-dependent diabetes melitis (NIDDM). There are 6–10 million individuals with NIDDM in the U.S., including 18% of the population of 65 years of age (Harris et al., 1987). Approximately 45% of males and 70% of females with NIDDM are obese, and their diabetes is substantially improved or eliminated by weight reduction (Harris, 1991). As described below, both obesity and NIDDM are strongly heritable, though the predisposing genes have not been identified. The molecular genetic basis of these metabolically related disorders is an important, poorly understood problem.

The assimilation, storage, and utilization of nutrient energy constitute a complex homeostatic system central to survival of metazoa. Among land-dwelling mammals, storage in adipose tissue of large quantities of metabolic fuel as triglycerides is crucial for surviving periods of food deprivation. The need to maintain a fixed level of energy stores without continual alterations in the size and shape of the organism requires the achievement of a balance between energy intake and expenditure. However, the molecular mechanisms that regulate energy balance remain to be elucidated. The isolation of molecules that transduce nutritional information and control energy balance will be critical to an understanding of the regulation of body weight in health and disease.

An individual's level of adiposity is, to a large extent, genetically determined. Examination of the concordance rates of body weight and adiposity amongst mono- and dizygous twins or adoptees and their biological parents have suggested that the heritability of obesity (0.4–0.8) exceeds that of many other traits commonly thought to have a substantial genetic component, such as schizophrenia, alcoholism, and atherosclerosis (Stunkard et al., 1990). Familial similarities in rates of energy expenditure have also been reported (Bogardus et al., 1986). Genetic analysis in geographically delimited populations has suggested that a relatively small number of genes may account for the 30%–50% of variance in body composition (Moll et al., 1991). However, none of the genes responsible for obesity in the general population have been genetically mapped to a definite chromosomal location. Rodent models of obesity include seven apparently single-gene mutations. The most intensively studied mouse obesity mutations are the ob (obese) and db (diabetes) genes. When present on the same genetic strain background, ob and db result in indistinguishable metabolic and behavioral phenotypes, suggesting that these genes may function in the same physiologic pathway (Coleman, 1978). Mice homozygous for either mutation are hyperphagic and hypometabolic, leading to an obese phenotype that is notable at one month of age. The weight of these animals tends to stabilize at 60–70 g (compared with 30–35 g in control mice). ob and db animals manifest a myriad of other hormonal and metabolic changes that have made it difficult to identify the primary defect attributable to the mutation (Bray et al., 1989).

Each of the rodent obesity models is accompanied by alterations in carbohydrate metabolism resembling those in Type II diabetes in man. In some cases, the severity of the diabetes depends in part on the background mouse strain (Leiter, 1989). For both ob and db, congenic C57BL/Ks mice develop a severe diabetes with ultimate β cell necrosis and islet atrophy, resulting in a relative insulinopenia. Conversely, congenic C57BL/6J ob and db mice develop a transient insulin-resistant diabetes that is eventually compensated by β cell hypertrophy resembling human Type II diabetes.

The phenotype of ob and db mice resembles human obesity in ways other than the development of diabetes—the mutant mice eat more and expend less energy than do lean controls (as do obese humans). This phenotype is also quite similar to that seen in animals with lesions of the ventromedial hypothalamus, which suggests that both mutations may interfere with the ability to properly integrate or respond to nutritional information within the central nervous system. Support for this hypothesis comes from the results of parabiosis experiments (Coleman, 1973) that suggest ob mice are deficient in a circulating satiety factor and that db mice are resistant to the effects of the ob factor (possibly due to an ob receptor defect). These experiments have led to the conclusion that obesity in these mutant mice may result from different defects in an afferent loop and/or integrative center of the postulated feedback mechanism that controls body composition.

Using molecular and classical genetic markers, the ob and db genes have been mapped to proximal chromosome 6 and midchromosome 4, respectively (Bahary et al., 1990; Friedman et al., 1991b). In both cases, the mutations map to regions of the mouse genome that are syntonic with human, suggesting that, if there are human homologs of ob and db, they are likely to map, respectively, to human chromosomes 7q and 1p. Defects in the db gene may result in obesity in other mammalian species: in genetic crosses between Zucker fa/fa rats and Brown Norway +/+ rats, the fa mutation (rat chromosome 5) is flanked by the same loci that flank db in mouse (Truett et al., 1991).

Because of the myriad factors that seem to impact body weight, it is difficult to speculate as to which of these factors, and more particularly, which homeostatic mechanism is actually primarily determinative. Nonetheless, the apparent connection between the ob gene and the extent and characteristics of obesity have prompted the further investigation and elucidation that is reflected by the present application. It is the identification of the sequence of the gene and corresponding peptide materials, to which the present invention following below directs itself.

The citation of any reference herein should not be construed as an admission that such reference is prior art to the instant invention. Full citations of references cited by author and year are found at the end of the specification.

SUMMARY OF THE INVENTION

In its broadest aspect, the present invention relates to the elucidation and discovery of nucleic acids, and proteins putatively expressed by such nucleic acids or degenerate variations thereof, that demonstrate the ability to participate in the control of mammalian body weight. The nucleic acids in object represent the coding sequences corresponding to the murine and human ob gene, that is postulated to play a critical role in the regulation of body weight and adiposity. Data presented herein indicates that the polypeptide product of the gene in question is secreted by the cells that express it and that the polypeptide functions as a hormone.

In addition, the Examples herein demonstrate that the ob polypeptide, alternatively termed herein "leptin," circulates in mouse, rat, and human plasma. Leptin is absent in plasma from ob/ob mice, and is present at ten-fold higher concentrations in plasma from db/db mice, and twenty-fold higher concentrations in fa/fa rats. Most significantly, daily injections of recombinant leptin dramatically reduces the body mass of ob/ob mice, significantly affects the body weight of wild-type mice, and has no effect on db/db mice.

In a further aspect, the ob polypeptide from one species is biologically active in another species. In particular, the human ob polypeptide is active in mice.

In a first instance, the modulators of the present invention comprise nucleic acid molecules, including recombinant DNA molecules (e.g., cDNA or a vector containing the cDNA or isolated genomic DNA) or cloned genes (i.e., isolated genomic DNA), or degenerate variants thereof, which encode polypeptides themselves serving as modulators of weight control as hereinafter defined, or conserved variants or fragments thereof, particularly such fragments lacking the signal peptide (alternatively referred to herein as mature ob polypeptide), which polypeptides possess amino acid sequences such as set forth in FIG. 1 (SEQ ID NO:2), FIG. 3 (SEQ ID NO:4), FIG. 5 (SEQ ID NO:5) and FIG. 6 (SEQ ID NO:6). In specific embodiments, amino acid sequences for two variants of murine and human ob polypeptides are provided. Both polypeptides are found in a form with glutamine 49 deleted, which may result from an mRNA splicing anomaly. The ob polypeptides from various species may be highly homologous; as shown in FIG. 4, murine and human ob polypeptides are greater than 80% homologous.

The nucleic acid molecules, recombinant DNA molecules, or cloned genes, may have the nucleotide sequences or may be complementary to DNA coding sequences shown in FIG. 1 (SEQ ID NO:1) and FIG. 2 (SEQ ID NO:3). In particular, such DNA molecules can be cDNA or genomic DNA isolated from the chromosome. Nucleic acid molecules of the invention may also correspond to 5' and 3' flanking sequences of the DNA and intronic DNA sequences. Accordingly, the present invention also relates to the identification of a nucleic acid having a nucleotide sequence selected from the sequences of FIG. 1 (SEQ ID NO:1) and FIG. 2 (SEQ ID NO:3) herein, and degenerate variants, allelic variations, and like cognate molecules.

A nucleic acid molecule of the invention can be DNA or RNA, including synthetic variants thereof having phosphate or phosphate analog, e.g., thiophosphate, bonds. Both single stranded and double stranded sequences are contemplated herein.

The present invention further provides nucleic acid molecules for use as molecular probes, or as primers for polymerase chain reaction (PCR) amplification, i.e., synthetic or natural oligonucleotides having a sequence corresponding to a portion of the sequences shown in FIG. 1 (SEQ ID NO:1), FIG. 2 (SEQ ID NO:3) and FIG. 20A (SEQ ID NO:22); or the 5' and 3' flanking sequences of the coding sequences; or intronic sequences of the genomic DNA. In particular, the invention contemplates a nucleic acid molecule having at least about 10 nucleotides, wherein a sequence of the nucleic acid molecule corresponds to a nucleotide sequence of the same number of nucleotides in the nucleotide sequences of FIG. 1 (SEQ ID NO:1), FIG. 2 (SEQ ID NO:3) and FIG. 20A (SEQ ID NO:22), or a sequence complementary thereto. More preferably, the nucleic acid sequence of the molecule has at least 15 nucleotides. Most preferably, the nucleic acid sequence has at least 20 nucleotides. In an embodiment of the invention in which the oligonucleotide is a probe, the oligonucleotide is detectably labeled, e.g., with a radionuclide (such as $^{32}P$), or an enzyme.

In further aspects, the present invention provides a cloning vector, which comprises the nucleic acids of the invention that encode the ob polypeptide; and a bacterial, insect, or a mammalian expression vector, which comprises the nucleic acid molecules of the invention encoding the ob polypeptide, operatively associated with an expression control sequence. Accordingly, the invention further relates to a host cell, such as a bacterial cell, yeast cell, insect cell, or a mammalian cell, transfected or transformed with an appropriate expression vector, and correspondingly, to the use of the above mentioned constructs in the preparation of the modulators of the invention.

In yet a further aspect, the present invention relates to antibodies that bind to the ob polypeptide. Such antibodies may be generated against the full length polypeptide, or antigenic fragments thereof. In one aspect, such antibodies inhibit the functional (i.e., body weight and fat composition modulating) activity of the ob polypeptide. In another aspect, antibodies can be used to determine the level of circulating ob polypeptide in plasma or serum. In yet a further aspect, regio-specific antibodies, particularly monoclonal antibodies, can be used as probes of ob polypeptide structure.

All of the foregoing materials are to be considered herein as modulators of body weight and fat composition, and as such, may be used in a variety of contexts. Specifically, the invention contemplates both diagnostic and therapeutic applications, as well as certain agricultural applications, all contingent upon the use of the modulators defined herein, including both nucleic acid molecules and peptides. Moreover, the modulation of body weight carries specific therapeutic implications and benefits, in that conditions where either obesity or, conversely, cachexia represent undesired bodily conditions, can be remedied by the administration of one or more of the modulators of the present invention.

Thus, a method for modulating body weight of a mammal is proposed that comprises controlling the expression of the protein encoded by a nucleic acid having nucleotide sequence selected from the sequence of FIG. 1 (SEQ ID NO:1), the sequence of FIG. 2 (SEQ ID NO:3) and degenerate and allelic variants thereof. Such control may be effected by the introduction of the nucleotides in question by gene therapy into fat cells of the patient or host to control or reduce obesity. Conversely, the preparation and administration of antagonists to the nucleotides, such as anti-sense molecules, would be indicated and pursued in the instance where conditions involving excessive weight loss, such as anorexia nervosa, cancer, or AIDS are present and under treatment. Such constructs would be introduced in similar fashion to the nucleotides, directly into fat cells to effect such changes.

Correspondingly, the proteins defined by FIG. 1, FIG. 3, FIG. 5, and FIG. 6 (SEQ ID NO:1, SEQ ID NO:4, SEQ ID NO:5, and SEQ ID NO:6), conserved variants, active fragments thereof, and cognate small molecules could be formulated for direct administration for therapeutic purposes, to effect reduction or control of excessive body fat or weight gain. Correspondingly, antibodies and other antagonists to the stated protein materials, such as fragments thereof, could be prepared and similarly administered to achieve the converse effect. Accordingly, the invention is advantageously directed to a pharmaceutical composition comprising an ob polypeptide of the invention, or alternatively an antagonist thereof, in an admixture with a pharmaceutically acceptable carrier or excipient.

In addition, the ob polypeptide of the invention may be administered for its cosmetic effects, e.g., to improve body appearance by reducing fat deposits. The ob polypeptide can be used independently or in conjunction with other cosmetic strategies, e.g., surgery, for its cosmetic effects.

The diagnostic uses of the present nucleotides and corresponding peptides extend to the use of the nucleic acids to identify further mutations of allelic variations thereof, so as to develop a repertoire of active nucleotide materials useful in both diagnostic and therapeutic applications. In particular, both homozygous and heterozygous mutations of the nucleotides in question could be identified that would be postulated to more precisely quantitate the condition of patients, to determine the at-risk potential of individuals with regard to obesity. Specifically, heterozygous mutations are presently viewed as associated with mild to moderate obesity, while homozygous mutations would be associated with a more pronounced and severe obese condition. Corresponding DNA testing could then be conducted utilizing the aforementioned ascertained materials as benchmarks, to facilitate an accurate long term prognosis for particular tendencies, so as to be able to prescribe changes in either dietary or other personal habits, or direct therapeutic intervention, to avert such conditions.

The diagnostic utility of the present invention extends to methods for measuring the presence and extent of the modulators of the invention in cellular samples or biological extracts (or samples) taken from test subjects, so that both the nucleic acids (genomic DNA or mRNA) and or the levels of protein in such test samples could be ascertained. Given that the increased activity of the nucleotide and presence of the resulting protein reflect the capability of the subject to inhibit obesity, the physician reviewing such results in an obese subject would determine that a factor other than dysfunction with respect to the presence and activity of the nucleotides of the present invention is a cause of the obese condition. Conversely, depressed levels of the nucleotide and/or the expressed protein would suggest that such levels must be increased to treat such obese condition, and an appropriate therapeutic regimen could then be implemented.

Further, the nucleotides discovered and presented in FIG. 1 and FIG. 2 represent cDNA in which, as stated briefly above, is useful in the measurement of corresponding RNA. Likewise, recombinant protein material corresponding to the polypeptides of FIG. 1 and FIG. 3 may be prepared and appropriately labeled, for use, for example, in radioimmunoassays, for example, for the purpose of measuring fat and/or plasma levels of the ob protein, or for detecting the presence and level of a receptor for ob on tissues, such as the hypothalamus.

Yet further, the present invention contemplates not only the identification of the nucleotides and corresponding proteins presented herein, but the elucidation of the receptor to such materials. In such context, the polypeptides of FIG. 1, FIG. 3, FIG. 5, and/or FIG. 6 could be prepared and utilized to screen an appropriate expression library to isolate active receptors. The receptor could thereafter be cloned, and the receptor alone or in conjunction with the ligand could thereafter be utilized to screen for small molecules that may possess like activity to the modulators herein.

Yet further, the present invention relates to pharmaceutical compositions that include certain of the modulators hereof, preferably the polypeptides whose sequences are presented in SEQ ID NO:2, SEQ ID NO:4, SEQ ID NO:5 and SEQ ID NO:6, their antibodies, corresponding small molecule agonists or antagonists thereof, or active fragments prepared in formulations for a variety of modes of administration, where such therapy is appropriate. Such formulations would include pharmaceutically acceptable carriers, or other adjuvants as needed, and would be prepared in effective dosage ranges to be determined by the clinician or the physician in each instance.

Accordingly, it is a principal object of the present invention to provide modulators of body weight as defined herein in purified form, that exhibit certain characteristics and activities associated with control and variation of adiposity and fat content of mammals.

It is a further object of the present invention to provide methods for the detection and measurement of the modulators of weight control as set forth herein, as a means of the effective diagnosis and monitoring of pathological conditions wherein the variation in level of such modulators is or may be a characterizing feature.

It is a still further object of the present invention to provide a method and associated assay system for the screening of substances, such as drugs, agents and the like, that are potentially effective to either mimic or inhibit the activity of the modulators of the invention in mammals.

It is a still further object of the present invention to provide a method for the treatment of mammals to control body weight and fat content in mammals, and or to treat certain of the pathological conditions of which abnormal depression or elevation of body weight is a characterizing feature.

It is a still further object of the present invention to prepare genetic constructs for use in genetic therapeutic protocols and or pharmaceutical compositions for comparable therapeutic methods, which comprise or are based upon one or more of the modulators, binding partners, or agents that may control their production, or that may mimic or antagonize their activities.

Other objects and advantages will become apparent to those skilled in the art from a review of the ensuing description which proceeds with reference to the following illustrative drawings.

BRIEF DESCRIPTION OF THE DRAWINGS

FIG. 2 depicts the nucleic acid sequence (SEQ ID NO:3) derived for the human ob cDNA. The nucleotides are numbered from 1 to 701 with a start site at nucleotide 46 and a termination at nucleotide 550.

FIG. 3 depicts the full deduced amino acid sequence (SEQ ID NO:4) derived for the human ob gene corresponding to the nucleic acid sequence of FIG. 2. The amino acids are numbered from 1 to 167. A signal sequence cleavage site is located after amino acid 21 (Ala) so that the mature protein extends from amino acid 22 (Val) to amino acid 167 (Cys).

FIG. 4 depicts the comparison between the murine (SEQ ID NO:2) and human (SEQ ID NO:4) deduced amino acid sequences. The sequence of the human ob deduced amino acid sequence was highly homologous to that of mouse. Conservative changes are noted by a dash, and non-conservative changes by an asterisk. The variable glutamine codon is underlined, as is the position of the nonsense mutation in C57BL/6J ob/ob (1J) mice. Overall, there is 84% identity at the amino acid level, although only six substitutions were found between the valine at codon 22 (immediately downstream of the signal sequence overage) and the cysteine at position 117.

FIG. 5 depicts the full length amino acid sequence (SEQ ID NO:5) derived for the murine ob gene as shown in FIG. 3, but lacking glutamine at position 49. The amino acids are numbered from 1 to 166. A signal sequence cleavage site is located after amino acid 21 (Ala) (and thus, before the glutamine 49 deletion) so that the mature protein extends from amino acid 22 (Val) to amino acid 166 (Cys).

FIG. 6 depicts the full deduced amino acid sequence (SEQ ID NO:6) derived for the human ob gene as shown in FIG. 4, but lacking glutamine at position 49. The amino acids are numbered from 1 to 166. A signal sequence cleavage site is located after amino acid 21 (Ala) (and thus, before the glutamine 49 deletion) so that the mature protein extends from amino acid 22 (Val) to amino acid 166 (Cys).

(FIG. 7B) The resulting YAC contig. One of the YACs in this contig, Y902A0925, was chimeric. Each of the probes used to genotype the recombinant animals is indicated in parentheses. (6) Corresponds to YAC 107; (5) corresponds to M16(+) (or M16(pLUS)); (4) corresponds to adu(+); (3) corresponds to aad(pICL); (2) corresponds to 53(pICL); and (1) corresponds to 53(+). (FIG. 7C) The P1 contig of bacteriophage P1 clones isolated with selected YAC end probes. The ob gene was isolated in a P1 clone isolated using the distal end of YAC YB6S2F12 (end (4)) (alternatively termed herein adu(+)).

FIG. 10 presents the sequence of the 2G7 clone (SEQ ID NO:7), which includes an exon coding for a part of the ob gene. The primer sequences used to amplify this exon are boxed in the figure (SEQ ID NOS:8 and 9).

FIG. 13 is a Northern analysis of additional 2J animals and control animals that confirms the absence of the ob mRNA from 2J animals. The Northern analysis was performed as in FIGS. 11 and 12. In this case, the control RNA was ap2, a fat specific transcript. There is no significance to the varying density of the ap2 bands.

FIG. 17 presents the expression cloning region of vector pET-15b (Novagen).

FIG. 20 (FIG. 20A) The sequence of the human ob gene (SEQ ID NO:22).

FIG. 21 presents a schematic drawing of one of the cloning strategies employed to achieve recombinant expression of ob in pichia yeast. (FIG. 21B) Schematic drawing of the structure of the recombinant fusion protein, including the amino acid sequence (SEQ ID NO:23) showing the XhoI site and putative KEX-2 and STE-13 cleavage sites, and the N-terminal surplus amino acids present after KEX-2 cleavage (SEQ ID NO:24). (FIG. 21C) An alternative strategy for producing mature ob under involves preparing a construct with an amino acid sequence corresponding to a XhoI cleavage site and a KEX-2 cleavage site immediately upstream of the mature ob polypeptide sequence (SEQ ID NO:25).

FIG. 22. Alternative expression strategy in pichia.

FIG. 24 shows the ob protein circulates in mouse plasma.

FIG. 25 shows that the ob protein circulates at variable levels in human plasma.

(FIG. 26B) The human protein expressed in yeast contains an intramolecular disulphide bond. Secreted proteins generally assume their correct conformation when expressed in the *Pichia pastoris* expression system. The 146 amino acid mature human protein was expressed in *Pichia pastoris* and purified from the yeast media by a two-step purification protocol involving IMAC and gel filtration. The purified recombinant protein was subjected to mass spectrometry before and after cyanogen bromide cleavage. Cyanogen bromide cleaves at the carboxy terminus of methionine residues. The molecular mass of the recombinant yeast protein was 16,024±3 Da (calculated molecular mass=16,024 Da). Cyanogen bromide cleaves after the three methionines in the protein sequence at amino acids 75, 89, and 157. The cyanogen bromide fragment with measured mass 8435.6 Da corresponds to amino acids 90–157 and 158–167 joined by a disulphide linkage between cys-117 and cys-167 (calculated molecular mass=8434.5 Da). N.D.= note detected.

FIG. 29 shows the results of pair feeding of ob mice.

FIG. 32 shows that ob RNA is expressed in all adipose tissue depots. All of the adipose tissue depots tested expressed ob RNA. The inguinal fat pad expressed somewhat lower RNA levels although there was variability in the levels of signals in different experiments.

(FIG. 33A) One month old CBA female mice were treated with GTG (0.2 mg/g), with a resulting increase of >20 g in treated animals relative to control animals (<5 g). (FIG. 33B) Hybridization of an ob probe to RNA from db/db and GTG treated mice revealed a twenty-fold increase in the abundance of ob RNA relative to control RNA (actin or GAPDH).

DETAILED DESCRIPTION

Figure 7:
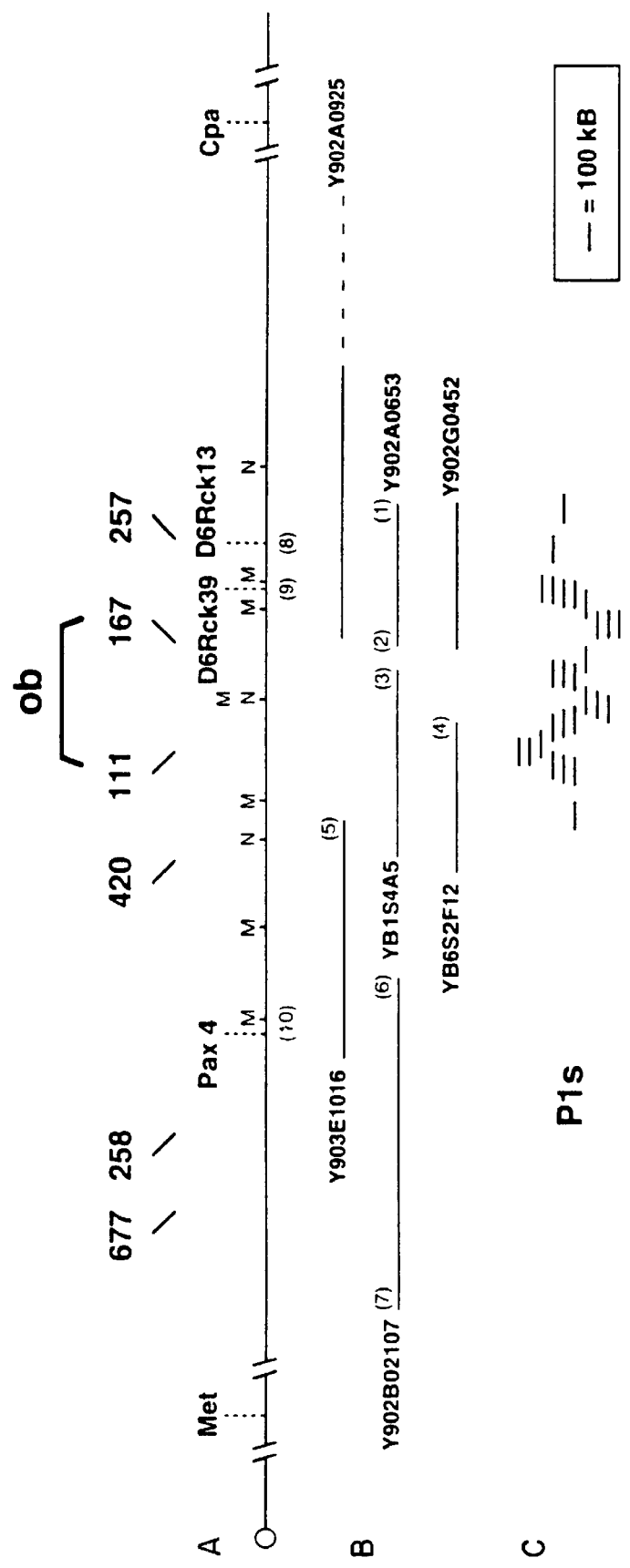
FIG. 7 (FIG. 7A) Physical map of the location of ob in the murine chromosome, and the YAC and P1 cloning maps. "M and N" corresponds to MuII and NotI restriction sites. The numbers correspond to individual animals that were recombinant in the region of ob of the 1606 meioses that were scored. Met, Pax 4, D6Rck39, D6Rck13, and Cpa refer to locations in the region of ob that bind to the DNA probes. YACs were isolated using D6Rck13 and Pax-4 as probes, and the ends were recovered using vectorette PCR and/or plasmid end rescue and used in turn to isolate new YACs.
Figure 8:
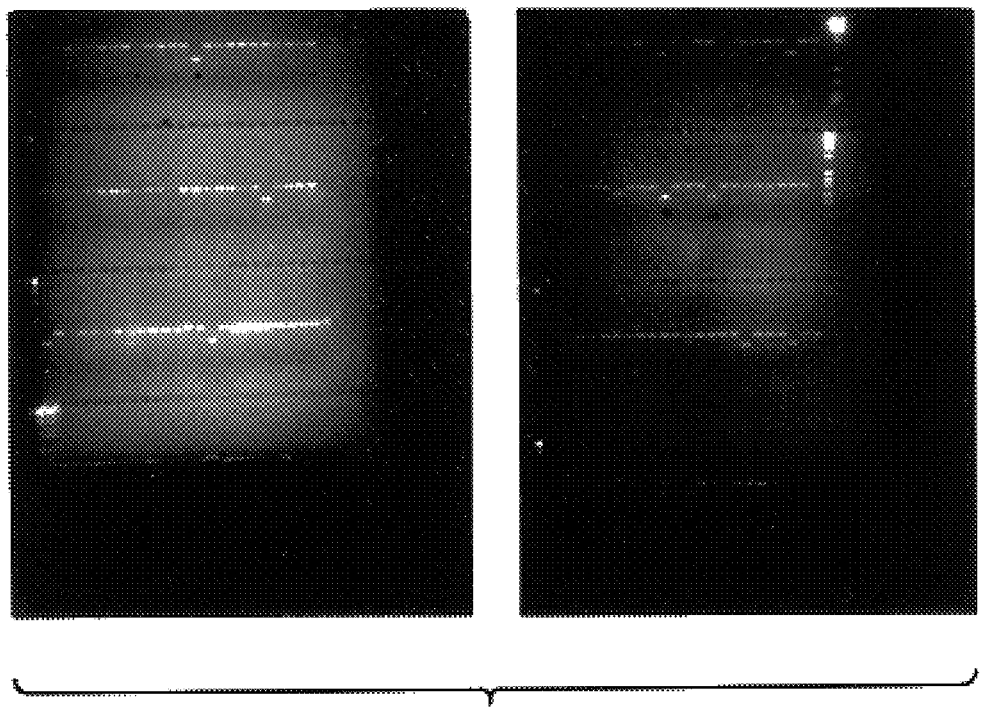
FIG. 8 presents a photograph of an ethidium bromide stain of 192 independent isolates of the fourth exon trapping experiment that were PCR amplified and characterized.
Figure 9:
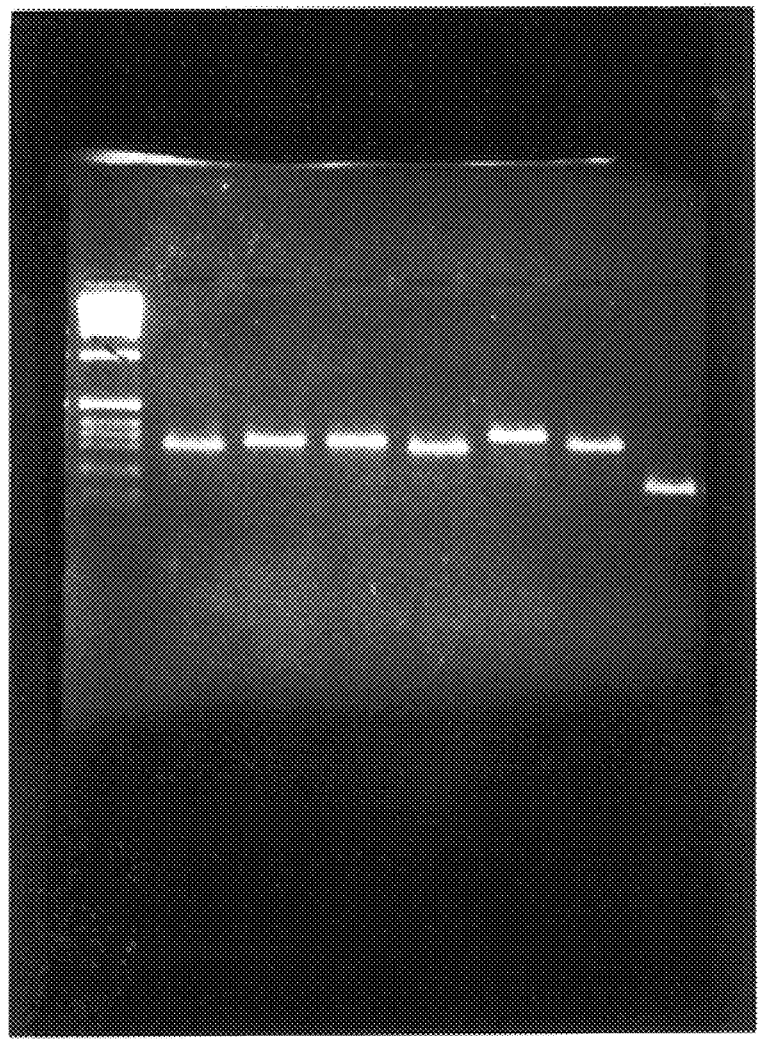
FIG. 9 is a photograph of an ethidium bromide stain of PCR-amplified clones suspected of carrying ob. Each of the 7 clones that did not carry the artifact was reamplified using PCR and electrophoresed on a 1% agarose gel in TBE and stained with ethidium bromide. The size markers (far left unnumbered lane) are the commercially available "1 kB ladder". Lane 1—clone 1D12, containing an "HIV sequence." Lane 2—clone 1F1, a novel clone outside of the ob region. Lane 3—clone 1H3. Lane 4—clone 2B2, which is the identical to 1F1. Lane 5—clone 2G7, which contains an ob exon. Lane 6—clone 2G11, which is identical to 1F1. Lane 7—clone 2H1, which does not contain an insert.

The present invention relates to the elucidation and discovery of a protein, termed herein ob polypeptide or leptin, nucleic acids encoding the protein, including degenerate variations thereof, e.g., that incorporate optimal codons for expression in a particular expression system, which protein demonstrates the ability to participate in the control of mammalian body weight. The nucleic acids in object represent the coding sequences corresponding to the murine and human ob polypeptide, which is postulated to play a critical role in the regulation of body weight and adiposity. Data presented herein indicates that the polypeptide product of a nuceic acid of the invention is secreted by the cells that express it, and that the polypeptide functions as a hormone. Additional experimental data demonstrate that the ob polypeptide is very effective in treating obesity in mice carrying a mutation of the ob gene. In addition, high bolus doses or moderate continuous doses of ob polypeptide effect weight reduction in normal (wildtype) mice.

In addition, the Examples herein demonstrate that the ob polypeptide, alternatively termed herein "leptin," circulates in mouse, rat, and human plasma. Leptin is absent in plasma from ob/ob mice, and is present at ten-fold higher concentrations in plasma from db/db mice, and twenty-fold higher concentrations in fa/fa rats. Most significantly, daily injections of recombinant leptin dramatically reduces the body mass of ob/ob mice, significantly effects the body weight of wild-type mice, and has no effect on db/db mice.

In a further aspect, the ob polypeptide from one species is biologically active in another species. In particular, the human ob polypeptide is active in mice.

In its primary aspect, the present invention is directed to the identification of materials that function as modulators of mammalian body weight. In particular, the invention concerns the isolation, purification and sequencing of certain nucleic acids that correspond to the ob gene or its coding region in both mice and humans, as well as the corresponding polypeptides expressed by these nucleic acids. The invention thus comprises the discovery of nucleic acids having the nucleotide sequences set forth in FIG. 1 (SEQ ID NO:1) and FIG. 2 (SEQ ID NO:3), and to degenerate variants, alleles and fragments thereof, all possessing the activity of modulating body weight and adiposity. The correspondence of the present nucleic acids to the ob gene portends their significant impact on conditions such as obesity as well as other maladies and dysfunctions where abnormalities in body weight are a contributory factor. The invention extends to the proteins expressed by the nucleic acids of the invention, and particularly to those proteins set forth in FIG. 1 (SEQ ID NO:2), FIG. 3 (SEQ ID NO:4), FIG. 5 (SEQ ID NO:5), and FIG. 6 (SEQ ID NO:6), as well as conserved variants, active fragments, and cognate small molecules.

As discussed earlier, the weight control modulator peptides or their binding partners or other ligands or agents exhibiting either mimicry or antagonism to them or control over their production, may be prepared in pharmaceutical compositions, with a suitable carrier and at a strength effective for administration by various means to a patient experiencing abnormal fluctuations in body weight or adiposity, either alone or as part of an adverse medical condition such as cancer or AIDS, for the treatment thereof. A variety of administrative techniques may be utilized, among them oral administration, nasal and other forms of transmucal administration, parenteral techniques such as subcutaneous, intravenous and intraperitoneal injections, catheterizations and the like. Average quantities of the recognition factors or their subunits may vary and in particular should be based upon the recommendations and prescription of a qualified physician or veterinarian.

In accordance with the above, an assay system for screening potential drugs effective to mimic or antagonize the activity of the weight modulator may be prepared. The weight modulator may be introduced into a test system, and the prospective drug may also be introduced into the resulting cell culture, and the culture thereafter examined to observe any changes in the activity of the cells, due either to the addition of the prospective drug alone, or due to the effect of added quantities of the known weight modulator.

As stated earlier, the molecular cloning of the ob gene described herein has led to the identification of a class of materials that function on the molecular level to modulate mammalian body weight. The discovery of the modulators of the invention has important implications for the diagnosis and treatment of nutritional disorders including, but not limited to, obesity, weight loss associated with cancer and the treatment of diseases associated with obesity such as hypertension, heart disease, and Type II diabetes. In addition, there are potential agricultural uses for the gene product in cases where one might wish to modulate the body weight of domestic animals. Finally, to the extent that one or more of the modulators of the invention are secreted molecules, they can be used biochemically to isolate their receptor using the technology of expression cloning. The discussion that follows with specific reference to the ob gene bears general applicability to the class of modulators that a part of the present invention, and is therefore to be accorded such latitude and scope of interpretation.

As noted above, the functional activity of the ob polypeptide can be evaluated transgenically. In this respect, a transgenic mouse model can be used. The ob gene can be used in complementation studies employing transgenic mice. Transgenic vectors, including viral vectors, or cosmid clones (or phage clones) corresponding to the wild type locus of candidate gene, can be constructed using the isolated ob gene. Cosmids may be introduced into transgenic mice using published procedures (Jaenisch, *Science* 240, 1468–1474, 1988). The constructs are introduced into fertilized eggs derived from an intercross between F1 progeny of a C57BL/6J ob/ob X DBA intercross. These crosses require the use of C57BL/6J ob/ob ovarian transplants to generate the F1 animals. DBA/2J mice are used as the counterstrain because they have a nonagouti coat color which is important when using the ovarian transplants. Genotype at the ob loci in cosmid transgenic animals can be determined by typing animals with tightly linked RFLPs or microsatellites which flank the mutation and which are polymorphic between the progenitor strains. Complementation will be demonstrated when a particular construct renders a genetically obese F2 animal (as scored by RFLP analysis) lean and nondiabetic. Under these circumstances, final proof of complementation will require that the ob/ob or db/db animal carrying the transgene be mated to the ob/ob or db/db ovarian transplants. In this cross, all N2 animals which do not carry the transgene will be obese and insulin resistant/diabetic, while those that do carry the transgene will be lean and have normal glucose and insulin concentrations in plasma. In a genetic sense, the transgene acts as a suppressor mutation.

Alternatively, ob genes can be tested by examining their phenotypic effects when expressed in antisense orientation in wild-type animals. In this approach, expression of the wild type allele is suppressed, which leads to a mutant phenotype. RNA.RNAduplex formation (antisense-sense) prevents normal handling of mRNA, resulting in partial or complete elimination of wild-type gene effect. This technique has been used to inhibit Tk synthesis in tissue culture and to produce phenotypes of the Kruppel mutation in Drosophila, and the shiverer mutation in mice (Izant and Weintraub, *Cell* 36, 1007–1015, 1984; Green et al., *Annu. Rev. Biochem.* 55,569–597, 1986; Katsuki et al., *Science* 241, 593–595, 1988). An important advantage of this approach is that only a small portion of the gene need be expressed for effective inhibition of expression of the entire cognate mRNA. The antisense transgene will be placed under control of its own promoter or another promoter expressed in the correct cell type, and placed upstream of the SV40 poly A site. This transgene will be used to make transgenic mice. Transgenic mice will also be mated ovarian transplants to test whether ob heterozygotes are more sensitive to the effects of the antisense construct.

In the long term, the elucidation of the biochemical function of the ob gene product (the ob polypeptide or protein) is useful for identifying small molecule agonists and antagonists that affect its activity.

Various terms used throughout this specification shall have the definitions set out herein, for example, below.

The term "body weight modulator", "modulator", "modulators", and any variants not specifically listed, may be used herein interchangeably, and as used throughout the present application and claims refers in one instance to both nucleotides and to proteinaceous material, the latter including both single or multiple proteins. More specifically, the aforementioned terms extend to the nucleotides and to the DNA having the sequences described herein and presented in FIG. 1 (SEQ ID NO:1), and FIG. 2 (SEQ ID NO:3). Likewise, the proteins having the amino acid sequence data described herein and presented in FIG. 1 (SEQ ID NO:2), and FIG. 3 (SEQ ID NO:4) are likewise contemplated, as are the profile of activities set forth with respect to all materials both herein and in the claims. Accordingly, nucleotides displaying substantially equivalent or altered activity are likewise contemplated, including substantially homologous analogs and allelic variations. Likewise, proteins displaying substantially equivalent or altered activity, including proteins modified deliberately, as for example, by site-directed mutagenesis, or accidentally through mutations in hosts that produce the modulators are likewise contemplated.

A composition comprising "A" (where "A" is a single protein, DNA molecule, vector, recombinant host cell, etc.) is substantially free of "B" (where "B" comprises one or more contaminating proteins, DNA molecules, vectors, etc., but excluding racemic forms of A) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

THE OB POLYPEPTIDES

The terms "protein," which refers to the naturally occurring polypeptide, and "polypeptide" are used herein interchangeably with respect to the ob gene product and variants thereof. The term "mature protein" or "mature polypeptide" particularly refers to the ob gene product with the signal sequence (or a fusion protein partner) removed.

As noted above, in specific embodiments ob polypeptides of the invention include those having the amino acid sequences set forth herein e.g., SEQ ID NOS: 2, 4, 5, 6, etc., including the ob polypeptide modified with conservative amino acid substitutions, as well as biologically active fragments, analogs, and derivatives thereof. The term "biologically active", is used herein to refer to a specific effect of the polypeptide, including but not limited to specific binding, e.g., to a receptor, antibody, or other recognition molecule; activation of signal transduction pathways on a molecular level; and/or induction (or inhibition by antagonists) of physiological effects mediated by the native ob polypeptide in vivo. Ob polypeptides, including fragments, analogs, and derivatives, can be prepared synthetically, e.g., using the well known techniques of solid phase or solution phase peptide synthesis. Preferably, solid phase synthetic techniques are employed. Alternatively, ob polypeptides of the invention can be prepared using well known genetic engineering techniques, as described infra. In yet another embodiment, the ob polypeptide can be purified, e.g., by immunoaffinity purification, from a biological fluid from, such as but not limited to plasma, serum, or urine, preferably human plasma, serum, or urine, and more preferably from a subject who overexpresses the polypeptide, such as an obese person suffering from a mutation in the ob receptor or from obesity related to a mutation corresponding to "fatty."

Fragments of the ob Polypeptide

In a particular embodiment, the present invention contemplates that naturally occurring fragments of the ob polypeptide may be important. The peptide sequence includes a number of sites that are frequently the target for proteolytic cleavage, e.g., arginine residues. It is possible that the full length polypeptide may be cleaved at one or more such sites to form biologically active fragments. Such biologically active fragments may either agonize or antagonize the functional activity of the ob polypeptide to reduce body weight.

Analogs of the Ob Polypeptide

The present invention specifically contemplates preparation of analogs of the ob peptide, which are characterized by being capable of a biological activity of ob polypeptide, e.g., of binding to a specific binding partner of ob peptide, such as the ob receptor. In one embodiment, the analog agonizes ob activity, i.e., it functions similarly to the ob peptide. Preferably, an ob agonist is more effective than the native protein. For example, an ob agonist analog may bind to the ob receptor with higher affinity, or demonstrate a longer half-life in vivo, or both. Nevertheless, ob peptide agonist analogs that are less effective than the native protein are also contemplated. In another embodiment, the analog antagonizes ob activity. For example, an ob analog that binds to the ob receptor but does not induce signal transduction can competitively inhibit binding of native ob to the receptor, thus decreasing ob activity in vivo. Such an ob antagonist analog may also demonstrate different properties from ob peptide, e.g., longer (or shorter) half-life in vivo, greater (or lesser) binding affinity for the ob receptor, or both.

In one embodiment, an analog of ob peptide is the ob peptide modified by substitution of amino acids at positions on the polypeptide that are not essential for structure or function. For example, since it is known that human ob peptide is biologically active in mouse, substitution of divergent amino acid residues in the human sequence as compared to the murine amino acid sequence will likely yield useful analogs of ob peptide. For example, the serine residue at position 53 or position 98, or both (in the unprocessed peptide sequence depicted in FIG. 4) from human may be substituted, e.g., with glycine, alanine, valine, cysteine, methionine, or threonine. Similarly, the arginine residue at position number 92 (FIG. 4) may be substituted, e.g., with asparagine, lysine., histidine, glutamine, glutamic acid, aspartic acid, serine, threonine, methionine, or cysteine. Referring still to FIG. 4, other amino acids in the human ob peptide that appear to be capable of substitution are histidine at position 118, tryptophan at position 121, alanine at position 122, glutamic acid at position 126, threonine at position 127, leucine at position 128, glycine at position 132, glycine at position 139, tryptophan at position 159, and glycine at position 166. In another embodiment, it may be possible to substitute one or more of residues 121 to 128 (as depicted in FIG. 4), e.g., with glycines or alanines, or substituting some of the residues with the exceptions of serine as position 123, or leucine at position 125.

In another embodiment, an analog of the ob polypeptide, preferably the human ob polypeptide, is a truncated form of the polypeptide. For example, it has already been demonstrated that the glutamine at residue 49 is not essential, and can be deleted from the peptide. Similarly, it may be possible to delete some or all of the divergent amino acid residues at positions 121–128. In addition, the invention contemplates providing an ob analog having the minimum amino acid sequence necessary for a biological activity. This can be readily determined, e.g., by testing the activity of fragments of ob for the ability to bind to ob-specific antibodies, inhibit the activity of the native ob peptide, or agonize the activity of the native ob peptide. In one embodiment, the invention provides a truncated ob peptide consisting of the loop structure formed by the disulfide bond that forms between cysteine residues 117 and 167 (as depicted in FIG. 4). In another embodiment, the truncated analog corresponds to the amino acids from residue 22 (which follows the putative signal peptide cleavage site) to 53 (the amino acid residue immediately preceding a flexible loop region detected with limited proteolysis followed by mass spectrometric analysis of the ob polypeptide; see Cohen et al., 1995, "Probing the Solution Structure of the DNA-Binding Protein Mass by a Combination of Proteolysis and Mass Spectrometry,"). In another embodiment, the truncated analog corresponds to amino acids from residue 61 (the residue immediately following the flexible loop region as detected with the limited proteolysis/mass spec analysis of the ob polypeptide) to amino acid residue 116 (the residue immediately preceding the first cysteine residue). In yet another embodiment, the truncated analog corresponds to amino acids from residue 61 to amino acid residue 167.

Furthermore, one or more of the residues of the putative flexible loop at residues number 54 to 60 are substituted. For example, one or more of the residues may be substituted with lysine, glutamic acid, or cysteine (preferably lysine) for cross linking, e.g., to a polymer, since flexible loop structures are preferred sites for dirivitization of a protein. Alternatively, the residues at the flexible loop positions may be substituted with amino acid residues that are more resistant to proteolysis but that retain a flexible structure, e.g., one or more prolines. In yet another embodiment, substitutions with amino acid residues that can be further derivitized to make them more resistant to degradation, e.g., proteolysis, is contemplated.

It will be appreciated by one of ordinary skill in the art that the foregoing fragment sizes are approximate, and that from one to about five amino acids can be included or deleted from each or both ends, or from the interior of the polypeptide or fragments thereof, of the recited truncated analogs, with the exception that in the disulfide bonded loop analogs, the cysteine residues must be maintained.

It has been found that murine ob peptide contains 50% α-helical content, and that the human ob peptide contains about 60% α-helical content, as detected by circular dichroism of the recombinant peptides under nearly physiological conditions. Accordingly, in another embodiment, amino acid residues can be substituted with residues to form analogs of ob peptide that demonstrate enhanced propensity for forming, or which form more stable, α-helix structures. For example, α-helix structure would be preferred if Glu, Ala, Leu, His, Trp are introduced as substitutes for amino acid residues found in the native ob peptide. Preferably, conservative amino acid substitutions are employed, e.g., substituting aspartic acid at residue(s) 29, 30, 44, 61, 76, 100, and/or 106 (as depicted in FIG. 4) with glutamic acid(s) (Glu); substituting isoleucine(s) with leucine; substituting glycine or valine, or any divergent amino acid, with alanine (e.g., serine at position 53 of the human ob peptide with alanine), substituting arginine or lysine with histidine, and substituting tyrosine and/or phenylalanine with tryptophan. Increasing the degree, or more importantly, the stability of α-helix structure may yield an ob analog with greater activity, increased binding affinity, or longer half-life. In a specific embodiment, the helix forming potential of the portion of the ob peptide corresponding to amino acid residues 22 through 53 is increased. In another embodiment, the helix-forming potential or stability of the amino acid residues 61–116 is increased. In yet another embodiment, the helix forming potential of the disulfide loop structure corresponding to amino acids 117 to 167 is increased. Also contemplated are ob analogs containing enhanced α-helical potential or stability in more than one of the foregoing domains. In a further embodiment, truncated ob peptide analogs are generated that incorporate structure forming, e.g., helix-forming, amino acid residues to compensate for the greater propensity of polypeptide fragments to lack stable structure.

Analogs, such as fragments, may be produced, for example, by pepsin digestion of weight modulator peptide material. Other analogs, such as muteins, can be produced by standard site-directed mutagenesis of weight modulator peptide coding sequences. Analogs exhibiting "weight modulator activity" such as small molecules, whether functioning as promoters or inhibitors, may be identified by known in vivo and/or in vitro assays.

Small Molecule Analogs and Peptidomimetics of Ob Polypeptide

The structure of the ob polypeptide, preferably human ob polypeptide, can be analyzed by various methods known in the art. The protein sequence can be characterized by a hydrophilicity analysis (e.g., Hopp and Woods, 1981, Proc. Natl. Acad. Sci. U.S.A. 78:3824). A hydrophilicity profile can be used to identify the hydrophobic and hydrophilic regions of the ob polypeptide, which may indicate regions buried in the interior of the folded polypeptide, and regions accessible on the exterior of the polypeptide. In addition, secondary structural analysis (e.g., Chou and Fasman, 1974, Biochemistry 13:222) can also be done, to identify regions of ob polypeptide that assume specific secondary structures. Manipulation of the predicted or determined structure, including secondary structure prediction, can be accomplished using computer software programs available in the art.

By providing an abundant source of recombinant ob polypeptide, the present invention enables quantitative structural determination of the polypeptide. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed. These include but are not limited to X-ray crystallography (Engstom, A., 1974, Biochem. Exp. Biol. 11:7–13).

In yet a further embodiment, an analog of ob polypeptide can be tested to determine whether it cross-reacts with an antibody specific for native ob polypeptide, or specific fragments thereof. The degree of cross reactivity provides information about structural homology or similarity of proteins, or about the accessibility of regions corresponding to portions of the polypeptide that were used to generate fragment-specific antibodies.

Screening for Ob Analogs

Various screening techniques are known in the art for screening for analogs of polypeptides. Various libraries of chemicals are available. Accordingly, the present invention contemplates screening such libraries, e.g., libraries of synthetic compounds generated over years of research, libraries of natural compounds, and combinatorial libraries, as described in greater detail, infra, for analogs of ob polypeptide. In one embodiment, the invention contemplates screening such libraries for compounds that bind to anti-ob polypeptide antibodies, preferably anti-human ob polypeptide antibodies. In another aspect, once the ob receptor is identified (see infra), Any screening technique known in the art can be used to screen for ob receptor agonists or antagonists. The present invention contemplates screens for small molecule ligands or ligand analogs and mimics, as well as screens for natural ligands that bind to and agonize or antagonize activates ob receptor in vivo.

Knowledge of the primary sequence of the receptor, and the similarity of that sequence with proteins of known function, can provide an initial clue as the agonists or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, 1990, Science 249:386–390; Cwirla, et al., 1990, Proc. Natl. Acad. Sci., 87:6378–6382; Devlin et al., 1990, Science, 249:404–406), very large libraries can be constructed ($10^6$–$10^8$ chemical entities). A second approach uses primarily chemical methods, of which the Geysen method (Geysen et al., 1986, Molecular Immunology 23:709–715; Geysen et al. 1987, J. Immunologic Method 102:259–274) and the recent method of Fodor et al. (1991, Science 251, 767–773) are examples. Furka et al. (1988, 14th International Congress of Biochemistry, Volume 5, Abstract FR:013; Furka, 1991, Int. J. Peptide Protein Res. 37:487–493), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., 1993, "Generation and screening of an oligonucleotide encoded synthetic peptide library," Proc. Natl. Acad. Sci. USA 90:10700–4; Lam et al., International Patent Publication No. WO 92/00252, each of which is incorporated herein by reference in its entirety), and the like can be used to screen for ob receptor ligands according to the present invention. With such libraries, receptor antagonists can be detected using cell that express the receptor without actually cloning the ob receptor (Lam et al., supra).

Alternatively, assays for binding of soluble ligand to cells that express recombinant forms of the ob receptor ligand binding domain can be performed. The soluble ligands can be provided readily as recombinant or synthetic ob polypeptide.

The screening can be performed with recombinant cells that express the ob receptor, or alternatively, using purified receptor protein, e.g., produced recombinantly, as described above. For example, the ability of labeled, soluble or solubilized ob receptor that includes the ligand-binding portion of the molecule, to bind ligand can be used to screen libraries, as described in the foregoing references.

Derivatives of Ob Polypeptides

Generally, the present protein (herein the term "protein" is used to include "polypeptide", unless otherwise indicated) may be derivatized by the attachment of one or more chemical moieties to the protein moiety. The chemically modified derivatives may be further formulated for intraarterial, intraperitoneal, intramuscular, subcutaneous, intravenous, oral, nasal, rectal, bucal, sublingual, pulmonary, topical, transdermal, or other routes of administration. Chemical modification of biologically active proteins has been found to provide additional advantages under certain circumstances, such as increasing the stability and circulation time of the therapeutic protein and decreasing immunogenicity. See U.S. Pat. No. 4,179,337, Davis et al., issued Dec. 18, 1979. For a review, see Abuchowski et al., in Enzymes as Drugs. (J. S. Holcerberg and J. Roberts, eds. pp. 367–383 (1981)). A review article describing protein modification and fusion proteins is Francis, *Focus on Growth Factors* 3: 4–10 (May 1992) (published by Mediscript, Mountview Court, Friern Barnet Lane, London N20, OLD, UK).

Chemical Moieties For Derivatization

The chemical moieties suitable for derivatization may be selected from among water soluble polymers. The polymer selected should be water soluble so that the protein to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For the present proteins and peptides, these may be ascertained using the assays provided herein.

Polymer Molecules

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols and polyvinyl alcohol. Polyethylene glycol propionaldenhyde may advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Polymer/Protein Ratio

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

Attachment of the Chemical Moiety to the Protein

The polyethylene glycol molecules (or other chemical moieties) should be attached to the protein with consideration of effects on functional or antigenic domains of the protein. There are a number of attachment methods available to those skilled in the art. E.g., EP 0 401 384 herein incorporated by reference (coupling PEG to G-CSF), see also Malik et al., Exp. Hematol. 20: 1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydrl groups may also be used as a reactive group for attaching the polyethylene glycol molecule(s). Preferred for therapeutic purposes is attachment at an amino group, such as attachment at the N-terminus or lysine group. Attachment at residues important for receptor binding should be avoided if receptor binding is desired.

N-terminally Chemically Modified Proteins

One may specifically desire N-terminally chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemically modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at pH which allows one to take advantage of the $pK_a$ differences between the $\epsilon$-amino groups of the lysine residues and that of the $\alpha$-amino group of the N-terminal residue of the protein. By such selective derivatization attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol proprionaldehyde, containing a single reactive aldehyde, may be used.

Nucleic Acids Associated With Ob Polypeptide

As noted above, the present invention is directed to nucleic acids encoding ob polypeptides, as well as associated genomic non-coding sequences 5', 3', and intronic to the ob gene. Thus, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984). Of particular relevance to the present invention are strategies for isolating, cloning, sequencing, analyzing, and characterizing a gene or nucleic acid based on the well known polymerase chain reaction (PCR) techniques.

A "replicon" is any genetic element (e.g., plasmid, chromosome, virus) that functions as an autonomous unit of DNA replication in vivo, i.e., capable of replication under its own control.

A "vector" is a replicon, such as a plasmid, phage or cosmid, to which another DNA segment may be attached so as to bring about the replication of the attached segment. A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

"Heterologous" DNA refers to DNA not naturally located in the cell, or in a chromosomal site of the cell. Preferably, the heterologous DNA includes a gene foreign to the cell.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at east about 10 nucleotides; more preferably at least about 15 nucleotides; most referably the length is at least about 20 nucleotides.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Isolation of ob Coding and Flanking Sequences

Figures 1, 20A:
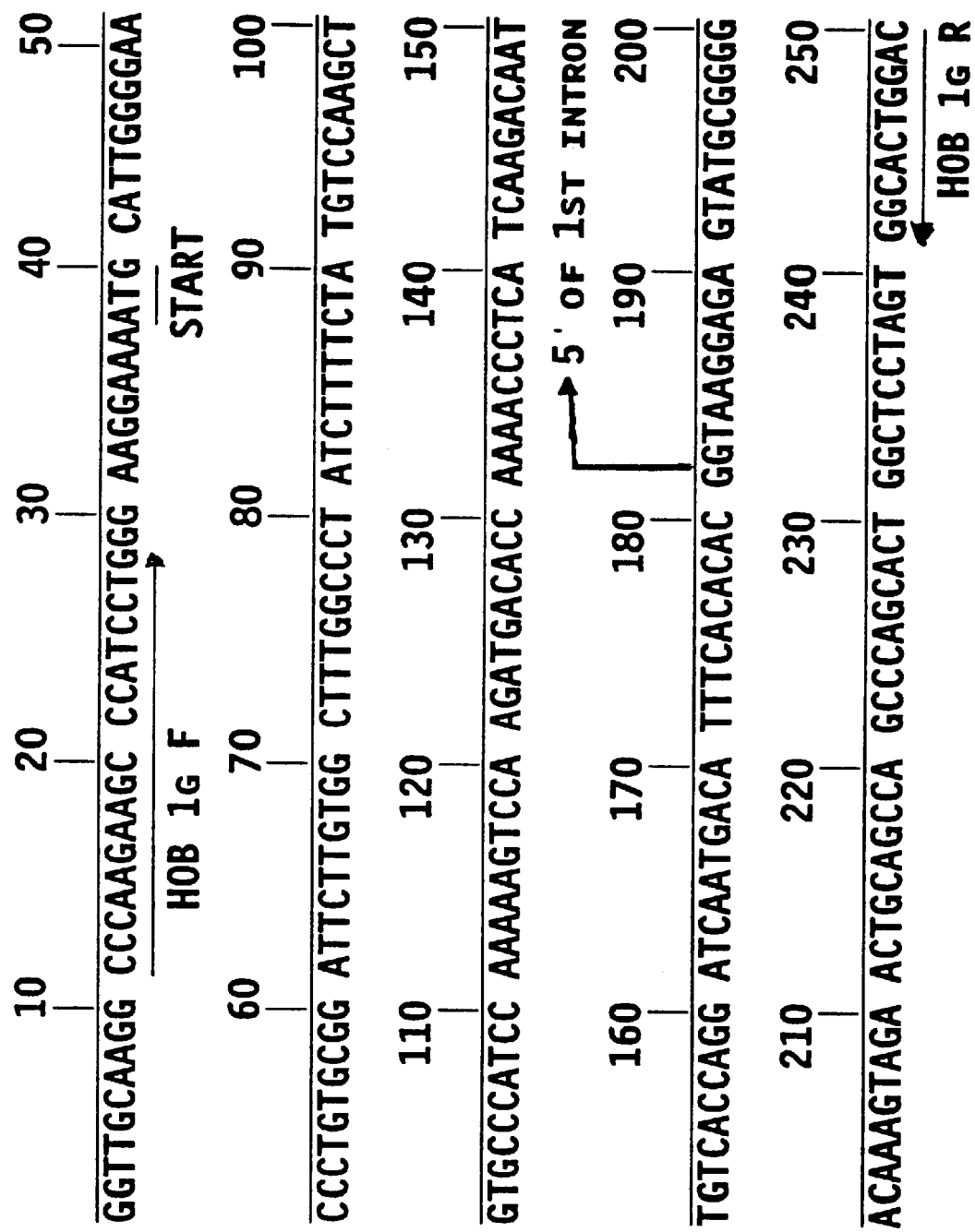
FIG. 1 depicts the nucleic acid sequence (SEQ ID NO:1) and deduced amino acid sequence (SEQ ID NO:2) derived for the murine ob cDNA. A 39 base pair 5' leader was followed by a predicted 167 amino acid open reading frame and an approximately 3700 kB 3' untranslated sequence. (In previously filed application Ser. No. 08/347,563 filed Nov. 30, 1994 and Ser. No. 08/438,431, filed May 10, 1995, an additional 58-base 5' sequence was determined subsequently, this non-coding sequence was identified as a cloning artifact. This artifact has no bearing on the coding region, the 39 base 5' non-coding region presently depicted in FIG. 1, or 3' non-coding region of the gene.) A total of about 2500 base pairs of the 3' untranslated sequence is shown. Analysis of the predicted protein sequence by observation and using the SigSeq computer program indicates the presence of a signal sequence (underlined). Microheterogeneity of the cDNA was noted in that approximately 70% of the cDNAs had a glutamine codon at codon 49 and 30% did not (see FIG. 5 and FIG. 6, infra). This amino acid is underlined, as is the arginine codon that is mutated in C57BL/6J ob/ob mice (1J mice).

The nucleic acids contemplated by the present invention extend as indicated, to other nucleic acids that code on expression for peptides such as those set forth in FIG. 1 (SEQ ID NO:2), FIG. 3 (SEQ ID NO:4), FIG. 5 (SEQ ID NO:5), and FIG. 6 (SEQ ID NO:6) herein. Accordingly, while specific DNA has been isolated and sequenced in relation to the ob gene, any animal cell potentially can serve as the nucleic acid source for the molecular cloning of a gene encoding the peptides of the invention. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, the genomic DNA can be amplified using primers selected from the cDNA sequences. Alternatively, DNA fragments are generated, some of which will encode the desired gene. The DNA may be cleaved at specific sites using various restriction enzymes. One may also use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired ob or ob-like gene may be accomplished in a number of ways. For example, if an amount of a portion of a ob or ob-like gene or its specific RNA, or a fragment thereof, is available and can be purified and labeled, the generated DNA fragments may be screened by nucleic acid hybridization to the labeled probe (Benton and Davis, 1977, *Science* 196:180; Grunstein and Hogness, 1975, *Proc. Natl. Acad. Sci. U.S.A.* 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in FIG. 1 (SEQ ID NO:1) or FIG. 2 (SEQ ID NO:3). Preferably, a fragment is selected that is highly unique to the modulator peptides of the invention. Those DNA fragments with substantial homology to the probe will hybridize. As noted above, the greater the degree of homology, the more stringent hybridization conditions can be used. In one embodiment, low stringency hybridization conditions are used to identify a homologous modulator peptide. However, in a preferred aspect, and as demonstrated experimentally herein, a nucleic acid encoding a modulator peptide of the invention will hybridize to a nucleic acid having a nucleotide sequence such as depicted in FIG. 1 (SEQ ID NO:1) or FIG. 2 (SEQ ID NO:3), or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, tyrosine phosphatase activity or antigenic properties as known for the present modulator peptides. For example, the antibodies of the instant invention can conveniently be used to screen for homologs of modulator peptides from other sources.

A gene encoding a modulator peptide of the invention can also be identified by mRNA selection, i.e., by nucleic acid hybridization followed by in vitro translation. In this procedure, fragments are used to isolate complementary mRNAs by hybridization. Such DNA fragments may represent available, purified modulator DNA. Immunoprecipitation analysis or functional assays (e.g., tyrosine phosphatase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against a modulator peptide.

A radiolabeled modulator peptide cDNA can be synthesized using the selected mRNA (from the adsorbed polysomes) as a template. The radiolabeled mRNA or cDNA may then be used as a probe to identify homologous modulator peptide DNA fragments from among other genomic DNA fragments.

As mentioned above, a DNA sequence encoding weight modulator peptides as disclosed herein can be prepared synthetically rather than cloned. The DNA sequence can be designed with the appropriate codons for the weight modulator peptide amino acid sequences. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express weight modulator analogs, as described above. Alternatively, DNA encoding analogs can be made by site-directed mutagenesis of native ob genes or cDNAs, and analogs can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs of the ob polypeptide with unnatural amino acids.

Non-coding Nucleic Acids

The present invention extends to the preparation of antisense nucleotides and ribozymes that may be used to interfere with the expression of the weight modulator proteins at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule (See Weintraub, 1990; Marcus-Sekura, 1988). In the cell, they hybridize to that mRNA, forming a double stranded molecule. The cell does not translate an mRNA complexed in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into weight modulator peptide-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988). Because they are sequence-specific, only mRNAs with particular sequences are inactivated.

Investigators have identified two types of ribozymes, Tetrahymena-type and "hammerhead"-type (Hasselhoff and Gerlach, 1988). Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against and ribozymes that cleave mRNAs for weight modulator proteins and their ligands, thus inhibiting expression of the ob gene, and leading to increased weight gain and adiposity.

In another embodiment, short oligonucleotides complementary to the coding and complementary strands of the ob nucleic acid, or to non-coding regions of the ob gene 5', 3', or internal (intronic) to the coding region are provided by the present invention. Such nucleic acids are useful as probes, either as directly labeled oligonucleotide probes, or as primers for polymerase chain reaction, for evaluating the presence of mutations in the ob gene, or the level of expression of ob mRNA. Preferably, the non-coding nucleic acids of the invention are from the human ob gene.

In a specific embodiment, the non-coding nucleic acids provide for homologous recombination for integration of an amplifiable gene and/or other regulatory sequences in proximity to the ob gene, e.g., to provide for higher level of expression of the ob polypeptide, or to overcome a mutation in the ob gene regulatory sequences that prevent proper levels of expression of the ob polypeptide (see International Patent Publication WO 91/06666, published May 16, 1991 by Skoultchi; International Patent Publication No. WO 91/09955, published Jul. 11, 1991 by Chappel; see also International Patent Publication No. WO 90/14092, published Nov. 29, 1990, by Kucherlaptati and Campbell).

Production of Ob Polypeptide: Expression and Synthesis

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is also used herein to refer to this sort of signal sequence. Translocation signal sequences can be found associated with a variety of proteins native to eukaryotes and prokaryotes, and are often functional in both types of organisms.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and Synthetic DNA sequences. Suitable vectors include derivatives of SV40 and known bacterial plasmids, e.g., *E. coli* plasmids col E1, pCR1, pBR322, pMB9, pUC or pUC plasmid derivatives, e.g., pGEX vectors, pET vectors, pmal-c, pFLAG, etc., and their derivatives, plasmids such as RP4; phage DNAs, e.g., the numerous derivatives of phage λ, e.g., NM989, and other phage DNA, e.g., M13 and Filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. In a preferred embodiment, expression of ob is achieved in methylotrophic yeast, e.g., *Pichia pastoris* yeast (see, e.g., International Patent Publication No. WO 90/03431, published Apr. 5, 1990, by Brierley et al.; International Patent Publication No. WO 90/10697, published Sep. 20, 1990, by Siegel et al.). In a specific embodiment, infra, an expression vector is engineered for expression of ob under control of the α-mating factor signal sequence.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the AOX 1 promoter of methylotrophic yeast, the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli*, Pseudomonas, Bacillus, Streptomyces; fungi such as yeasts (Saccharomyces, and methylotrophic yeast such as Pichia, Candida, Hansenula, and Torulopsis); and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

In a specific embodiment, an ob fusion protein can be expressed. An ob fusion protein comprises at least a functionally active portion of a non-ob protein joined via a peptide bond to at least a functionally active portion of an ob polypeptide. The non-ob sequences can be amino- or carboxy-terminal to the ob sequences. More preferably, for stable expression of a proteolytically inactive ob fusion protein, the portion of the non-ob fusion protein is joined via a peptide bond to the amino terminus of the ob protein. A recombinant DNA molecule encoding such a fusion protein comprises a sequence encoding at least a functionally active portion of a non-ob protein joined in-frame to the ob coding sequence, and preferably encodes a cleavage site for a specific protease, e.g., thrombin or Factor Xa, preferably at the ob-non-ob juncture. In a specific embodiment, the fusion protein is expressed in *Escherichia coli* or in *P. pastoris*.

In a specific embodiment, infra, vectors were prepared to express the murine and human ob genes, with and without the codon for gln-49, in bacterial expression systems and yeast (Pichia) expression systems as fusion proteins. The ob gene is prepared with an endonuclease cleavage site, e.g., using PCR and novel primers. It is desirable to confirm sequences generated by PCR, since the probability of including a point mutation is greater with this technique. A plasmid containing a histidine tag (HIS-TAG) and a proteolytic cleavage site is used. The presence of the histidine makes possible the selective isolation of recombinant proteins on a Ni-chelation column, or by affinity purification. The proteolytic cleavage site, in a specific embodiment, infra, a thrombin cleavage site, is engineered so that treatment with the protease, e.g., thrombin, will release the full length mature (i.e., lacking a signal sequence) ob polypeptide.

In another aspect, the pGEX vector (Smith and Johnson, 1988, Gene 67:31–40) can be used. This vector fuses the schistosoma japonicum glutathionine S-transferase cDNA to the sequence of interest. Bacterial proteins are harvested and recombinant proteins can be quickly purified on a reduced glutathione affinity column. The GST carrier can subsequently be cleaved from fusion proteins by digestion with site-specific proteases. After cleavage, the carrier and uncleaved fusion protein can be removed by absorption on glutathione agarose. Difficulty with the system occasionally arises when the encoded protein is insoluble in aqueous solutions.

Expression of recombinant proteins in bacterial systems may result in incorrect folding of the expressed protein, requiring refolding. The recombinant protein can be refolded prior to or after cleavage to form a functionally active ob polypeptide. The ob polypeptide may be refolded by the steps of (i) incubating the protein in a denaturing buffer that contains a reducing agent, and then (ii) incubating the protein in a buffer that contains an oxidizing agent, and preferably also contains a protein stabilizing agent or a chaotropic agent, or both. Suitable redox (reducing/oxidizing) agent pairs include, but are not limited to, reduced glutathione/glutathione disulfide, cystine/cysteine, cystamine/cysteamine, and 2-mercaptoethanol/2-hydroxyethyldisulfide. In a particular aspect, the fusion protein can be solubilized in a denaturant, such as urea, prior to exchange into the reducing buffer. In preferred embodiment, the protein is also purified, e.g., by ion exchange or Ni-chelation chromatography, prior to exchange into the reducing buffer. Denaturing agents include but are not limited to urea and guanidine-HCl. The recombinant protein is then diluted about at least 10-fold, more preferably about 100-fold, into an oxidizing buffer that contains an oxidizing agent, such as but not limited to 0.1 M Tris-HCl, pH 8.0, 1 mM EDTA, 0.15 M NaCl, 0.3 M oxidized glutathione. The fusion protein is then incubated for about 1 to about 24 hours, preferably about 2 to about 16 hours, at room temperature in the oxidizing buffer. The oxidizing buffer may comprise a protein stabilizing agent, e.g., a sugar, an alcohol, or ammonium sulfate. The oxidizing buffer may further comprises a chaotropic agent at low concentration, to destabilize incorrect intermolecular interactions and thus promote proper folding. Suitable chaotropic agents include but are not limited to a detergent, a polyol, L-arginine, guanidine-HCl and polyethylene glycol (PEG). It is important to use a low enough concentration of the chaotropic agent to avoid denaturing the protein. The refolded protein can be concentrated by at least about 10-fold, more preferably by the amount it was diluted into the oxidizing buffer.

Bacterial fermentation processes can also result in a recombinant protein preparation that contains unacceptable levels of endotoxins. Therefore, the invention contemplates removal of such endotoxins, e.g., by using endotoxin-specific antibodies or other endotoxin binding molecules. The presence of endotoxins can be determined by standard techniques, such as by employing E-TOXATE Reagents (Sigma), or with bioassays.

In addition to the specific example, the present inventors contemplate use of baculovirus, mammalian, and yeast expression systems to express the ob protein. For example, in baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)).

Mammalian expression vectors contemplated for use in the invention include vectors with inducible promoters, such as dihydrofolate reductase (DHFR), e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12, 1991). Alternatively, a glutamine synthetase/methionine sulfoximine co-amplification vector, such as pEE14 (HindIII, XbaI, SmaI, SmaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker; Invitrogen), pREP8 (BamH1, XhoI, NotI, HindIII, NheI, and KpnI cloning site, RSV LTR promoter, histidinol selectable marker; Invitrogen), pREP9 (KpnI, NheI, HindIII, NotI, XhoI, SfiI, and BamHI cloning site, RSV LTR promoter, G418 selectable marker; Invitrogen), and pEBVHis (RSV LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and HpA cloning site, TK or XPRT selection).

Yeast expression systems can also be used according to the invention to express ob polypeptide. For example, the non-fusion pYES2 vector (XbaI, SphI, ShoI, NotI, GstXI, EcoRI, BstXI, BamH1, SacI, KpnI, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

It is further intended that body weight modulator peptide analogs may be prepared from nucleotide sequences derived within the scope of the present invention.

In addition to recombinant expression of ob polypeptide, the present invention envisions and fully enables preparation of ob polypeptide, or fragments thereof, using the well known and highly developed techniques of solid phase peptide synthesis. The invention contemplates using both the popular Boc and Fmoc, as well as other protecting group strategies, for preparing ob polypeptide or fragments thereof. Various techniques for refolding and oxidizing the cysteine side chains to form a disulfide bond are also well known in the art.

Antibodies to the Ob Polypeptide

According to the invention, ob polypeptide produced recombinantly or by chemical synthesis, and fragments or other derivatives or analogs thereof, including fusion proteins, may be used as an immunogen to generate antibodies that recognize the ob polypeptide. Such antibodies include but are not limited to polyclonal, monoclonal, chimeric, single chain, Fab fragments, and an Fab expression library.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. No. Nos. 4,816,397 and 4,816,567, as well as antigen binding portions of antibodies, including Fab, F(ab')$_2$ and Fr (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant. saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to ob polypeptide, or fragment, derivative or analog thereof. For the production of antibody, various host animals can be immunized by injection with the ob polypeptide, or a derivative (e.g., fragment or fusion protein) thereof, including but not limited to rabbits, mice, rats, sheep, goats, etc. In one embodiment, the ob polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the ob polypeptide, or fragment, analog, or derivative thereof, any technique that provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for an ob polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce ob polypeptide-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for an ob polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an ob polypeptide, one may assay generated hybridomas for a product which binds to an ob polypeptide fragment containing such epitope. For selection of an antibody specific to an ob polypeptide from a particular species of animal, one can select on the basis of positive binding with ob polypeptide expressed by or isolated from cells of that species of animal.

The foregoing antibodies can be used in methods known in the art relating to the localization and activity of the ob polypeptide, e.g., for Western blotting, imaging ob polypeptide in situ, measuring levels thereof in appropriate physiological samples, etc.

In a specific embodiment, antibodies that agonize or antagonize the activity of ob polypeptide can be generated. Such antibodies can be tested using the assays described infra for identifying ligands.

In a specific embodiment, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, the gex vector can be used to express the polypeptide (Smith and Johnson, supra). Alternatively, one can use only hydrophilic domains to generate the fusion protein. The expressed protein will be prepared in quantity and used to immunize rabbits in Freunds adjuvant.

In another specific embodiment, recombinant ob polypeptide is used to immunize chickens, and the chicken anti-ob antibodies are recovered from egg yolk, e.g., by affinity purification on an ob-column. Preferably, chickens used in immunization are kept under specific pathogen free (SPF) conditions.

In another embodiment, antibodies against leptin are generated in ob/ob mice, which lack circulating ob protein, and thus are expected to be capable of generating an anti-ob polypeptide response since they will not be tolerized to the polypeptide, and wild-type mice. Spleen cells from both groups of mice can be fused with myeloma cells to prepare hybridomas for monoclonal antibodies.

In yet another embodiment, recombinant ob polypeptide is used to immunize rabbits, and the polyclonal antibodies are immunopurified prior to further use. The purified antibodies are particularly useful for semi-quantitative assays, particularly for detecting the presence of circulating ob polypeptide in serum or plasma.

Panels of monoclonal antibodies produced against modulator peptides can be screened for various properties; i.e., isotype, epitope, affinity, etc. Of particular interest are monoclonal antibodies that neutralize the activity of the modulator peptides. Such monoclonals can be readily identified in activity assays for the weight modulators. High affinity antibodies are also useful when immunoaffinity purification of native or recombinant modulator is possible.

Preferably, the anti-modulator antibody used in the diagnostic and therapeutic methods of this invention is an affinity purified polyclonal antibody. More preferably, the antibody is a monoclonal antibody (mAb). In addition, it is preferable for the anti-modulator antibody molecules used herein be in the form of Fab, Fab', F(ab')$_2$ or F(v) portions of whole antibody molecules.

DIAGNOSTIC IMPLICATIONS

The present invention also relates to a variety of diagnostic applications, including methods for detecting the presence of conditions and/or stimuli that impact abnormalities in body weight or adiposity, by reference to their ability to elicit the activities which are mediated by the present weight modulators. As mentioned earlier, the weight modulator peptides can be used to produce antibodies to themselves by a variety of known techniques, and such antibodies could then be isolated and utilized as in tests for the presence of particular transcriptional activity in suspect target cells. alternatively, the nucleic acids of the invention can be employed in diagnosis.

Antibody-based Diagnostics

As suggested earlier, a diagnostic method useful in the present invention comprises examining a cellular sample or medium by means of an assay including an effective amount of an antagonist to a modulator protein, such as an anti-modulator antibody, preferably an affinity-purified polyclonal antibody, and more preferably a mAb. In addition, it is preferable for the anti-modulator antibody molecules used herein be in the form of Fab, Fab', F(ab')$_2$ or F(v) portions or whole antibody molecules. As previously discussed, patients capable of benefiting from this method include those suffering from cancer, AIDS, obesity or other condition where abnormal body weight is a characteristic or factor. Methods for isolating the modulator and inducing anti-modulator antibodies and for determining and optimizing the ability of anti-modulator antibodies to assist in the examination of the target cells are all well-known in the art.

Also, antibodies including both polyclonal and monoclonal antibodies, and drugs that modulate the production or activity of the weight control modulators recognition factors and/or their subunits may possess certain diagnostic applications and may for example, be utilized for the purpose of detecting and/or measuring conditions where abnormalities in body weight are or may be likely to develop. For example, the modulator peptides or their active fragments may be used to produce both polyclonal and monoclonal antibodies to themselves in a variety of cellular media, by known techniques such as the hybridoma technique utilizing, for example, fused mouse spleen lymphocytes and myeloma cells. These techniques are described in detail below. Likewise, small molecules that mimic or antagonize the activity(ies) of the receptor recognition factors of the invention may be discovered or synthesized, and may be used in diagnostic and/or therapeutic protocols.

The presence of weight modulator in cells can be ascertained by the usual immunological procedures applicable to such determinations. A number of useful procedures are known. Three such procedures which are especially useful utilize either the receptor recognition factor labeled with a detectable label, antibody $Ab_1$ labeled with a detectable label, or antibody $Ab_2$ labeled with a detectable label. The procedures may be summarized by the following equations wherein the asterisk indicates that the particle is labeled, and "WM" stands for the weight modulator:

A. $WM^* + Ab_1 = WM^*Ab_1$

B. $WM + Ab^* = WMAb_1^*$

C. $WM + Ab_1 + Ab_2^* = Ab_1 WMAb_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure B is representative of the well known competitive assay techniques. Procedure C, the "sandwich" procedure, is described in U.S. Pat. No. Nos. RE 31,006 and 4,016,043. Still other procedures are known such as the "double antibody", or "DASP" procedure.

In each instance, the weight modulators form complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-weight modulator antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The weight modulators or their binding partners can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, test kits suitable for use by a medical specialist may be prepared to determine the presence or absence of predetermined transcriptional activity or predetermined transcriptional activity capability in suspected target cells. In accordance with the testing techniques discussed above, one class of such kits will contain at least the labeled weight modulator or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for predetermined transcriptional activity, comprising:

(a) a predetermined amount of at least one labeled immunochemically reactive component obtained by the direct or indirect attachment of the present weight modulator or a specific binding partner thereto, to a detectable label;

(b) other reagents; and (c) directions for use of said kit.

More specifically, the diagnostic test kit may comprise:

(a) a known amount of the weight modulator as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the weight modulator to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the weight modulator and a specific binding partner thereto.

Nucleic Acid-based Diagnostics

As demonstrated in the examples, infra, nucleic acids of the invention can be used to detect defects associated with defects in the ob polypeptide that result in obese phenotypes. For example, nucleic acid probes (e.g., in Northern analysis or RT-PCR analysis) can be used to determine whether an obese phenotype is associated with lack of expression of ob mRNA, or expression of non-functional ob mRNA, e.g., as in db/db mice (where the deficiency results from lack of an ob receptor) or where a mutation yields a non-transcribed mRNA. Moreover, the nucleic acid-based diagnostic techniques of the invention can be used in conjunction with antibody-based techniques to further develop a molecular understanding of obese or anorexic phenotypes.

The human cDNA clones that have recently been isolated have been sequenced as presented herein. This facilitates the determination of the complete sequence of the human gene (see FIG. 20). DNA sequences from the introns of the human ob gene have been obtained (FIG. 20), and these have been used to prepare PCR primers to PCR amplify the coding sequence of the ob gene from human genomic DNA so as to identify mutations or allelic variants of the ob gene, all in accordance with protocols described in detail earlier herein. Specific PCR primers for amplifying human genomic ob are described in a specific Example, infra.

The current hypothesis is that heterozygous mutations in the ob gene will be associated with mild/moderate obesity while homozygous mutations would be associated with several DNA sequence based diagnostic tests obesity. If this is true, it would allow the ascertainment of people at risk for the development of obesity and make possible the application of drug treatment and/or lifestyle changes before an increased body weight is fully developed.

Alternatively, the presence of microsatellites that segregate with mutant forms of human ob can be used for diagnosis. Various PCR primers, including those based on the nucleotide sequence provided in FIG. 20A, can be used in this respect.

The ob gene may also be useful diagnostically for measurements of its encoded RNA and protein in nutritional disorders. It will be of importance to know, in a particular nutritional disorder, whether ob RNA and/or protein is unregulated or downregulated. Thus, if an obese person has increased levels of ob, it would appear that the problem is downstream of ob, while if ob is reduced, it would appear that inappropriately low levels of ob may be cause of obesity (whether or not the defect is in the ob gene). Conversely, if a cancer or AIDS patient who lost weight had elevated levels of ob, it may be concluded that inappropriately high expression of ob is responsible for the weight loss.

The cloned human cDNA will be of use for the measurement of the levels of human ob RNA. In addition, recombinant human protein will be prepared and used to develop immunoassays to enable measurement of the fat and perhaps plasma levels of the ob protein.

Therapeutic Implications

The polypeptides, nucleic acids, and antibodies of the invention have significant therapeutic potential. Preferably, a therapeutically effective amount of such an agent is administered in a pharmaceutically acceptable carrier, diluent, or excipient.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Administration of recombinant ob polypeptide results in weight loss, in particular, a decrease in fat tissue. Ob polypeptide can be prepared using standard bacterial and/or mammalian expression vectors, synthetically, or purified from plasma or serum, all as stated in detail earlier herein. Alternatively, increased expression of native ob polypeptide may be induce by homologous recombination techniques, as described supra.

Reduction of ob polypeptide activity (by developing antagonists, inhibitors, use of neutralizing antibodies, or antisense molecules) should result in weight gain as might be desirable for the treatment of the weight loss associated with cancer, AIDS or anorexia nervosa. Modulation of ob activity can be useful for reducing body weight (by increasing its activity) or increasing body weight (by decreasing its activity).

Polypeptide-based Therapeutic Treatment

In the simplest analysis the ob gene determines body weight in mammals, in particular mice and man. The ob gene product, and, correspondingly, cognate molecules, appear to be part of a signaling pathway by which adipose tissue communicates with the brain and the other organs. It is believed that the ob polypeptide is itself a signaling molecule, i.e., a hormone.

The ob polypeptide, or functionally active fragment thereof, or an antagonist thereof, can be administered orally or parenterally, preferably parenterally. Because metabolic homeostasis is a continuous process, controlled release administration of ob polypeptide is preferred. For example, the polypeptide may be administered using intravenous infusion, an implantable osmotic pump, a transdermal patch, liposomes, or other modes of administration. In one embodiment, a pump may be used (see Langer, supra; Sefton, CRC *Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target. i.e., the brain. thus requiring only a fraction of the systemic dose (see, e.g., Goodson, in *Medical Applications of Controlled Release*, supra, vol. 2, pp. 115–138 (1984)). Other controlled release systems are discussed in the review by Langer (*Science* 249:1527–1533 (1990)). In another embodiment, the therapeutic compound can be delivered in a vesicle, in particular a liposome (see Langer, *Science* 249:1527–1533 (1990); Treat et al., in *Liposomes in the Therapy of Infectious Disease and Cancer*, Lopez-Berestein and Fidler (eds.), Liss, N.Y., pp. 353–365 (1989); Lopez-Berestein, ibid., pp. 317–327; see generally ibid.)

In a further aspect, recombinant cells that have been transformed with the ob gene and that express high levels of the polypeptide can be transplanted in a subject in need of ob polypeptide. Preferably autologous cells transformed with ob are transplanted to avoid rejection; alternatively, technology is available to shield non-autologous cells that produce soluble factors within a polymer matrix that prevents immune recognition and rejection.

The ob polypeptide can be delivered by intravenous, intraarterial, intraperitoneal, intramuscular, or subcutaneous routes of administration. Alternatively, the ob polypeptide, properly formulated, can be administered by nasal or oral administration. A constant supply of ob can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

Pharmaceutical Compositions

In yet another aspect of the present invention, provided are pharmaceutical compositions of the above. Such pharmaceutical compositions may be for administration for injection, or for oral, pulmonary nasal or other forms of administration. In general, comprehended by the invention are pharmaceutical compositions comprising effective amounts of protein or derivative products of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which are herein incorporated by reference. The compositions may be prepared in liquid form, or may be in dried powder, such as lyophilized form.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (E.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the protein (or chemically modified protein), and inert ingredients which allow for protection against the stomach environment, and release of the biologically active material in the intestine.

Also specifically contemplated are oral dosage forms of the above derivatized proteins. Protein may be chemically modified so that oral delivery of the derivative is efficacious. Generally, the chemical modification contemplated is the attachment of at least one moiety to the protein (or peptide) molecule itself, where said moiety permits (a) inhibition of proteolysis; and (b) uptake into the blood stream from the stomach or intestine. Also desired is the increase in overall stability of the protein and increase in circulation time in the body. Examples of such moieties include: Polyethylene glycol, copolymers of ethylene glycol and propylene glycol, carboxymethyl cellulose, dextran, polyvinyl alcohol, polyvinyl pyrrolidone and polyproline. Abuchowski and Davis, Soluble Polymer-Enzyme Adducts. In: "Enzymes as Drugs", Hocenberg and Roberts, eds., Wiley-Interscience, New York, N.Y., (1981), pp 367–383; Newmark, et al., J. Appl. Biochem. 4: 185–189 (1982). Other polymers that could be used are poly-1,3-dioxolane and poly-1,3,6-tioxocane. Preferred for pharmaceutical usage, as indicated above, are polyethylene glycol moieties.

For the protein (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia. tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the protein (or derivative) are for instance the fatty acids oleic acid, linoleic acid and linolenic acid.

Controlled release formulation may be desirable. The drug could be incorporated into an inert matrix which permits release by either diffusion or leaching mechanisms i.e. gums. Slowly degenerating matrices may also be incorporated into the formulation. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Some entric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary Delivery

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., PHARMACEUTICAL RESEARCH, VOL. 7, No. 6, pp. 565–569 (1990); Adjei et al., *International Journal of Pharmaceutics*, Vol. 63, pp. 135–144 (1990)(leuprolide acetate); Braquet et al., *Journal of Cardiovascular Pharmacology*, Vol. 13, suppl. 5, s. 143–146 (1989) (endothelin-1);Hubbard et al., *Annals of Internal Medicine*, Vol. III, No. 3, pp. 206–212(1989)($\alpha$1-antitrypsin); Smith et al., *J. Clin. Invest.*, Vol. 84, pp. 1145–1146 (1989)($\alpha$1-proteinase); Oswein et al., "Aerosolization of Proteins", Proceedings of Symposium on Respiratory Drug Delivery II, Keystone, Colo., March, 1990 (recombinant human growth hormone); Debs et al., *The Journal of Immunology*, Vol. 140, pp. 3482–3488 (1988)(interferon-$\gamma$ and tumor necrosis factor alpha) and Platz et al., U.S. Pat. No. 5,284, 656 (granulocyte colony stimulating factor). Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of protein (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations suitable for use with a nebulizer, either jet or ultrasonic, will typically comprise protein (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing protein (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 $\mu$m (or microns), most preferably 0.5 to 5 $\mu$m, for most effective delivery to the distal lung.

Nasal Deliver

Nasal delivery of the protein (or derivative) is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Methods of Treatment, Methods of Preparing a Medicament

In yet another aspect of the present invention, methods of treatment and manufacture of a medicament are provided. Conditions alleviated or modulated by the administration of the present derivatives are those indicated above.

Dosages

For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing. Generally, for injection or infusion, dosage will be between 0.01 $\mu$g of biologically active protein/kg body weight, (calculating the mass of the protein alone, without chemical modification), and 10 mg/kg (based on the same). The dosing schedule may vary, depending on the circulation half-life of the protein or derivative used, whether the polypeptide is delivered by bolus dose or continuous infusion, and the formulation used.

Administration with Other Compounds

For therapy associated with obesity, one may administer the present protein (or derivatives) in conjunction with one or more pharmaceutical compositions used for treating other clinical complications of obesity, such as those used for treatment of diabetes (e.g., insulin), high blood pressure, high cholesterol, and other adverse conditions incident to obesity. Also, other appetite suppressants may be co-administered, e.g., amphetamines. Administration may be simultaneous (for example, administration of a mixture of the present protein and insulin) or may be in serriatim.

Nucleic Acid-based Therapeutic Treatment

The ob gene could be introduced into human fat cells to develop gene therapy for obesity. Such therapy would be expected to decrease body weight. Conversely, introduction of antisense constructs into human fat cells would reduce the levels of active ob polypeptide and would be predicted to increase body adiposity.

In one embodiment, a gene encoding an ob polypeptide is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HSV1) vector (Kaplitt et al., 1991, Molec. Cell. Neurosci. 2:320–330), an attenuated adenovirus vector, such as the vector described by Stratford-Perricaudet et al. (1992, J. Clin. Invest. 90:626–630), and a defective adeno-associted virus vector (Samulski et al., 1987, J. Virol. 61:3096–3101; Samulski et al., 1989, J. Virol. 63:3822–3828).

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreases liver, kidney, and the brain. Lipids may be chemically coupled to other molecules for the purpose of targeting (see Mackey, et. al., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Agricultural Applications

The ob gene can also be isolated from domestic animals, and the corresponding ob polypeptide obtained thereby. In a specific example, infra the a probe derived from the murine ob gene hybridizes to corresponding homologous coding sequences from a large number of species of animals. As discussed for human therapies, recombinant proteins can also be prepared and administered to domestic animals. Administration of the polypeptide can be implemented to produce leaner food animals, such as beef cattle, swine, poultry, sheep, etc. Preferably, an autologous ob polypeptide is administered, although the invention contemplates administration of anti-autologous polypeptide as well. Since the ob polypeptide consists of approximately 160 amino acid residues, it may not be highly immunogenic. Thus, administration of non-autologous polypeptide may not result in an immune response.

Alternatively, the introduction of the cloned genes into transgenic domestic animals would allow one to potentially decrease body weight and adiposity by overexpressing an ob transgene. The simplest means of achieving this would be to target an ob transgene to fat using its own or another fat specific promoter.

Conversely, increases in body fat might be desirable in other circumstances such as for the development of Kobe beef or fatty liver to make foie gras. This could be accomplished by targeting an antisense ob transgene to fat, or by using gene knockout technology. Alternatively, where an increase in body weight at percentage of fat is desired, an inhibitor or antagonist of the ob polypeptide can be administered. Such inhibitors or antagonists include, but are not limited to, antibodies reactive with the polypeptide, and fragments of the polypeptide that bind but do not activate the ob receptor, i.e., antagonists of ob polypeptide.

Cosmetic Implications

The ob polypeptide has significant value for cosmetic use, in addition to the health benefits. In particular, since the ob polypeptides of the invention, including derivatives and agonist analogs thereof, are useful for modulation of the rate and quantity of fat cell deposition in an animal, they are useful for reducing unsightly fat tissue, e.g., fat deposits in the abdomen, hips, thighs, neck, and chin that do not necessarily amount to an obese condition, but which nevertheless detract from an individual's appearance. The fat reduction effect is thought to be accomplished, in part, by a reduction in appetite, i.e., a reduction in food intake, by an increase in basal metabolism, or both. Thus, the present ob polypeptide, or its derivatives or agonist analogs, is useful for administration to a subject to effect cosmetic changes in fat tissue deposits, whether by modulating fat deposition, reducing appetite, or both.

In addition, the present compositions and methods may be used in conjunction with various procedures, such as cosmetic surgeries designed to alter the overall appearance of a body (e.g., liposuction or laser surgeries designed to reduce body mass by aspirating or ablating fat tissue), exercise (especially running and weight training), low fat diet, hypnosis, biofeedback, to mention some of the ways one may attempt to decrease the percentage of fat tissue and improve the appearance of the body.

Accordingly, the present invention relates to a method for effecting cosmetic fat tissue modulation in an individual comprising administering a fat modulating amount of an ob polypeptide, or derivative or agonist analog thereof, to an individual who desires cosmetic fat tissue modulation to improve overall body appearance. In a particular aspect, the fat tissue modulation is a consequence of appetite suppression. Preferably, the fat tissue modulation is a reduction in fat tissue.

In a further embodiment, the invention relates to a method for effecting cosmetic fat tissue loss comprising combining a procedure for changing body appearance with administration of a fat modulating amount of an ob polypeptide, or derivative or agonist analog thereof, to an individual who desires cosmetic fat tissue modulation to improve overall body appearance.

The ob Receptor

Development of small molecule agonists and antagonists of the ob factor will be greatly facilitated by the isolation of its receptor. This can be accomplished by preparing active ob polypeptide and using it to screen an expression library using standard methodology. Receptor binding in the expression library can be tested by administering recombinant polypeptide prepared using either bacterial or mammalian expression vectors, and observing the effects of short term and continuous administration of the recombinant polypeptide on the cells of the expression library, or by directly detecting binding of ob polypeptide to the cells.

As it is presently believed that the ob receptor is likely to be located in the hypothalamus and perhaps liver, preferably cDNA libraries from these tissues will be constructed in standard expression cloning vectors. These cDNA clones would next be introduced into COS cells as pools and the resulting transformants would be screened with active ligand to identify COS cells expressing the ob receptor. Positive clones can then be isolated so as to recover the cloned receptor. The cloned receptor would be used in conjunction with the ob ligand (assuming it is a hormone) to develop the necessary components for screening of small molecule modulators of ob.

A particular assay system that is to be utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the weight modulator may be radiolabeled and combined, for example, with antibodies or other inhibitors thereto, after which binding studies would be carried out. Solutions would then be prepared that contain various quantities of labeled and unlabeled uncombined weight modulator. and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic. In turn, a receptor assay will be particularly useful in the identification of the specific receptors to the present modulators, such as the db receptor.

A further assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

Once a recombinant which expresses the ob receptor gene sequence is identified, the recombinant ob receptor can be analyzed. This is achieved by assays based on the physical or functional properties of the ob receptor, including radioactive labelling of the receptor followed by analysis by gel electrophoresis, immunoassay, ligand binding, etc. Furthermore, antibodies to the ob receptor could be generated as described above.

The structure of the ob receptor can be analyzed by various methods known in the art. Preferably, the structure of the various domains, particularly the ob binding site, is analyzed. Structural analysis can be performed by identifying sequence similarity with other known proteins, particular hormone and protein receptors. The degree of similarity (or homology) can provide a basis for predicting structure and function of the ob receptor, or a domain thereof. In a specific embodiment, sequence comparisons can be performed with sequences found in GenBank, using, for example, the FASTA and FASTP programs (Pearson and Lipman, 1988, Proc. Natl. Acad. Sci. USA 85:2444–48).

The protein sequence can be further characterized by a hydrophilicity analysis (e.g., Hopp and Woods, 1981, Proc. Natl. Acad. Sci. U.S.A. 78:3824). A hydrophilicity profile can be used to identify the hydrophobic and hydrophilic regions of the ob receptor protein, which may in turn indicate extracytoplasmic, membrane binding, and intracytoplasmic regions.

Secondary structural analysis (e.g., Chou and Fasman, 1974, Biochemistry 13:222) can also be done, to identify regions of the ob receptor that assume specific secondary structures.

Manipulation, translation, and secondary structure prediction, as well as open reading frame prediction and plotting, can also be accomplished using computer software programs available in the art.

By providing an abundant source of recombinant ob polypeptide, and the opportunity to isolate the ob receptor (i.e., the db gene product), the present invention enables quantitative structural determination of the active conformation of the ob polypeptide and the ob receptor, or domains thereof. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed. These include but are not limited to X-ray crystallography (Engstom, A., 1974, Biochem. Exp. Biol. 11:7–13).

More preferably, co-crystals of ob polypeptide and ob receptor can be studied. Analysis of co-crystals provides detailed information about binding, which in turn allows for rational design of ligand agonists and antagonists. Computer modeling can also be used, especially in connection with NMR or X-ray methods (Fletterick, R. and Zoller, M. (eds.), 1986, Computer Graphics and Molecular Modeling, in *Current Communications in Molecular Biology*, Cold Spring Harbor Laboratory, Cold Spring Harbor, N.Y.).

Identification and isolation of a gene encoding an ob receptor of the invention provides for expression of the receptor in quantities greater than can be isolated from natural sources, or in indicator cells that are specially engineered to indicate the activity of a receptor expressed after transfection or transformation of the cells. According, in addition to rational design of agonists and antagonists based on the structure of ob polypeptide, the present invention contemplates an alternative method for identifying specific ligands of ob receptor using various screening assays known in the art.

The invention may be better understood by reference to the following Examples, which are intended to be exemplary of the invention and not limiting therof.

EXAMPLE SECTION

The following outlines the method used to identify the genetic material that is exemplary of the present invention. This endeavor comprises four sequential steps: A) Genetic Mapping, B) Physical Mapping, C) Candidate Gene Isolation, and D) Mutation detection. Following confirmation that the murine gene in object was isolated (Step D), the homologous human gene was sought, and both the murine and human genes and putative proteins were characterized. The steps are summarized in greater detail, below.

A. Genetic Mapping

The ob mutation was segregated in genetic crosses and standard linkage analysis was used to position the mutation relative to RFLPs (restriction fragment length polymorphisms). These data placed the ob gene in an ~5 cM interval on proximal mouse chromosome 6. (5 cM is a measurement of genetic distance corresponding to 5 apparent genetic crossovers per 100 animals.) A total of 771 informative meioses were generated and used in subsequent genetic mapping (Friedman et al. *Genomics* 11: 1054–1062, 1991). The genetic loci that were mapped relative to ob were all previously published. The two closest RFLPs described were defined by probes derived from the carboxypeptidase and met oncogene genes.

The genetic resolution of the experiments described above was inadequate to clone ob, principally because none of the genetic markers were in tight linkage. In order to identify the requisite tightly linked RFLPs, additional probes were isolated and the genetic cross was expanded. A method known as chromosome microdissection was used to isolate random pieces of DNA from proximal mouse chromosome 6 (Bahary et al., *Mammalian Genome* 4: 511–515, 1993). Individual cloned probes were tested for tight linkage to ob. On the basis of these studies one probe, D6Rck13, also termed psd3, was selected for further analysis owing to its genetic proximity to ob.

This probe was used to genotype 835 ob progeny from interspecific and intersubspecific crosses, which indicated that D6Rck13 is nonrecombinant in all 835 animals as reported in Bahary et al. In the course of physical mapping, a new polymorphic marker was identified from a cosmid subclone derived from YAC 53A6. This new marker was positioned between D6Rck13 and the ob gene and was used to genotype the additional 771 informative meioses from intraspecific intercross and backcross. A single animal #167 was identified to bear a recombination crossover between ob and D6Rck39. These studies indicated that D6Rck39/D6RcK13 is ~0.06 cM from ob. An additional probe, Pax-4, was identified that was 0.12 cM proximal to ob. Pax-4 was recombinant in two animals; #111 and 420. Pax-4 is a pseudogene that was previously mapped to proximal mouse chromosome 6 by Gruss and co-workers (Gruss et al. *Genomics* 11:424–434, 1991). On this basis, it was determined that the ob gene resides in the ~0.2 cM interval between Pax-4 and D6Rck13. This led to efforts to clone the interposing DNA in an effort to isolate ob.

B. Physical Mapping

The cloning of the DNA in this interval made use of yeast artificial chromosomes (YACs), a relatively new cloning vector that allows the cloning of long stretches of contiguous DNA often more than 1 million base pairs in length.

Firstly, yeast artificial chromosomes were isolated using D6Rck13 and Pax-4. This was accomplished by preparing purified DNA probes and using them to isolate the corresponding YACs. These YACs (#8, 16, 107 and 24) were isolated and initially characterized, and on the basis of the resulting analyses it was concluded that YAC 16 was the YAC that extended furthest distally, i.e., closest to ob. The key end of YAC #16 was then recovered, and it was determined that this end was closer to ob than Pax-4. This end was termed 16M(+). This conclusion was reached because it was shown that this probe was not recombinant in animal #420 (as was Pax-4). This end was sequenced and used to develop a PCR assay. This PCR assay was used to screen a YAC library. Four positive clones were isolated. Subsequent characterization of these YACs by end-rescuing, restriction mapping, pulse field gel electrophoresis, and Southern blots with the genetic crosses determined that two of these YACs, adu and aad, were critical for subsequent studies. YAC aad is a 550 kB nonchimeric YAC which extended furthest distally. Therefore, the distal end of this YAC, aad(pICL) was used to complete the physical map. YAC adu is 370 kB nonchimeric YAC and its distal end, adu(+), was determined to be nonrecombinant in all the ob progeny of the genetic crosses including animals #111 and 167, suggesting that the ob gene might reside in this YAC.

A PCR assay for these two ends, aad(pICL) and adu(+) was developed and used for isolating moire YACs and P1 clones to continue physical mapping. The important P1 clones isolated by this effort included 498, 499, 500 (isolated using a probe derived from aad(pICL)) and 322, 323 and 324 (using a probe from adu(+)).

In the meantime, YACs isolated by D6Rck13 (53A6, 25A8, 25A9, 25A10) were characterized. These studies determined that 53A6 extended furthest proximally toward the aad YAC. The size of the gap between 53A6 and aad was determined ~70 kB. The key end of 53A6, 53(pICL) was then used to screen three available YAC libraries and a P1 library. A critical P1 clone, 325, was isolated. This P1 clone overlapped with the P1 clones isolated by aad(pICL) as described above, and therefore served to close the gap between 53(pICL) and aad(pICL). As a result, the whole contig, containing YACs and P1 clones, of ~2.5 million base pairs in length, and which spanned Pax4, 16M(+), adu(+), aad(pICL), 53(pICL), D6Rck39 and D6Rck13, was cloned. By carefully mapping the sites of recombination apparent in animal #111 and 167, it was concluded that ob was situated in a 400 kB interval. To provide a working DNA source for isolating the ob gene, about 500 kB covering this nonrecombination region was isolated in a total of 24 P1 clones. These P1 clones, including 322 and 323, which later were proved to be useful clones, were used for exon trapping.

The physical map of the portion of the chromosome carrying ob is shown in FIG. 7A. FIG. 7B represents the YAC contig. FIG. 7C represents the P1 contig.

C. Isolation of Candidate Genes

The method used to isolate genes in this interval was exon trapping. This method used a commercial vector to identify exon DNA (i.e., coding sequences) by selecting for functional splice acceptor and donor sequences in genomic DNA introduced into a test construct. The DNA from these P1s were grown and subcloned into the exon trapping vector. These clones were short inserts cloned into a Bluescript vector. Each clone was PCR amplified with PCR primers corresponding to plasmid sequences that flanked the insert. The PCR amplification was performed directly on the bacteria that carried the plasmid. The reactions were set up using a Biomek robot. The PCR products were electrophoresed on a 1% agarose gel in TBE buffer that contained ethidium bromide. The exon trapping technique was modified to eliminate contaminating $E.\ coli$ DNA from the P1 clones, and to screen out the abundant artifactual exons, which exceeded 80–90% of the putative exons trapped. The exon trapping vector includes HIV sequences; a short segment of these vector sequences corresponds to this artifact.

The exon trapping experiment was performed using various P1 clones. Exon trapping products were then amplified by PCR, selected, and sequenced. Sequences of putative "exons" were compared with those in Genbank using the Blast computer program. About 15 exons were selected for further examination by RT-PCR, Northern analysis, and zoo blot for the presence of corresponding RNA or conservative sequences. Seven of the 15 putative exons, 325-2, 323-9, 322-5, D1-F7, 1H3, and 2G7, were found to encode an RNA transcript. 325-2 is a testis specific gene; 323-8 and 323-9 are likely two exons from the same gene expressed mainly in brain and kidney. IH3 and 322-5 represent two low level brain transcripts. D1-F7 is an exon from a previously cloned gene, inosine monophosphate dehydrogenase (IMPDH), which has ubiquitous expression pattern. None of these genes appeared to encode ob. 2G7, which is the ob exon, is discussed further below.

After three unsuccessful efforts to exon trap the ob gene, another attempt was made by pooling DNA from all the P1s from the critical ob region. These included P1s: 258, 259, 322, 323, 324, 325, 498, 499, 500, 653, 654 and others. Thereafter P1s 258, 260, 322, 498 and 499 were subcloned into the exon trapping vector, and subsequently several plates were prepared with bacterial clones, each of which carried a putative exon. Approximately 192 clones representing putative ob candidates were obtained. As noted above, a consistent artifact such that many of the isolates contained two trapped exons derived from the vector was observed.

Thus, clones were identified both by their size and the fact that hybridization of DNA probes corresponding to this artifact hybridized to the corresponding bands on a Southern blot of the gel. In this way, 185 out of 192 clones were excluded from further evaluation. Exclusion of the artifacts on the basis of size alone was not possible, as this could have, in the end, led to exclusion of the exon corresponding to ob.

Thus, of the 192 exons, a total of seven exons were selected for further study. Templates for sequencing the seven exons were prepared, and sequencing was performed. The sequences for the 7 exons were analyzed and it was found that 4 were identical and one was an apparent artifact. In particular, clone 1D12 contained the "HIV sequence," i.e., the artifact band. This left three exons for further analysis: 1F1, 2G7 and 1H3. 1F1 was eliminated because it mapped outside the critical region. PCR primers for both 1H3 and 2G7 were selected and synthesized.

The sequence of the exon on 2G7 was determined, and is shown in FIG. 10 (SEQ ID NO:7). PCR primers for 2G7 were selected and synthesized. The portions of the sequence corresponding to the PCR primers are underlined. The primers used were:

5' CCA GGG CAG GAA AAT GTG (Tm=60.0) (SEQ ID NO:8)

3' CAT CCT GGA CTT TCT GGA TAG G (Tm=60.0) (SEQ ID NO:9)

These primers amplified genome DNA with PCR conditions as follows: 25–30 cycles at 55° annealing×2', 72° extension×2', 94° denaturation×1' in standard PCR buffer. These primers were also used to generate a labeled probe by including $^{32}$P dCTP in the PCR reaction with a corresponding reduction in the amount of cold dCTP.

Figure 11A:
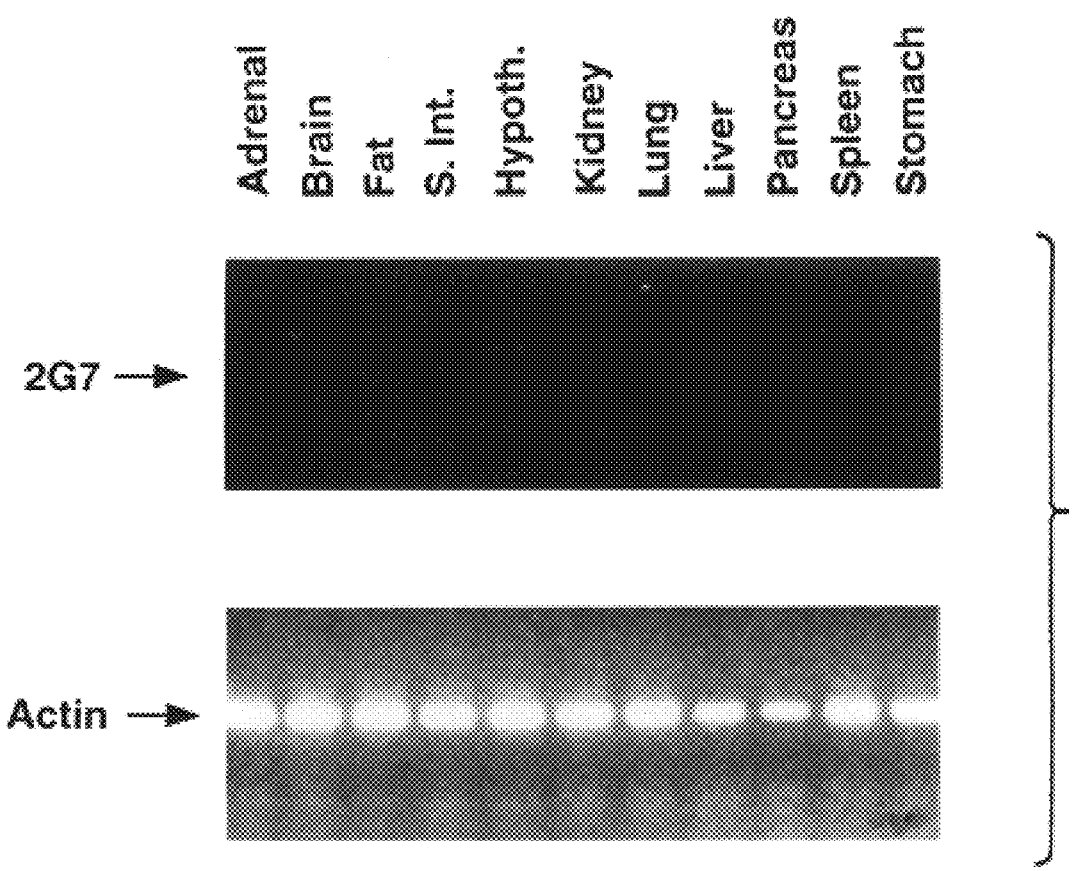
FIG. 11 (FIG. 11A) Reverse transcription-PCR analysis of mRNA from different tissues of the same mouse with the 2G7 primers and actin primers. The RT-PCR reactions were performed using 100 ng of total RNA reverse transcribed with oligo dT as a primer for first strand cDNA. PCR amplification was performed for 35 cycles with 94° denaturation×1'; 55° hybridization×1'; and 72 extensions for 2' with a 1' second autoextension per cycle. RT-PCR products were resolved in a 2% low melting point agarose gel run in 1×TBE buffer.
(FIG. 11B) Northern blot of mRNA from different organs of the mouse using PCR labeled 2G7 as a probe. Ten $\mu$g of total RNA from each of the tissues was electrophoresed on an agarose gel with formaldehyde. The probe was hybridized at 65° C. in Rapid Hybe (Amersham). Autoradiographic signals were apparent after 1 hour of exposure; the experiment shown was the result of a 24 hour exposure.
Figure 11B:
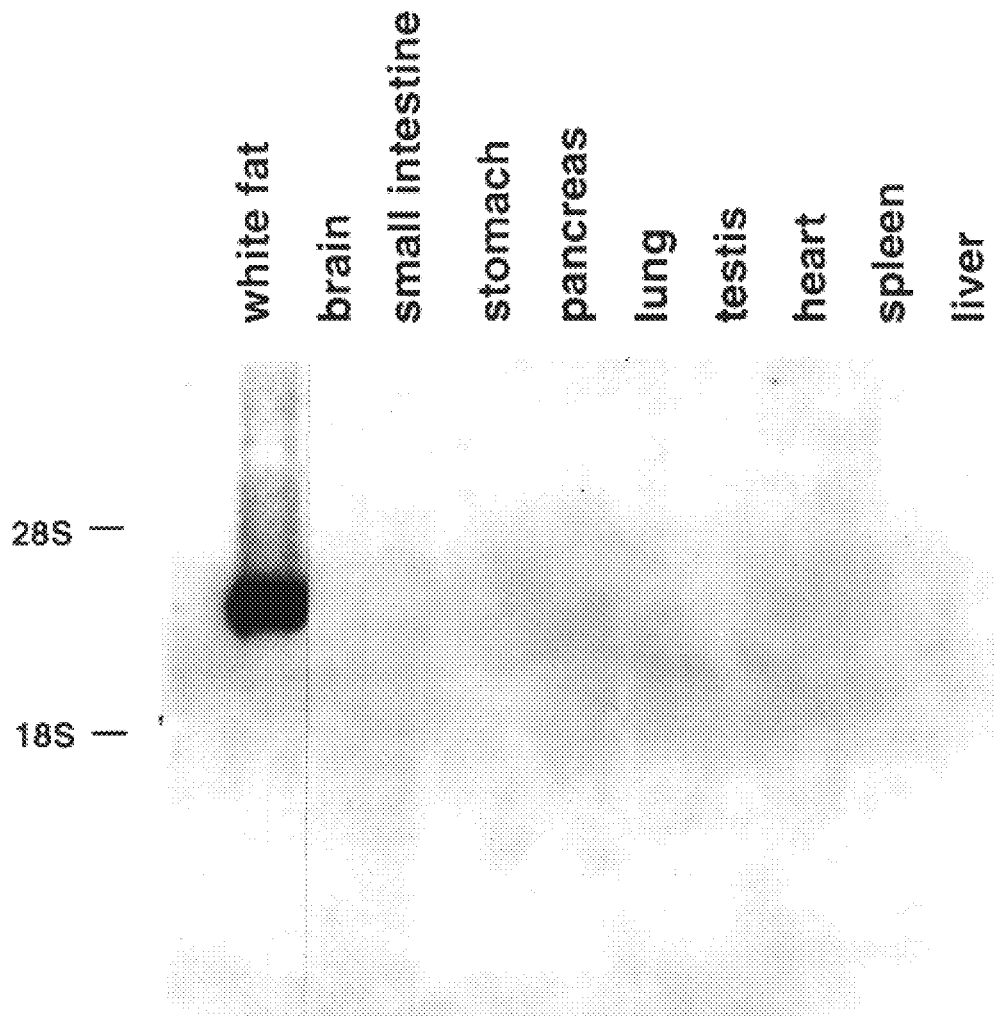

A RT PCR was performed on a variety of tissue RNAs and it was concluded that 2G7 was expressed exclusively in white fat among the tissues examined (FIG. 11A). Thereafter, $^{32}$P-labelled 2G7 was hybridized to a Northern blot of tissue RNAs (FIG. 11B) and showed that its RNA was expressed at high level in fat tissue but was either not expressed or expressed at very low levels in all other tissues (where the signals may be the result of fat contaminating the tissue preparations). Ten µg of total RNA from each of the tissues listed was electrophoresed on an agarose gel with formaldehyde. The probe was hybridized at 65° in a standard hybridization buffer, Rapid Hype (Amersham). The size of the RNA was approximately 4.9 kB. At this point 2G7 was considered to be a viable candidate gene for ob and was analyzed further.

D. Mutation Detection

Figure 12A:
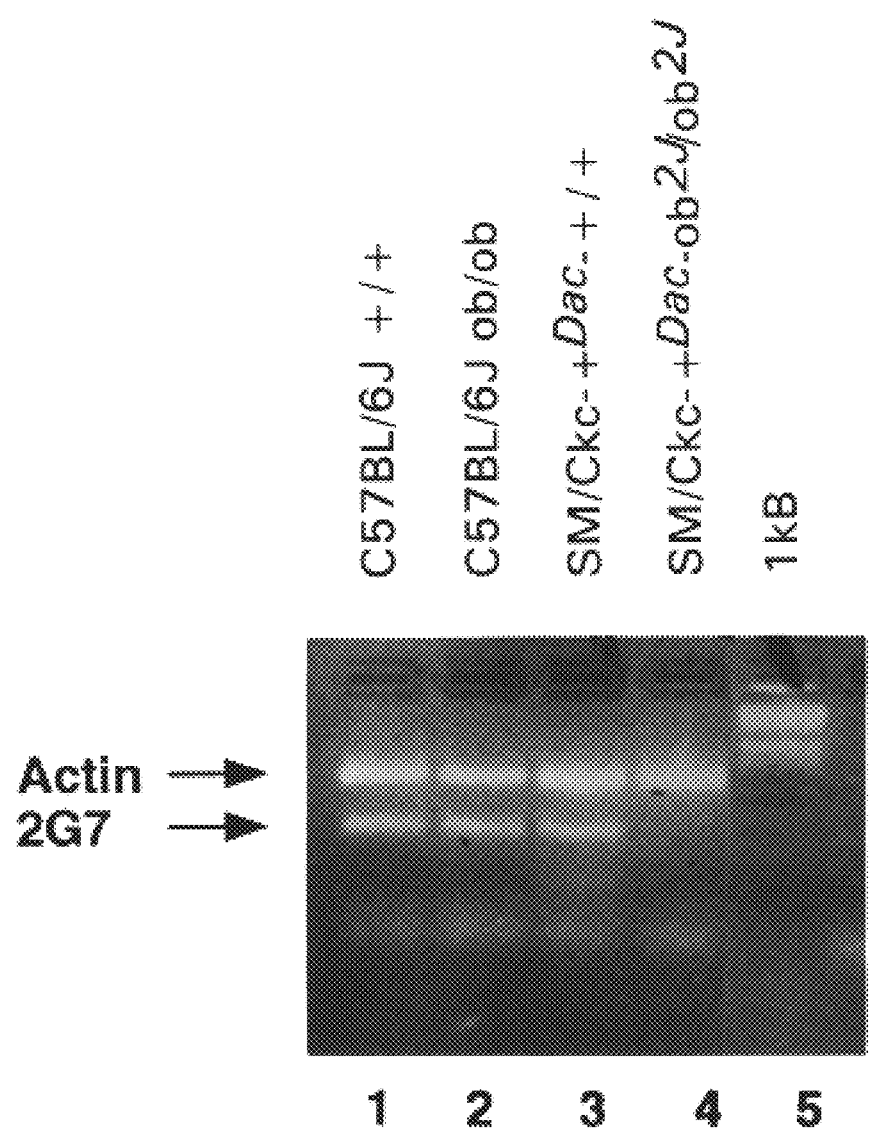
FIG. 12 (FIG. 12A) An ethidium bromide stain from an RT PCR reaction on fat cell (white adipose tissue) RNA from each of the mouse strains listed. Total RNA (100 ng) for each sample was reverse transcribed using oligo dT and reverse transcriptase, and the resulting single stranded cDNA was PCR amplified with the 2G7 primers (lower bands) or actin primers (upper bands). Both the 2G7 and actin primers were included in the same PCR reaction. The products were run on a 1% agarose TBE gel.
(FIG. 12B) Northern analysis corresponding to (FIG. 12A). Ten $\mu$g of fat cell (white adipose tissue) RNA from each of the strains indicated were run out and probed with the PCR labeled 2G7 probe as in FIG. 11B, above. An approximately 20-fold increase in the level of 2G7 mRNA was apparent in white fate RNA from the C57BL/6J ob/ob (1J) strain relative to lean littermates. In both the RT-PCR and Northern experiments there was no detectable signal in 2G7 RNA from the SM/Ckc-+$^{Dac}$ob$^2$J/ob$^{2J}$ (2J) mice even after a 2 week exposure. A 24 hour autoradiographic exposure is shown. The same filter was hybridized to an actin probe (bottom portion of the panel).

In order to confirm that 2G7 encoded the ob gene, it was necessary to demonstrate differences in the levels of RNA expression of DNA sequence of this gene in mutant as compared to wild type animals. Two separate mutations of the ob gene are available for study, C57BL/6J ob/ob (1J) and Ckc/Smj ob/ob (2J). These will be referred hereinafter as 1J and 2J, respectively. (Informal nomenclature is used to refer to the mouse strains studied. Throughout this specification and in the drawings, it will be understood that C57BL/6J refers to C57BL/6J+/+; CKC/smj refers to SM/Ckc-+$^{Dac}$-+/+; CKC/smj ob/ob refers to SM/Ckc-+$^{Dac}$-ob$^{2J}$/ob$_{2J}$). RNA was prepared from fat tissue that had been isolated from 1J, 2J, and control animals. Total RNA for each sample was treated with DNase and then reverse transcribed using oligo-dT as a primer and reverse transcriptase. The resulting single stranded cDNA was then PCR amplified either with the 2G7 primers (conditions shown above) for the lower band or commercially available actin primers for the upper band. The RT PCR products were run on a 1% agarose TBE gel that was stained with ethidium bromide (FIG. 12A). Using RT-PCT it was found that while 2G7 mRNA was expressed in 1J and all the other control mice, it was completely missing in 2J mouse. No signal was detected after 30 cycles of amplification. This experiment provided direct evidence that 2G7 corresponded to an exon from the ob gene.

Since 2J mutation is relatively recent and is maintained as a coisogenic strain, this result was the first available evidence that indicated that 2G7 is an exon from the ob gene. The mutation is likely located in the promoter region which leads to total abortion of the mRNA synthesis. The presence of signal in 1J mouse in this RT-PCT experiment suggested that 1J might carry a point mutation which does not result in a gross change in size of the RNA sample. In addition, 2G7 mRNA was absent, when tested by RT PCR, from four additional 2J animals.

Figure 12B:
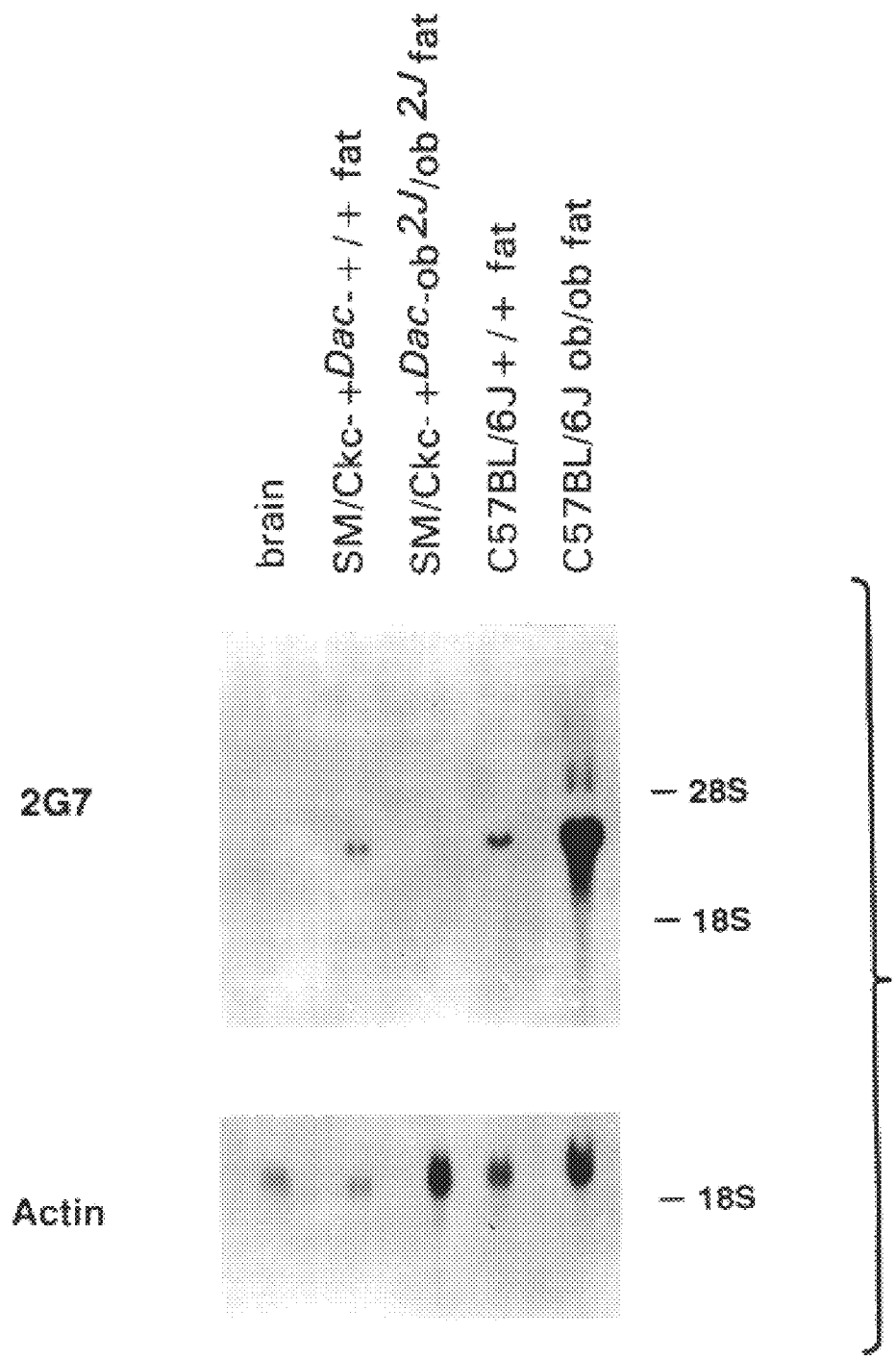

This result was confirmed on a Northern blot (FIG. 12B). Fat cell RNA was prepared from each of the strains (C57Bl/6J, 1J, CKC/smj, and 2J). Ten µg of these RNAs were run out. The blot was probed with the 2G7 probe that was PCR labeled, by amplification of the material, i.e., band, in FIG. 11 using $^{32}$P-dCTP in the PCR reaction. Actin is a control for the amount of RNA loaded. The actin signal is fairly similar in all of the samples. The ob signal is absent in brain because the mRNA is specific to fat cells.

The results of the Northern analysis confirm that 2G7 RNA was absent in 2J mice. The ob RNA is absent in the CKC/smj ob/ob mice because in this obese mutant strain the gene is disrupted such that no RNA is made. In addition, the level of 2G7 RNA was increased ~10–20 fold in 1J as well as db/db fat. These results are compatible with the hypothesis that ob either encodes circulating hormone or is responsible for the generation of a signal from fat cells that modulates body weight. These results supported the conclusion that 2G7 is the ob gene and predicted that 1J mice have a point mutation, probably a nonsense mutation leading to a premature translation termination.

These Northern results have been replicated using fat cell RNA preparations from four different 2J animals (FIG. 13). In this assay, ap2 is a fat-specific transcript that was used as a control much the same as actin in FIG. 12B. There is no significance to the varying density of the ap2 band. ap2 was labeled by designing PCR primers form the published ap2 sequence. The RT PCR products of fat cell RNA were then relabeled using the same protocol for PCR labeling. This analysis demonstrates the presence of ob mRNA in normal homozygous or heterozygous animals, and its absence from 2J mutant animals.

Figure 14:
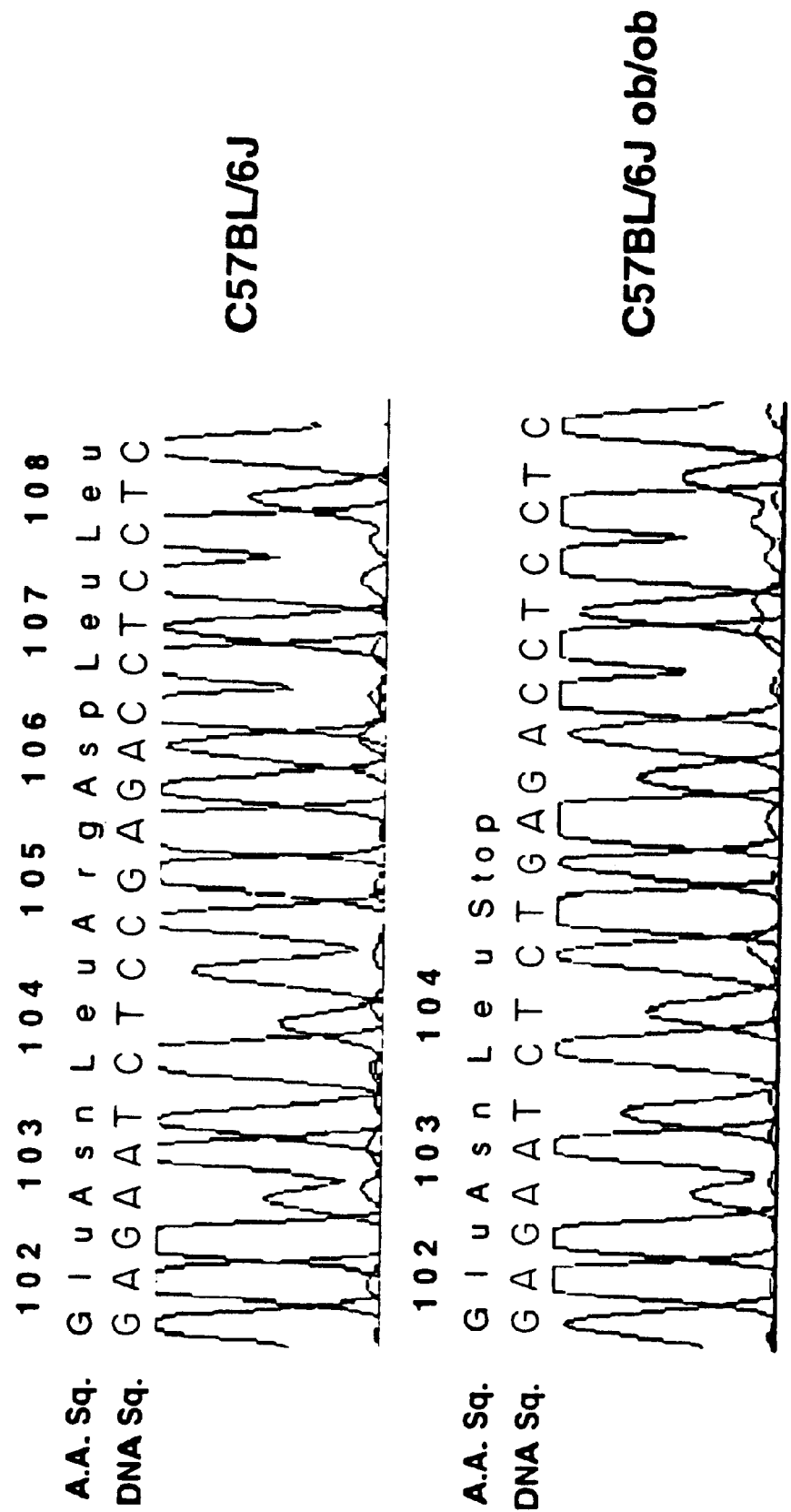
FIG. 14 compares the DNA sequence of the C57BL/6J (normal) and the C57BL/6J ob/ob (1J) mice in the region of the point mutation that leads to introduction of a premature stop codon (nonsense mutation) in the mutant strain cDNA. The ob/ob mice had a C→T mutation that changed an arginine residue at position 105. This base change is shown as the output from the automated DNA sequencer. RT-PCR was performed using white fat RNA from both strains (+/+ and ob/ob) using primers from the 5' and 3' untranslated regions. The PCR reaction products were gel purified and directly sequenced manually and using an ABI 373A automated sequencer with primers along both strands of the coding sequence.

The mutation has been identified in 1J mice. The mutation is a C to T base change that results in change of an arginine to an apparent premature stop codon at amino acid 108, and in all likelihood accounts for the 1J mutation (FIG. 14) despite high level expression of the ob mRNA (see FIG. 12 and FIG. 13, C57BL/6J ob/ob lanes).

More recently, Southern blots have been used to conclude that the 2J mutation is the result of a detectable DNA change at the 5' end of ob that appears to completely abolish RNA expression. The exact nature of this possible rearrangement remains to be determined.

Figure 15A:
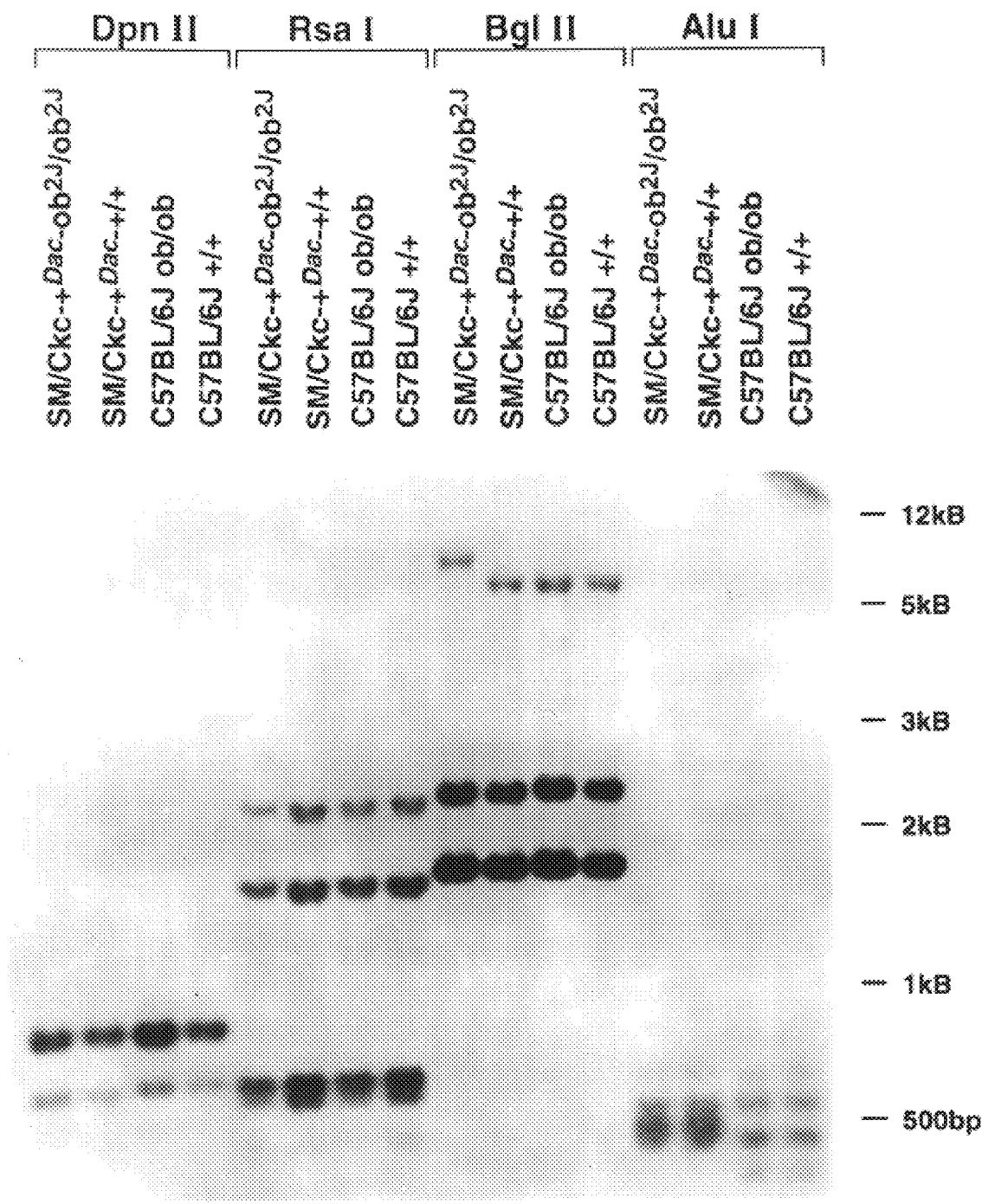
FIG. 15 (FIG. 15A) Genomic southern blot of genomic DNA from each of the mouse strains listed. Approximately 5 µg of DNA (derived from genomic DNA prepared from liver, kidney or spleen) was restriction digested with the restriction enzyme indicated. The DNA was then electrophoresed in a 1% agarose TBE gel and probed with PCR labeled 2G7. Restriction digestion with BglII revealed an increase in the size of an approximately 9 kB (the largest) BglII fragment in SM/Ckc-+Dacob$^{2J}$/ob$^{2J}$ (2J) DNA. RFLPs were not detectable with any other restriction enzymes. Preliminary restriction mapping of genomic DNA indicated that the polymorphic BglII site is about 7 kB upstream of the transcription start site. None of the other enzymes tested extend past the mRNA start site.
(FIG. 15B) Segregation of a BglII polymorphism in the SM/Ckc-+ Dacob$^{2J}$/ob$^{2J}$ strain. Six obese and five lean progeny from the same generation of the coisogenic SM/Ckc-+$^{Dac}$ob$^{2J}$/ob$^{2J}$ (2J) colony were genotyped by scoring the BglII polymorphism as shown in (FIG. 15A). All of the phenotypically obese animals were homozygous for the larger allele of the polymorphic Bgl fragment. The DNA in the "control" lane was prepared from an unrelated SM/Ckc-+ $^{Dac}$+/+ mouse, bred separately from the SM/Ckc-+$^{Dac}$ob$^{2J}$/ob$^{2J}$ colony.

A genomic Southern blot of DNA from the CKC/smj (SM/Ckc-+$^{Dac}$) and C57BL/6J mice using four different restriction endonucleases was performed in order to determine whether the mutant ob yielded a unique fragment pattern (FIG. 15A). Approximately 10 µg of DNA (derived from genomic DNA prepared from liver, kidney, or spleen) was restriction digested with the restriction enzyme indicated. The DNA was then electrophoresed in a 1% agarose TBE gel. The DNA was transferred to an imobilon membrane and hybridized to the PCR labeled 2G7 probe. The key band is the uppermost band in the BglII digest for the CKC/smj ob/ob (SM/Ckc-+$^{DAC}$ ob$^{2J}$/ob$^{2J}$) DNA. This band is of higher molecular weight than in the other strain, indicating a mutation in this strain.

Figure 15B:
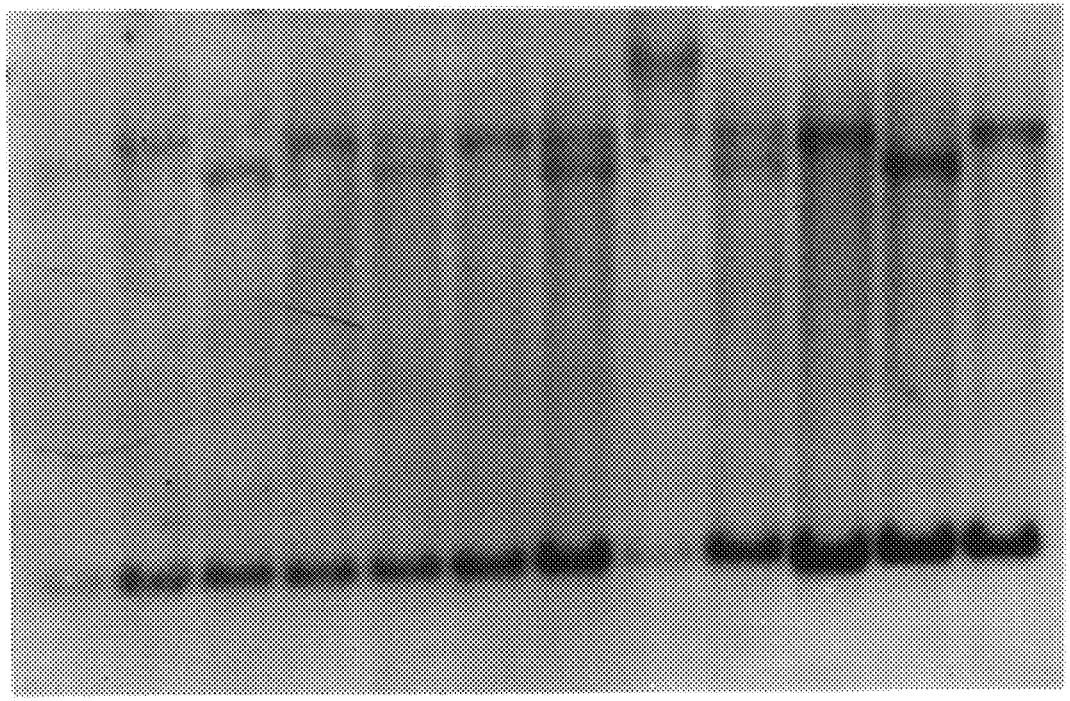

FIG. 15B is a southern blot of a BglII digest of genomic DNA from the progeny of an ob$^{2J}$/+×ob$^{2J}$/+cross. Some of the DNAs have only the upper band, some only the lower band, and some have the both bands. The animals with only the upper band are allo-obese, i.e., ob$^{2J}$/ob$^{2J}$. These data show that the polymorphism (i.e., mutation) shown in FIG. 15A segregates in a genetic sense.

EXAMPLE 1 cDNA Cloning and Sequence Determination of ob

Using the labeled 2G7 PCR probe, a total of 50 mouse cDNA clones from a murine fat cell λgt11 cDNA library (Clonetech 5'-STRETCH cDNA from testicular fat pads of Swiss mice, #ML3005b), and thirty cross hybridizing human cDNA clones from a human fat cell λgt10 cDNA library (Clonetech 5'-STRETCH cDNA from abdomen #HL1108a) were isolated. Library screening was performed using the plaque lift procedure. The filters from the plaque lift were denatured using the autoclave method. The filters were hybridized in duplicate with the PCR labeled 2G7 probe (Rapid Hybe buffer, 65° C., overnight). After a 2–4 hour prehybridization, the filters were washed in 2×SSC, 2%

SDS, twice for 30 minutes at 65° C. and exposed to SRy Llim. Duplicate positives were plaque purified. Plaque purified phage were PCR amplified using commercially available vector primers, e.g., λgt10 and λgt11. The resulting PCR products corresponded to the cDNA insert for each phage with a small amount of vector sequence at either end. The bands were gel purified and sequenced using the ABI automated sequencer and the vector primers to probe the DNA polymerase.

The raw sequencing data were then manually examined base by base to correct mishearing from the computer program. As the correct sequence became available, the downstream primers were synthesized and used to continue sequencing. Such experiments were repeated until each available cDNA clone was sequenced and synthesized into a contig. To date, ~3000 base pairs from the 5' end of the mRNA has been compiled. One of the cDNA clones extended to the 5' end of the mRNA since its sequence was identical to that of the 5' RACE product of fat tissue RNA (data not shown).

The sequence data revealed that there is a 167 amino acid open reading frame (FIG. 1). A Kozak translation initiation consensus sequence was present with an adenosine residue three bases upstream of the ATG. Two classes of cDNA were found differing by inclusion or exclusion of a single glutamine codon. This residue is found in a position immediately 3' to the splice acceptor of the 2G7 exon. Since the CAG codon of glutamine includes a possible AG splice acceptor sequence, it appears that there is slippage at the splice acceptor site with an apparent 3 base pairs deletion in a subset of the cDNA, as shown below.

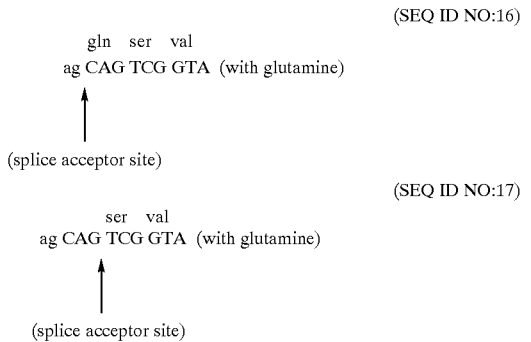

The "ag" in the sequences above corresponds to the assumed intron sequence upstream of the glutamine codon, and AG is the putative alternative splice site. This glutamine residue is located in a highly conserved region of the molecule and its importance for biological activity is as yet unknown.

A putative N-terminal signal sequence was detected, the signal cleavage site of which is predicted to be carboxy terminal to the alanine residue at amino acid position 21. This putative signal sequence was confirmed by application of a computer algorithm to the method of von Heijne (*Nucl. Acids Res.* 14, 4683, 1986). Using this technique, the most probable signal sequence was identified in the polypeptide coding region corresponding to amino acids 1–23, having the sequence:

MCWRPLCRFLWLWSYLSYVQA ↑ VP (SEQ ID NO:10) in which the arrow indicates the putative signal sequence cleavage site. The rest of the amino acid sequence was largely hydrophilic and did not have any notable structural motifs or membrane spanning domains other than the N-terminal signal sequence. Specifically, we did not find consensus sequences for N-linked glycosylation or dibase amino acid sequences indicative of protein cleavage in the predicted processed protein (Sabatini and Adesnik, *The metabolic basis of inherited disease*, C. V. Scriver et al. eds., McGraw-Hill: New York, pp. 177–223). Data base search using Blast and Block programs did not identify any homologous sequence.

Human fat tissue RNA was analyzed on Northern blot, RNA species of similar size to the mouse ob gene was detected. Sequencing and analysis of cDNA clones revealed that human ob also encodes 167 amino acid polypeptide (FIG. 2 and FIG. 3). Two classes of cDNA with or without three base pairs deletion were found in human as well (FIG. 6). The mouse and human ob genes were highly homologous in the predicted coding region, but had only 30% homology in the available 3' and 5' untranslated regions. An N-terminal signal sequence was also present in the human ob polypeptide. Comparison of the human and mouse ob polypeptide sequences showed that the two molecules share an overall 84% identity at amino acid level (FIG. 4). The N-termini of the mature proteins from both species share even higher homology, with only four conservative and three nonconservative amino acid substitutions among the N-terminal 100 amino acid residues.

Figure 16:
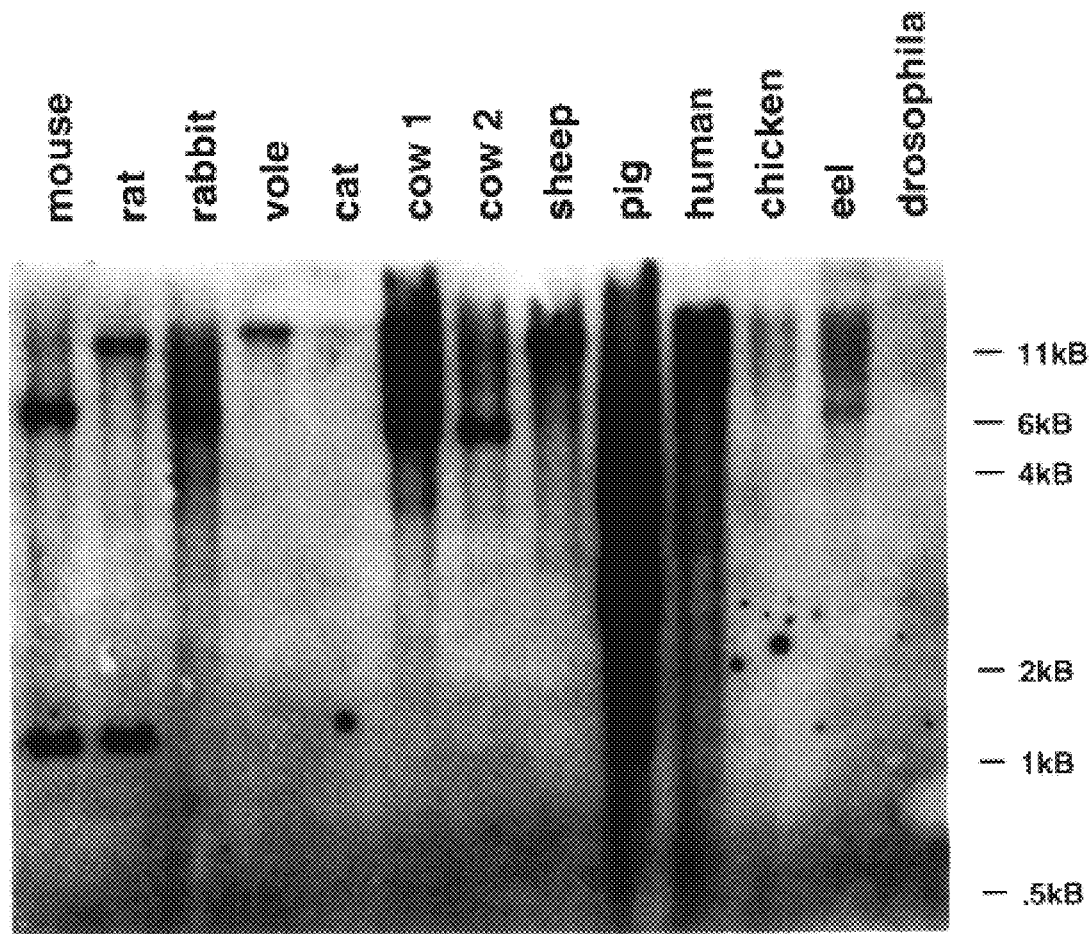
FIG. 16 is a Southern blot of EcoRI digested genomic DNA from the species listed, using an ob cDNA as a probe (i.e., a zoo blot). Hybridization signals were detectable in every vertebrate sample, even after a moderate stringency hybridization. The cat DNA in this experiment was slightly degraded. The restricted DNA was run on a 1% agarose TBE gel, and transferred to an imobilon membrane for probing. The filter was hybridized at 65° C. and washed in 2×SSC/ 0.2% SDS at 65° C. twice for twenty minutes and exposed for 3 days using Kodak X-OMAT film.

Genomic DNA was isolated from mouse, rat, rabbit, vole, cat, cow, sheep, pig, human, chicken, eel, and drosophila, and restriction digested with EcoR1. The digests were electrophoresed on 1% agarose TBE gel. DNA was transferred to an imobilon membrane and probed with the PCR labeled 2G7 probe. The filter was hybridized at 65° C. and washed with 2×SSC, 0.2% SDS at 65° C. twice for twenty minutes each wash, i.e., there were two buffer changes. These data indicate that ob is conserved among vertebrates (FIG. 16). Note in this regard that there is a 2+ signal in eel DNA; eel is a fish.

In summary, available evidence suggests that body weight and adiposity are physiologically controlled. Seven years ago efforts began to identify two of the key components of this system: the ob and db genes. As shown in this example, the ob gene has now been identified as a fat specific gene that plays a key role in regulating body weight. The product of this gene, which is most probably a secreted hormone, will have important implications for the diagnosis and treatment of nutritional disorders in man and non-human animals.

EXAMPLE 2

Expression of ob In Bacteria

Both murine and human cDNAs encoding ob have been cloned into a pET-15b expression vector (Novagen). This vector contains a T7 promoter in conjunction with a lac operator, and expresses a fusion protein containing a histidine tag (His-Tag) and a thrombin cleavage site immediately upstream of the coding sequence insertion site (FIG. 17) (SEQ ID NO:11).

The mouse and human cDNAs were modified such that the alanine at the end of the signal sequence was turned into an NdeI site, as was a separate sequence in the 3' region. Insertion of the NdeI site was accomplished using PCR with novel primers:

Mnde-5' (murine five prime primer):
CTTATGTTCA TATGGTGCCG ATCCAGAAAG TC (SEQ ID NO:12)

Mnde-3' (murine three prime primer):

TCCCTCTACA TATGTCTTGG GAGCCTGGTG GC (SEQ ID NO:13)

Hnde-5' (human five prime primer):
TCTATGTCCA TATGGTGCCG ATCCAAAAAG TC (SEQ ID NO:14)

Hnde-3' (human three prime primer):
TTCCTTCCCA TATGGTACTC CTTGCAGGAA GA (SEQ ID NO:15)

The primers contain a 6-base pair mismatch in the middle that introduces NdeI restriction sites at each end of the PCR fragment. Phage carrying either the mouse or human cDNA were PCR amplified using those primers. The PCR product was digested with NdeI and gel purified on a 1% low melting point agarose gel. The gel purified bands were subcloned into the pET vector. The resulting plasmids were sequenced to ensure that mutations were not introduced during the PCR amplification step of cloning. Constructs for the human and murine cDNA that encodes and that lacks glutamine 49 have been prepared. In particular, pET 15b constructs containing either the human or the mouse ob coding sequence, minus signal sequence and fused to a Hig-Tag, have been made using a PCR cloning method. The constructs have been sequenced to ensure no sequence errors were introduced into the coding region of the ob gene during the PCR amplification step.

Figure 18A:
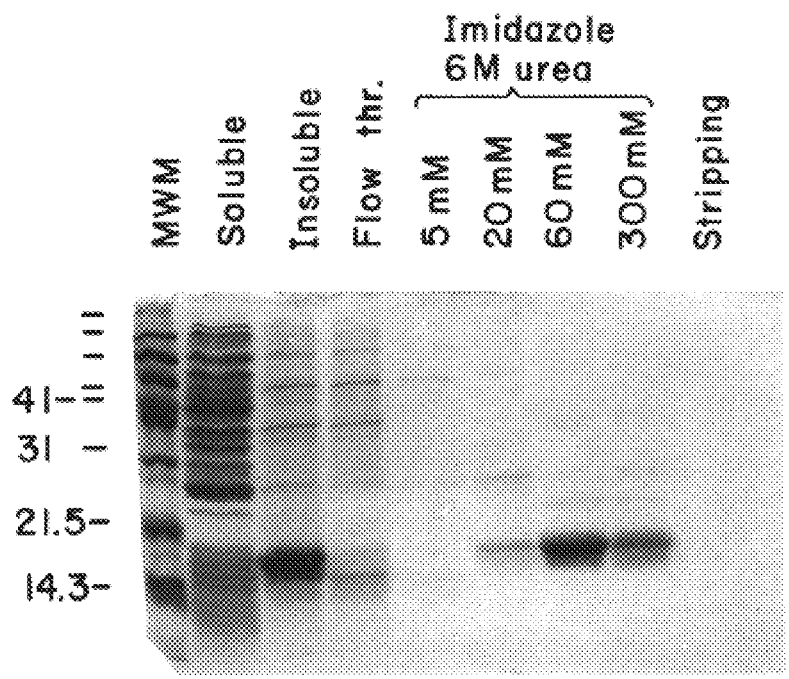
FIG. 18 presents analysis of the eluate from a His-binding resin (Ni) column for a recombinant mature murine ob fusion to a His-tag (FIG. 18A) and mature human ob fusion to a His-tag (FIG. 18B). Bacteria were transformed with vectors pETM9 and pETH14, respectively. Upon induction with 1 mM IPTG at optimal conditions, the transformed bacteria were able to produce 100–300 µg/ml of ob fusion protein, primarily in the inclusion body. The inclusion body was solubilized with 6M guanidine-HCl or urea, and fusion protein (present in the lysis supernatant) was loaded on the His-binding resin (Ni) column in 10 ml of 1×binding buffer with urea. The column was eluted stepwise with 5 ml aliquots of 20 µM, 60 µM, and 300 µM imidazole, and finally with strip buffer. The aliquots were analyzed for the presence of ob polypeptide fusion on a 15% acrylamide gel. Each lane contains the equivalent of 100 µl of bacterial extract.
Figure 18B:
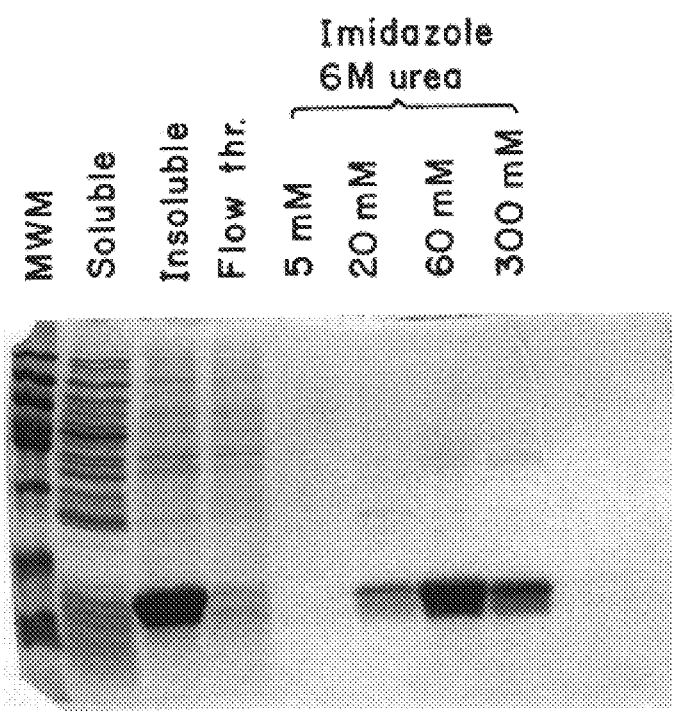

Two resultant plasmid constructs, pETM9 and pETH14, were selected to transform a bacterial expression host. Upon induction with 1 mM IPTG under optimal conditions, the transformed bacteria were able to produce 100–300 μg/ml of the ob fusion. The majority of the ob fusion protein was found in the inclusion body. After solubilization with 6M guanidine-HCl or urea, the fusion protein was purified through a His-binding (Ni-chelation) resin column. The conditions for column purification of the ob fusion protein (including binding, washing, and eluting) were established experimentally. The ob fusion protein binds to the resin at 5 mM imidazol/6M guanidine-HCl and stays bound at up to 20 mM imidazol/6M guanidine-HCl. The protein can be eluted form the resin at 60 mM imidazol/6M guanidine (FIGS. 18A and 18B). Both the purified human and mouse ob fusion proteins were further dialyzed in PBS to remove guanidine-HCl from the preparation and used to raise polyclonal antibodies.

In order to test the biological activity of the fusion protein products, the refolding conditions for the purified protein was tested and developed. This involves initial dialysis of the fusion protein in 1 M guanidine solution, followed by dilution with 0.4 M arginine solution. The His-Tag was removed from the fusion proteins before biological function assay. The tag removal was achieved by treating the fusion protein with thrombin from human placenta.

In addition, human and mouse ob gene coding sequence minus the signal sequence is being inserted into a pET 12c vector using PCR cloning method. These constructs can direct the synthesized ob fusion proteins into the periplasmic space of the bacterial host cell. The ob fusion protein recovered from the periplasmic space may only need a simple gel filtration to be purified from other host proteins and will not be denatured during such process.

EXAMPLE 3

Preparation of Antibodies to the ob Polypeptide

In addition to use of the recombinant protein to generate polyclonal antibodies, a set of four peptide sequences from the deduced murine ob sequence were identified using immunogenicity plot software (GCG Package). The four carboxyl terminal peptide fragments are:

(SEQ ID NO:18):
Val-Pro-Ile-Gln-Lys-Val-Gln-Asp-Asp-Thr-Lys-Thr-Leu-Ile-Lys-Thr (SEQ ID NO:19):
Leu-His-Pro-Ile-Leu-Ser-Leu-Ser-Lys-Met-Asp-Gln-Thr-Leu-Ala (SEQ ID NO:20):
Ser-Lys-Ser-Cys-Ser-Leu-Pro-Gln-Thr-Ser-Gly-Leu-Gln-Lys-Pro-Glu-Ser-Leu-Asp (SEO ID NO:21):
Ser-Arg-Leu-Gln-Gly-Ser-Leu-Gln-Asp-Ile-Leu-Gln-Gln-Leu-Asp-Val-Ser-Pro-Glu-Cys

These peptides were conjugated to KLH, and the peptide-KLH conjugates were used to immunize rabbits using standard techniques. Polyclonal antisera specific for each peptide is recovered from the rabbits.

EXAMPLE 4

In Vitro Translocation of an ob Polypeptide

In order to confirm the presence of a functional signal sequence, a human cDNA that included the entire open reading frame was subcloned into the pGEM vector.

Figure 19A:
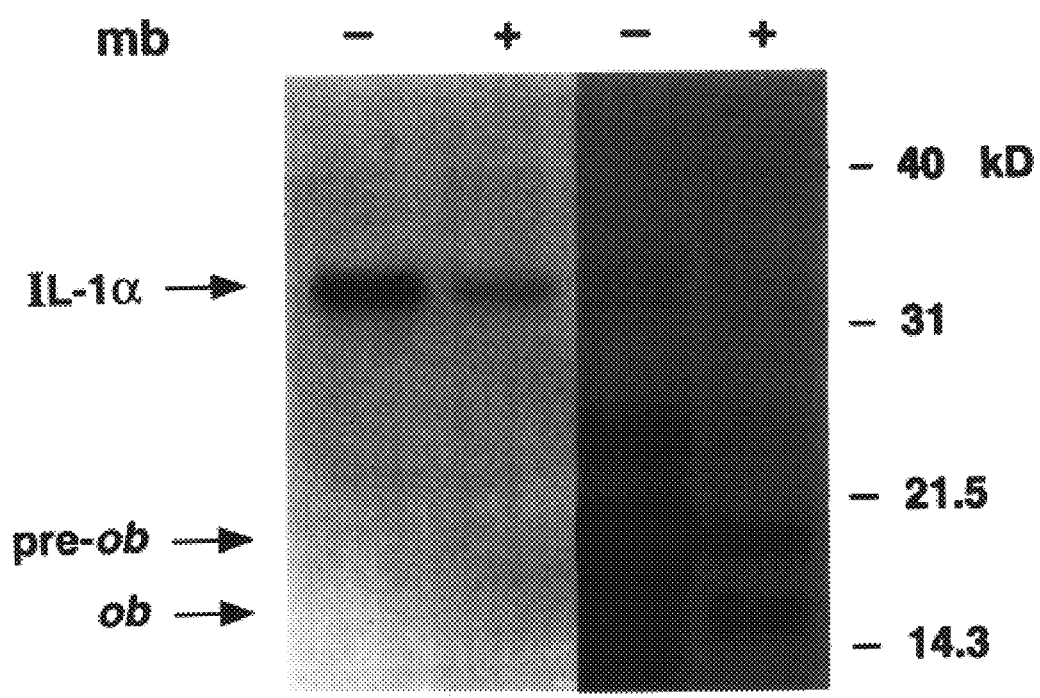
FIG. 19 (FIG. 19A) In vitro translation of ob RNA. A human ob cDNA was subcloned into the pGEM vector. The plasmid was linearized and plus strand RNA was synthesized using sp6 polymerase. The in vitro synthesized RNA was translated in the presence or absence of canine pancreatic microsomal membranes. An approximately 18 kD primary translation product was seen after in vitro translation. The addition of microsomal membranes to the reaction led to the appearance of a second translation product about 2 kD smaller than the primary translation product. The size of the translation product of interleukin-1α RNA, which lacks an encoded signal sequence, was unchanged by the addition of microsomal membranes. These data indicated the presence of a functional signal sequence.
(FIG. 19B) In vitro translation in the presence or absence of proteinase K. Protease treatment resulted in complete proteolysis of the 18 kD primary translation product, while the 16 kD processed form was unaffected. Permeabilization of the microsome with 0.1% TRITON-X100 rendered the processed from protease sensitive. These results indicate that the product had translated into the lumen of the microsome.
Figure 19B:
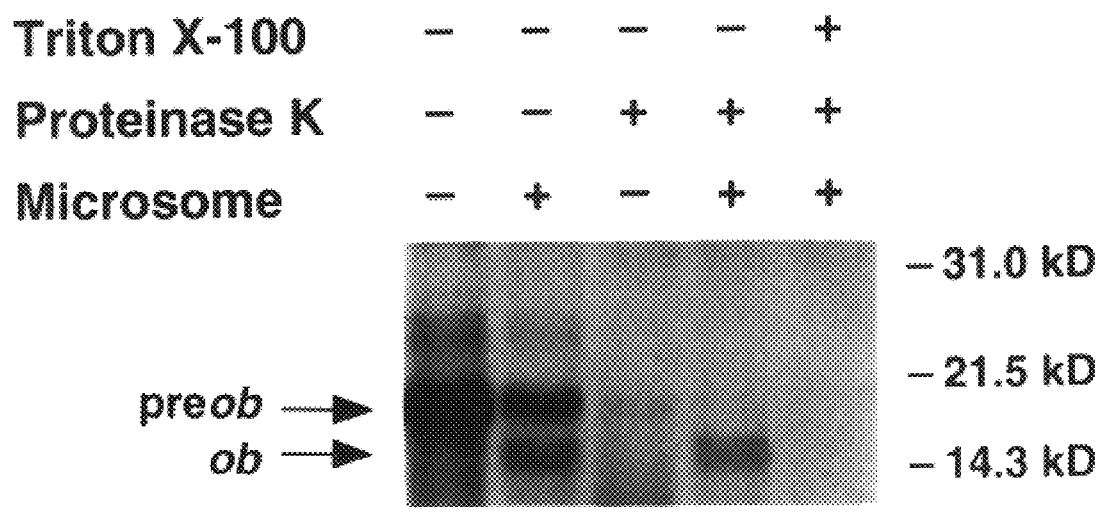

Only the human cDNA was used in this experiment because suitable mouse subclones were not recovered. Positive strand human ob RNA was transcribed using sp6 polymerase and used in an in vitro translation reaction with and without canine pancreatic microsomal membranes. The primary translation product migrated with an apparent molecular weight of ~18 kD, which is consistent with that predicted by the cDNA sequence. Inclusion of the microsomal membranes in the reaction inhibited the overall efficiency of translation ~5 fold. Nevertheless, approximately 50–70% of the ob primary translation product was truncated by approximately 2 kD in the presence of the membrane preparation, suggesting that the signal sequence is functional (FIG. 19A). The size of the primary translation product of interleukin-1α RNA, which does not encode a signal sequence, was unchanged when microsomal membranes were included in the reaction. In order to confirm that translocation of the ob protein had taken place, the in vitro translation products were treated with Proteinase-K. Protease treatment resulted in the complete proteolysis of the 18 kD primary translation product while the 16 kD processed form was unaffected by the enzyme treatment, indicating that it had translocated into the lumen of the microsomes (FIG. 19B). These data are compatible with the hypothesis that ob is a secreted molecule.

After signal sequence cleavage, two cysteine residues would remain within the predicted protein raising the possibility that the molecule contains a disulfide bond characteristic of other secreted polypeptides (Shen anti Rutter, 1984, Science 224:168–171).

EXAMPLE 5

Characterization of the ob Gene

To establish the relationship between obesity and genetic alterations in the ob gene in humans, the sequence of the human ob gene was determined (FIG. 20A) (SEQ ID NO:). Specific primers from the human coding sequence were used to screen a human P1 library. Three different P1 clones were obtained, grown up, and PCR amplified using primers flanking the splicing site between the first and second coding exon. The entire intron region, around 2 kB, was amplified and partially sequenced (see FIG. 20A; and as indicated in SEQ ID NO:22).

Figure 20B:
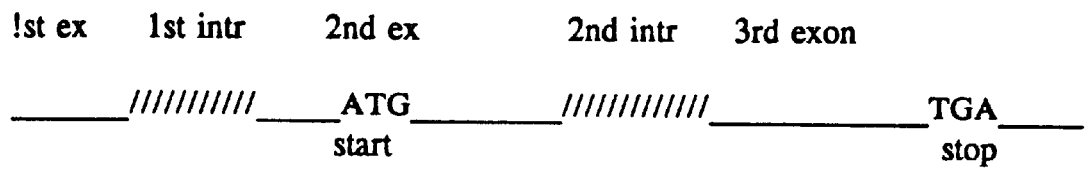
(FIG. 20B) A schematic diagram of the murine ob gene.
Figure 20C:
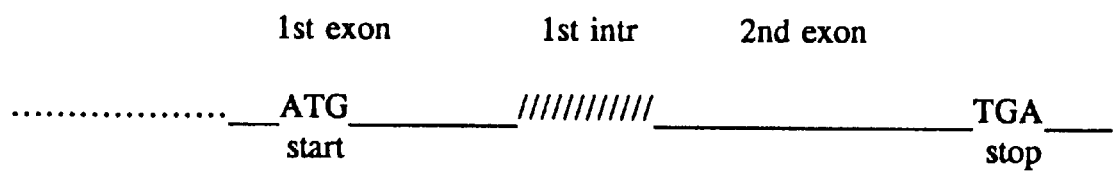
(FIG. 20C) A schematic diagram of the human ob gene. In both (FIG. 20B) and (FIG. 20C), the start and stop codons are underlined. There is no evidence of a first intron homologous to the mouse first intron in the human gene, but its existence cannot be excluded.

The gene structure of both the murine and human genes was characterized using PCR assays and other standard techniques. The mouse ob gene was found to consist of 3 exons, the second and third of which account for the coding sequence (FIG. 20B). The coding region of the human ob gene shares the same structure; however, the human gene lacks a 5' exon and intron (FIG. 20C).

Two sets of primers generated from the intronic sequences of the human gene have been prepared (FIG. 20A). The sequences of the primers follows (F and R refer to forward and reverse, respectively):

HOB 1gF 5'-CCCAAGAAGCCCATCCTG-3' (SEQ ID NO:26)
HOB 1gR 5'-GACTATCTGGGTCCAGTGCC-3' (SEQ ID NO:27)
HOB 2gF 5'-CCACATGCTGAGCACTTGTT-3' (SEQ ID NO:28)
HOB 2gR 5'-CTTCAATCCTGGAGATACCTGG-3' (SEQ ID NO:29)

DNA samples have been obtained from various sources, and these sets of primers are being used to amplify human genomic DNA from severely obese people. The PCR products were run on a low melting point agarose gel, and the bands were cut out and digested with agarase. The sequences were obtained using the ABI 373A DNA sequencer and Taq dideoxy terminator kit (abi, Perkin-Elmer). One point mutation in an ob gene from a patient sample has been detected to date. This mutation is on the first exon and does not change the amino acid sequence. Preliminary data indicate that an insertion sequence may be present in the first exon of another patient.

A different automated sequencing method with Sequenase instead of Taq DNA polymerase may be employed to yield more easily readable sequences for mutation detection.

EXAMPLE 6

Expression of ob in Yeast

Following the positional cloning of ob, it became important to uncover the physiological mechanism by which the ob protein reduces food intake and body weight. The first step in this direction was to recombinantly produce a functional protein using an expression system. In addition to the successful bacterial expression system, a yeast expression system was also selected. Yeast expression has several attractive features for expressing ob. The most important is that biologically active eukaryotic proteins are more likely to be produced. The ob polypeptide is secreted by mammalian cells. Protein secretion is very similar for all eukaryotes, which means that the yeast secretory apparatus is much more similar to the mammalian secretory pathway than bacterial secretory pathways would be. In particular, protein modifications of ob seen in mammalian cells would likely also be seen in the expression through the yeast secretory system. In addition, protein folding is carried out in passage through the secretory apparatus and thus delivering ob through the yeast secretory apparatus is likely to give a properly folded protein with native biological activity. This is significant for ob because the two cystein residues may form a disulfide bridge. In contrast to secretory pathways, the reducing environment of the cell cytoplasm prevents formation of disulfide bridges, and therefore it is essential that ob pass through the secretory pathway in order for this disulfide bond to form in vivo. Other advantages have to do with the ease and quickness of manipulating yeast, the availability of vectors and strains, and the vast experience in yeast recombinant technology.

Figure 21A:
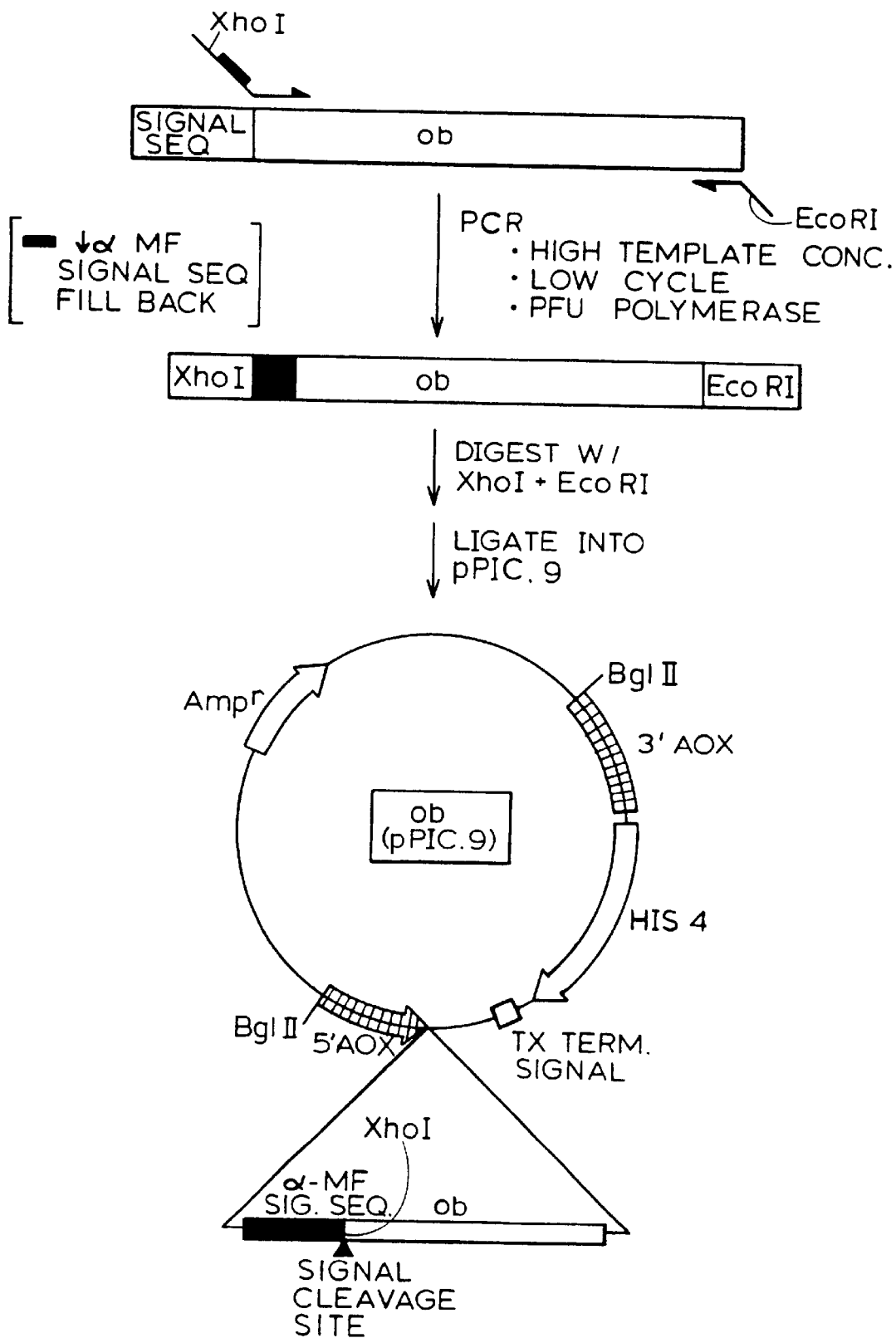
(FIG. 21A) Expression vector of ob with an α-mating factor signal sequence.

A *Pichia pastoris* expression system was chosen for four reasons: (1) it has higher levels of heterologous protein expression than other yeast systems such as *S. cerevisiae*; (2) protein glycosylation is more similar to the mammalian system in *P. pastoris* than *S. cerevisiae* (although glycosylation sites were not detected in ob using a computer search, there still remained the possibility of glycosylation at unrecognized sites); (3) *P. pastoris* secretes very few proteins natively, and thus it is generally straightforward to purify the expressed foreign protein; and (4) the vectors and yeast strains are commercially available (from Invitrogen). Two strategies for generating yeast expression vectors are shown in FIG. 21 and FIG. 22.

The vector chosen was pPIC.9. This vector contains a cloning site just downstream of the alpha-mating factor prepro coding sequence which directs the protein encoded by the gene cloned into the cloning site to be secreted by the secretory pathway. The other important feature of the vector is a HIS4 gene that allows selection for uptake of the vector using a yeast auxotrophic strain grown on histidine-deficient media following transformation of the yeast with the vector. The cloning strategy was the following: PCR amplify ob cDNA using a 5' primer that contained at its 3' end sequence complementary to the sequence of ob just following the predicted leader peptide cleavage site, and at its most 5' end a sequence complementary to the 3' end of the alpha-mating factor sequence of the vector. The 5' primer also contains an XhoI site. The 3' primer was designed to have at its 3' end a sequence complementary to the last few amino acids of ob and an EcoRI site at its 5' end. Following PCR amplification, the PCR product was digested with XhoI and EcoRI and cloned into similarly digested pPIC.9. Following the cloning of both the mouse and human ob cDNAs, each with and without the glutamine at codon 49, individual clones were isolated for all four individual constructs and sequenced to verify that the constructs were cloned in the correct orientation and frame and contained no mutatibns from the PCR amplification step. Following identification of clones with the correct sequence, these were transformed into *P. pastoris* strain GS115, a histidine auxotroph.

Figure 23A:
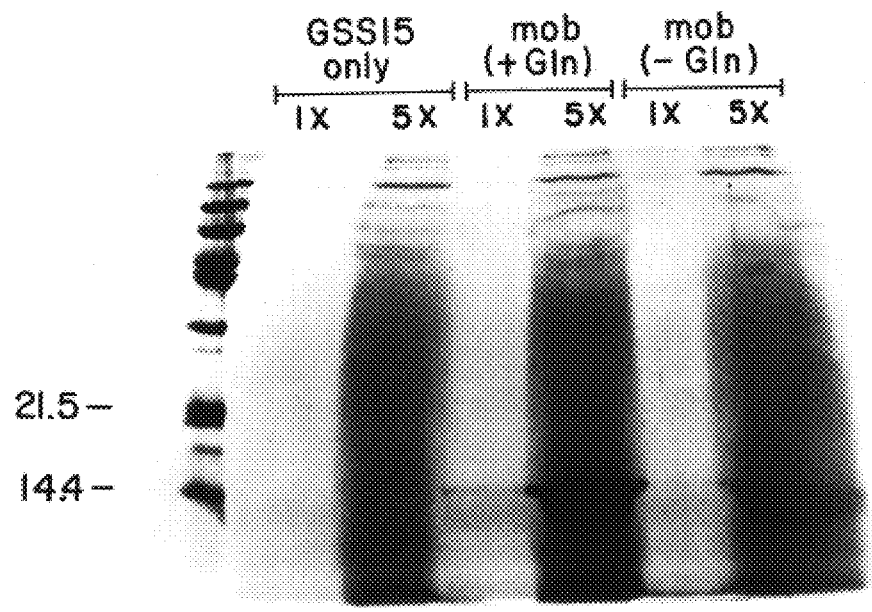
FIG. 23 (FIG. 23A) PAGE analysis of expression of murine ob (both the microheterogenous forms, i.e., containing and missing Gln 49) in transformed pichia yeast. The expected band of approximately 16 kD is visible in the transformed yeast culture fluid (second and third lanes), but not in culture fluid from non-transformed yeast (first lane).
(FIG. 23B) PAGE analysis of partially purified recombinant ob polypeptide on carboxymethyl cellulose, a weak cation exchanger. A band of about 16 kD is very visible in fractions 3 and 4 from the column, which was eluted with 250 mM NaCl. Lane 1—loaded sample; lane 2—flow through; lanes 3–5—fractions eluted with 250 mM NaCl.
Figure 23B:
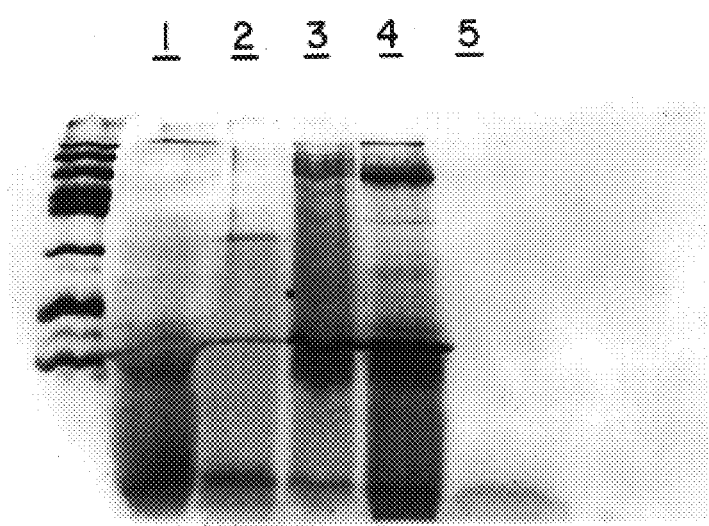

For the two mouse ob constructs, transformed yeast clones were screened for protein expression. As evidence that the transformed yeast contain ob, a DNA dot-blot assay and a colony hybridization assay were done which both showed ob sequence within the transformed yeast but not within the untransformed yeast. Furthermore, the transformed yeast now secreted a 16 kDa protein into the culture media whereas the untransformed yeast does not secrete a protein of this size (FIG. 23A). This is the predicted size of ob. Individual clones for both mouse constructs have been identified that are high expressors for ob, and currently a purification strategy is being developed to purify ob to homogeneity. One strategy has been to purify ob on a cation exchange column (FIG. 23B); preliminary data suggest that a strong cation exchanger may be useful. However, after cation exchange chromatography, the putative ob product is lost. This indicates the presence of a protease in the sample.

Figure 22A:
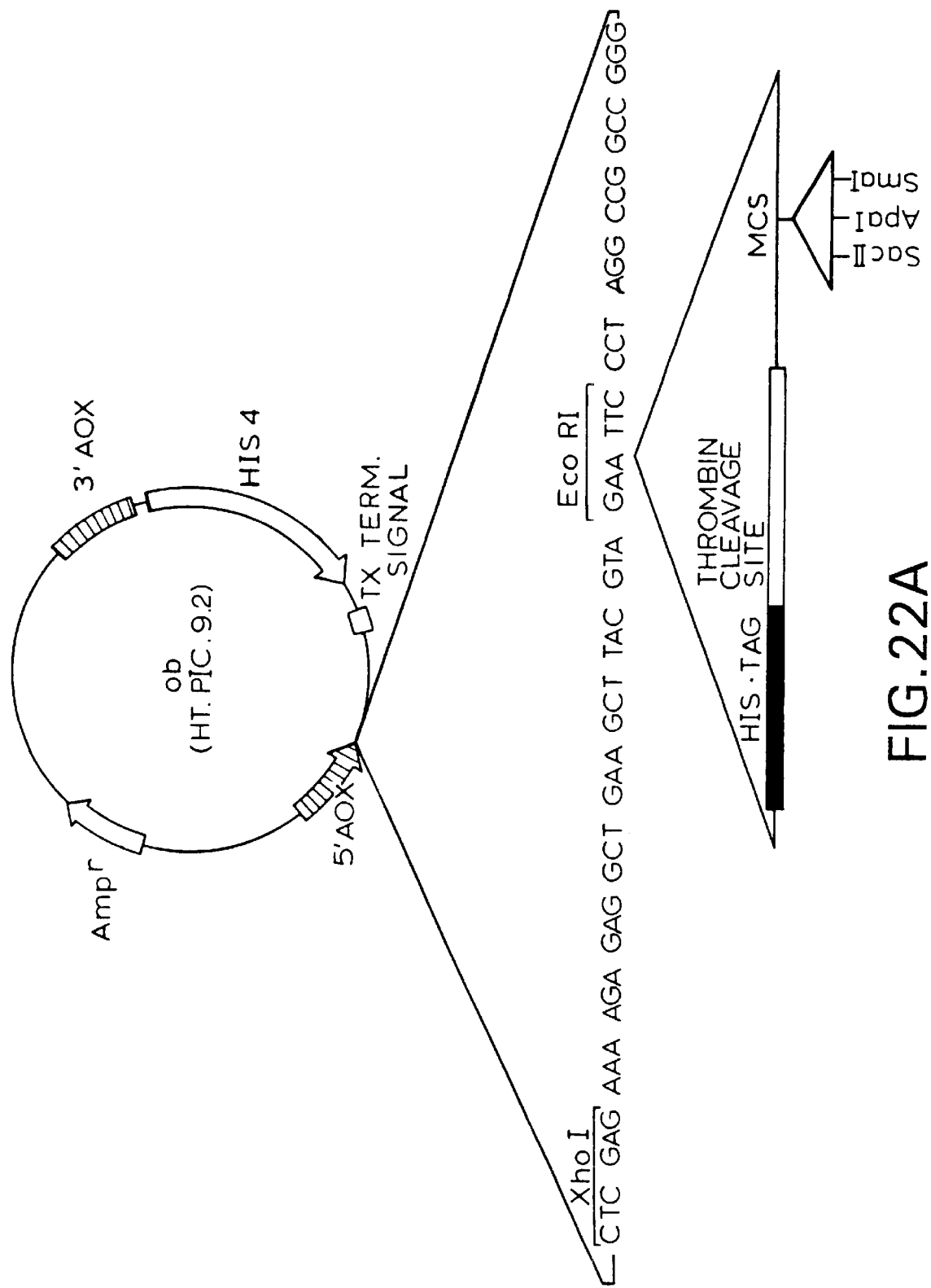
(FIG. 22A) Expression vector of an ob fusion with a His tag adopted from the pET expression system under control of the α-mating factor signal sequence.
Figure 22B:
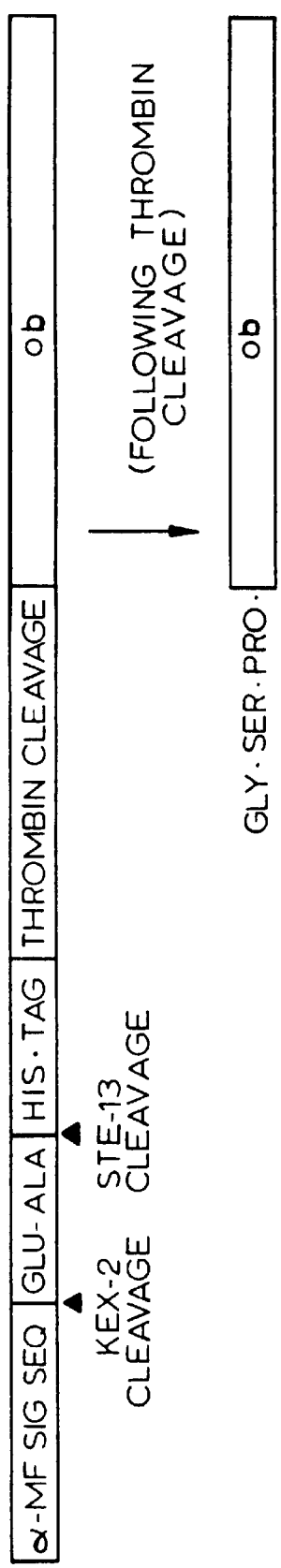
(FIG. 22B) Schematic drawing of the structure of the recombinant ob fusion protein containing a His tag, which includes the α-mating factor signal sequence, putative KEX-2 and STE-13 cleavage sites, the His-tag, and a thrombin cleavage site, and which would yield ob with three surplus N-terminal amino acid residues.

One strategy to overcome this problem is to prepare ob-His tag fusions for expression in yeast (FIG. 22). Further evaluation has demonstrated that ob without a His tag associates tightly with a Ni-chelation column. Purification of the ob polypeptide by Ni-chelation, followed by gel filtration, yielded a product of sufficient purity for mass spectral analysis. Mass spec confirms the molecular weight of the expressed protein is identical to the expected molecular weight, which strongly confirms that ob has been successfully expressed in Pichia.

However, the Ni-chelation/gel filtration purification protocol does not yield a ob polypeptide in sufficiently pure form. Additional small molecules are present. It does appear that the proteolytic activity elutes from the Ni-chelation column in the void volume. Accordingly, a three step purification process is planned: Ni-chelation, followed by cation exchange (which eliminates the small molecule contaminants), followed by gel filtration.

Estimating expression level by Coomassie blue staining of SDS-PAGE gels reveals approximately 10 mg/L when yeast are grown in shaker flasks. These levels are expected to increase in fermentation vessels, and we are about to initiate fermentation with the hopes of obtaining larger quantities of protein. Regarding the human ob constructs, transformed yeast clones containing high copy numbers of the ob gene have been identified, and these are expected to express ob protein. As antibodies are developed, these will be used to confirm the identity of the secreted 16 kDa protein.

EXAMPLE 7

High Level Expression of an Ob Fusion Peptide in Bacteria

Preparation of Freezer Stocks:

To each of the two 4 ml aliquots of sterilized M9ZB media without the carbon source, 40 $\mu$l stock dextrose (0.4 g/ml, filter sterilized) 10 $\mu$l ampicillin stock (200 mg/ml and 5 $\mu$l chlorampenicol stock (34 mg/ml, in ethanol) were added. A single colony each of *E. coli* with cloned mouse and human OB1 protein in a Novagen pET-14b vector was used to inoculate these. The tubes were incubated at 37° C. overnight.

0.5 ml of the overnight cultures were used to inoculate 50 ml M9ZB media with dextrose, ampicillin and chloramphenicol. These were incubated at 30° C. and the absorbance at 600 nm ($A_{600}$) was monitored periodically. At $A_{600}$ of about 1–1.2, 175 $\mu$l aliquots of the culture were mixed with 25 ul 60% glycerol in 2 ml eppendorf tubes, flash frozen in liquid nitrogen and stored at –80° C.

Culture Growth:

50 ml M9ZB media with 0.5 ml 40% dextrose, 125 $\mu$l ampicillin stock and 50 $\mu$l chloramphenicol stock was inoculated with 1 ml freezer stock and incubated at 30° C. At $A_{600}$ of 1–1.2, 10 ml of this culture was used to inoculate each of four 2 l flasks with 500 ml M9ZB media with dextrose, ampicillin and chloramphenicol. These were incubated at 30° C. until induction at $A_{600}$ of about 1–1.2 with a final concentration of 0.5 mM IPTG. The cultures were incubated overnight. The cells were harvested by centrifugation at 4000 rpm for 20 minutes. This expression system yield a recombinant O6 polypeptides as a fairly high percentage of total protein; on the order of gm perlit of *E. coli*.

Cell Lysis and Resuspension of Inclusion Bodies:

Cell paste was resuspended in a minimal volume of 20 mM HEPES, pH 7.2, 10% glycerol, 0.1 M KCl, 5 mM $MgCl_2$, 1% aprotinin, 1 mM PMSF, 5 $\mu$g/ml leupeptin and 50 $\mu$g/ml DNase I. The suspension was freeze thawed three times using liquid nitrogen and lukewarm water. Lysed cells were centrifuged at 18000 rmpm, 30 minutes and resuspended in 20 mM HEPES, pH 7.5, 0.1 M NaCl. The suspension was sonicated and Triton X100 was added to it to a final concentration of 2%. This was centrifuged for 15 minutes at 18000 rpm. After two more such cycles, three cycles of Triton free washes were given. Finally the pallet was dissolved in 6 M GdHCl, 20 mM HEPES, pH 7.5 by sonication followed by centrifugation. The supernatant was used for further purification.

The OB protein was purified in the unfolded state by immobilized metal ion affinity chromatography (IMAC). The solution was applied to a 40 ml column of Pharmacia chelating fast flow sepharose column charged by 5 column volumes of 50 mM $NiSO_4$ and equilibrated in 6 M GdHCl, 20 mM HEPES, pH 7.5. The column was washed with 6 M GdHCl, 30 mM imidazole, 20 mM HEPES, pH 7.5. Finally the protein was eluted with the same buffer containing 0.2 M imidazole. Unfolded protein in 6 M GdHCl was stored at 4° C. after adding sodium acetate (NaAc) to 10 mM and adjusting the pH to about 4.5 with acetic acid.

Refolding and the Purification of the Protein:

6 M GdHCl solution containing 100 mg protein was treated with 67 $\mu$l 1 M dithiothreitol (DTT) and diluted to about 67 ml with 6 M GdHCl, 10 mM NaAc, pH 4.5. It was left stirring at room temperature for about an hour. It was then diluted into 4 l of 20% glycerol, 2.5 mM $CaCl_2$, 20 mM Tris, pH 8.4 buffer with stirring. After proper mixing, the solution was left at room temperature for about 8 hours without further stirring. Then 2000 units of purified bovine thrombin (from thrombostat, a Parke-Davis product) was added and the solution was left with gentle stirring. After 2.5 hours it was redosed with 2000 units of thrombin and the cleavage of the histidine tag was continued for 3 more hours. The thrombin cleavage was arrested by adding PMSF to a final concentration of 0.1 mM. The solution was filtered and stored at 4° C.

The cleaved protein was further purified on the same IMAC column as above, equilibrated in 1 M KCl, 20% glycerol, 20 mM HEPES, pH 8.4 buffer. After loading the protein solution, it was washed with the same buffer and the cleaved protein was eluted with 1M KCl, 20% glycerol, 40 mM imidazole, 20 mM HEPES, pH 8.4. Uncleaved protein eluted at 0.2 M imidazole.

Purified cleaved protein was concentrated, treated with 50–100 mM EDTA, 10 mM potassium ferricyanide (to complete any incomplete oxidation) and gel filtered on superdex 75 16/60 column. Yields using this procedure approached 50% of the starting peptide.

Once purified the expressed protein has been characterized by several methods. Physical characterization includes dynamic light-scattering to determine homogeneity of structure and is used as a measure of proper folding. Light scattering data indicate that the human ob polypeptide is expressed predominantly or exclusively as a monomer, while the murine ob polypeptide can be found as a dimer as well as a monomer.

Assays with Ellman's reagent and mass spectroscopic analysis confirm that the cyteine residues form a disulfide bond in the protein. This oxidized form of the polypeptide was administered to mice, as described infra, and demonstrated biological activity.

Circular dichroism has been used to roughly determine the structural geometry of the protein. CD spectra in a physiological buffer (pH about 8, approximately physiological ionic strength) indicate that the human ob polypeptide has about 60% $\alpha$-helix structure and about 40% random coil structure. The murine ob polypeptide was found to have about 50% $\alpha$-helix and 50% random coil by CD spectroscopy.

Limited proteolysis, followed by mass spectrometry (see Cohen et al., 1995, "Probing the Solution Structure of the DNA-Binding Protein Mass by a Combination of Proteolysis and Mass Spectrometry,", has been employed to identify portions of ob polypeptide that are accessible to proteolysis. This analysis has demonstrated the presence of a flexible loop structure of amino acid residues 54 to 60 (as depicted in FIG. 4). It is likely that this flexible loop connects two domains of defined 2° structure, e.g., α-helix.

Importantly, as shown in the following Examples, bioactivity of the purified protein was assayed by administering the protein to both lean and obese rodents via an osmotic pump (e.g., an ALZET osmotic pump from Alza Corporation, Palo Alto, Calif.) or by daily bolus dose i.p. over at least a two-week period and effects on feeding behavior and body weight were observed.

EXAMPLE 8

Weight Reducing Effects of the ob Polypeptide (Leptin)

The gene product of the mouse ob locus plays an important role in regulating body weight. The present Example establishes that the ob protein circulates in mouse, rat and human plasma. The circulating form in all three species has an identical molecular weight by SDS-PAGE to the deduced polypeptide sequence without the signal sequence, suggesting that, in vivo, the protein is not processed after cleavage of the signal sequence. The ob protein was absent in plasma from C57/B16J ob/ob mice and present at ten-fold higher concentrations in plasma of db/db mice and twenty-fold higher levels in plasma of fa/fa rats relative to controls. It is suggested that these obese animal mutants are resistant to the effects of ob. There were seven-fold differences in plasma levels of the ob protein within a group of six lean human subjects. Daily injections of the recombinant mouse ob protein dramatically reduced body mass in ob/ob mice, had significant effects on body weight of wild type mice but had no effect on db/db mice. These data suggest that the gene product of the ob locus serves an endocrine function to regulate body weight.

Materials and Methods

Rabbits were immunized with recombinant protein in Freunds adjuvant (HRP, Inc). Immunopurified anti-mouse ob antibodies were prepared by passage of antiserum over a sepharose 4B column conjugated to the recombinant protein as described [Harlow, 1988 #444]. Immunoprecipitation of mouse plasma was carried out as follows: 0.5 ml of plasma from mouse, rat and human containing approximately 2.5 mM EDTA was pre-cleared with unconjugated sepharose-4B at room temperature with rocking for 2 hours. The sepharose was removed by spinning and 50 ml of a 50% slurry of antibody-conjugated sepharose containing affinity purified antibody at a concentration of 1 mg/ml of packed sepharose was added. One half ml of 2× RIPA buffer was added to give final binding conditions as follows: 50 mM Tris-HCl, pH 7.5, 100 mM NaCl, 1% NP-40, 0.1% SDS, 0.5% sodium deoxycholate and 0.025% sodium azide. The reaction was carried out overnight at 4° C. with rocking. The antibody-conjugated sepharose was washed 8 times using RIPA buffer, followed by rinsing three times with PBS, and run on 15% SDS-PAGE. The proteins were transferred to nitrocellulose and Western blotted with a biotinylated immunopurified antibody against the recombinant protein. The secondary antibody used was HRP-streptavidin and ECL was used for detection.

To quantitate the amount of ob in mouse serum, increasing amounts of the refolded recombinant mouse ob protein (0.01, 0.1, 0.5, 2.0, 15.0 ng) was added to 100λ of C57BL/6J ob/ob plasma and incubated at 4° C. for 3 hours with the protein A sepharose conjugated antibody. After extensive washing with buffer A (10 mM Sodium Phosphate buffer, pH 7.4; 100 mM NaCl; 1% Triton X-100, 5 mM EDTA, 1 mM PMSF), samples were resuspended in sample buffer, loaded on a 15% SDS-PAGE and transferred to a nitrocellulose membrane. Western blotting was performed using an immunopurified biotinylated anti-amino terminus antibody as a primary antibody and HRP-Streptavidin as a secondary antibody followed by ECL detection.

Cytoplasmic extracts were prepared by homogenizing adipose tissue in NDS buffer (10 mM Tris, pH 7.5, 10 mM NaCl, 60 mM ICCI, 0.15 mM spermine, 0.5 mM spermidine, 14 mM b-Mercaptoethanol, 0.5 m EGTA, 2 mM EDTA, 0.5% NP-40) by polytron and dounce homogenization and removal of nuclei was accomplished by centrifuging at 700 g.

Immunoprecipitations were performed as described above except that immunopurified anti-human ob antibodies were used. For the ELISA, 100 ml of a 1 mg/ml solution of immunopurified anti-human ob antibody was dissolved in a borate buffered PBS solution and applied overnight to microtiter (Corning cat. #2595) plates at 4° C. The plates were then washed 4 times with borate saline solution containing 0.05% Tween 20 and excess liquid was removed. Plates were blocked by incubation at room temperature for 2 hours with 240 ml per well of borate saline buffer containing 0.3% gelatin and then washed and dried. Either known amounts of a refolded human ob protein or plasma samples in 100 ml volume were incubated in individual wells overnight at 4° C. After washing, the plates were incubated with 100 ml of a biotinylated immunopurified anti-human antibody (0.1 mg/ml in a gelatine borate buffered solution) for 4 hours at room temperature. After washing, Horse Radish Peroxidase (HRP)-Streptavidin was added to the plates (0.1 mg/ml in borate buffer, 0.3% gelatin). HRP substrate solution (ABTS, 0.3 mg/ml and $H_2O_2$, 0.01% in citric acid) was then used for detection and the OD was measured at 414 nM to quntitate the antibody binding.

The mouse and human ob gene coding sequences were PCR amplified from plasmids containing ob cDNA sequences and subcloned into the pPIC.9 plasmid (Invitrogen). The human 5' primer used was

5' GTATCTCTCGAGAAAAGAGTGCCCATC-CAAAAAGTCCAAG 3' (SEQ ID NO:34)

and the 3' primer was

5' GCGCGAATTCTCAGCACCCAGGGCTGAGGTC 3' (SEQ ID NO:35).

For mouse, the 5' primer was

5' GTATCTCTCGAGAAAAGAGTGCCTATC-CAGAAAGTCCAGG 3' (SEQ ID NO:36)

and the 3' primer was

5' GCGCGAATTCTCAGCATTCAGGGCTAACATC 3' (SEQ ID NO:37).

The 5' primer for both mouse and human contains a XhoI site at the 5' end and coding sequences for the last 4 amino acids of the alpha-mating factor signal sequence present in the vector pPIC.9. This vector directs secretion of heterologously expressed genes from the cell into the culture media. The 5' PCR primer also includes the first 19 nucleotides of the ob gene open reading frame after the signal sequence cleavage site before the alanine at amino acid position 21. The 3' primer contains an EcoRI site at its 5' end which is immediately followed by sequences complementary to the putative ob stop codon. The PCR conditions were as follows: denaturing for 1 min. at 94° C., annealing for 1 min. at 55° C. and extension for 2.5 min. at 72° C. Low-cycle PCR (15 cycles) and the proof-reading polymerase PFU (Stratagene) were used to limit the number of PCR-generated mutations. The PCR products were digested with XhoI and EcoRI and cloned into similarly digested vector pPIC.9. All constructs were sequenced on both strands to ensure the absence of any PCR-generated mutations. Clones were transformed into *Pichia pastoris* (His-) by the spheroplast method and selected on histidine deficient media. Approximately 200 clones of mouse and human were screened for high-copy number integration by a colony hybridization assay and the high copy number clones were then assayed for ob expression initially by Coomassie staining showing the presence of a novel 16 kD protein present in the culture media of transformed yeast. The 16 kD band was confirmed to be ob using antibodies raised against the bacterially expressed ob protein. The recombinant proteins were purified by a two-step purification method described below. Mass spectrometry and cyanogen bromide treatment were performed as described Beavis, 1990 #804.

The entire ob coding sequence of the mouse and human ob genes C-terminal to the signal sequence were subcloned into the Pet15b expression vector (Novagen) and overexpressed in *Escherichia coli* [BL21(DE3)plYsS] using the T7 RNA polymerase system Studier, 1990 #803. Cells grown at 30° C. to an absorbency of 0.7 at 595 nM and induced with 0.5 mM isopropyl-b-D-thiogalcto-pyranoside overnight were collected by low-speed centrifugation. Lysis was performed by three cycles of freeze thaw and DNA digestion was perform with DNaseI. Membrane extraction was performed by sonication and detergent solubilization, and the final inclusion body pellet was dissolved in 6M guanidine-HCl, 20 mM HEPES, pH8.4. Recombinant ob proteins were purified under denaturing conditions by IMAC using a Ni-ion affinity column and washing with increasing amounts of imidazole. Purified denatured ob protein was then stored in 6 M guanidine-HCl, 10 mM sodium acetate (NaAc), pH 5, and reduced using 1 mM DTT at room temperature for 1 hour. Denaturation was performed by diluting the reduced protein into 20% glycerol, 5 mM $CaCl_2$, 5 mM NaAc, pH 5, through mixing and incubation at room temperature for 8–12 hours. After denaturation the pH was adjusted to 8.4 by addition of Tris to 10 mM, and the hexahistidine tag was removed by thrombin cleavage. Cleaved, renatured protein was repurified by IMAC to separate product from thrombin and uncleaved fusion protein. Cleaved, renatured protein elutes from the Ni-ion affinity column at 40 mM imidazole, whereas thrombin is not retained and uncleaved fusion protein elutes at 0.2 mM imidazole. Product was then concentrated, treated with 100 mM EDTA and 10 mM potassium ferricyanide and further purified by gel filtration using Pharmacia superdex 75 16/60 column.

An Ellman's assay was conducted as described Ellman, 1959, Arch. Biochem. Biophy. 82:70–77). Ellman's reagent was prepared by dissolving 39.6 mg 5,5'-dithio-bis(2-nitrobenzoic acid) (DTNB) in 10 ml 0.05 M phosphate, pH 8. A calibration curve was constructed in the concentration range of 10–120 mM free sulfhydryl (using a 1 mM stock solution of reduced DTT) at 412 nm. Each assay was performed using 0.02 ml Ellman's reagent and a total reaction mixture of 0.5 ml. The measured extinction coefficient was 12974 $M^{-1}cm^{-1}$ for free sulfhydryl group (correlation coefficient 0.99987), which is within 5% of the previously reported value of 13600 $M^{-1}cm^{-1}$.

Fifty ml of 2 mg/ml pure gel filtered protein, corresponding to a possible free sulfhydryl concentration of about 24 mM in the final reaction mixture, was subjected to Ellman's assay. The resulting solution gave $A_{412}$ of about 0.02, suggesting that two cysteine residues in the protein are in an oxidized state to form cystine or that their free sulfhydryl groups are completely buried within the inaccessible core of the folded protein. Identical results were obtained by conducting the same assay on unfolded protein in the presence of 6 M guanidine-HCl.

Mice were individually caged in a pathogen-free environment and acclimated to a diet containing 35% (w/w) Laboratory Rodent Diet 5001 (PMP Feeds, Inc.), 5.9% (w/w) tapioca pudding mix (General Foods) and 59.1% water which has an energy content of 1.30 kcal/gm. The diet was sterilized by autoclave and packed into 60 mm plastic dishes which were fixed to the tops of 100 mm petri dishes. Tapioca gives the diet a pasty texture making it difficult for the animal to spread the food in the cage. The 100 mm lid recovers the small amount of food spilled by the animal. A fresh dish of food was placed into the cage each morning and the previous day's dish was removed and weighed. The difference in weight provided a measure of daily food consumption. Effects of recombinant protein on food intake and body weight were measured in three strains of mice: C57Bl/6J ob/ob, C57Bl/Ks db/db and CBA/J+/+, purchased from the Jackson Laboratory. Thirty mice from each strain were divided into groups of 10. One group from each strain received daily intraperitoneal (i.p.) injections of the refolded bacterial ob protein at a dose of 5 mg/g/day in 300 ml of PBS. A second group received i.p. injections of the same volume of PBS. These control mice received injections of the PBS dialysate of the recombinant protein. The PBS was cleared of endotoxin using an Acticlean ETOX column. A third group of animals did not receive injections. Food intake was recorded daily and body weight measurements were recorded regularly over a 3.5 week interval. For the pair feeding experiment, the food intake of a separate group of ob mice was matched on a daily basis to that consumed by the ob mice receiving protein.

Results

The ob Protein Circulates in Mouse, Rat and Human Plasma. Recombinant mouse and human ob protein was prepared using the PET 15b bacterial expression vector (Novagen) and by cloning into *Pichia pastoris*, a yeast expression system that secretes recombinant proteins directly into the culture media. The ob protein expressed in yeast includes the 146 amino acids carboxy terminal to the signal sequence. Rabbits were immunized with the bacterial proteins (HRP, Inc.). Antibodies were immunopurified (Research Genetics) and used for immunoprecipitations and Western blots of protein from plasma and adipose tissue.

The ob protein from mouse plasma migrates with an apparent molecular weight of 16 kD by SDS-PAGE. The electrophoretic mobility is identical to the recombinant ob protein secreted by yeast after signal sequence removal (FIG. 24A) The protein was not detected in plasma from C57BL/6J ob/ob mice that have a nonsense mutation at codon 105. Several different antisera failed to identify the truncated 105 residue polypeptide chain predicted by the cDNA sequence.

Figure 24A:
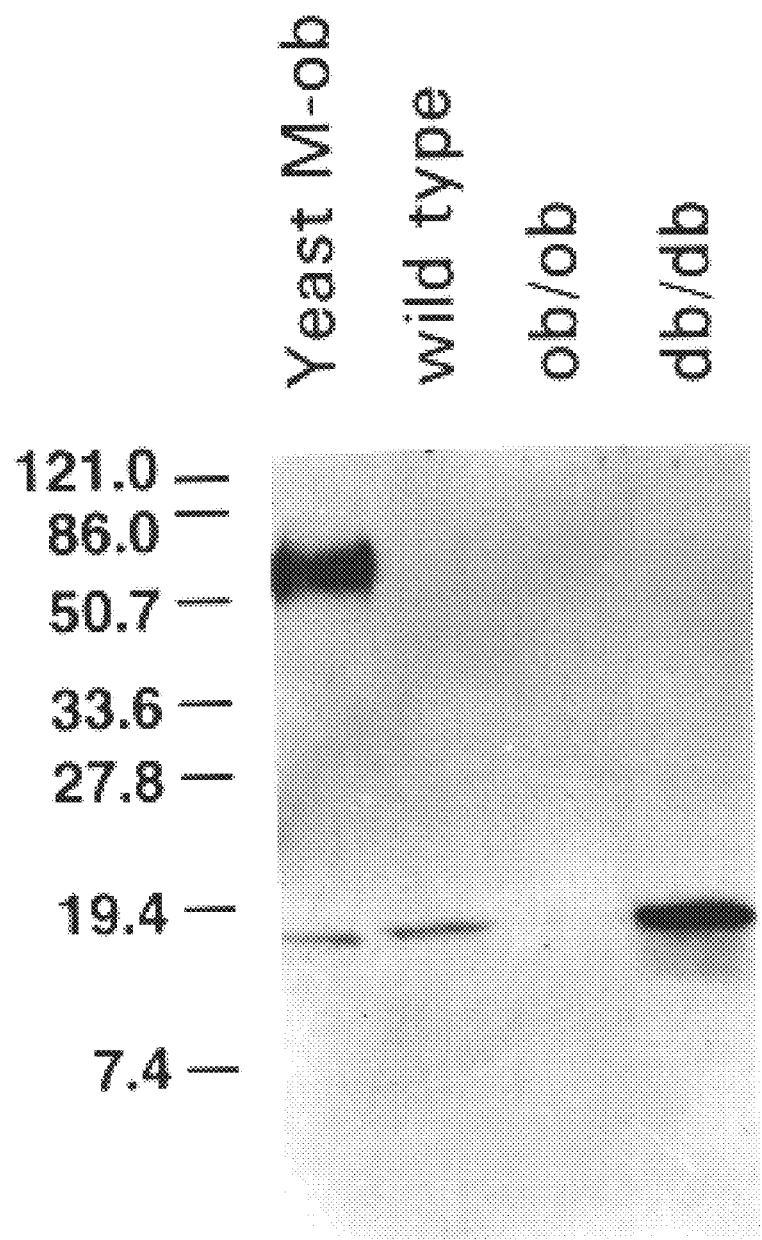
(FIG. 24A) Immunoprecipitations from mouse blood. 0.5 ml of mouse plasma was pre-cleared with unconjugated sepharose and incubated overnight with immunopurified anti-ob antibodies conjugated to sepharose 4B beads. The immunoprecipitate was separated on a 15% SDS-PAGE gel, transferred and Western blotted with an anti-ob antibody. The protein migrated with a molecular weight of approximately 16 kD, to the same position as the mature mouse ob protein expressed in yeast. The protein was absent in plasma from C57BL/6J ob/ob mice and increased ten-fold in plasma from C57BLB/Ks db/db mice relative to wild type mice. db mice have been suggested to overproduce the ob protein, secondary to resistance to its effects.
Figure 24B:
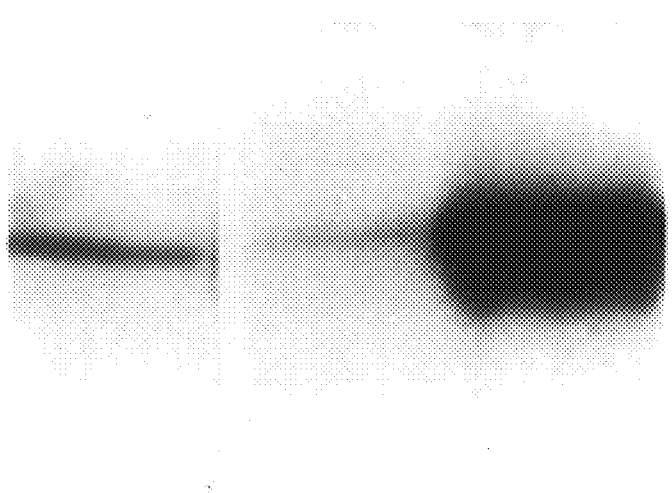
(FIG. 24B) Increased levels of ob in fatty rats. The fatty rat is obese as a result of a recessive mutation on rat chromosome 5. Genetic data has suggested a defect in the same gene mutated in db mice. Plasma from fatty rats and lean littermates was immunoprecipitated and run on Western blots. A twenty-fold increase in the circulating level of ob is seen in the mutant animals.
Figure 24C:
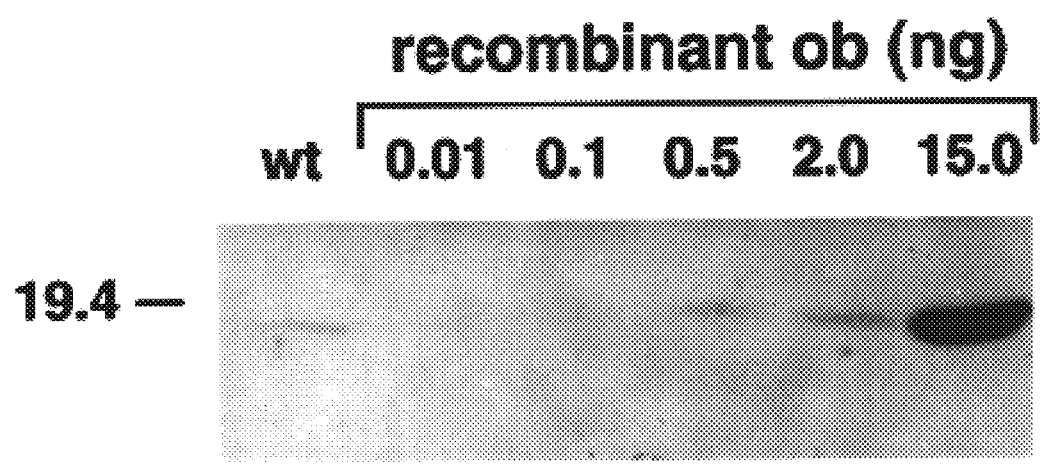
(FIG. 24C). Quantitation of the ob protein in mouse plasma. Increasing amounts of the recombinant mouse protein were added to 100λ of plasma from ob mice and immunoprecipitated. The signal intensity on Western blots was compared to that from 100λ of plasma from wild type mice. A linear increase in signal intensity was seen with increasing amounts of recombinant protein demonstrating that the immunoprecipitations were performed under conditions of antibody excess. Similar signals were seen in the wild type plasma sample and the sample with 2 ng of recombinant protein indicating the circulating level in mouse plasma is approximately 20 ng/ml.
Figure 24D:
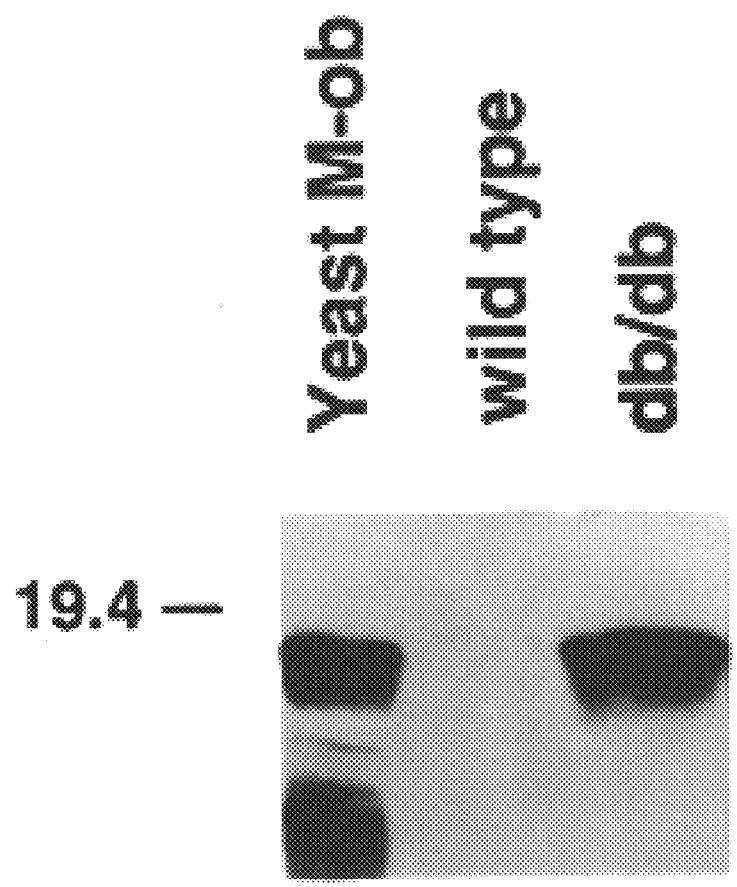
(FIG. 24D) ob protein in adipose tissue extracts. Cytoplasmic extracts of mouse adipose tissue were prepared from db and wild type mice. Western blots showed increased levels of the 16 kD protein in extracts prepared from db mice.

A ten-fold increase in the level of circulating protein was observed in db/db mice relative to a control animal (FIG. 24A). Immunoprecipitation of plasma from wild type and fa/fa rats revealed a twenty-fold increase in the level of ob protein in the mutant rat compared to wild type (FIG. 24B). The db mutation results in an obese phenotype identical to that seen in ob mice (Bahary et al., 1990, Proc. Nat. Acad. Sci. USA. 87:8642–8646). fatty rats are obese as a result of a recessive mutation in a gene homologous to db (Truett et al., 1991, Proc. Natl. Acad. Sci. USA. 88:7806–7809). In order to quantitate the level of ob in mouse plasma, increasing amounts of recombinant protein were added to ob serum and immunoprecipitated (FIG. 24C). A linear increase of the signal intensity on Western blots was seen with increasing amounts of recombinant protein. Comparison of the signal intensity of the native protein in mouse plasma to the standards indicated that the circulating level of the ob protein in wild type mice is approximately 20 ng/ml. These data demonstrate that the immunoprecipitations and Western blots were performed under conditions of antibody excess. Increased levels of the ob protein were also seen in protein extracts of adipose tissue from db/db mice relative to controls (FIG. 24D). As expected for a secreted protein, the protein from the adipose tissue fractionated with the crude membrane fraction (data not shown).

Figure 25A:
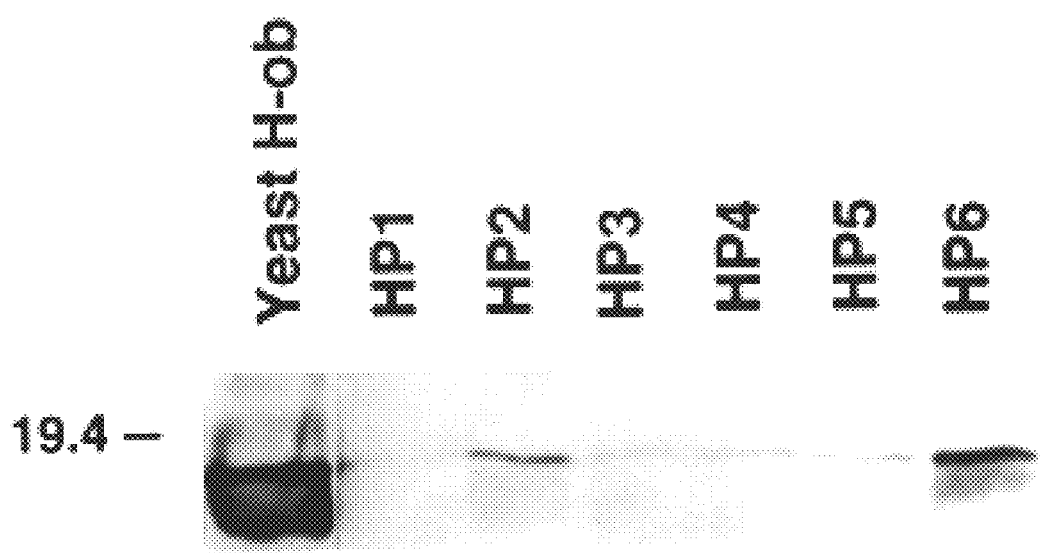
(FIG. 25A) Western blots of human plasma. Plasma samples were obtained from six lean volunteers. Immunoprecipitation and Western blotting revealed the presence of an immunoreactive 16 kD protein, identical in size to a recombinant 146 amino acid human protein expressed in yeast. Variable levels of the protein were seen in each of the six samples.
Figure 25B:
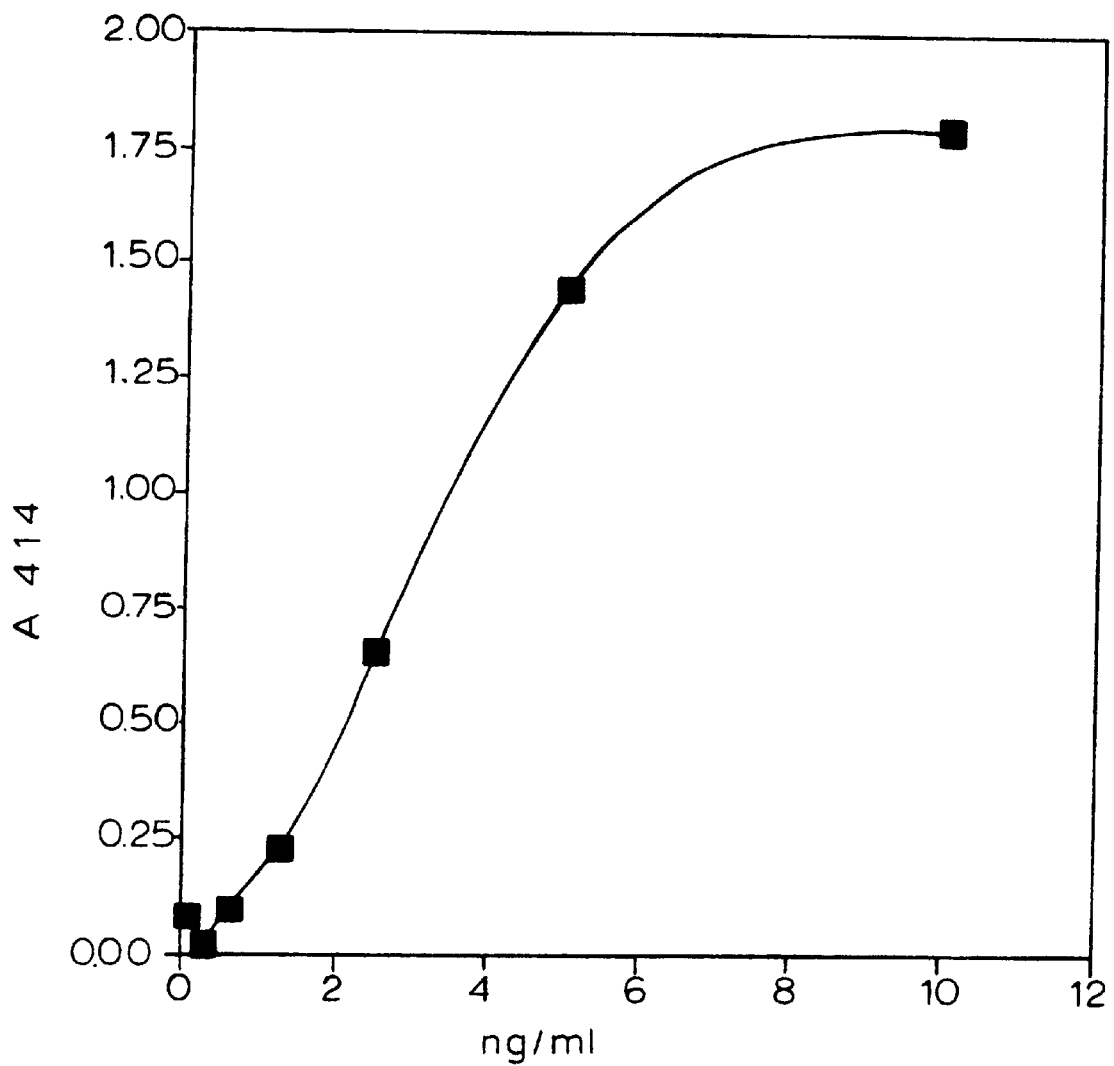
(FIG. 25B) An ELISA (Enzyme Linked Immunoassay) for human ob. Microtiter plates were coated with immunopurified anti-human ob antibodies. Known amounts of recombinant protein were added to the plates and detected using immunopurified biotinylated anti-ob antibodies. Absorbance at 414 nm was plotted against concentration of ob standard to yield a standard curve. The resulting standard curve showed that the assay was capable of detecting 1 ng/ml or more of the human ob protein.
Figure 25C:
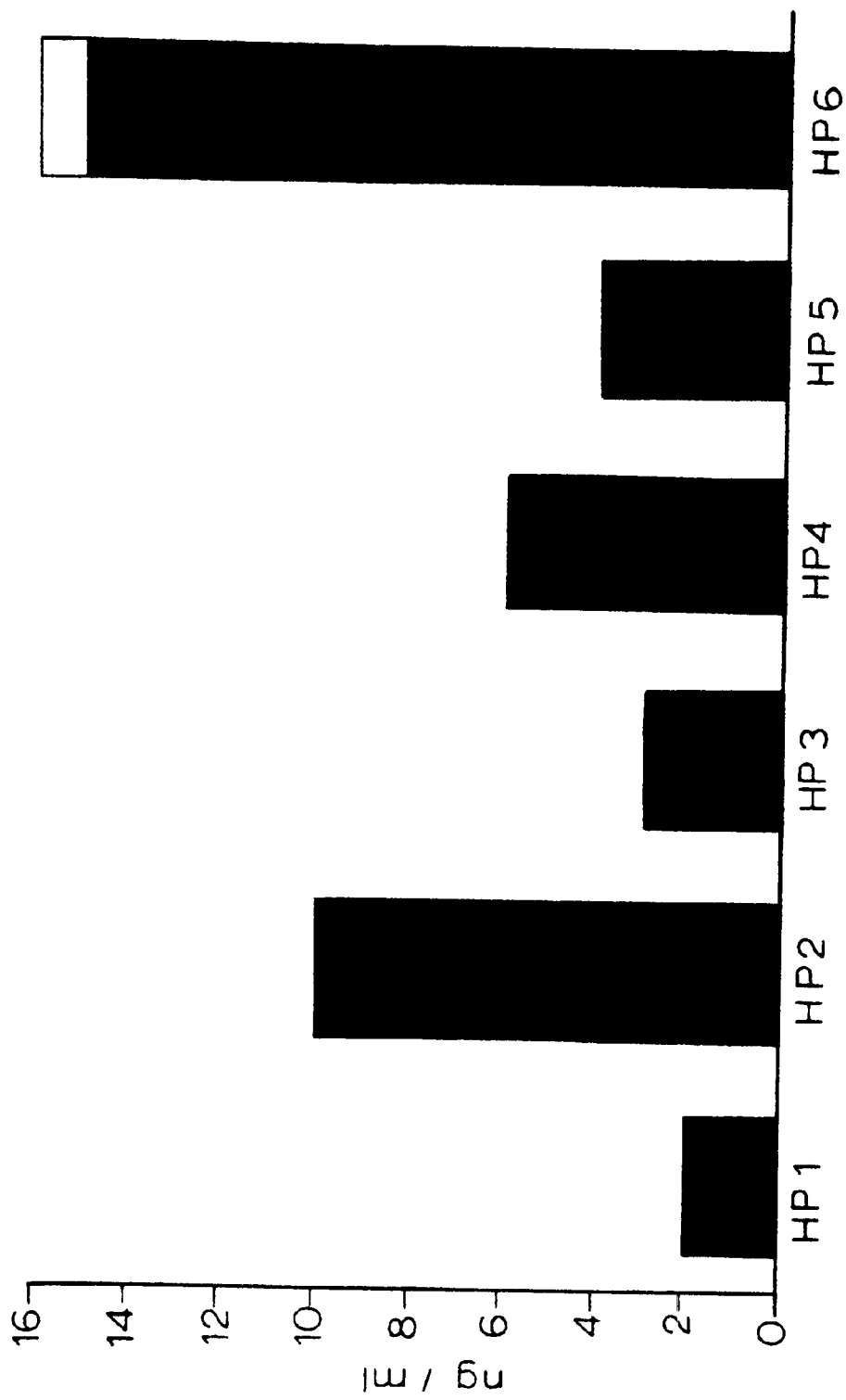
(FIG. 25C) Quantitation of the ob protein in human plasma. An ELISA immunoassay was performed using 100λ of plasma from the six lean volunteers and the standards used in FIG. 25B. Levels of the ob protein ranging from 2 ng/ml in HP1 to 15 ng/ml in HP6 were seen. These data correlated with the Western blot data in FIG. 25A.

Plasma samples from six lean human subjects with a Body Mass Index less than 25 (BMI=weight/length$^2$) were immunoprecipitated using immunopurified antibodies to the human protein. The immunoprecipitated material migrated with an electrophrotic mobility identical to that seen for the 146 amino acid human protein expressed in yeast. The intensity of the signals varied significantly among the six samples (FIG. 25A). Densitometry of the autoradiograph revealed an approximately five-fold difference in the levels in individuals HP1 and HP6 with intermediate levels in the other subjects. An enzyme linked immunoassay (ELISA) was developed using the immunopurified antibody and the refolded bacterial protein as a standard (see below). The resulting standard curve is shown in FIG. 25B. Using this assay, the plasma levels of the ob protein in the six human plasma samples varied between 2–15 ng/ml (FIG. 25C). The level of the ob protein in plasma from HP 6 was outside of the linear range of the immunoassay and is $\geq$ or 15 ng/ml. These quantitative differences correlated with those seen on Western blots.

Preliminary data suggest that leptin may circulate, at least in part, complexed to another protein or proteins. This conclusion was based on heterogeneity of the shape of the titration curve for serum compared with recombinant standard. Analysis of a large amount of leptin immunopurified on a rabbit anti-ob column by gel filtration HPLC under denaturing and non-denaturing conditions, with monitoring by ELISA and SDS-PAGE suggested that the ob polypeptide behaved like a high molecular weight complex. However, these data remain preliminary; the ob binding protein, if any, has yet to be characterized.

Figure 26A:
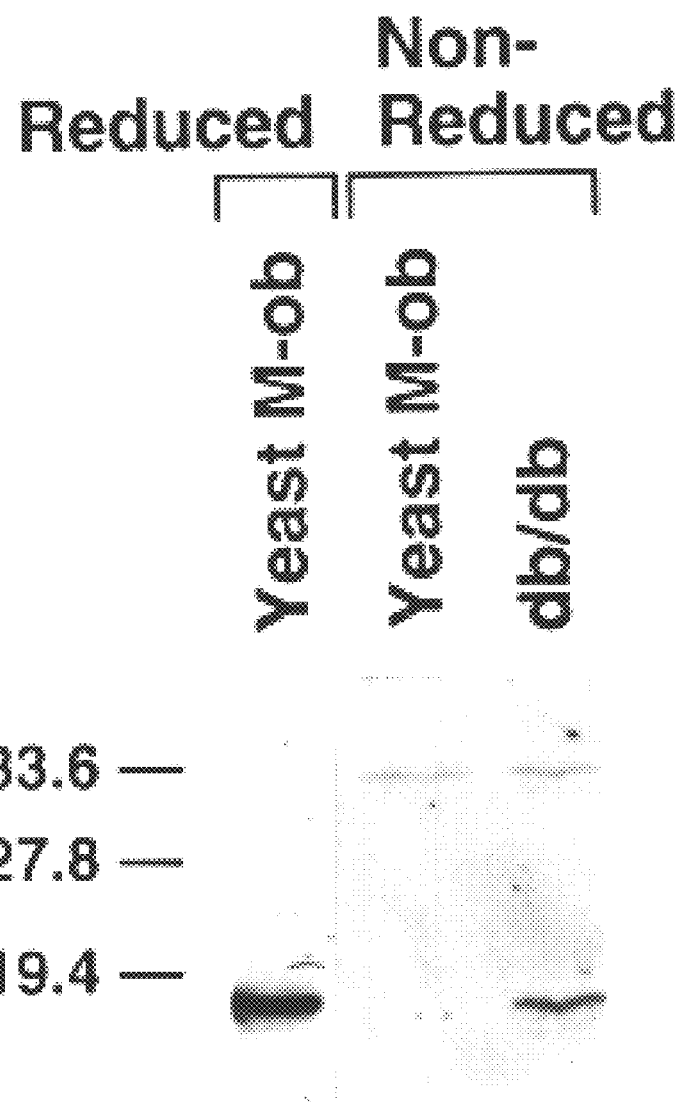
(FIG. 26A) Western blots under reducing and non-reducing conditions. The western blots of mouse and human plasma were repeated with and without the addition of reducing agents to the sample buffer. When β-mercaptoethanol is omitted from the sample buffer, immunoprecipitates from db plasma migrate with an apparent molecular mass of 16 kD and 32 kD. Addition of β-mercaptoethanol to the buffer leads to the disappearance of the 32 kD moiety (see FIG. 24). This result is recapitulated when the mouse protein is expressed in the yeast, *Pichia pastoris*. In this case, the mouse ob protein migrates to the position of a dimer. Under reducing conditions the purified recombinant mouse protein migrates with an apparent molecular weight of 16 kD, indicating that the 32 kD molecular form is the result of one or two intermolecular disuphide bonds. The human protein expressed in vivo and in *Pichia pastoris* migrates with a molecular mass of 16 kD under both reducing and non-reducing conditions (data not shown).
Figure 26:
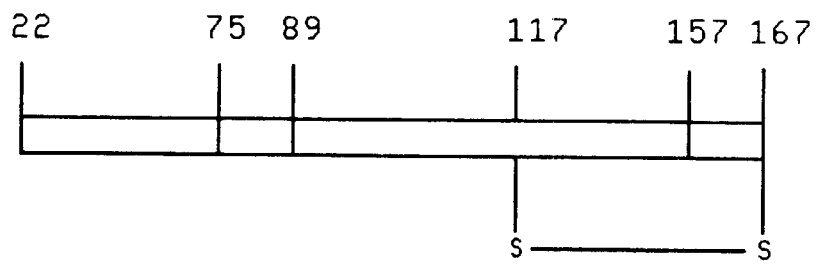
FIG. 26 shows that the ob protein forms inter- or intramolecular disulphide bonds.

Structural Features of the ob Protein. Since the ob protein has two cysteine residues, it could form either intra- or intermolecular disulphide bonds under oxidizing conditions in vivo. Western blots were repeated with and without the addition of reducing agents to the sample buffer. Under both conditions, the ob protein in human serum migrated as a monomer (data not shown). Under nonreducing conditions, protein immunoprecipitated from db mouse serum was detected at positions consistent with that of both a monomer of 16 kD and a dimer of approximately 32 kD (FIG. 26A). The higher molecular weight moiety disappeared under reducing conditions suggesting that a fraction of mouse ob circulates as a higher molecular weight species via formation of an intermolecular disulphide bond. Approximately 80% of mouse ob circulates as the approximately 16 kD protein and 20% as the approximately 32 kD form.

The same molecular forms are seen when the mouse and human proteins are expressed in *Pichia pastoris* (Abrams et al., 1992, Immunol. Rev.: 5–24). In these studies, the DNA sequence corresponding to the 146 amino acid mature ob protein was cloned downstream of the yeast alpha mating factor signal sequence in the pPIC.9 vector (Invitrogen). The ob protein was purified from the yeast media of strains expressing the mouse and human proteins and electrophoresed under reducing and nonreducing conditions (FIG. 26A). The mouse protein was expressed in yeast mainly as a dimer under nonreducing conditions, and only as a monomer in the presence of reducing agents. The recombinant human protein migrated to the position of a monomer under both conditions (data not shown).

The purified human protein expressed in Pichia had a molecular mass of 16,024±3 Da as determined by mass spectrometry (Beavis, 1990 #804). This value is in agreement with the mass calculated from the amino acid sequence of the protein containing a single intramolecular disulfide bridge (16,024 Da). Matrix-assisted laser desorption mass spectometric analysis of cyanogen bromide cleavage products of the protein indicates that cysteines 117 and 167 are linked through an intramolecular disulphide bond (FIG. 26B) Cyanogen bromide cleaves carboxyterminal to methionine residues.

Figure 27:
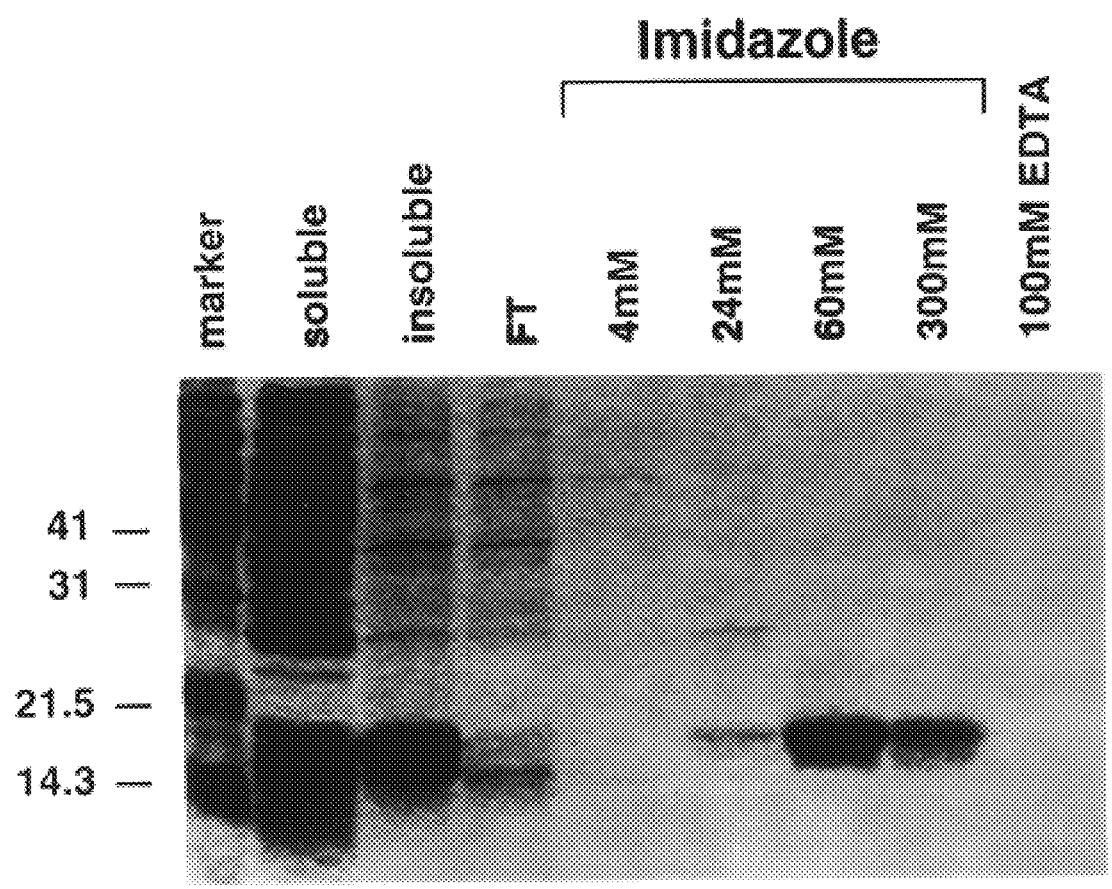
FIG. 27 depicts the preparation of the bioactive recombinant protein. The nucleotide sequence corresponding to the 145 amino acid mature mouse ob protein was cloned into the PET 15b expression vector. This PET vector inserts a polyhistidine tract (His-tag) upstream of the cloned sequence which allows efficient purification using Immobilized Metal Affinity Chromatography (IMAC). The recombinant bacterial protein initially partitioned in the insoluble membrane fraction after bacterial lysis. The membrane fraction was solubilized using guanidium hydrochloride and loaded onto an IMAC column. The protein was eluted stepwise with increasing concentrations of imidazole as shown. The eluted protein was refolded and treated with thrombin to remove the His-tag, as described below. The final yield of soluble protein was 45 ng/ml of bacterial culture.
Figure 28A:
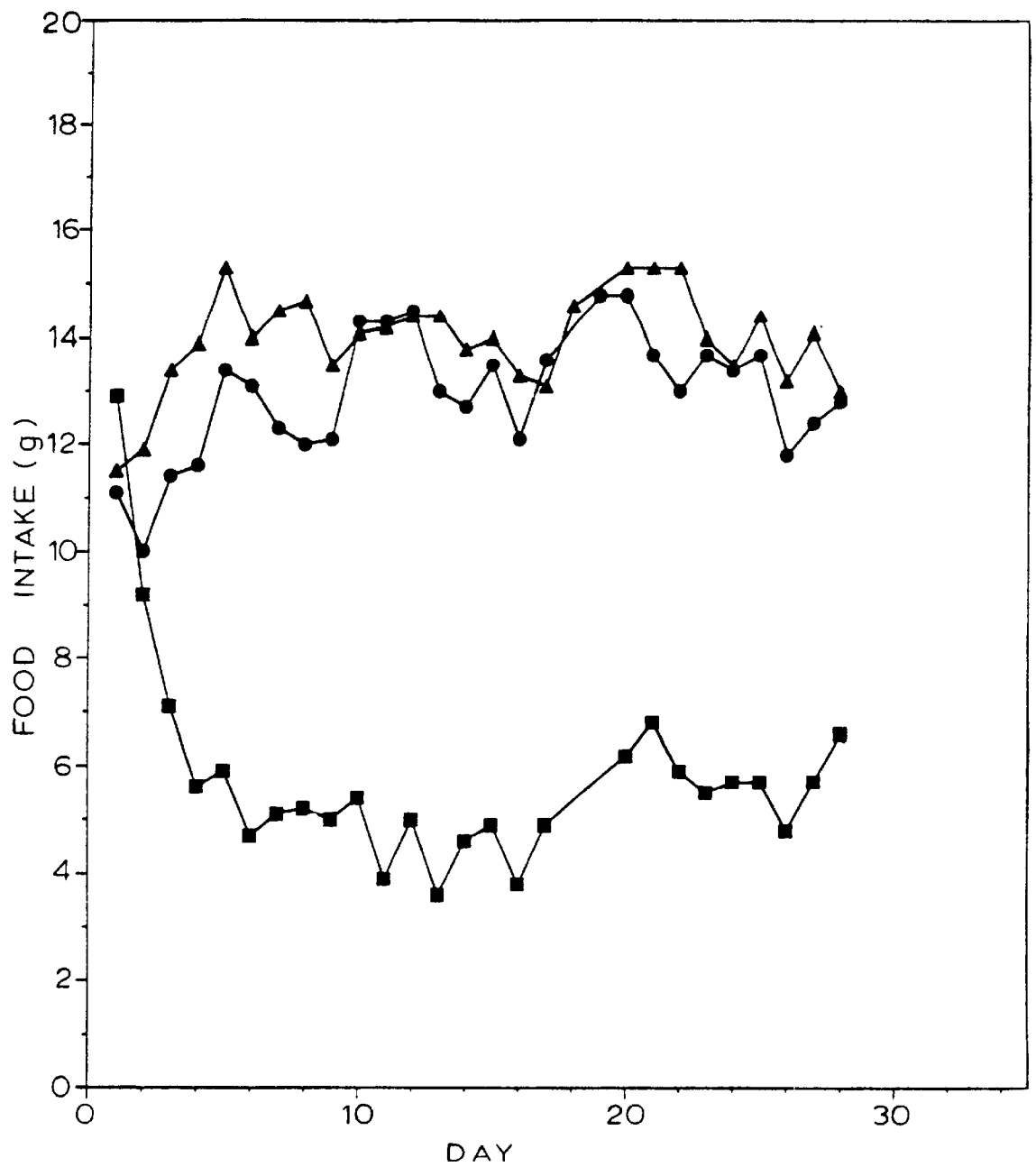
FIG. 28 shows the biologic effects of the ob protein. Time course of food intake (FIGS. 28A–28C) and body weight (FIGS. 28D–28F). Groups of ten animals received either daily intraperitoneal injections of the ob protein at a dose of 5 mg/kg/day (solid squares), daily injections of PBS (solid circles) or no treatment (solid triangles). The treatment groups included C57Bl/6J ob/ob mice (FIGS. 28A and 28D), C57Bl/Ks db/db mice (FIGS. 28B and 28E) and CBA/J+/+ mice (FIGS. 28C and 28F). The food intake of the mice was measured daily and the body weight was recorded at three to four day intervals as indicated. (The scale of the body weight in grams is different for the wild type mice vs. the ob and db mice.) The food intake of the ob mice receiving protein was reduced after the first injection and stabilized after the fourth day at a level approximately 40% of that seen in the sham injected group (p<0.001). The body weight of these animals decreased an average of 1.3 grams/day and stabilized after three weeks to a level approximately 60% of the starting weight (p<0.0001). No effect of the protein was demonstrable in db mice. Small but significant effects on body weight were observed in CBA/J mice at two early time points (p<0.02). The standard error of each measure is depicted by a bar and the statistical significance of these results is shown in Table 1.
Figure 28B:
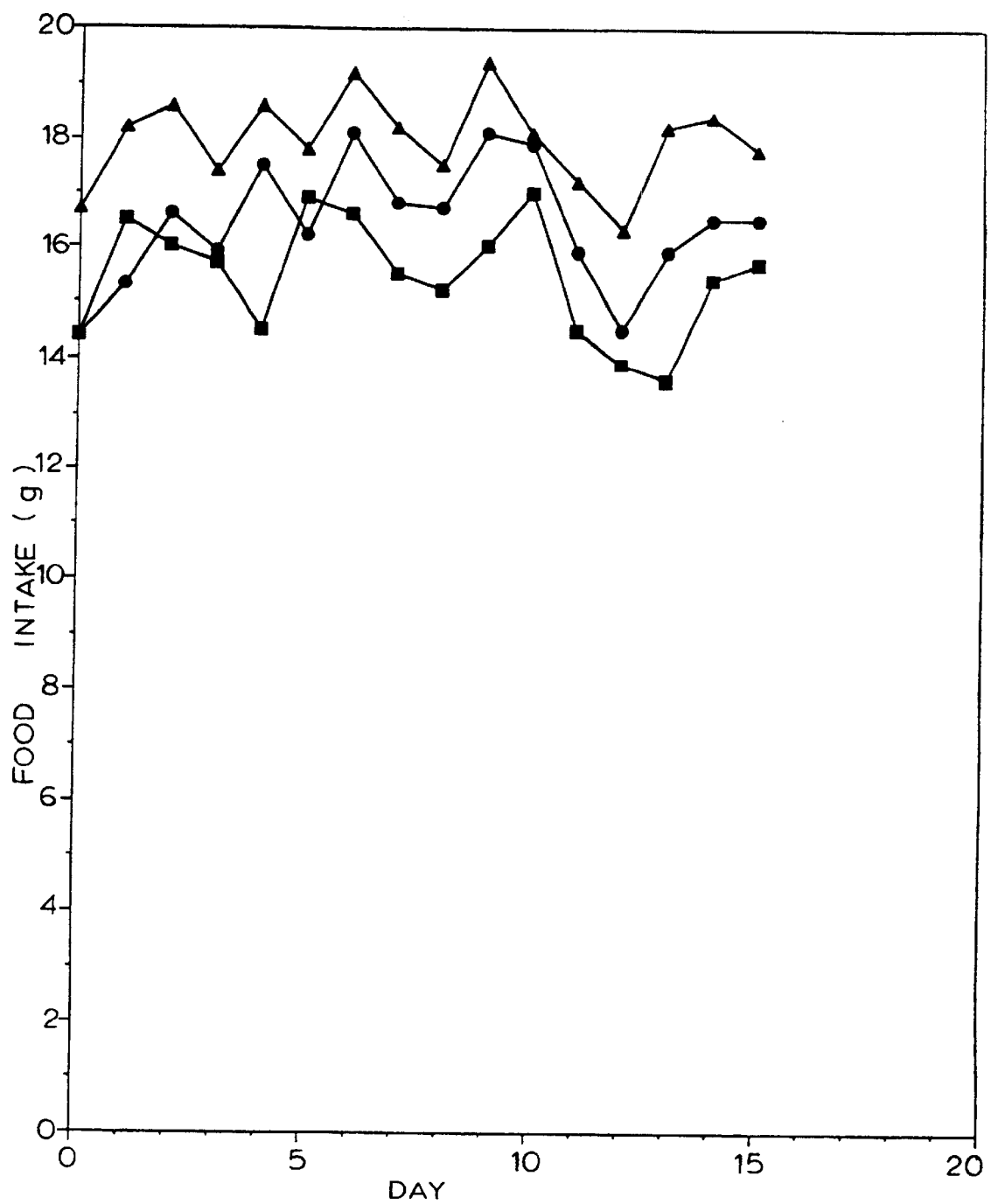
Figure 28C:
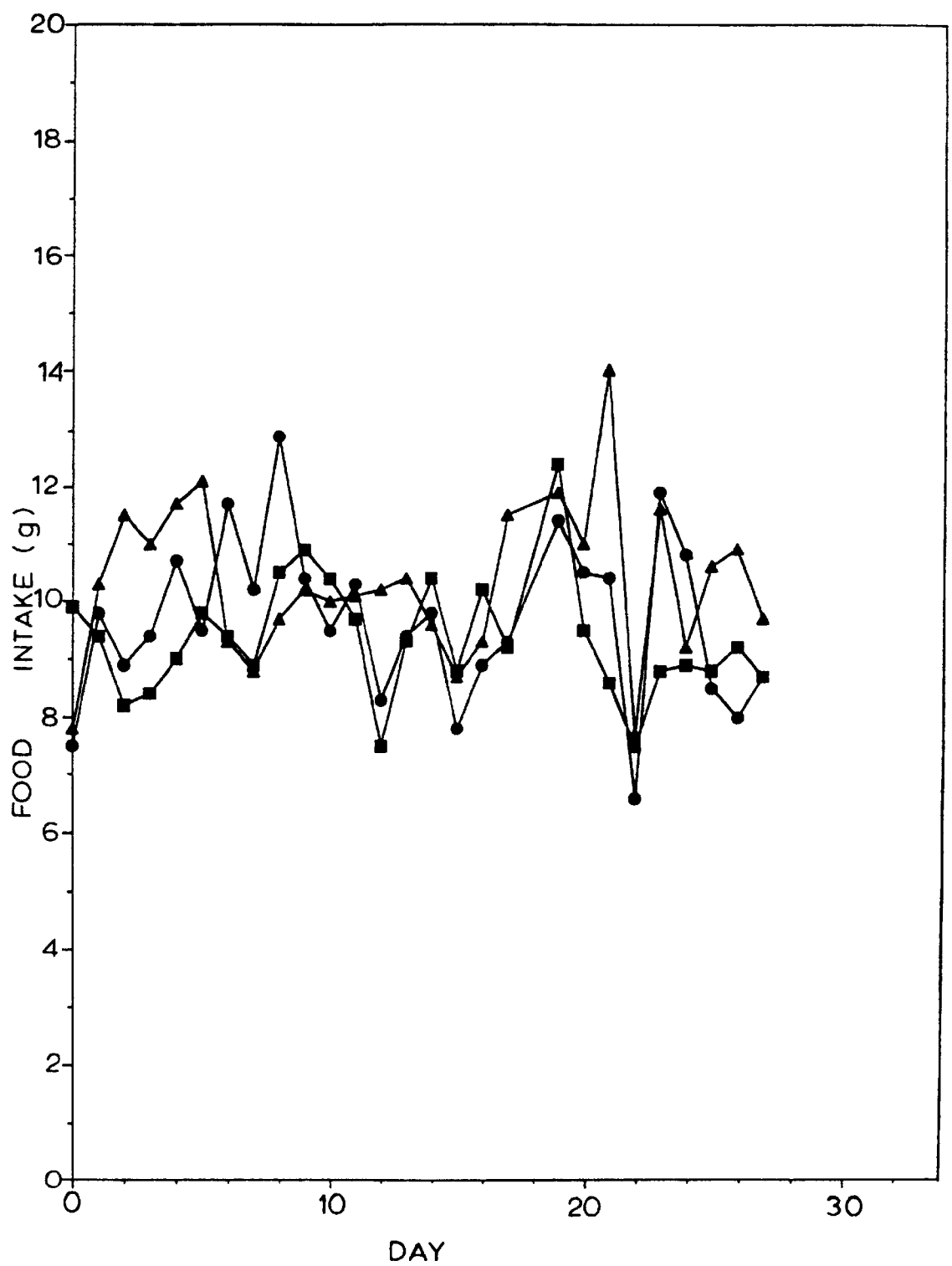
Figure 28D:
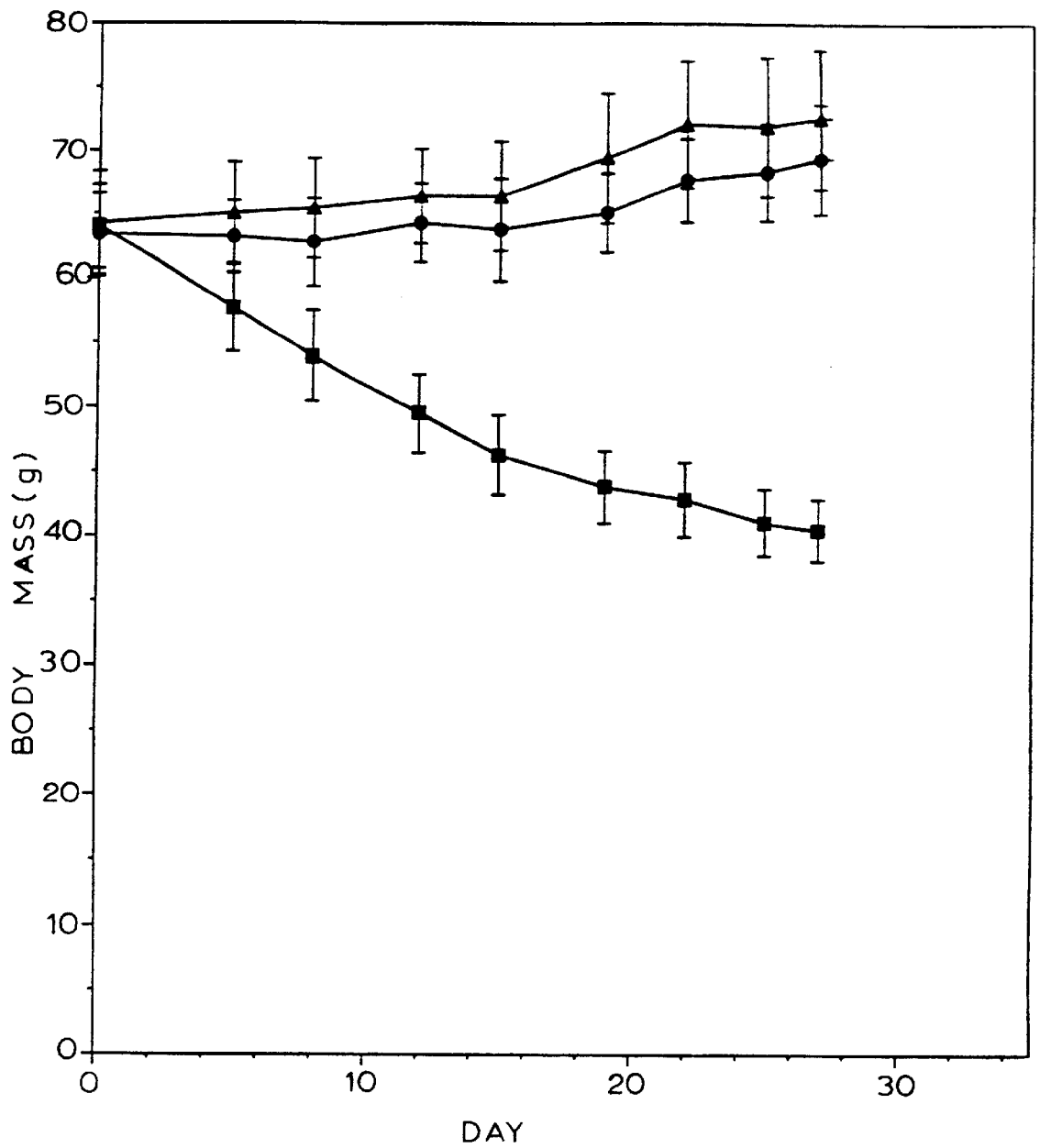
Figure 28E:
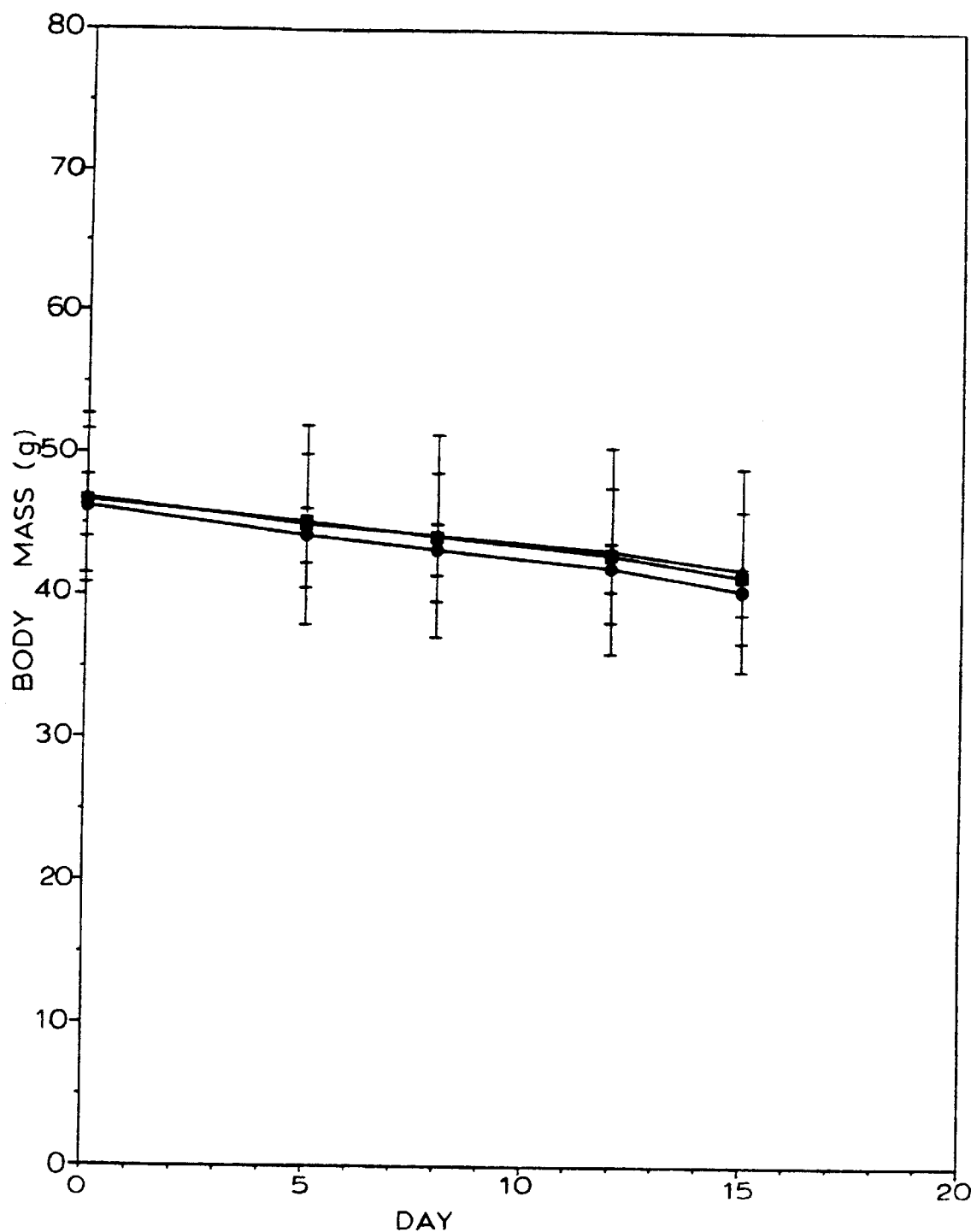
Figure 28F:
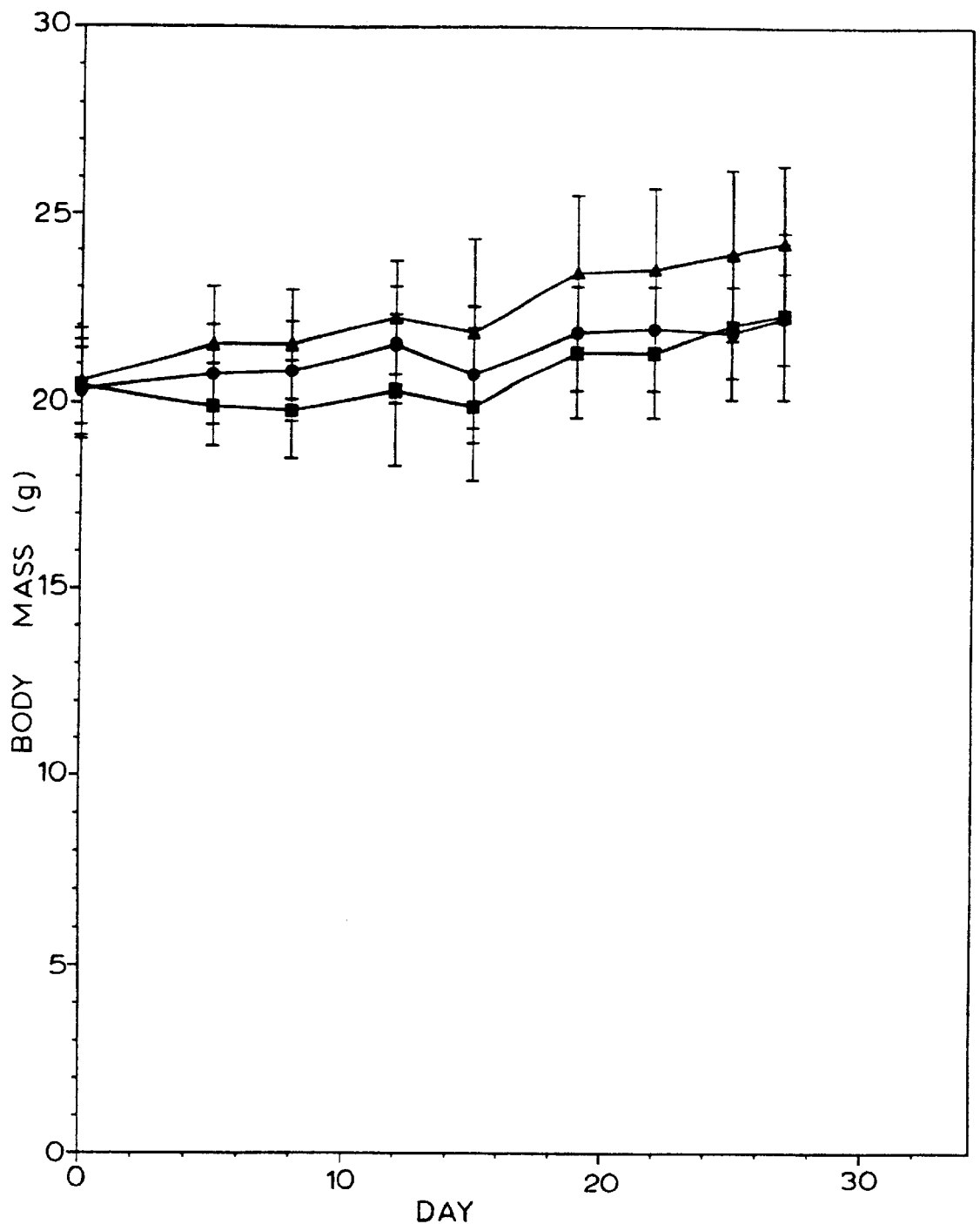

Preparation and Characterization of Bioactive Recombinant Protein. Mouse ob protein was expressed in *E. coli* from a PET 15b plasmid as an insoluble fusion protein, with a 20 residue, N-terminal hexa-histidine tag containing a thrombin cleavage site. Bacterial inclusion bodies were solubilized using guanidine-HCl and purified under denaturing conditions using immobilized metal ion affinity chromatography (IMAC) (FIG. 27). Purified, denatured fusion protein was reduced, diluted and permitted to refold in aqueous solution at room temperature. Following thrombin cleavage, renatured mouse ob protein containing four additional N-terminal residues (Gly-Ser-His-Met) was repurified by IMAC to >98% homogeneity, as judged by SDS-PAGE and mass spectrometry. Matrix-assisted laser desorption mass spectrometry gave a measured mass of 16,414±3 Da (predicted mass=16,415 Da). Both reducing and non-reducing SDS-PAGE gels demonstrated a single molecular species with apparent and molecular weight of 16 kD (data not shown).

Dynamic light scattering using a DP801 Molecular Size Detector (Protein Solutions, Inc.) demonstrated that the renatured mouse ob protein was largely monomeric, with some higher-order aggregates. The protein was treated with EDTA and chemically oxidized. Higher molecular weight species were then removed by gel filtration. Further dynamic light scattering confirmed that the purified, renatured recombinant mouse ob protein was monodispersed. Following dialysis against phosphate buffered saline (PBS), bacterial endotoxin was removed using an Acticlean ETOX column (Sterogene Bioseparations, Inc.). The final yield of protein was 45 mg/l.

Ellman's assay was performed on the purified, renatured recombinant mouse ob protein to assess its oxidation state (Ellman, 1959, Arch. Biochem. Biophy. 82:70–77). Both renatured protein and protein unfolded by 6M guanidine-HCl demonstrated <0.5% free suifhydryl content, demonstrating that the monomeric product contains an intramolecular disulphide bond. This was confirmed by mass spectrometry of the cyanogen bromide cleavage products of the refolded bacterial protein (data not shown).

Figure 29A:
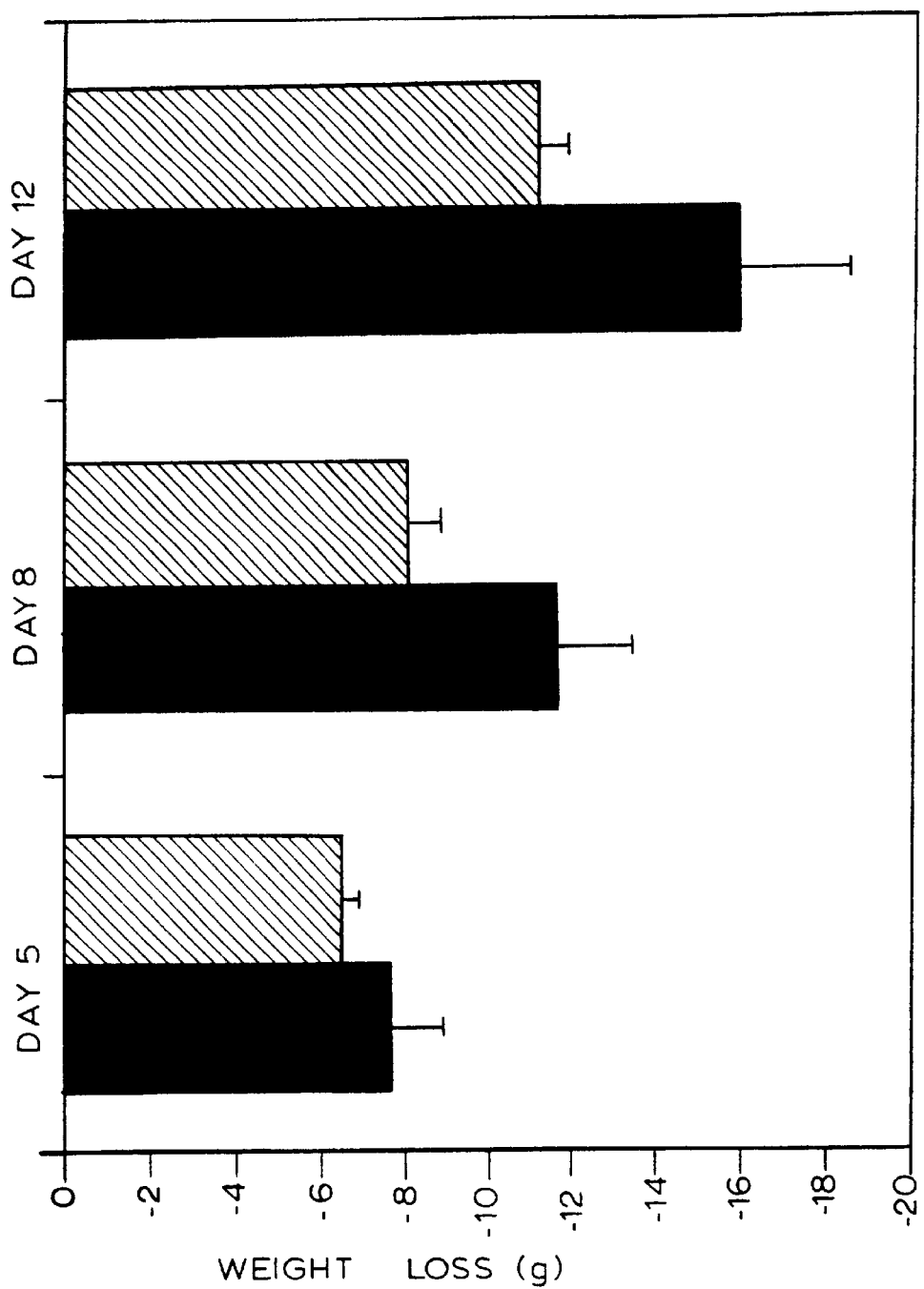
(FIG. 29A) A group of four C57Bl/6J ob/ob mice were fed an amount of food equal to that consumed by the group of ob mice receiving recombinant protein. The weight loss for both groups was calculated after five, eight, and twelve days. The food restricted mice lost (hatched bar) less weight than the ob mice receiving protein (solid bar) (p<0.02). This result indicates that the weight reducing effect of the ob protein is the result of effects on both food intake and energy expenditure.
Figure 29B:
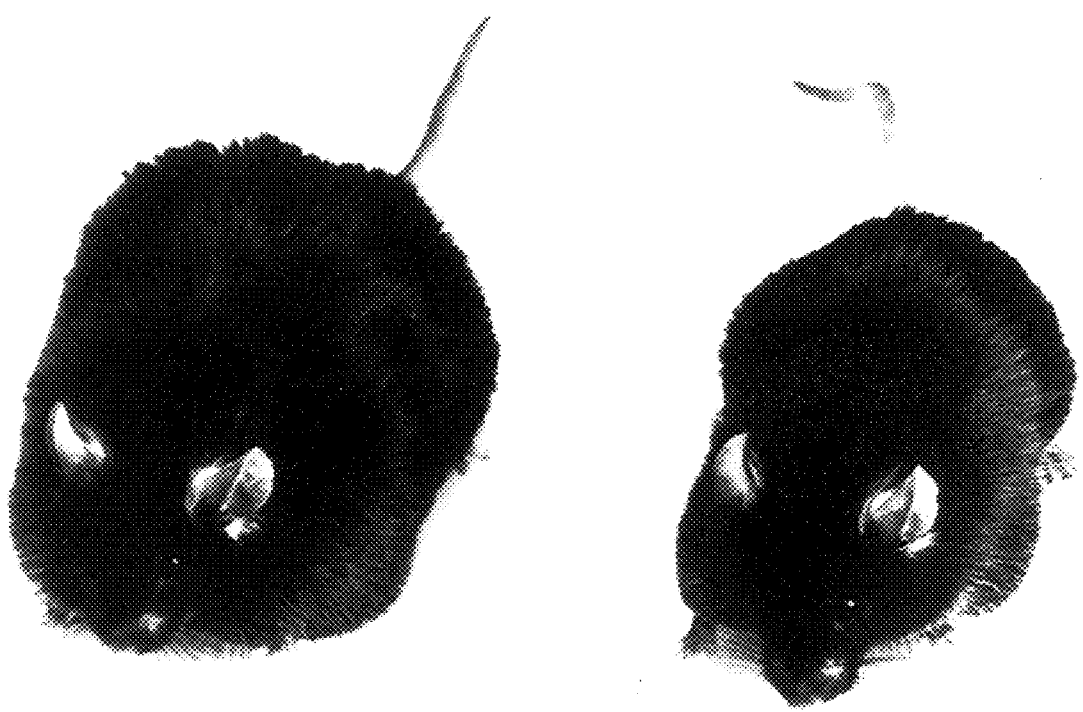
(FIG. 29B) Photograph of a treated ob mouse. Shown are two C57Bl/6J ob/ob mice. The mouse on the left received PBS and weighed 65 grams which was the starting weight. The mouse on the right received daily injections of the recombinant ob protein. The starting weight of this animal was also 65 grams, and the weight after three weeks of protein treatment was 38 grams.
Figure 29C:
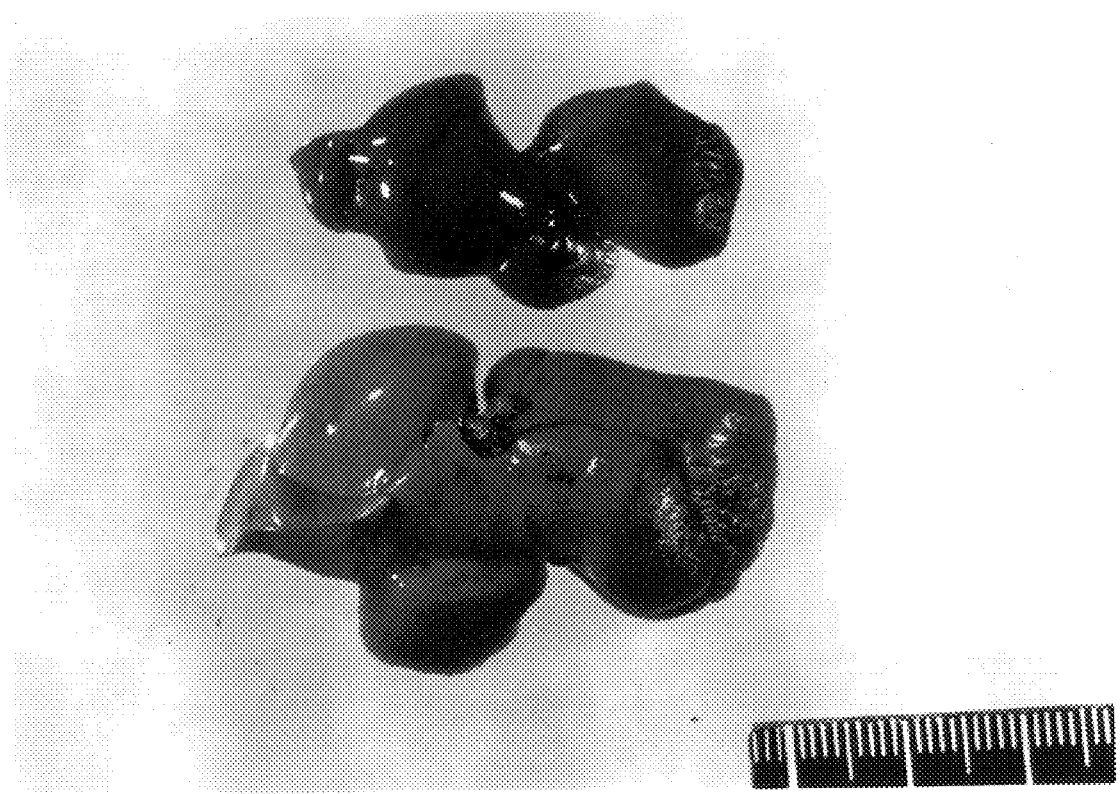
(FIG. 29C) Livers from treated and untreated ob mice. Shown are livers from treated and untreated C57Bl/6J ob/ob mice. The liver from the mouse receiving PBS had the gross appearance of a fatty liver and weighed 5.04 grams. The liver from the mouse receiving the recombinant ob protein had a normal appearance and weighed 2.23 grams.

Bioactivity of the ob Protein. The purified, renatured recombinant mouse ob protein was administered as a daily intraperitoneal injection of 5 mg/kg/day to groups of 10 C57Bl/6J ob/ob (age, 16 weeks), C57Bl/Ks db/db (age, 12 weeks) and CBA/J+/+ (age, 8 weeks) mice. An equal number of animals received PBS as a daily injection. The PBS used for the control injections was derived from the dialysate after equilibration of the protein. Ten additional animals from the three mouse strains did not receive injections. The food intake of individual animals was monitored daily and the weights of the animals were recorded at three or four day intervals. The cumulative results for food intake and body weight from each of the 9 groups of mice are shown in FIG. 28A–FIG. 28F, and the statistical significance of the data are shown in Table 1. The food intake of the C57Bl/6J ob/ob mice injected with protein was significantly decreased after the first injection and continued to decrease until the fifth day when it stabilized at a level equal to approximately 40% of the intake of the animals receiving injections of PBS (p<0.001). The sham injected ob mice did not lose weight over the three week study period. The C57Bl/6J ob/ob mice receiving protein lost approximately 10% of their body weight after 5 days (p<0.001). These animals continued to lose weight over the three week treatment at which point the weight of the ob animals receiving protein had decreased to an average of 60% of their initial body weight (p<0.0001). A separate group of ob mice were pair fed to the ob mice receiving protein. The data in FIG. 29B show that the pair fed mice lost significantly less weight than the animals receiving the recombinant protein (p<0.02). A photograph of two mice receiving injections of either protein or vehicle shows the gross difference in appearance resulting from the protein treatment (FIG. 29B). In order to further ascertain the effects of the protein, autopsies of two mice in each of the groups were performed. Gross inspection of the ob mice receiving protein revealed a dramatic decrease in body fat as well as the size of the liver. The liver weights of the db and wild type mice were unchanged with treatment. The livers from the ob mice receiving the injections of PBS weighed 5.04 and 5.02 grams vs. 2.23 and 2.03 grams in the animals receiving the recombinant protein. In contrast to the pale fatty liver characteristic of ob mice, the liver from the ob mice receiving protein acquired the darker color characteristic of normal liver (FIG. 29C). Histologic sections of the liver indicated that the untreated animals had a fatty liver that was markedly improved by protein treatment (data not shown).

In contrast to the ob mice, there were no significant differences in body weight or food intake in the C57BL/Ks db/db mice receiving protein relative to the control group receiving vehicle (FIG. 28A–FIG. 28F, Table 1). All three groups of db/db mice lost between 2–5 grams during the treatment period. The average blood glucose of the db mice was measured using a glucometer, and was ≧500 mg/dl in all of the mice indicating that these animals had developed diabetes secondary to obesity. The injections of db mice were terminated after two weeks.

In wild type mice there was a small but significant decrease in body weight following administration of the recombinant ob protein (FIG. 28A–FIG. 28F, Table 1). After five days of protein injection, the treated mice lost an average of 0.5 grams while control mice gained 0.4 grams (p<0.02). At two subsequent time points the animals receiving protein weighed significantly less than the mice receiving daily injections of PBS. The significance of the weight change was reduced at the later time points. In the animals that lost weight, the food intake was not significantly different from control animals. The injections of PBS had a small but significant effect on food intake and body weight in ob, db and wild type mice as compared to mice not receiving injections (p<0.05).

TABLE 1

| Animal Group | Treatment Group | Days | n | Mean | Std. Error | p |
|---|---|---|---|---|---|---|
| ob/ob | protein | 1–5 | 10 | −6.38600000 | 0.47628190 | <0.001 |
| | vehicle | | 9 | −0.14444444 | 0.24444444 | |
| | protein | 1–12 | 10 | −14.45000000 | 0.70793126 | <0.001 |
| | vehicle | | 9 | 0.98888889 | 0.38058597 | |
| | protein | 1–27 | 6 | −24.28333333 | 0.69924563 | <0.0001 |
| | vehicle | | 5 | 4.30000000 | 0.79874902 | |
| db/db | protein | 1–5 | 10 | −1.47000000 | 0.36939891 | 0.240 |
| | vehicle | | 10 | −2.00000000 | 0.23142073 | |
| | protein | 1–12 | 10 | −3.75000000 | 0.77348418 | 0.610 |
| | vehicle | | 10 | −4.19000000 | 0.34655447 | |
| CBA/J | protein | 1–5 | 10 | −0.48000000 | 0.17876117 | 0.006 |
| | vehicle | | 10 | 0.38000000 | 0.21489015 | |
| | protein | 1–12 | 10 | −0.12000000 | 0.45748103 | 0.015 |
| | vehicle | | 10 | 1.20000000 | 0.18378732 | |
| | protein | 1–27 | 5 | 1.98000000 | 0.48723711 | <0.651 |
| | vehicle | | 6 | 2.23333333 | 0.20763215 | |

Discussion

An endocrine function for the protein product of the ob locus was first suggested by Coleman, who showed that the body weight of ob/ob mice was reduced after parabiotic union to normal or db mice (Coleman, 1978, Diabetologia 14:141–148). The results indicated above support this hypothesis by showing that ob protein circulates in the bloodstream and that injections of recombinant protein reduce body weight. The molecular weight of the gene product encoded by the ob gene is approximately 16 kD, which is equal to the 146 amino acid sequence carboxy terminal to the signal sequence. The recombinant ob protein is not modified when expressed in *Pichia pastoris*. Expression of mammalian genes in Pichia generally results in the formation of the correct protein structure (Cregg et al., 1993, Bio/Technology 11:905–914). These findings suggest that the ob protein is not glycosylated and is not post-translationally processed in vivo. The data do not exclude the possibility that the ob protein is noncovalently bound to itself or other proteins in plasma or adipose tissue. Although proteolytic cleavage of the protein has not been excluded, lower molecular weight forms of the ob protein were not detected by any of the antisera used, including four anti-peptide antibodies.

The ob protein has two cysteine residues and circulates as a monomer in human, and as a monomer and dimer in mouse. An intramolecular disulphide bond typical of secreted molecules is found when the human protein is expressed in *Pichia pastoris* suggesting that it is likely to be present in vivo. This is supported by the bioactivity of the recombinant bacterial protein, which has an intramolecular disulphide bond. The mouse ob protein can be found in plasma as a monomer and as a dimer. The monomer and dimer are seen when the mouse ob protein is expressed in yeast shows that the propensity of the m6use protein to form a dimer is a result of differences in the primary sequence relative to human. While it is clear that the monomer has bioactivity, the functional activity of the dimer is unknown.

The effect of the ob protein on food intake and body weight in ob mice is dramatic. After three weeks treatment, the ob mice receiving daily injections of recombinant protein had lost 40% of their weight and were consuming 40% as much food as control animals. Moreover, the weight of the treated ob mice had not yet equilibrated at the time the experiment was terminated. The results of the pair feeding experiment indicate weight loss is a result of effects on both food intake and energy expenditure. Thus, a separate group of ob mice whose caloric intake was restricted to that of ob mice receiving protein lost significantly less weight than the animals receiving protein. The reduction in food intake in ob/ob mice to a level lower than that of wild type mice, within a day of receiving the ob protein, indicates that they are especially sensitive to its effects. Indeed, the ob receptor may be upregulated in these animals. Food intake of treated ob mice became relatively constant after five days of treatment. If this is the result of the protein having reached steady state levels, it would suggest that the protein has a relatively long half life (Goodman, 1990, *The Pharmacological Basis of Therapeutics*, A. Gilman, ed., Pergamon Press: New York, pp. 19–45). This conclusion is consistent with data from parabiosis experiments (Coleman, 1978, Diabetologia 14:141–148; Weigle, 1988, Int. J. Obesity 12:567–578).

Effects of recombinant protein on the body weight of wild type mice were small but statistically significant during the first two weeks of the study. While the difference in weight between wild type mice receiving protein vs. PBS was sustained at later time points, the statistical significance of the data had greatly diminished after three weeks. The early weight loss could not be accounted for by a difference in food intake. Presumably, the measurement of food intake was not precise enough to detect a decrease resulting in a one gram difference in body weight during treatment. These observations differ from the results of previous experiments in which wild type rodents have been joined by parabiotic union to db mice, fa rats, rats with hypothalamic lesions and rats rendered obese by a high calorie diet (Coleman, 1978, Diabetologia 14:141–148; Harris et al., 1987, Int. J. Obes. 11:275–283; Harris and Martin, 1989, "Physiological and metabolic changes in parabiotic partners of obese rats", *Hormones, Thermogenesis and Obesity*, H. Lardy and F. Straatman, eds., Elsevier Science Publishing Co.: New York; Hervey, 1959, J. Physiol. 145:336–352). In each case, the wild type animals become anorectic and lose copious amounts of weight. As the levels of ob protein are increased in db mice and fa rats and the level of ob RNA is increased in mice with hypothalamic lesions, it is likely that wild type mice can respond to ob when it circulates in plasma at a sufficiently high level. The findings reported here are consistent with the possibility that the levels of the administered protein were below endogenous levels, leading to equilibration at a slightly lower body weight. Quantitation of the circulating levels of the ob protein in the treated mice will resolve this issue. While an immunoassay of the mouse protein is not yet available, immunoprecipitations have suggested that the levels of the circulating ob protein were not substantially elevated in the wild type mice receiving protein.

The lesser effect of the protein on wild type mice and the absence of a response in db mice makes it unlikely that the treatment has nonspecific or aversive effects. All of the db mice lost a small amount of weight during the treatment period, whether or not they were receiving the ob protein. The db animals were markedly hyperglycemic and the weight loss is likely to be the result of diabetes and not the experimental protocol. C57BL/Ks db/db mice often develop diabetes and begin to lose small amounts of weight when of the age of the animals used in this study (Coleman, 1978, Diabetologia 14:141–148). C57Bl/6J ob/ob mice of a similar age do not develop significant hyperglycemia. These phenotypic differences are thought to be the result of genetic differences in the strains (C57Bl6J vs. C57Bl/Ks) carrying the mutations (Coleman, 1978, Diabetologia 14:141–148).

The failure to detect the truncated 105 amino acid protein predicted by the cDNA sequence of the ob gene in C57Bl/6J ob/ob mice suggests that the mutant protein is either degraded or not translated. However, the possibility that the antisera used do not detect this truncated protein cannot be excluded. The observed ten-fold increase in the levels of the ob protein in db mice compared to wild type suggests that the ob protein is overproduced when there is resistance to its effects. These data correlate with studies of the ob mRNA. As mentioned, previous experiments have shown that mutations of the mouse dband the rat fa genes, which map to homologous chromosomal regions, result in overproduction of a plasma factor that suppresses body weight (Truett et al., 1991, Proc. Natl. Acad. Sci. USA. 88:7806–7809; Coleman, 1978, Diabetologia 14:141–148; Hervey, 1959, J. Physiol. 145:336–352). In both cases, it has been suggested that the mutant animals are resistant to the effects of the ob protein. This possibility is confirmed by the observation that the ob protein has no effect on body weight or food intake when administered to db mice.

Obesity in humans could be associated with increased levels of the ob protein in plasma in individuals who are relatively unresponsive to the hormone. On the other hand, reduced expression of ob could also lead to obesity in which case "normal" (i.e; inappropriately low) levels of the protein might be found. Thus, the levels of ob protein in human plasma could be a marker for different forms of obesity. In a small group of lean subjects with BMI <25, low nanogram levels of circulating ob protein are detectable by ELISA. Significantly, variable concentrations were noted suggesting that the level of expression and/or sensitivity to the protein may play a role in determining body weight.

The site of action of the ob protein is unknown. The protein affects both food intake and energy expenditure, a finding consistent with clinical studies indicating that alterations of both systems act to regulate body weight (Leibel et al., 1995, N. Engl. J. Med. 332:621–628; Keesey and Corbett, 1984, "Metabolic defense of the body weight set-point", *Association for Research in Nervous and Mental Disease*, Stunkard and Stellar, eds., Raven Press: New York. p. 87–96). The hypothalamus is likely to be downstream of ob in the pathway that controls body weight, although direct effects on a variety of organs are possible.

EXAMPLE 9

Increased Expression in Adipocytes of ob RNA in Mice with Lesions of the Hypothalamus and with Mutations at the db Locus The gene product of the recently cloned mouse obese gene (ob) plays an important role in regulating the adipose tissue mass. ob RNA is expressed specifically by mouse adipocytes in vivo in each of several different fat cell depots including brown fat. It is also expressed in cultured 3T3-442A preadipocyte cells that have been induced to differentiate. Mice with lesions of the hypothalamus, as well as mice mutant at the db locus, express a twenty-fold higher level of ob RNA in adipose tissue. These data suggest that both the db gene and the hypothalamus are downstream of the ob gene in the pathway that regulates the adipose tissue mass and are consistent with previous experiments suggesting that the db locus encodes the ob receptor. In the db/db and lesioned mice, quantitative differences in the level of expression of ob RNA correlated with the lipid content of adipocytes. The molecules that regulate the level of expression of the ob gene in adipocytes are likely to play an important role in determining body weight as are the molecules that mediate the effects of ob at its site of action.

Materials and Methods

In Situ Hybridization. White fat tissues from identical abdominal regions of wild type (wt) and db mice were processed simultaneously according to the modified ethod described by Richardson et al. (1992, Growth, Development & Aging 56:149–157). Briefly, tissues were fixed in Bouin's solution for 2 hours at 4° C. They were then dehydrated by serial treatment of increasing concentrations of ethanol from 10% to 100%, each for 5 min. at 4° C. Further incubation of tissues with xylene (1 h) and paraffin (2 h) were performed at 65° C. Embedded wt and db/db fat tissues were sectioned and mounted on to the same conditions later. Sections were baked at 65° C. for 1 h and treated with xylene and serial dilutions of ethanol from 100% to 50%, each for 3 min. at room temperature. Antisense RNA probe of ob gene was synthesized by in vitro transcription of linearized ob gene coding sequence upstream of a Sp6 RNA polymerase promoter. In situ hybridization was carried out exactly according to Schaeren-Wiemers and Gerfin-Moser (Schaeren-Wiemers and Gerfin-Moser, 1993, Histochemistry 100:431–440).

RNA Preparation and Cell Culture. Total RNA and Northern blots were prepared as described. Stromal vascular cells and adipocytes were prepared according to Rodbell and RNA from both fractions was prepared according to Dani et al. (Dani et al., 1989, Mol. Cell. Endocrinol. 63:199–208; Rodbell, J. Biol. Chem. 239:375–380) After sub-cloning, 3T3-F442 cells were grown in Dulbecco's modified Eagle medium containing 10% foetal bovine serum (defined as standard medium) (Dani et al., 1989, "Molecular biology techniques in the study of adipocyte differentiation", *Obesity in Europe* vol. 88, Bjorntorp and Rossner, Eds., John Libbey Company Ltd.: London, England. p. 371–376). At confluence, cells were treated in standard medium supplemented with 2 nM triiodothyronine (T3) and 17 nM insulin. Twelve days later, RNA was prepared as above.

Gold ThioGlucose Treatment. Two month old female CBA/J mice were treated with a single intraperitoneal injection of aurothioglucose (Sigma A0632) at a dose of 0.2 mg/g in normal saline. Control animals were injected with normal saline. Mice were weighed one month after the treatment. Adipose tissue RNA was isolated from those treated animals whose weight had increased more that twenty grams post GTG treatment.

Results

Figure 30:
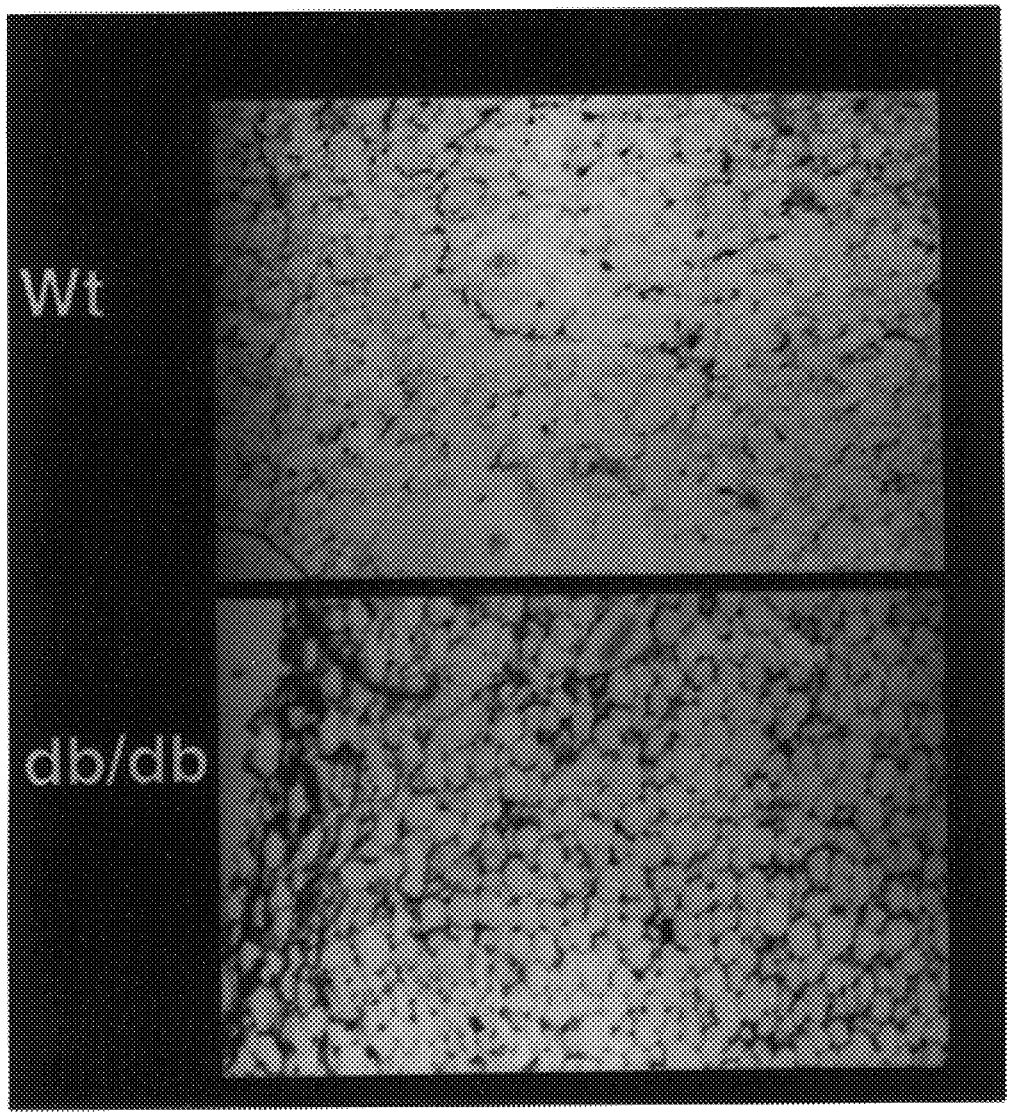
FIG. 30 shows the in situ hybridization of ob to adipose tissue. Sense and Antisense ob RNA was labeled in vitro using Sp6 and t7 polymerase and digoxigenin. The labeled RNAs were hybridized to paraffin embedded sections of adipose tissue from epididymal fat pads of eight week old C57Bl/Ks mice (labelled wild type) and C57Bl/Ks db/db mice (labelled db). In the figure, the lipid droplets appear as unstained vacuoles within cells. The cytoplasm is a thin rim at the periphery of the cells and is indistinguishable from the cell membrane X 65. Hybridization to all the adipocytes in the field was detected in the wild type sections only using the antisense probe and greatly increased levels were seen in the tissue sections from the db/db animals.
Figure 31:
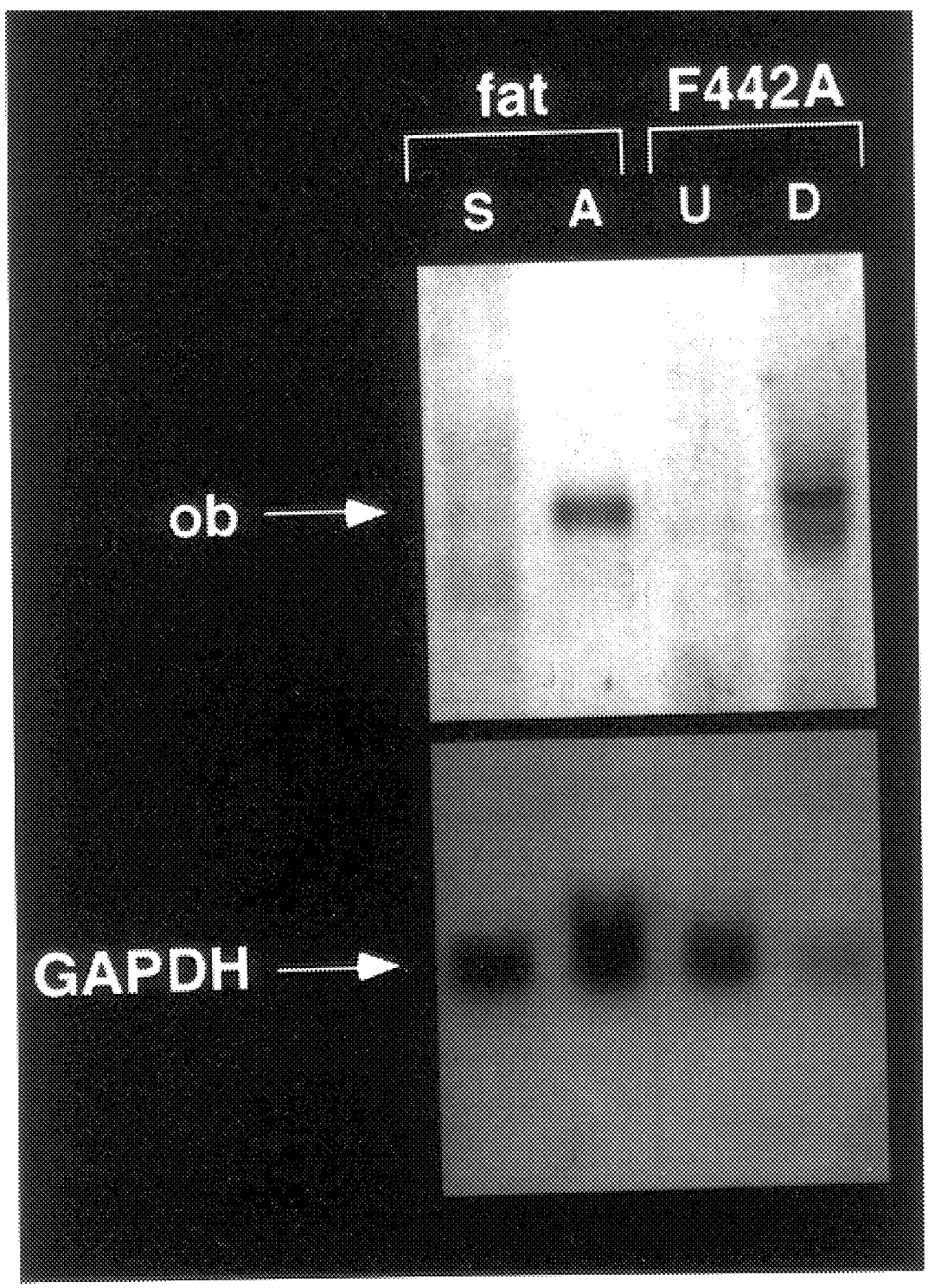
FIG. 31 shows that ob RNA is expressed in adipocytes in vivo and in vitro. Total RNA (10 micrograms) from several different sources was electophoresed on Northern blots and hybridized to an ob probe. Firstly, differences in cell buoyancy after collagenase digestion was used to purify adipocytes. ob RNA was present only in the adipocyte fraction. Lane S indicates the stromovascular fraction and A indicates the adipocyte fraction. In addition, ob RNA was not expressed in the undifferentiated 3T3-442 preadipocyte cells lane U. Differentiated adipocytes from these cell lines expressed clearly detectable levels of ob mRNA (lane D).

The ob gene was recently found to be expressed in adipose tissue (Zhang et al., 1994, Nature 372:425–432). As adipose tissue is composed of many cell types including adipocytes, preadipocytes, fibroblasts and vascular cells, in situ hybridization was performed to sections of epididymal fat pads from normal animals with sense and antisense ob riboprobes (Richardson et al., 1992, Growth, Development & Aging 56:149–157; Wasserman, 1964, "The concept of the fat organ: in Rodahl, Issekutz, fat as a tissue", *Rodahl, Issekutz, Fat as a tissue*, McGraw Hill: New York, p. 22–92). When using the antisense probe, positive signals were detectable in all of the adipocytes in the section (FIG. 30—labeled Wt). Signals were not noted when the antisense probe was hybridized to sections of brain (data not shown). Hybridization of the antisense probe to sections of adipose tissue from C57Bl/Ks db/db mice was greatly increased, confirming the adipocyte specific expression of ob RNA and demonstrating a large increase in the level of ob RNA per adipocyte in these animals (FIG. 30—labeled db/db). Mice mutant at the db locus are massively obese as part of a syndrome that is phenotypically identical to that seen in C57Bl/6J ob/ob mice (Bahary et al., 1990, Proc. Nat. Acad. Sci. USA 87:8642–8646).

ob RNA was not synthesized by adipose tissue stromal cells separated from adipocytes. As expected, cells in the adipocyte fraction expressed ob RNA using Northrn blots (FIG. 31). The same result was obtained using RT-PCR (data not shown). These data support the conclusion that only adipocytes express the ob gene. Data from cultured adipocytes confirm this conclusion. In these studies, 3T3-F442A cells were cultured using conditions that lead to lipid accumulation, as part of a cellular program leading to differentiation into adipocytes. ob RNA was not expressed in exponentially growing cells as well as in confluent 3T3-F442A preadipocyte cells which express early markers while differentiation of these cells into adipocytes led to the expression of detectable levels of ob RNA (FIG. 31) (Dani et al., J. Biol. Chem. 264:10119–10125). The level of ob RNA is extremely sensitive to the culture conditions as no message was observed in late post-confluent cells not exposed to insulin.

Figure 32A:
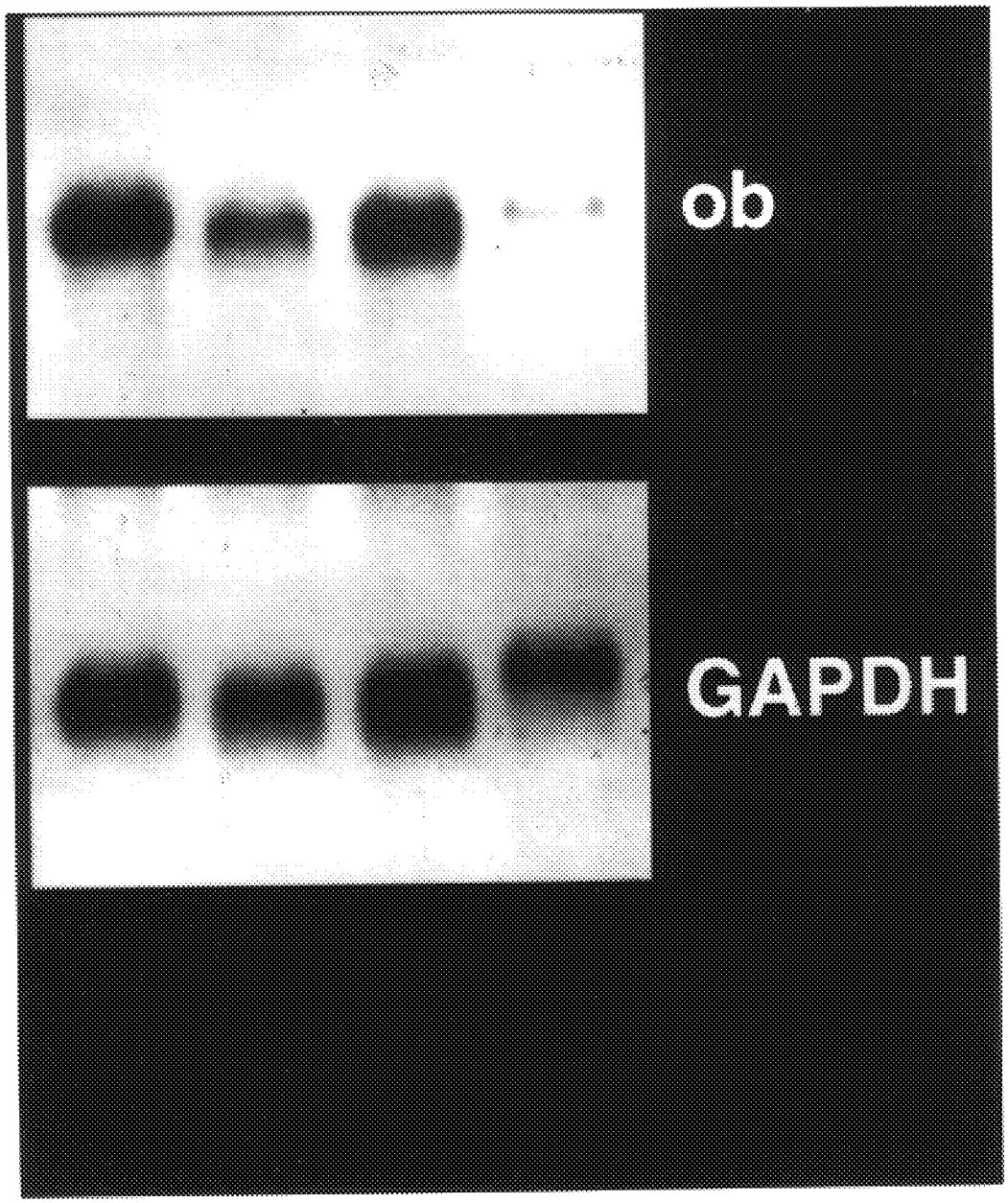
(FIG. 32A) Lanes (1) epididymal (2) inguinal (3) abdominal (4) parametrial fat pads. Brown fat also expressed a low level of ob RNA.
Figure 32B:
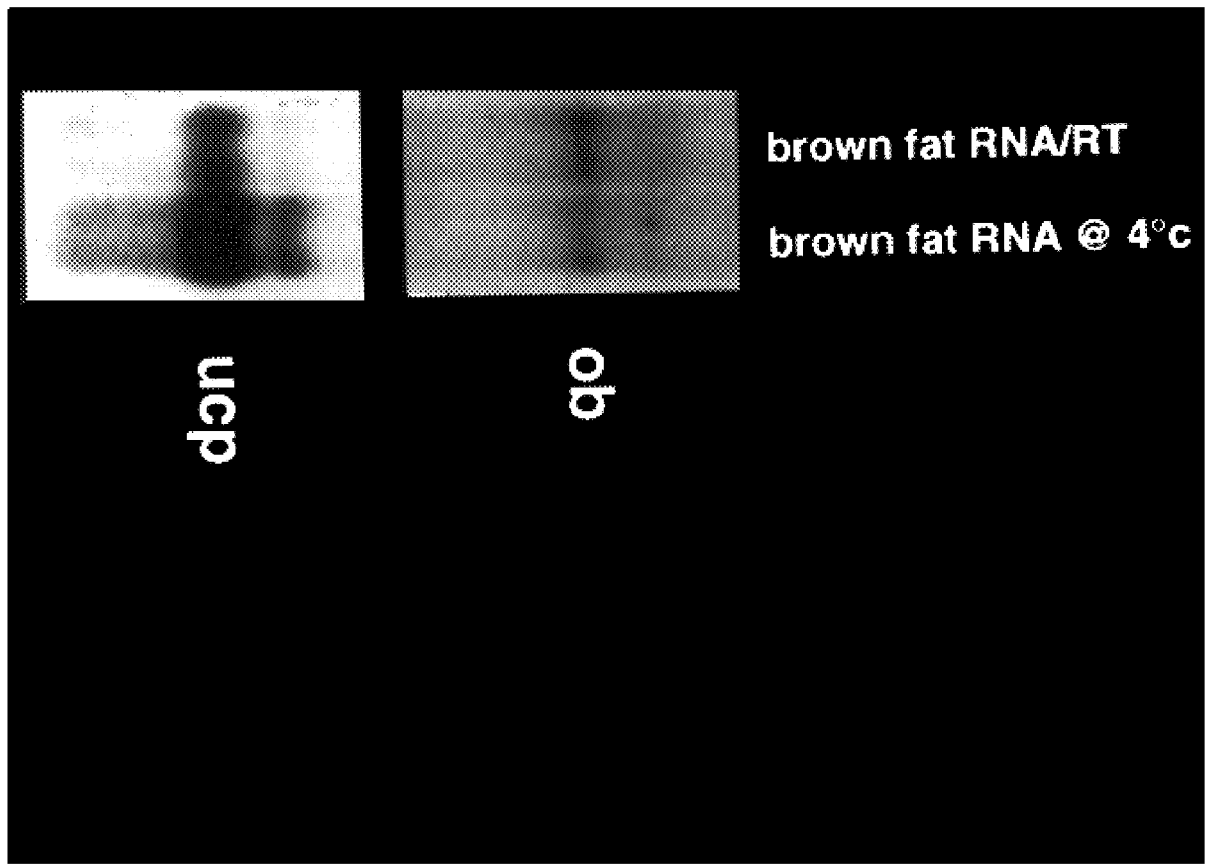
(FIG. 32B) The level of ob expression in brown fat was unchanged in animals housed at 4° C. for one week while the abundance of the brown fat specific UCP RNA, known to be cold inducible, increased five-fold.

Hybridization studies showed that ob RNA is expressed in vivo in several different fat depots including the epididymal, parametrial, abdominal, perirenal, and inguinal fat pads (FIG. 32A). The precise level of expression in each of the depots was somewhat variable, with inguinal and parametrial fat expressing lower levels of ob RNA. ob RNA is also expressed in brown adipose tissue although the level of expression is approximately 50 fold lower in brown fat relative to the other adipose tissue depots. These quantitative differences correlated loosely with previously reported differences in cell size among the different fat cell depots (Johnson and Hirsch, 1972, J. Lipid Res. 13: 2–11). The amount of ob RNA in brown fat is unaffected by cold exposure (FIG. 32B). In this experiment, the level of uncoupling protein RNA (UCP) increased in brown fat after cold exposure while the level of ob RNA did not change (Jacobsson et al., 1985, J. Biol. Chem. 260:16250–16254). In aggregate, these data confirm that all adipocytes are capable of producing ob RNA and demonstrate a variable level of expression in different fat depots. These data support the possibility that the level of the encoded protein correlates with the total adipose tissue mass.

Levels of ob RNA in db/db mice and mice with lesions of the hypothalamus were measured. Lesions of the ventromedial hypothalamus (VMH) result in obesity as part of a syndrome resembling that seen in ob/ob and db/db mice (Bray and Campfield, 1975, Metabolism 24:99–117). Parabiosis experiments suggest such lesions result in over expression of a blood borne factor that suppresses food intake and body weight (Hervey, 1959, J. Physiol. 145:336–352). Similar results are noted when mice mutant at the db locus are parabiosed to normal mice, suggesting the ob receptor may be encoded by the db locus (Coleman et al., 1978, Diabetologia 14:141–148). Thus, obesity resulting from VMH lesions and the db mutation may be the result of resistance to the effects of the ob protein. If so, a secondary increase in the levels of ob RNA in adipose tissue would be predicted.

Figure 33:
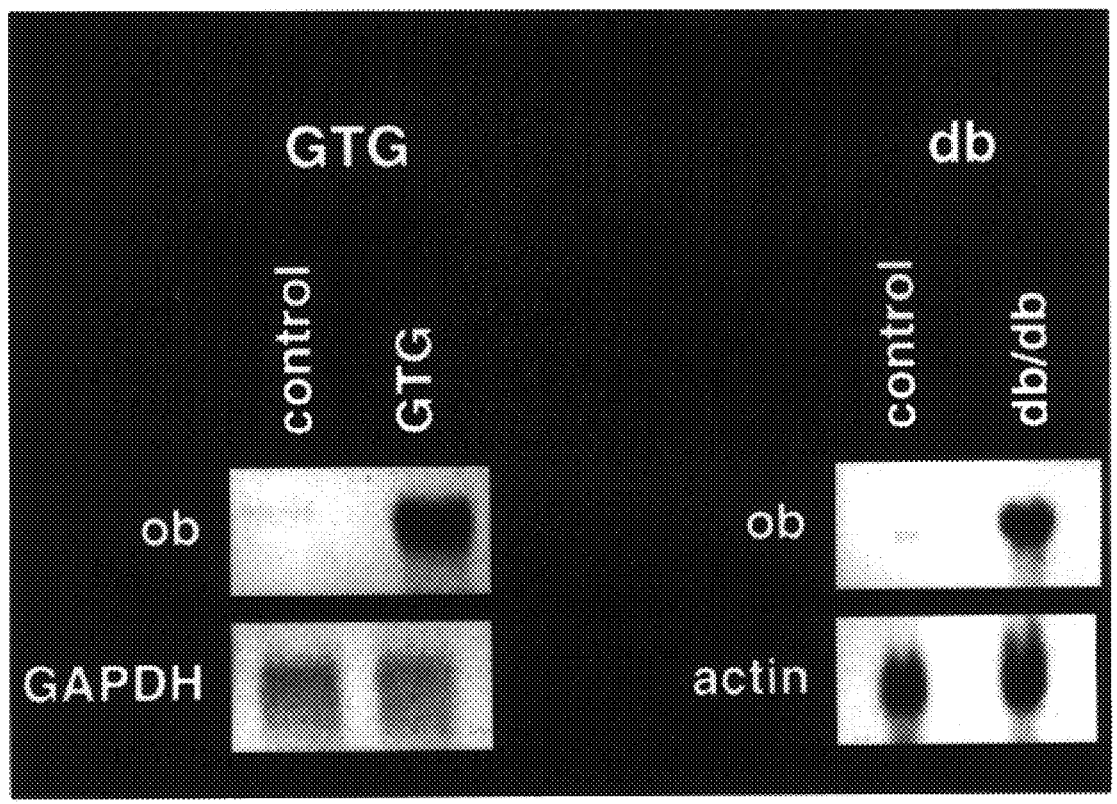
FIG. 33 depicts the expression of ob RNA in db/db and gold thioglucose treated mice. Total RNA from the parametrial fat pads of Gold Thioglucose (GTG) and db/db treated mice was electrophoresed on a Northern blot. GTG administered as a single dose is known to cause obesity by inducing specific hypothalamic lesions.

Hypothalamic lesions were induced in female CBA mice using the chemical Gold ThioGlucose (GTG) (Debons et al., 1977, Fed. Proc.36:143–147). This treatment results in specific hypothalamic lesions, principally in the ventromedial hypothalamus (VMH), with the subsequent development of obesity within several weeks. Usually, a single intraperitoneal injection of GTG of 0.2 mg/gm body weight results in the development of obesity within four weeks. One month old female CBA/J mice (20–25 grams) were treated with GTG and the subsequent weight gain of treated and control animals is shown (Table 2). Adipose tissue RNA was prepared from db/db mice and from those GTG treated animals that gained >20 gm. Northern blots showed a twenty-fold increase in the level of ob RNA in two month old db/db and GTG treated mice compared to normal animals (FIG. 33).

TABLE 2

Weight Gain in Gold ThioGlucose Treated Mice

|  | control (n = 41) | GTG (n = 93) |
|---|---|---|
| <10 g | 41, (100%) | 4, (4%) |
| 10 g–20 g | 0, (0%) | 15, (16%) |
| >20 g | 0, (0%) | 74, (80%) |

Two month old female CBA/J mice were treated with goldthioglucose (GTG). Goldthioglucose (Sigma A0632) was administered intraperitonealy in normal saline solution at a dosage of 2.0 mg/g. Body weight of control and injected animals was recorded before and one month after the injection. Animals were housed five to a cage and were fed ad libitum. The amount of weight gained one month post-injection is shown in the Table. Animals with a body weight gain greater that 20 g one month after injection were selected for further study.

Discussion

The gene product of the mouse ob gene circulates in mouse and human plasma where it may act to regulate the adipose tissue mass. Further studies on the regulation of expression and mechanism of action of ob will have important implications for our understanding of the physiologic pathway that regulates body weight.

The present Example shows that the ob gene product is expressed exclusively by adipocytes in all adipose tissue depots. This result is consistent with the possibility that the protein product of the ob gene correlates with the bodies lipid stores. Moreover ob RNA is upregulated twenty fold in db mice and mice with hypothalamic lesions. In these animals, the actual increase in the level of ob RNA per cell is likely to be even higher than twenty fold since the adipocyte cell size is increased approximately five fold in these animals (see FIG. 30) (Debons et al., 1977, Fed. Proc. 36:143–147). These data position the db gene and the hypothalamus downstream of ob in the pathway that controls body weight and is consistent with the hypothesis that the ob receptor is encoded at the db locus (Coleman et al., 1978, Diabetologia 14:141–148). The molecular cloning of the ob receptor and/or the db gene will resolve this issue. The increase in the level of ob RNA in db/db and GTG treated mice also suggests a non cell-autonomous function of the ob gene product in fat cells (Ashwell et al., 1977, Proc. R. Soc. Lond. 195:343–353; Ashwell and Meade, Diabetologia 15:465–470). Thus, if the encoded protein acted directly on fat cells to inhibit growth or differentiation, the overexpression of the wild type ob gene in GTG treated mice would result in a lean phenotype.

The most parsimonious explanation of these data is that the ob protein functions as an endocrine signaling molecule that is secreted by adipocytes and acts, directly or indirectly, on the hypothalamus. Direct effects on the hypothalamus would require that mechanisms exist to allow passage of the ob gene product across the blood brain barrier. Mechanisms involving the circumventricular organ and/or specific transporters could permit brain access of a molecule the size of that encoded by the ob gene (Johnson and Gross, 1983, FASEB J. 7:678–686; Baura et al., 1993, Jr. Clin. Investigation, Inc. 92:1824–1830; Pardridge, 1986, Endocrine Reviews 7:314–330). However, this hypothesis must be considered with caution until the means by which the protein might cross the blood brain barrier have been identified. Moreover, possible effects on other target organs will need to be evaluated.

The fat cell signal(s) that are fesponsible for the quantitative variation in the expression level of the ob gene is not yet known but correlates with differences in adipocyte cell size. Adipocytes from db/db mice are five times as large as those from normal mice, with a cell size of approximately 1.0 μg lipid/cell (Johnson and Hirsch, 1972, J. Lipid Res. 13: 2–11). Prior evidence has indicated that fat cell lipid content and/or size is an important parameter in determining body weight (Faust et al., 1978, Am. J. Physiol. 235:E279–86; Faust et al., 1977, Science 197:393–396). It could be that each fat cell expresses a low level of ob RNA that further increases in proportion to the cell size. It is also possible that cell size is not the sensed parameter and merely correlates with the intracellular signal that increases the expression of the ob gene in adipocytes from db/db and VMH lesioned mice. In any case, the components of the signal transduction pathway regulating the synthesis of ob RNA are likely to be important in determining body weight. Genetic and environmental influences that reduce the level of expression of ob would act to increase body weight as would influences that decreased sensitivity to the encoded protein. The specific molecules that regulate the level of expression levels of the ob gene are as yet unknown, and await a determination of the level(s) of gene control that leads to quantitative variation in the level of ob RNA and an examination of the regulatory elements of the ob gene. The identification of the molecules that regulate the expression of the ob gene in adipocytes and those that mediate the effects of the encoded protein at its site(s) of action will greatly enhance our understanding of the physiologic mechanisms that regulate body weight.

EXAMPLE 10

RNA Expression Pattern and Mapping on the Physical, Cytogenetic, and Genetic Maps of Chromosome 7 ob RNA is expressed at high levels in human adipose tissue and at substantially lower levels in placenta and heart. The human ob gene maps to a large yeast artificial chromosome (YAC) contig derived from chromosome 7q31.3. In addition to confirming the relative location of the gene based on mouse-human comparative mapping, this study has identified 8 established microsatellite markers in close physical proximity to the human ob gene. Since mutations in mouse ob can result in a syndrome that closely resembles morbid obesity in humans, these genetic markers represent important tools for studying the possible role of the ob gene in inherited forms of human obesity.

Materials and Methods

Northern blot analysis. Total RNA was prepared from adipose tissue using the method of Chirgwin et al. (1979, Biochem. 18:5294–5299). Northern blots, radiolabelling, and hybridizations were performed as described (Zhang et al., 1994, Nature 372:425–432). Northern blots of polyA$^+$ RNA (human MTN, human MTN II, and human fetal MTN II) were obtained from CLONTECH (Palo Alto, Calif.), as were PCR primers used to generate the radiolabelled human actin probe.

STS development. Sequence tagged-site (STS)-specific PCR assays were developed and optimized essentially as described (Green and Green, 1991, PCR Methods Applic. 1:77–90; Green et al., 1991, Genomics 11:548–564; Green, 1993, "Physical mapping of human chromosomes: generation of chromosome-specific sequence-tagged sites", *Methods in Molecular Genetics* Vol. 1: Gene and Chromosome Analysis (Part A). (ed. K. W. Adolph), Academic Press, Inc.: San Diego, pp. 192–210; Green et al., 1994, Hum. Mol. Genet. 3:489–501). Each STS is named using the prefix 'sWSS' followed by a unique number. Details about the 19 STSs reported here are provided in Table 3, with additional information (e.g., PCR reaction conditions, complete DNA sequence) available in GenBank and/or the Genome Data Base (GDB). For the microsatellite-specific STSs, the oligonucleotide primers used in the PCR assays (Table 3) corresponded either to those employed for genotype analysis (Table 4) or those designed (most often with the computer program OSP) (Hillier and Green, 1991, PCR Methods Applic. 1:124–128) using the DNA sequence available in GenBank.

(isolated insert end of a YAC) (Green, 1993, supra), 'Lambda Clone' (random chromosome 7-specific lambda clone) (Green et al. 1991, supra; Green, 1993, supra), 'Genetic Marker' (microsatellite marker, see Table 2) (Green et al. 1994, supra), 'YAC Insert' (random segment from YAC insert), and 'Gene' (gene-specific STS). Note that for some genetic marker-specific STSs, the PCR primers used for identifying YACs (listed in this table) are different from those used for performing genotype analysis (Table 4), since the detection of YACs containing a genetic marker does not require amplification of the polymorphic tract itself. All of the indicated PCR assays utilized an annealing temperature of 55° C., except for sWSS494, sWSS883, sWSS1529, and sWSS2619 (which used 50° C.), sWSS999 and sWSS1174 (which used 60° C.), and sWSS808 (which used 65° C.). Additional details regarding the STS-specific PCR assays are available in GDB.

TABLE 3

| STS Name | Alias | Locus | Source | PCR Primers | Size (bp) | GDB ID No. |
|---|---|---|---|---|---|---|
| sWSS1734 | | D7S2185 | YAC End | CAAGACAAATGAGATAAGG AGAGTTACAGCTTTACAG | 72 | G00-455-235 |
| sWSS494 | | D7S2016 | Lambda Clone | CTAAACACCTTTCCATTCC TTATATTCACTTTTCCCCTCTC | 112 | G00-334-404 |
| sWSS883 | UT528 | D7S1498 | Genetic Marker | TGCAGTAAGCTGTGATTGAG GTGCAGCTTTAATTGTGAGC | 490 | G00-455-262 |
| sWSS2359 | AFMa065zg9 | D7S1873 | Genetic Marker | AGTGTTGTGTTTCTCCTG AAAGGGGATGTGATAAGTG | 142 | G00-455-247 |
| sWSS2336 | AFMa125wh1 | D7S1874 | Genetic Marker | GGTGTTACGTTTAGTTAC GGAATAATGAGAGAAGATTG | 112 | G00-455-244 |
| sWSS1218 | AFM309yf1 | D7S686 | Genetic Marker | GCTCAACTGACAGAAAAC GACTATGTAAAAGAAATGCC | 154 | G00-307-733 |
| sWSS1402 | | D7S1916 | YAC End | AAAGGGCTTCTAATCTAC CCTTCCAACTTCTTTGAC | 137 | G00-344-044 |
| sWSS999 | | D7S1674 | YAC Insert | TAAACCCCTTTCTGTTC TTGCATAATAGTCACACCC | 105 | G00-334-839 |
| sWSS1751 | | D7S2186 | YAC End | CCAAAATCAGAATTGTCAGAAG AAACCGAAGTTCAGATACAG | 186 | G00-455-238 |
| sWSS1174 | AFM218xf10 | D7S514 | Genetic Marker | AATATCTGACATTGGCAC TTAGACCTGAGAAAAGAG | 144 | G00-307-700 |
| sWSS2061 | | D7S2184 | YAC End | GTTGCACAATACAAAATCC CTTCCATTAGTGTCTTATAG | 200 | G00-455-241 |
| sWSS2588 | | D7S2187 | YAC End | ATCACTACACACCTAATC CCATTCTACATTTCCACC | 117 | G00-455-253 |
| sWSS808 | PAX4 | PAX4 | Gene | GGCTGTGTGAGCAAGATC-CTAGGA TTGCCAGGCAAAGAGGGCTGGAC | 153 | G00-455-259 |
| sWSS1392 | AFM206xc1 | D7S635 | Genetic Marker | CTCAGGTATGTCTTTATC TGTCTCTGCATTCTTTTC | 75 | G00-307-815 |
| sWSS1148 | AFM199xh12 | D7S504 | Genetic Marker | GACACATACAAACACAAG ATTGAGTTGAGTGTAGTAG | 60 | G00-307-652 |
| sWSS1529 | | D7S1943 | YAC End | CAGGGATTTCTAATTGTC AAAAGATGGAGGCTTTTG | 116 | G00-334-119 |
| sWSS2619 | ob | ob | Gene | CGTTAAGGGAAGGAACTCTGG TGGCTTAGAGGAGTCAGGGA | 106 | G00-455-256 |
| sWSS404 | | D7S1956 | Lambda Clone | ACCAGGGTCAATACAAAG TAATGTGTCCTTCTTGCC | 122 | G00-334-251 |
| sWSS2367 | AFMa345wc9 | D7S1875 | Genetic Marker | CAATCCTGGCTTCATTTG AAGGTGGGTAGGATGCTA | 81 | G00-455-250 |

Table 3. STSs in the YAC contig containing the human ob gene

The 19 chromosome 7-specific STSs mapped to the YAC contig containing the human ob gene (FIG. 35) are listed. In each case, the designated 'sWSS' name, relevant alias, GD-assigned locus name, STS source, PCR primer sequences, STS size, and GDB identification number are indicated. The sources of STSs are as follows: 'YAC End'

Table 4. Microsatellite markers in the YAC contig containing the human ob gene

The 8 microsatellite markers mapped to the YAC contig containing the human ob gene (FIG. 35) are listed. In each case, the marker name (indicated as the alias in Table 3), type of microsatellite motif (tetranucleotide- 'Tetra' repeat or $(CA)_n$ repeat), GDB-assigned locus name, primer sequences utilized for PCR-based genotype analysis, and GDB identification number are indicated. Additional details regarding the PCR assays and the polymorphisms are available in GDB.

| Marker Name | Type   | Locus   | Primers                                       | GDB ID No.  |
|-------------|--------|---------|-----------------------------------------------|-------------|
| UT528       | Tetra. | D7S1498 | TGCAGTAAGCTGTGATTGAG GTGCAGCTTTAATTGTGAGC     | G00-312-446 |
| AFMa065zg9  | $(CA)_n$ | D7S1873 | AGCTTCAAGACTTTNAGCCT GGTCAGCAGCACTGTGATT   | G00-437-253 |
| AFMa125wh1  | $(CA)_n$ | D7S1874 | TCACCTTGAGATTCCATCC AACACCGTGGTCTTATCAAA   | G00-437-263 |
| AFM309yf10  | $(CA)_n$ | D7S680  | CATCCAAGTTGGCAGTTTTT AGATGCTGAATTCCCAGACA  | G00-200-283 |
| AFM218xf10  | $(CA)_n$ | D7S514  | TGGGCAACACAGCAAA TGCAGTTAGTGCCAATGTCA      | G00-188-404 |
| AFM206xc1   | $(CA)_n$ | D7S635  | CCAGGCCATGTGGAAC AGTTCTTGGCTTGCGTCAGT      | G00-199-240 |
| AFM199xh12  | $(CA)_n$ | D7S504  | TCTGATTGCTGGCTGC GCGCGTGTGTATGTGAG          | G00-188-280 |
| AFMa345wc9  | $(CA)_n$ | D7S1875 | AGCTCTTGGCAAACTCACAT GCCTAAGGGAATGAGACACA  | G00-437-259 |

The human ob-specific STS (sWSS2619) was designed using DNA sequence obtained from the 3' untranslated region of the cDNA. The human PAX4-specific STS (sWSS808) was developed using the following strategy. Oligonucleotide primers specific for the mouse Pax4 gene (GGCTGTGTGAGCAAGATCCTAGGA and GGGAGCCTTGTCCTGGGTACAAAG (Walther et al., 1991, Genomics 11:424–434)) were used to amplify a 204-bp fragment from human genomic DNA (which was the same size product as that generated from mouse genomic DNA). This PCR assay was not suitable for identifying corresponding YACs, since a similarly-sized (200-bp) product was also amplified from yeast DNA. However, DNA sequence analysis of the PCR product generated from human DNA revealed substitutions at 20 positions among the 156 bases analyzed (data not shown). Using this human-specific sequence, a new primer (TTGCCAGGCAAAGAGGGCTGGAC) was designed and used with the first of the above mouse Pax4-specific primers (see Table 3). The resulting human PAX4-specific PCR assay did not amplify a significant product from yeast DNA and was thus used for identifying corresponding YACs.

Identification of YACs by PCR-based screening. Most of the YACs depicted in FIG. 35 were derived from a collection of clones highly enriched for human chromosome 7 DNA (the 'chromosome 7 YAC resource') (Green et al., 1995, Genomics 25: 170–183) using a PCR-based screening strategy (Green et al., 1995, Genomics 25: 170–183; Greena and Olson, 1990, Proc. Natl. Acad. Sci. USA 87:1213–1217). In a few cases, clones were isolated by PCR-based screening (Greena and Olson, 1990, Proc. Nati. Acad. Sci. USA 87:1213–1217) of available total human genomic YAC libraries constructed at CEPH (Dausset et al., 1992, Behring Inst. Mitt. 91:13–20; Albertsen et al., 1990, Proc. Natl. Acad. Sci. USA 87:4256–4260) or ICI (Anand et al., 1989, Nucl. Acids Res. 17:3425–3433; Anand et al., 1990, Nucl. Acids Res. 18:1951–1956). Each YAC is named using the prefix 'yWSS' followed by a unique number.

Results and Discussion

Figure 34:
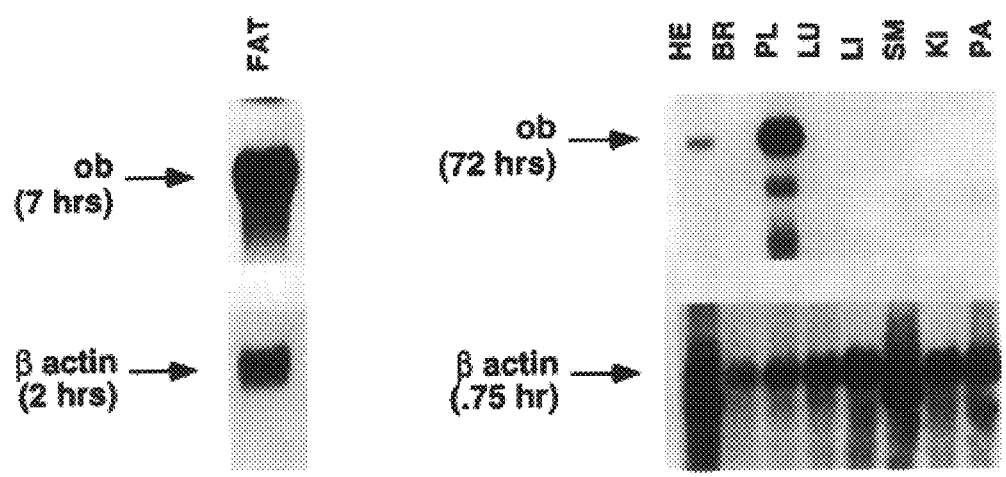
FIG. 34 represents a northern blot analysis of human RNA. Northern blots containing 10 mg of total RNA from human adipose tissue (FAT, FIG. 34A) and 2 mg of polyA+ RNA from other human tissues (FIG. 34B) were hybridized to human ob or human β-actin probes as indicated. An intense signal at approximately 4.5 kb was seen with the adipose tissue total RNA. Hybridization to the polyA+ RNA revealed detectable signals in heart (HE) and placenta (PL), whereas ob RNA was not detected in brain (BR), lung (LU), liver (LI), skeletal muscle (SM), kidney (KI), and pancreas (PA). In each case, the length of the autoradiographic exposure is indicated. Of note, the genesis of the lower molecular bands seen in placental RNA (e.g., alternate splicing, RNA degradation) is not known.

Examination of the tissue expression of the human ob gene by northern blot analysis revealed that ob RNA is expressed at a high level in human adipose tissue and much lower levels in placenta and heart (FIG. 34). The size of the RNA (approximately 4.5 kb) was equivalent in human and mouse as well as in each of the expressing tissues. In these studies, five-fold higher signals were seen in 10 $\mu$g of total adipose tissue RNA as in 2 $\mu$g of polyA$^+$ placental RNA. A five-fold lower signal was seen in polyA$^+$ RNA from heart compared to placenta. It is estimated that the level of ob RNA is approximately 250-fold lower in placenta than in adipose tissue. In this experiment, ob RNA was not detected in any of the other tissues analyzed, including brain, lung, liver, skeletal muscle, kidney, and pancreas. Additional experiments did not reveal ob RNA in spleen, thymus, prostate, testis, ovary, small intestine, colon, peripheral blood leukocytes, or in fetal brain, liver, or kidneys (data not shown). It is possible that ob is expressed at an undetectable level (by northern blot analysis) in these latter tissues or in other tissues that were not studied. The observed pattern of expression in human differs somewhat from mouse, in which ob RNA is detected almost exclusively in adipose tissue.

Comparative mapping of the ob gene region in the mouse and human genomes. The mouse ob gene is located on proximal chromosome 6 in a region homologous with a portion of human chromosome 7q. Genes within this segment include (from proximal to distal): Met protooncogene, the cystic fibrosis transmembrane conductance regulator (Cftr), paired box-containing gene 4 (Pax4), ob, and carboxypeptidase A (Cpa) (Zhang et al., 1994, Nature 372:425–432; Friedman et al., 1991, Genomics 11:1054–1062). In mouse, genetic mapping was used to demonstrate that Pax4 is tightly linked to ob (Walther et al., 1991, Genomics 11:424–434; Zhang et al. 1994, supra). The physical distance between ob and Pax4 was found to be approximately 1 megabase pairs (Mb) (Zhang et al. 1994, supra). Based on these comparative mapping studies, it was expected that the human ob gene would reside between PAX4 and CPA on chromosome 7q. Furthermore, since human CFTR (Heng et al., 1993, Cell Genet. 62:108–109) and PAX4 (Tamura et al., 1994, Cytogenet. Cell Genet. 66:132–134) were mapped by fluorescence in situ hybridization (FISH) to 7q31.3 and 7q32, respectively, the most likely cytogenetic position of the human ob gene would be in the vicinity of the 7q31.3–q32 boundary.

Mapping the ob gene on human chromosome 7. An STS (sWSS2619) amplifying a small segment of the 3' untranslated region of the human ob gene was used to screen a collection of YAC clones that is highly enriched for human chromosome 7 DNA (Green et al., 1995a, Genomics 25: 170–183), and 9 YACs were identified (yWSS691, yWSS1332, yWSS1998, yWSS2087, yWSS3319, yWSS3512, yWSS4875, yWSS4970, and yWSS5004). To verify that these YACs contain the authentic human ob gene, 2 additional experiments were performed. First, each of the YACs was tested with a second human ob-specific PCR assay, and all were found to be positive (data not shown). Second, yeast DNA from each clone was digested with EcoRI and analyzed by gel-transfer hybridization using a human ob cDNA-derived probe. In all instances, a single hybridizing band was seen, and this band was the same size in the YACs and a P1 clone known to contain the human ob gene (data not shown).

Using the computer program SEGMAP (Green and Green, 1991, supra) and other YAC-based STS-content data that we have generated for chromosome 7 (Green et al. 1991, supra; Green et al. 1994, supra; Green et al. 1995, supra), the human ob gene was found to reside within the YAC contig depicted in FIG. 35. Specifically, this contig consists of 43 overlapping YACs and 19 uniquely-ordered STSs. Details about each of the 19 STSs are provided in Table 3. In addition to the ob-specific STS, the contig also contains an STS (sWSS808) specific for the human PAX4 gene (Tamura et al. 1994, supra; Stapleton et al., 1993, Nature Genet. 3:292–298), 7 STSs derived from chromosome 7-specific YACs, 2 STSs derived from chromosome 7-specific lambda clones, and, importantly, 8 microsatellite-specific STSs. Additional details about these 8 genetic markers, including sequences of the primers used for genotype analysis, are provided in Table 2. Of note, there is redundant YAC-based connectivity throughout the contig (i.e., there are 2 or more YACs connecting each adjacent pair of STSs), lending strong support for the relative order of STSs shown in FIG. 35.

Figure 35A:
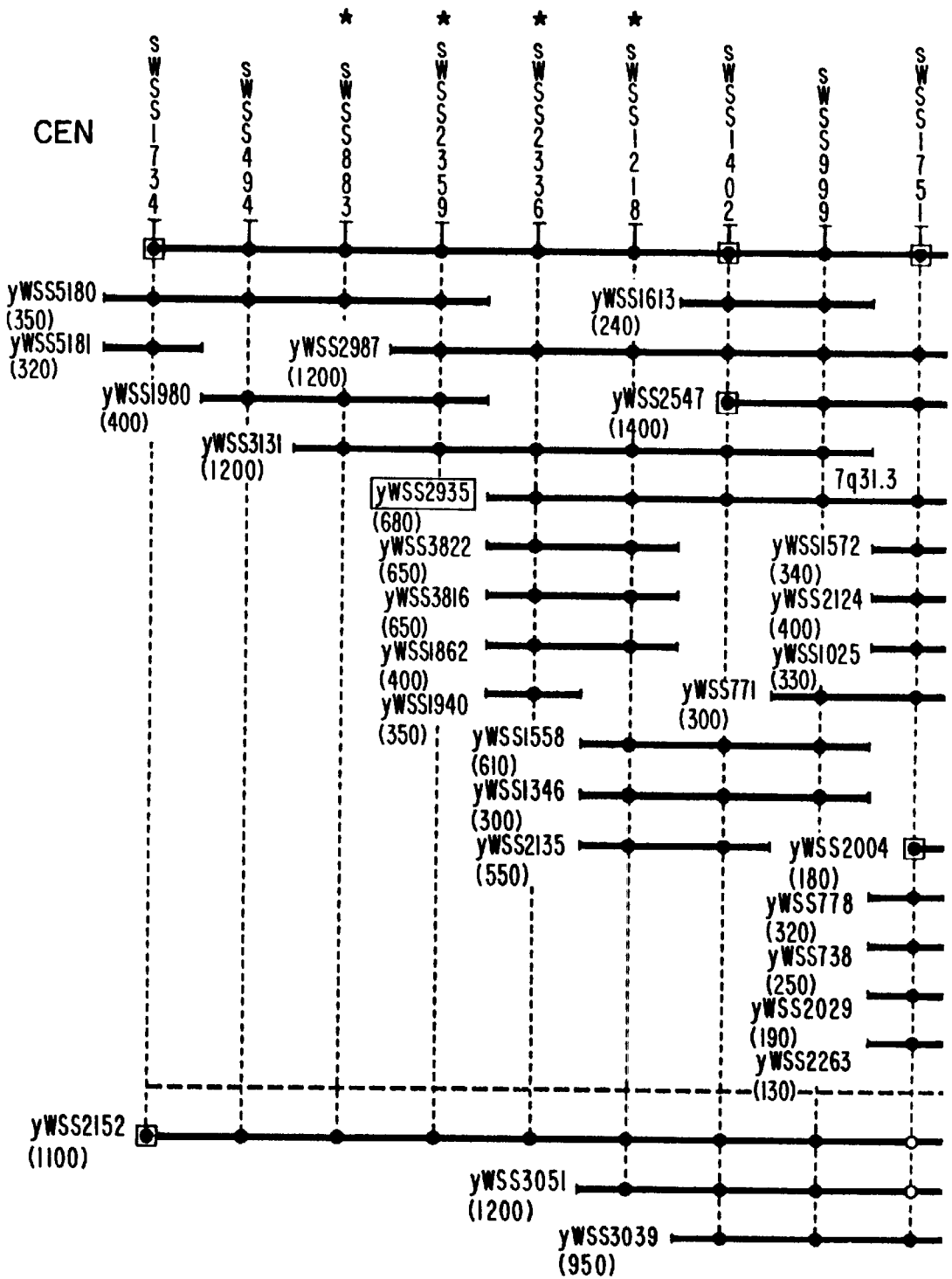
FIG. 35 represents YAC contig containing the human ob gene and 8 microsatellite markers. The YAC-based STS-content map of the region of chromosome 7 containing the human ob gene is depicted, as deduced by SEGMAP/Version 3.29 (Green and Green, 1991a; C. L. Magness and P. Green, unpublished data). The 19 uniquely-ordered STSs (see Table 3) are listed along the top. The 8 microsatellite-specific STSs are indicated with stars (see Table 4). Also indicated are the STSs corresponding to the PAX4 and ob genes as well as the predicted positions of the centromere (CEN) and 7q telomere (TEL) relative to the contig. Each of the 43 YAC clones is depicted by a horizontal bar, with its name given to the left and estimated YAC size (in kb, measured by pulsed-field gel electrophoresis) provided in parenthesis. The presence of an STS in a YAC is indicated by a darkened circle at the appropriate position. When an STS corresponds to the insert end of a YAC, a square is placed around the corresponding circle, both along the top (near the STS name) and at the end of the YAC from which it was derived. For the 5 YACs at the bottom (below the horizontal dashed line), 1 or more STS(s) expected to be present (based on the established STS order) was not detected (as assessed by testing the individual YACs with the corresponding STS-specific PCR assay(s) at least twice), and these are depicted as open circles at the appropriate positions. Most of the YACs were isolated from a human-hamster hybrid cell-derived library (Green et al., 1995, Genomics 25:170–83), with their original names as indicated. The remaining YACs were isolated from total human genomic libraries, and their original library locations are provided in Table 3. Boxes are placed around the names of the 3 YACs (yWSS691, yWSS999, and yWSS2935) that were found by FISH analysis to map to 7q31.3. The contig is displayed in its 'uncomputed' form, where YAC sizes are not used to estimate clone overlaps or STS spacing, and all of the STSs are therefore spaced in an equidistant fashion. In the 'computed' form, where YAC sizes are used to estimate the relative distance separating each pair of adjacent STSs as well as the extent of clone overlaps, the total YAC contig appears to span just over 2 Mb.
Figure 35B:
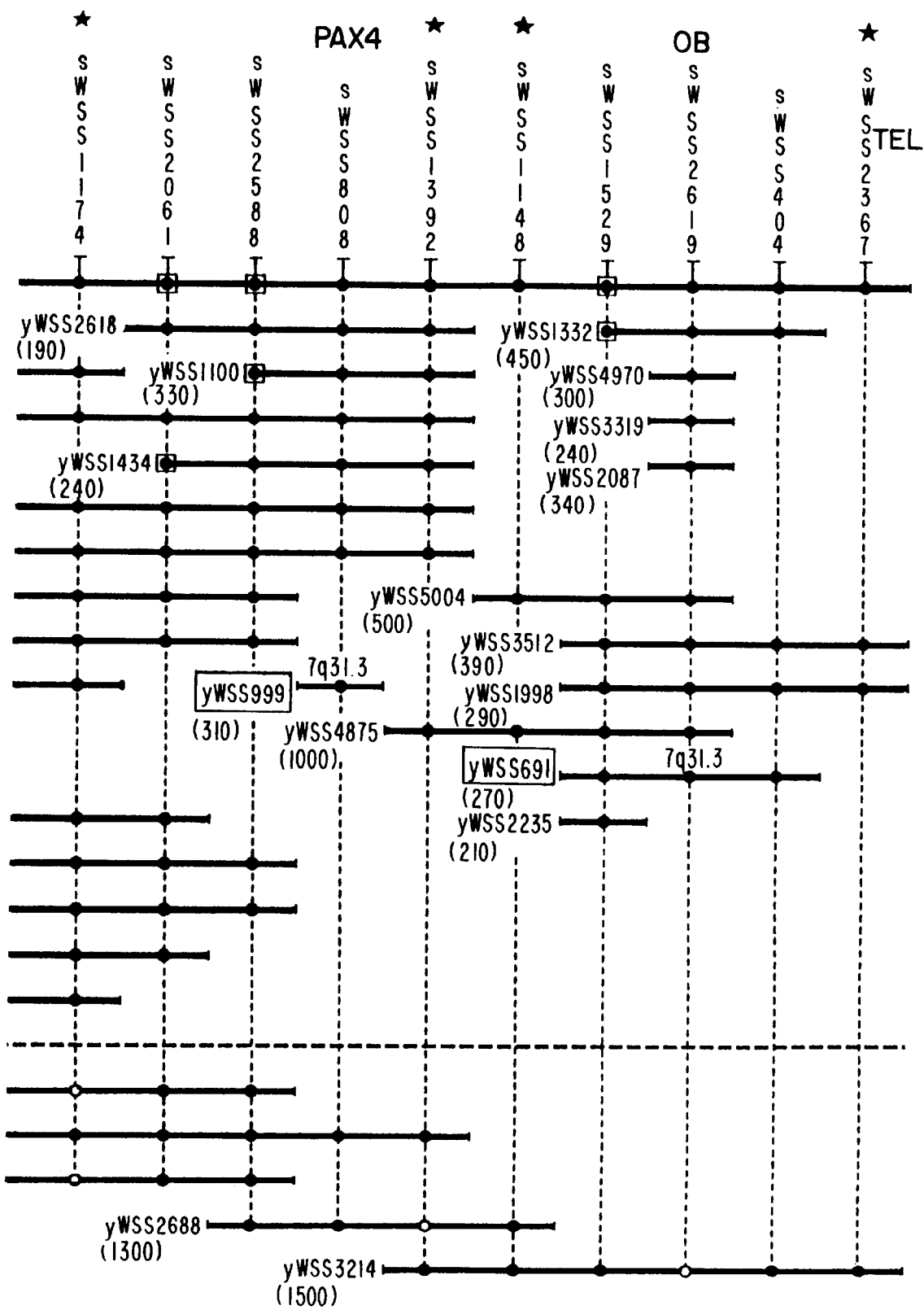

As depicted in FIG. 35, the predicted orientation of the human ob-containing YAC contig is such that sWSS1734 is the centromeric-most STS (i.e., closest to CFTR) while sWSS2367 is the telomeric-most STS (i.e., closest to CPA). This orientation is predominantly based on comparative mapping data, which places Pax4 proximal and ob distal within the syntenic block present in mouse and human DNA (Zhang et al. 1994, supra). The ob gene maps near the telomeric end of the contig, based on the placement of the ob-specific STS (sWSS2619).

While the contig shown in FIG. 35 was deduced by SEGMAP without consideration of YAC sizes (thereby displaying STSs equidistant from one another), a similar analysis of the data by SEGMAP that accounted for YAC sizes indicated that the total size of the region covered by the contig is just over 2 Mb (data not shown). Thus, while all 8 of the microsatellite-specific STSs (Table 4) are contained within a genomic interval spanning roughly 2 Mb, the 3 closest to the telomeric end of the contig (sWSS1392, sWSS1148, and sWSS2367) are particularly close to the ob gene itself (perhaps within an interval as small as approximately 500 kb). In fact, all 3 of the latter STSs are present in at least 1 of the human ob-containig YACs. Of note, the interval between human PAX4 (sWSS808) and ob (sWSS2619) is estimated to be approximately 400 kb, whereas this region was predicted to span approximately 1 Mb in mouse (Zhang et al. 1994). Finally, 3 of the YACs within the contig (yWSS691, yWSS999, and yWSS2935) have also been analyzed by FISH, and each was found to hybridize exclusively to 7q31.3. One of these YACs (yWSS691) contains the ob-specific STS, while the other 2 clones contain the PAX4-specific STS. The latter results are generally consistent with the previous cytogenetic assignment of human PAX4 to 7q32 (Tamura et al. 1994, supra). Based on these data, the human ob gene can be assigned to cytogenetic band 7q31.3.

EXAMPLE 11

Human Ob Polypeptide is Biologically Active in Mice

Groups of 10 ob/ob mice were treated by i.p. injection with 10 μg/g/day recombinant (bacterial) human and murine ob polypeptide or saline. After four days, the group receiving saline gained 0.3 g. The group receiving murine ob lost 3.2 g. The group receiving human ob lost 2 g ($p<0.01$ compared to saline controls). These groups were also tested for food intake. The data for food intake are shown in Table 5; the data for body mass are shown in Table 6.

TABLE 5

Food intake/day (g) of treated ob/ob mice (value ± S.Dev)

| Treatment | Day 0 | Day 1 | Day 2 | Day 3 | Day 4 | Day 5 | Day 6 | Day 7 |
|---|---|---|---|---|---|---|---|---|
| saline | 13.4 ±2.6 | 12.8 | 12.8 | 13.1 | 14.0 | 12.3 | 12.4 | 8.3 |
| murine ob | 14.9 | 3.7 | 4.4 | 5.1 | 8.9 | 8.1 | 8.7 | 3.5 |
| human ob | 14.3 | 10.3 | 8.7 | 7.0 | 8.9 | 5.3 | 3.8 | 13.0 |

TABLE 6

Body weight and weight change in treated ob/ob mice (value ± S.Dev)

| Treatment | Body Weight (Day 0) | Body Weight (Day 4) | Percent change (Day 0 to 4) | Body Weight (Day 6) | Percent Change (Day 0 to 6) |
|---|---|---|---|---|---|
| saline | 39.9 ± 1.8 | 40.7 ± 1.6 | 0.8 ± 0.5 | 41.1 ± 2.2 | 1.2 ± 1.1 |
| murine ob | 39.5 ± 2.1 | 36.2 ± 2.0 | −3.3 ± 1.2 | 36.3 ± 2.2 | −3.1 ± 1.2 |
| human ob | 39.5 ± 2.0 | 37.6 ± 1.7 | −2.0 ± 1.0 | 36.1 ± 1.3 | −3.5 ± 1.3 |

These data demonstrate that human ob is biologically active in mice.

EXAMPLE 12

A High Dose of Ob Affects Wild-type Mice

Wild type mice (C57Bl6J+/?) were treated with 10 μg/g/day i.p. of recombinant murine ob, and body mass measured every four days. The results are shown in Table 7.

TABLE 7

Body mass (g) of normal mice receiving ob

| Treatment | Day 0 | Day 4 | Day 8 | Day 12 | Day 16 |
|---|---|---|---|---|---|
| saline | 22.6 ± 1.4 | 22.2 ± 1.2 | 22.5 ± 1.3 | 23 | 22.5 |
| murine ob | 22.4 ± 1.5 | 20.6 ± 1.5 | 20.8 ± 1.3 | 20.8 | 21.8 |

These data demonstrate that ob affects the body mass of wild-type as well as obese (ob/ob) mice, albeit to a much smaller degree.

EXAMPLE 13

Ob Polypeptide Administered By Continuous Pump Infusion

This example demonstrates that continuous infusion of ob polypeptide results in weight loss in normal mice. Normal (non-obese) mice were administered murine ob polypeptide via osmotic pump infusion. A dosage of 0.5 mg protein/kg body weight/day resulted in a 4.62% loss (+/−1.34%) from baseline weight by the 6th day of infusion.

Materials and Methods

Animals. Wild type (+/+) C57B16 mice were used in this Example. The age of the mice at the initial time point was 8 weeks, and the animals were weight stabilized. Ten mice were used for each cohort (vehicle vs. protein).

Animal Handling:

Feeding and weight measurement. Mice were given ground rodent chow (PMI Feeds, Inc.) in powdered food feeders (Allentown Caging and Equipment), which allowed a more accurate and sensitive measurement of food intake than use of regular block chow. Weight was measured at the same time each day (2:00 p.m.), for a period of 6 days. Body weight on the day prior to infusion was defined as baseline weight.

Housing. Mice were single-housed, and maintained under humane conditions.

Administration of Protein or Vehicle. Protein (as described below) or vehicle (phosphate buffered saline, pH 7.4) were administered by osmotic pump infusion. Alzet osmotic minipumps (Alza, Palo Alto, Calif., model no. 1007D) were surgically placed in each mice in a subcutaneous pocket in the subscapular area. The pumps were calibrated to administer 0.5 ml protein in solution per hour for a dosage of 0.5 mg protein/kg body weight/day.

Controls. Control animals were infused with phosphate buffered saline (pH 7.4) via an Alzet osmotic minipump.

Protein. Recombinant murine ob polypeptide was used for the present experiments, generally at a concentration of about 0.9 mg/ml phosphate buffered saline, pH 7.4. The amino acid sequence (and DNA sequence) used was the following:

Recombinant murine met ob (double stranded) DNA and amino acid sequence. (SEQ. ID. NO:94 and SEQ. ID. NO:95, respectively.

The cloning of the murine ob DNA for expression in $E.\ coli$ was performed as follows. The DNA sequence as deduced from the published peptide sequence that appeared in Zhang et al. (1994, Nature 372:425–432, i.e., Example 1, supra) was reverse translated using $E.\ coli$ optimal codons. The terminal cloning sites were XbaI to BamHI. A ribosomal binding enhancer and a strong ribosomal binding site were included in front of the coding region. The duplex DNA sequence was synthesized using standard techniques. Correct clones were confirmed by demonstrating expression of the recombinant protein and presence of the correct ob DNA sequence in the resident plasmid.

Expression Vector and Host Strain. The plasmid expression vector used was pCFM1656, American Type Culture Collection (ATCC) Accession No. 69576. The above DNA was ligated into the expression vector pCFM1656, which had been linearized with XbaI and BamHI and transformed into the $E.\ coli$ host strain, FM5. $E.\ coli$ FM5 cells were derived at Amgen Inc., Thousand Oaks, Calif. from $E.\ coli$ K-12 strain (Bachmann, et al., Bacteriol. Rev. 40: 116–167 (1976)) and contain the integrated lambda phage repressor gene, $cI_{857}$ (Sussman et al., C.R. Acad. Sci. 254: 1517–1579 (1962)). Vector production, cell transformation, and colony selection were performed by standard methods. e.g., Sambrook, et al., Molecular Cloning: A Laboratory Manual, 2d Edition, Cold Spring Harbor Laboratory Press, Cold Spring Harbor, N.Y. Host cells were grown in LB media.

Fermentation Process. A three-phase fermentation protocol known as a fed-batch process was used. Media compositions are set forth below.

Batch. A nitrogen and phosphate source were sterilized (by raising to 122° C. for 35 minutes, 18–20 psi) in the fermentation vessel (Biolafitte, 12 liter capacity). Upon cooling, carbon, magnesium, vitamins, and trace metal sources were added aseptically. An overnight culture (16

```
        TCTAGATTTGAGTTTTAACTTTTAGAAGGAGGAATAACATATGGTACCGATCCAGAAAGT
      9 -+---------+---------+---------+---------+---------+--------   68
        AGATCTAAACTCAAAATTGAAAATCTTCCTCCTTATTGTATACCATGGCTAGGTCTTTCA
                                                   M  V  P  I  Q  K  V  -
        TCAGGACGACACCAAAACCTTAATTAAAACGATCGTTACGCGTATCAACGACATCAGTCA
     69 -+---------+---------+---------+---------+---------+--------  128
        AGTCCTGCTGTGGTTTTGGAATTAATTTTGCTAGCAATGCGCATAGTTGCTGTAGTCAGT
         Q  D  D  T  K  T  L  I  K  T  I  V  T  R  I  N  D  I  S  H  -
        CACCCAGTCGGTCTCCGCTAAACAGCGTGTTACCGGTCTGGACTTCATCCCGGGTCTGCA
    129 -+---------+---------+---------+---------+---------+--------  188
        GTGGGTCAGCCAGAGGCGATTTGTCGCACAATGGCCAGACCTGAAGTAGGGCCCAGACGT
         T  Q  S  V  S  A  K  Q  R  V  T  G  L  D  F  I  P  G  L  H  -
        CCCGATCCTAAGCTTGTCCAAAATGGACCAGACCCTGGCTGTATACCAGCAGGTGTTAAC
    189 -+---------+---------+---------+---------+---------+--------  248
        GGGCTAGGATTCGAACAGGTTTTACCTGGTCTGGGACCGACATATGGTCGTCCACAATTG
         P  I  L  S  L  S  K  M  D  Q  T  L  A  V  Y  Q  Q  V  L  T  -
        CTCCCTGCCGTCCCAGAACGTTCTTCAGATCGCTAACGACCTCGAGAACCTTCGCGACCT
    249 -+---------+---------+---------+---------+---------+--------  308
        GAGGGACGGCAGGGTCTTGCAAGAAGTCTAGCGATTGCTGGAGCTCTTGGAAGCGCTGGA
         S  L  P  S  Q  N  V  L  Q  I  A  N  D  L  E  N  L  R  D  L  -
        GCTGCACCTGCTGGCATTCTCCAAATCCTGCTCCCTGCCGCAGACCTCAGGTCTTCAGAA
    309 -+---------+---------+---------+---------+---------+--------  368
        CGACGTGGACGACCGTAAGAGGTTTAGGACGAGGGACGGCGTCTGGAGTCCAGAAGTCTT
         L  H  L  L  A  F  S  K  S  C  S  L  P  Q  T  S  G  L  Q  K  -
        ACCGGAATCCCTGGACGGGGTCCTGGAAGCATCCCTGTACAGCACCGAAGTTGTTGCTCT
    369 -+---------+---------+---------+---------+---------+--------  428
        TGGCCTTAGGGACCTGCCCCAGGACCTTCGTAGGGACATGTCGTGGCTTCAACAACGAGA
         P  E  S  L  D  G  V  L  E  A  S  L  Y  S  T  E  V  V  A  L  -
        GTCCCGTCTGCAGGGTTCCCTTCAGGACATCCTTCAGCAGCTGGACGTTTCTCCGGAATG
    429 -+---------+---------+---------+---------+---------+--------  488
        CAGGGCAGACGTCCCAAGGGAAGTCCTGTAGGAAGTCGTCGACCTGCAAAGAGGCCTTAC
         S  R  L  Q  G  S  L  Q  D  I  L  Q  Q  L  D  V  S  P  E  C  -
        TTAATGGATCC
    489 -+---------
        AATTACCTAGG
``` hours or more) of the above recombinant murine protein-producing bacteria of 500 mL (grown in LB broth) was added to the fermentor.

Feed I. Upon reaching between 4.0–6.0 $OD_{600}$, Feed I was added to cultures. The glucose was added at a limiting rate in order to control the growth rate ($\mu$). An automated system (called the Distributive Control System) was programmed to control the growth rate at 0.15 generations $hr^{-1}$.

Feed II. When the OD reached 30, temperature was slowly increased to 42° C. and the feed was changed to Feed II, described below. The fermentation was then allowed to continue for 10 hours with sampling every 2 hours. After 10 hours, the contents of the fermentor were chilled to below 20° C. and harvested by centrifugation.

| Media Composition: | | |
|---|---|---|
| Batch: | 10 g/L | Yeast extract |
| | 5.25 g/L | $(NH_4)_2SO_4$ |
| | 3.5 g/L | $K_2HPO_4$ |
| | 4.0 g/L | $KH_2PO_4$ |
| | 5.0 g/L | Glucose |
| | 1.0 g/L | $MgSO_4.7H_2O$ |
| | 2.0 mL/L | Vitamin Solution |
| | 2.0 mL/L | Trace Metal Solution |
| | 1.0 mL/L | P2000 Antifoam |
| Feed I: | 50 g/L | Bacto-tryptone |
| | 50 g/L | Yeast extract |
| | 450 g/L | Glucose |
| | 8.75 g/L | $MgSO_4.7H_2O$ |
| | 10 mL/L | Vitamin Solution |
| | 10 mL/L | Trace Metal Solution |
| Feed II: | 200 g/L | Bacto-tryptone |
| | 100 g/L | Yeast extract |
| | 110 g/L | Glucose |

Vitamin Solution (Batch, Feed I): 0.5 g Biotin, 0.4 g Folic acid, and 4.2 g riboflavin, were dissolved in 450 ml $H_2O$ and 3 ml 10 N NaOH, and brought to 500 ml with $H_2O$. Fourteen g pyridoxine-HCl and 61 g niacin were dissolved 150 ml $H_2O$ and 50 ml 10 N NaOH, and brought to 250 ml with $H_2O$. Fifty-four g pantothenic acid was dissolved in 200 ml $H_2O$, and brought to 250 ml. The three solutions were combined and brought to 10 liters total volume.

Trace Metal Solution (Batch, Feed I):

Ferric Chloride ($FeCl_3.6H_2O$): 27 g/L

Zinc Chloride ($ZnCl_2.4H_2O$): 2 g/L

Cobalt Chloride ($CoCl_2.6H_2O$): 2 g/L

Sodium Molybdate ($NaMoO_4.2H_2O$): 2 g/L

Calcium Chloride ($CaCl_2.2H_2O$): 1 g/L

Cupric Sulfate ($CuSO_4.5H_2O$): 1.9 g/L

Boric Acid ($H_3BO_3$): 0.5 g/L

Manganese Chloride ($MnCl_2.4H_2O$): 1.6 g/L

Sodium Citrate dihydrate: 73.5 g/L

Purification Process for Murine ob polypeptide.

Purification was accomplished by the following steps (unless otherwise noted, the following steps were performed at 4° C.):

1. Cell paste. *E. coli* cell paste was suspended in 5 times volume of 7 mM of EDTA, pH 7.0. The cells in the EDTA were further broken by two passes through a microfluidizer. The broken cells were centrifuged at 4.2 k rpm for 1 hour in a Beckman JB-6 centrifuge with a J5-4.2 rotor.

2. Inclusion body wash #1. The supernatant from above was removed, and the pellet was resuspended with 5 times volume of 7 mM EDTA, pH 7.0, and homogenized. This mixture was centrifuged as in step 1.

3. Inclusion body wash #2. The supernatant from above was removed, and the pellet was resuspended in ten times volume of 20 mM tris, pH 8.5, 10 mM DTT, and 1% deoxycholate, and homogenized. This mixture was centrifuged as in step 1.

4. Inclusion body wash #3. The supernatant from above was removed and the pellet was resuspended in ten times volume of distilled water, and homogenized. This mixture was centrifuged as in step 1.

5. Refolding. The pellet was refolded with 15 volumes of 10 mM HEPES, pH 8.5, 1% sodium sarcosine (N-lauryl sarcosine), at room temperature. After 60 minutes, the solution was made to be 60 mM copper sulfate, and then stirred overnight.

6. Removal of sarcosine. The refolding mixture was diluted with 5 volumes of 10 mM tris buffer, pH 7.5, and centrifuged as in step 1. The supernatant was collected, and mixed with agitation for one hour with Dowex 1-X4 resin, 20–50 mesh, chloride form (at 0.066% total volume of diluted refolding mix). This mixture was poured into a column and the eluant was collected. Removal of sarcosine was ascertained by HPLC.

7. Acid precipitation. The eluant from the previous step was collected, and pH adjusted to pH 5.5, and incubated for 30 minutes at room temperature. This mixture was centrifuged as in step 1.

8. Cation exchange chromatography. The pH of the supernatant from the previous step was adjusted to pH 4.2, and loaded on CM Sepharose Fast Flow. Twenty column volumes of salt gradient were done at 20 mM NaOAC, pH 4.2, 0 M to 1.0 M NaCl.

9. HIC chromatography. The CM Sepharose pool of peak fractions ascertained from ultraviolet analysis) from the above step was made to be 0.2 M ammonium sulfate. A 20 column volume reverse salt gradient was done at 5 mM NaOAC, pH 4.2, with 0.4 M to 0 M ammonium sulfate. This material was concentrated and diafiltered into PBS.

Results

Presented below are the percent (%) differences from baseline weight in C57Bl6J mice (8 wks old):

TABLE 8

Weight Loss Upon Continuous Infusion

| Time (days) | Vehicle (PBS) | Recombinant ob polypeptide |
|---|---|---|
| Days 1–2 | 3.24 +/− 1.13 | 1.68 +/− 1.4 |
| Days 3–4 | 4.3 +/− .97 | −2.12 +/− .79 |
| Days 5–6 | 4.64 +/− .96 | −4.62 +/− 1.3 |

As can be seen, at the end of a 6 day continuous infusion regime, animals receiving the ob polypeptide lost over 4% of their body weight, as compared to baseline. This is a substantially more rapid weight loss than has been observed with intraperitoneal (i.p.) injection. Weight loss of only was 2.6–3.0% was seen at the end of a 32-day injection period, in wild type (normal) mice, with daily i.p. injections of recombinant murine ob polypeptide at a 10 mg/kg dose, and had not been more than 4% at any time during the dosing schedule (data not shown). The present data indicate that with continuous infusion, a 20-fold lower dosage (0.5 mg/kg vs. 10 mg/kg) achieves more weight loss in a shorter time period.

The results seen here are statistically significant, e.g., −4.62% with $p<0.0001$.

EXAMPLE 14

Cloning and Expression of a Recombinant Human Ob Polypeptide

This example provides compositions and methods for preparation of a recombinant human version of the ob polypeptide.

The human version of ob DNA was constructed from the murine ob DNA, as in Example 13, above, by replacing the region between the MluI and BamHI sites with duplex DNA (made from synthetic oligonucleotides) in which 20 codon substitutions had been designed. The MluI site is shown under the solid line in the sequence below. This DNA was put into the pCFM 1656 vector (ATCC Accession No. 69576), in the same fashion as the recombinant murine protein, as described above.

Recombinant human met ob (Double Stranded) DNA and amino acid sequence (SEQ. ID. NO:96 and SEQ. ID. NO:97, respectively.

Fermentation. Fermentation of the above host cells to produce recombinant human ob polypeptide was accomplished using the conditions and compositions as described above for recombinant murine material. The results were analyzed for yield (grams/liter), pre-purification, of the recombinant human ob material (and minor amounts of bacterial protein), and correlated to analyze bacterial expression:

TABLE 9

Analysis of Human Ob Polypeptide Expression

| Timepoint | OD (@ 600 nm) | Yield (g/L) | Expression (mg/OD · L) |
|---|---|---|---|
| Ind. + 2 hrs. | 47 | 1.91 | 41 |
| Ind. + 4hrs. | 79 | 9.48 | 120 |
| Ind. + 6 hrs. | 95 | 13.01 | 137 |

TABLE 9-continued

Analysis of Human Ob Polypeptide Expression

| Timepoint | OD (@ 600 nm) | Yield (g/L) | Expression (mg/OD · L) |
|---|---|---|---|
| Ind. + 8 hrs. | 94 | 13.24 | 141 |
| Ind. + 10 hrs. | 98 | 14.65 | 149 | abbreviations: Ind. + _ hours means the hours after induction of protein expression, as described in Example 12 for the recombinant murine material using pCFM 1656
OD: optical density, as measured by spectrophotometer milligrams per OD unit per liter
mg/OD · L: expression in terms of mg of protein per OD unit per liter.

Purification of the recombinant human ob polypeptide. Recombinant human protein may be purified using methods similar to those used for purification of recombinant murine protein, as in Example 13, above. For preparation of recombinant human ob polypeptide, step 8 was performed by adjusting the pH of the supernatant from step 7 to pH 5.0,

```
    CATATGGTACCGATCCAGAAAGTTCAGGACGACACCAAAACCTTAATTAAAACGATCGTT
  1 ---------+---------+---------+---------+---------+---------+  60
    GTATACCATGGCTAGGTCTTTCAAGTCCTGCTGTGGTTTTGGAATTAATTTTGCTAGCAA
       M  V  P  I  Q  K  V  Q  D  D  T  K  T  L  I  K  T  I  V  -
    ACGCGTATCAACGACATCAGTCACACCCAGTCGGTGAGCTCTAAACAGCGTGTTACAGGC
 61 ---------+---------+---------+---------+---------+---------+ 120
    TGCGCATAGTTGCTGTAGTCAGTGTGGGTCAGCCACTCGAGATTTGTCGCACAATGTCCG
     T  R  I  N  D  I  S  H  T  Q  S  V  S  S  K  Q  R  V  T  G  -
    CTGGACTTCATCCCGGGTCTGCACCCGATCCTGACCTTGTCCAAAATGGACCAGACCCTG
121 ---------+---------+---------+---------+---------+---------+ 180
    GACCTGAAGTAGGGCCCAGACGTGGGCTAGGACTGGAACAGGTTTTACCTGGTCTGGGAC
     L  D  F  I  P  G  L  H  P  I  L  T  L  S  K  M  D  Q  T  L  -
    GCTGTATACCAGCAGATCTTAACCTCCATGCCGTCCCGTAACGTTCTTCAGATCTCTAAC
181 ---------+---------+---------+---------+---------+---------+ 240
    CGACATATGGTCGTCTAGAATTGGAGGTACGGCAGGGCATTGCAAGAAGTCTAGAGATTG
     A  V  Y  Q  Q  I  L  T  S  M  P  S  R  N  V  L  Q  I  S  N  -
    GACCTCGAGAACCTTCGCGACCTGCTGCACGTGCTGGCATTCTCCAAATCCTGCCACCTG
241 ---------+---------+---------+---------+---------+---------+ 300
    CTGGAGCTCTTGGAAGCGCTGGACGACGTGCACGACCGTAAGAGGTTTAGGACGGTGGAC
     D  L  E  N  L  R  D  L  L  H  V  L  A  F  S  K  S  C  H  L  -
    CCATGGGCTTCAGGTCTTGAGACTCTGGACTCTCTGGGCGGGGTCCTGGAAGCATCCGGT
301 ---------+---------+---------+---------+---------+---------+ 360
    GGTACCCGAAGTCCAGAACTCTGAGACCTGAGAGACCCGCCCCAGGACCTTCGTAGGCCA
     P  W  A  S  G  L  E  T  L  D  S  L  G  G  V  L  E  A  S  G  -
    TACAGCACCGAAGTTGTTGCTCTGTCCCGTCTGCAGGGTTCCCTTCAGGACATGCTTTGG
361 ---------+---------+---------+---------+---------+---------+ 420
    ATGTCGTGGCTTCAACAACGAGACAGGGCAGACGTCCCAAGGGAAGTCCTGTACGAAACC
     Y  S  T  E  V  V  A  L  S  R  L  Q  G  S  L  Q  D  M  L  W  -
    CAGCTGGACCTGTCTCCGGGTTGTTAATGGATCC
421 ---------+---------+---------+---- 454
    GTCGACCTGGACAGAGGCCCAACAATTACCTAGG
     Q  L  D  L  S  P  G  C  *
``` and loading this onto a CM Sepharose fast flow column. The 20 column volume salt gradient was performed at 20 mM NaOAC, pH 5.5, 0M to 0.5 M NaCl. Step 9 was performed by diluting the CM Sepharose pool four fold with water, and adjusting the pH to 7.5. This mixture was made to 0.7 M ammonium sulfate. Twenty column volume reverse salt gradient was done at 5 mM NaOAC, pH 5.5, 0.2 M to 0M ammonium sulfate. Otherwise, the above steps were identical.

EXAMPLE 15

Dose Response Studies

An additional study demonstrated that there was a dose response to continuous administration of Ob protein. In this study, wild-type mice (non-obese, CD-1 mice, weighing 35–40 g) were administered recombinant murine Ob protein using methods similar to Examples 12 and 13. The results were as follows (with % body weight lost as compared to baseline, measured as above):

TABLE 10

Dose Response With Continuous Administration

| DOSE | TIME | % REDUCTION IN BODY WEIGHT |
|---|---|---|
| 0.03 mg/kg/day | Day 2 | 3.5% |
| 1 mg/kg/day | Day 2 | 7.5% |
| 1 mg/kg/day | Day 4 | 14% |

As can be seen, increasing the dose from 0.03 mg/kg/day to 1 mg/kg/day increased the weight lost from 3.5% to 7.5%. It is also noteworthy that at day 14, the 1 mg/kg/day dosage resulted in a 14% reduction in body weight.

EXAMPLE 16

Effects of Leptin on Body Composition of ob/ob Mice

C57Bl/6J ob/ob 16 week old mice were treated with 5 μg/g/day of murine leptin, vehicle, or received no treatment for 33 days. In a second experiment, 7 week old ob/ob mice were treated with 10 μg/g/day of human leptin, murine leptin, or vehicle for 12 days. The mice were sacrificed and total body weight, body composition, insulin levels, and glucose levels were evaluated. The data from these experiments are reported in Table 11.

body mass, and water mass. The date indicate that leptin significantly decreases body fat mass and has a marginal effect on lean body mass. However, the effects on lean body mass were not statistically significant.

Comparison of the insulin and glucose levels in leptin treated and control (untreated) mice indicates that leptin reduces blood sugar and insulin levels, and thus ameliorates these indicia of diabetes.

EXAMPLE 17

High Dose Effects of Leptin on Wild-type Mice

Lean controls of the ob/ob mice (C57Bl/6J+/?) were injected once a day i.p. with 10 μg/g murine leptin or vehicle (PBS), and body weight and food intake were measured over the next two weeks. There was a significant decrease in body weight from day 4 onward and a significant decrease in food intake for the first week. However, after one week, the levels of food intake became indistinguishable between both groups of mice. The animals were sacrificed at the end of the two weeks and body composition was determined. The results of the body composition analysis are shown on Table

TABLE 11

Body Weight, Composition, Insulin Levels, and Glucose Levels of Treate Mice

| Treatment Group | | 16 Week Old Mice, 5 μg/g/day leptin | | | 7 Week Old Mice, 10 μg/g/day leptin | | |
|---|---|---|---|---|---|---|---|
| Treatment | | Murine leptin | Vehicle | Control | Human Leptin | Murine Leptin | Vehicle |
| Total Body Weight | | 31.90 ± 2.8 | 64.10 ± 4.5 | 67.50 ± 6.2 | 31.00 ± 1.3 | 33.40 ± 2.4 | 42.70 ± 1.5 |
| Fat | Total (g) | 9.10 ± 1.7 | 38.30 ± 4.0 | 40.87 ± 6.1 | | | |
| | % | 28.40 ± 3.4 | 59.70 ± 2.1 | 60.34 ± 3.7 | | | |
| Lean Mass | Total (g) | 6.80 ± 1.0 | 7.60 ± 0.4 | 7.73 ± 0.5 | | | |
| | % | 21.30 ± 1.7 | 11.90 ± 1.2 | 11.57 ± 1.6 | | | |
| Water | Total (g) | 16.00 ± 0.8 | 18.20 ± 0.7 | 18.90 ± 1.0 | | | |
| | % | 50.30 ± 4.2 | 28.40 ± 1.0 | 28.10 ± 2.2 | | | |
| Insulin (UIU/ml) | | <2.0 | <2.0 | <2.0 | <2.0 | <2.0 | 21.4 |
| Glucose (mg/dl) | | 170.0 ± 20.9 | 337 ± 30.3 | 317.5 ± 51.0 | 258.3 ± 26.8 | 320.0 ± 44.0 | 789.0 ± 152.1 |

The body composition data demonstrate the effect of leptin on three compartments of the body: fat mass, lean 12. The data show a decrease in body fat of the animals receiving leptin versus the animals receiving PBS.

TABLE 12

Body Composition and Weight of Wildtype (+/?) Mice

| GROUP | C57B1/6J | BODY WT | FAT | | LEAN BODY MASS | | WATER | |
|---|---|---|---|---|---|---|---|---|
| | | | Total | % | Total | % | Total | % |
| Protein | 1 | 17.3 | 0.30 | 1.71% | 5.00 | 28.93% | 12.00 | 69.36% |
| | 2 | 20.5 | 2.39 | 11.65% | 5.41 | 26.40% | 12.70 | 61.95% |
| | 3 | 16.9 | 0.34 | 1.99% | 4.76 | 28.19% | 11.80 | 69.82% |
| | 4 | 18.3 | 0.84 | 4.62% | 5.16 | 28.17% | 12.30 | 67.21% |
| | 5 | 17.7 | 0.44 | 2.51% | 4.96 | 28.00% | 12.30 | 69.49% |
| | 6 | 18.7 | 2.56 | 13.72% | 4.84 | 25.86% | 11.30 | 60.43% |
| | 7 | 15.7 | 0.37 | 2.38% | 4.53 | 28.83% | 10.80 | 68.79% |
| | 8 | 16.4 | 0.29 | 1.79% | 4.51 | 27.48% | 11.60 | 70.73% |
| | 9 | 16.5 | 0.83 | 5.05% | 4.67 | 28.29% | 11.00 | 66.67% |
| | 10 | 14.9 | | | | | 10.40 | 69.80% |

TABLE 12-continued

Body Composition and Weight of Wildtype (+/?) Mice

| GROUP | C57B1/6J | BODY WT | FAT Total | % | LEAN BODY MASS Total | % | WATER Total | % |
|---|---|---|---|---|---|---|---|---|
| | Avg. | 17.3 | 0.93 | 5.04% | 4.87 | 27.79% | 11.62 | 67.43% |
| | Std. Dev. | 1.6 | 0.90 | 4.52% | 0.30 | 1.05% | 0.74 | 3.52% |
| Vehicle | 11 | 18.8 | 1.30 | 6.93% | 5.00 | 26.58% | 12.50 | 66.49% |
| | 12 | 17.6 | 2.17 | 12.34% | 4.53 | 25.73% | 10.90 | 61.93% |
| | 13 | 18.0 | 2.29 | 12.74% | 4.61 | 25.59% | 11.10 | 61.67% |
| | 14 | 19.6 | 3.79 | 19.34% | 4.61 | 23.52% | 11.20 | 57.14% |
| | 15 | 18.6 | 2.35 | 12.65% | 4.75 | 25.52% | 11.50 | 61.83% |
| | 16 | 17.3 | 1.96 | 11.32% | 4.54 | 26.25% | 10.80 | 62.43% |
| | 17 | 19.3 | 1.38 | 7.12% | 5.02 | 26.04% | 12.90 | 66.84% |
| | 18 | 20.6 | 4.16 | 20.19% | 4.94 | 23.98% | 11.50 | 55.83% |
| | 19 | 17.7 | 1.08 | 6.13% | 4.72 | 26.64% | 11.90 | 67.23% |
| | 20 | 19.5 | | | | | 12.30 | 63.08% |
| | Avg. | 18.7 | 2.28 | 12.09% | 4.75 | 25.54% | 11.66 | 62.45% |
| | Std. Dev. | 1.1 | 1.07 | 5.08% | 0.20 | 1.10% | 0.72 | 3.83% |

A second experiment showed the effects of twice a day i.p. injections of 12.5 µg/g of murine leptin on wild type C57Bl/6J mice. There was a significant decrease in body weight and food intake associate with twice daily injections of the polypeptide. For this experiment, the animals were placed in metabolic chambers. Food consisted of a powdered Purina #5001 chow diet. This diet differed from earlier experiments, which used the diet consisting of chow diet, tapioca, and water. Thus the food used in the metabolic chambers had a higher caloric content, which explains why the amount of food consumed differs from those animals on the water-containing diet.

The following is a list of references related to the above disclosure and particularly to the experimental procedures and discussions.

Bahary, N.; G. Zorich; J. D. Pachter; R. L. Leibel; and J. M. Friedman. 1991. Molecular genetic linkage maps of mouse chromosomes 4 and 6. *Genomics* 11:33–47.

Bahary, N.; D. McGraw; R. L. Leibel; and J. M. Friedman. 1991. Chromosomal microdissection of midmouse chromosome 4: Mapping of microclones relative to the mouse db gene. Submitted.

Bahary, N.; J. Pachter; R. Felman; R. L. Leibel; K. A. Albright; S. Cram; and J. M. Friedman. 1991. Molecular mapping of mouse chromosomes 4 and 6: Use of a flow-sorted Robertsonian chromosome. Submitted.

Blank, R.; J. Eppig; F. T. Fiedorek; W. N. Frankel; J. M. Friedman; K. Huppi; I. Jackson; and B. Mock. 1991. Mouse chromosome 4. *Mammalian Genome* 1(suppl): s51–s78.

Bogardus, C.; Ravussin, E.; Abbot, W.; Zasakzku, J. K.; Young, A.; Knowler, W. C.; Friedman, J. M.; R. L. Leibel; N. Bahary; D. A. Siegel; and G. Truett, G. 1991. Genetic analysis of complex disorders: Molecular mapping of obesity genes in mice and humans. *Annals of the New York Academy of Sciences* 630:100–115.

Friedman, J. M.; R. L. Leibel; and N. Bahary. 1991. Molecular mapping of obesity genes. *Mammalian Genome* 1: 130–144.

Friedman, J. M.; R. L. Leibel; N. Bahary; and G. Zorich. 1991. Molecular mapping of the mouse ob mutation. *Genomics* 11:1054–1062.

Harris, M. I. (1991). Diabetes Care 14 (suppl. 3), 639–648.

Harris, M. I.; Hadden, W. C.; Knowler, W. C.; and Bennett, P. H.(1987). Diabetes 36, 523–534.

Harris, R. B. S. (1990). FASEB J. 4, 3310–3318.

Jacobowitz, R., and Moll, P. O. (1986). N. Engl. J. Med. 315, 96–100.

Kessey, R. E. (1980). In Obesity, A. Stunkard, eds. (Philadelphia: W.B. Sauders Co.), pp. 144–166.

Kessey, R. E., and Pawley, T. L. (1986). Annu. Rev. Psychol. 37, 109–133.22.

Leibel, R. L., N. Bahary and J. M. Friedman. 1990. Genetic variation and nutrition in obesity: Approaches to the molecular genetics of obesity. In *Genetic variation and Nutrition* (Simopoulos, A. P. and Childs, B., eds.), S. Karger, Basel, pp. 90–101.

Siegel, D.; N. G. Irving; J. M. Friedman; and B. J. Wainwright. 1991. Localization of the cystic fibrosis transmembrane conductance regulator to mouse chromosome 6. *Cytogenetics Cell Genetics*, submitted.

Truett, G. E.; N. Bahary; J. M. Friedman; and R. L. leibel. 1991. The rat obesity fatty (fa) maps to chromosome 5:Evidence for homology with the mouse gene diabetes (db). *Proc. Natl. Acad. Sci. USA* 88:7806–7809.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various references are cited throughout this specification, each of which is incorporated herein by reference in its entirety.

What is claimed is:

1. A method for modifying body weight of an animal, the method comprising administering to the animal an effective amount of an OB polypeptide analog, capable of modulating body weight, comprising amino acids 22–167 of SEQ ID NOS: 2 or 4, wherein one or more amino acids selected from the group consisting of amino acids 53, 56, 71, 85, 89, 92, 95, 98, 110, 118, 121, 122, 126, 127, 128, 129, 132, 139, 157, 159, 163, and 166 is substituted with another amino acid.

2. A method for modifying body weight of an animal, the method comprising administering to the animal an effective amount of an OB polypeptide analog, capable of modulating body weight, comprising amino acids 22–167 of SEQ ID NO: 4 wherein the analog is selected from the group consisting of polypeptides wherein:

(a) the serine residue at position 53 is substituted with glycine, alanine, valine, cysteine, methionine, or threonine;

(b) the serine residue at position 98 is substituted with glycine, alanine, valine, cysteine, methionine, or threonine; and (c) the arginine residue at position number 92 is substituted with asparagine, lysine, histidine, glutamine, glutamic acid, aspartic acid, serine, threonine, methionine, or cysteine.

3. A method for modifying body weight of an animal, the method comprising administering to the animal an effective amount of an OB polypeptide, capable of modulating body weight, comprising amino acids 22–167 of SEQ ID NOS: 2 or 4 or amino acids 22–166 of SEQ ID NO: 5 or 6 wherein said polypeptide has an N-terminal amino acid sequence selected from the group consisting of:

(a) SEQ ID NO: 38;
   (b) SEQ ID NO: 98;
   (c) SEQ ID NO: 26;
   (d) SEQ ID NO: 27;
   (e) SEQ ID NO: 28;
   (f) SEQ ID NO: 99; and
   (g) glycine-serine-proline.

4. A method for modifying body weight of an animal, the method comprising administering to the animal an effective amount of an OB polypeptide analog, capable of modulating body weight, comprising amino acids 22–167 of SEQ ID NOS: 2 or 4, wherein one or more amino acids selected from the group consisting of amino acids 53, 56, 71, 85, 89, 92, 95, 98, 110, 118, 121, 122, 126, 127, 128, 129, 132, 139, 157, 159, 163, and 166 is substituted with another amino acid and wherein said analog has an N-terminal amino acid sequence selected from the group consisting of:

(a) SEQ ID NO: 38;
   (b) SEQ ID NO: 98;
   (c) SEQ ID NO: 26;
   (d) SEQ ID NO: 27;
   (e) SEQ ID NO: 28;
   (f) SEQ ID NO: 99; and
   (g) glycine-serine-proline.

5. A method for modifying body weight of an animal, the method comprising administering to the animal an effective amount of an OB polypeptide analog, capable of modulating body weight, comprising amino acids 22–166 of SEQ ID NOS: 5 or 6, wherein one or more amino acids selected from the group consisting of amino acids 52, 55, 70, 84, 88, 91, 94, 97, 109, 117, 120, 121, 125, 126, 127, 128, 131, 138, 156, 158, 162, and 165 is substituted with another amino acid.

6. A method for modifying body weight of an animal, the method comprising administering to the animal an effective amount of an OB polypeptide analog, capable of modulating body weight, comprising amino acids 22–166 of SEQ ID NO: 6 wherein the analog is selected from the group consisting of polypeptides wherein:

(a) the serine residue at position 52 is substituted with glycine, alanine, valine, cysteine, methionine, or threonine;

(b) the serine residue at position 97 is substituted with glycine, alanine, valine, cysteine, methionine, or threonine; and (c) the arginine residue at position number 91 is substituted with asparagine, lysine, histidine, glutamine, glutamic acid, aspartic acid, serine, threonine, methionine, or cysteine.

7. A method for modifying body weight of an animal, the method comprising administering to the animal an effective amount of an OB polypeptide analog, capable of modulating body weight, comprising amino acids 22–166 of SEQ ID NOS: 5 or 6, wherein one or more amino acids selected from the group consisting of amino acids 52, 55, 70, 84, 88, 91, 94, 97, 109, 117, 120, 121, 125, 126, 127, 128, 131, 138, 156, 158, 162, and 165 is substituted with another amino acid and wherein said analog has an N-terminal amino acid sequence selected from the group consisting of:

(a) SEQ ID NO: 38;

(b) SEQ ID NO: 98;

(c) SEQ ID NO: 26;

(d) SEQ ID NO: 27;

(e) SEQ ID NO: 28;

(f) SEQ ID NO: 99; and (g) glycine-serine-proline.

8. The method according to claim 1, 2, 3, 4, 5, 6, or 7 wherein the OB polypeptide or polypeptide analog is a recombinant polypeptide or polypeptide analog.

9. The method according to claim 1, 2, 3, 4, 5, 6, or 7 wherein the OB polypeptide or polypeptide analog is a chemically synthesized polypeptide or polypeptide analog.

10. The method according to claim 1, 2, 3, 4, 5, 6, or 7 wherein the OB polypeptide or polypeptide analog has one or more polymers attached thereto.

11. The method according to claim 10, wherein at least one of said polymers is a water-soluble polymer.

12. The method according to claim 11, wherein the water-soluble polymer is polyethylene glycol.

13. The method according to claim 12, wherein the polypeptide or polypeptide analog is mono-, di-, tri- or tetrapegylated.

14. The method according to claim 13 wherein the polypeptide or polypeptide analog is N-terminal monopegylated.

15. The method according to claim 10, wherein at least one of said polymers is a pharmaceutically acceptable polymer.

16. The method according to claim 15, wherein said pharmaceutically acceptable polymer is a water soluble polymer.

17. The method according to claim 10, wherein at least one of said polymers is a polyamino acid.

18. The method according to claim 10, wherein at least one of said polymers is a branched or unbranched polymer.

19. The method according to claim 10, wherein at least one of said polymers is N-terminally attached to said polypeptide or polypeptide analog.

20. The method according to claim 10, wherein at least one of said polymers is C-terminally attached to said polypeptide or polypeptide analog.

21. The method according to claim 10, wherein at least one of said polymers is attached by at least one covalent bond through an amino acid residue of said polypeptide or polypeptide analog via a reactive group.

22. The method according to claim 21, wherein said reactive group is a free amino or carboxyl group.

23. The method according to claim 21, wherein said amino acid residue is selected from the group consisting of lysine, aspartic acid and glutamic acid.

24. The method according to claim 10, wherein the number of said polymers attached is one, two, three or four.

25. The method according to claim 24 wherein said two, three or four polymers are the same polymer.

26. The method according to claim 24 wherein said two, three or four polymers are two, three or four different polymers.

27. The method according to claim 1, 2, 3, 4, 5, 6 or 7 wherein the OB polypeptide or polypeptide analog is administered by intravenous, intraarterial, intraperitoneal, intramuscular, subcutaneous, nasal, oral or pulmonary delivery.

* * * * *

UNITED STATES PATENT AND TRADEMARK OFFICE
CERTIFICATE OF CORRECTION

PATENT NO.    : 6,350,730 B1
DATED         : February 26, 2002
INVENTOR(S)   : Jeffrey M. Friedman, Yiying Zhang and Ricardo Proenca It is certified that error appears in the above-identified patent and that said Letters Patent is hereby corrected as shown below:

<u>Title page,</u>
Item [54], please change the Title from "OB POLYPEPTIDES AND MODIFIED FORM AS MODULATORS OF BODY WEIGHT" to read -- OB POLYPEPTIDES, AS MODULATORS OF BODY WEIGHT --.

Signed and Sealed this

Twentieth Day of August, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 98

(2) INFORMATION FOR SEQ ID NO: 1:

(i) SEQUENCE CHARACTERISTICS:
        (A) LENGTH: 2793 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: Murine ob cDNA (iii) HYPOTHETICAL: NO (iv) ANTI-SENSE: NO (vi) ORIGINAL SOURCE:
        (A) ORGANISM: Murine (ix) FEATURE:
        (A) NAME/KEY: CDS
        (B) LOCATION: 57..560

(xi) SEQUENCE DESCRIPTION: SEQ ID NO: 1:

```
GGATCCCTGC TCCAGCAGCT GCAAGGTGCA AGAAGAAGAA GATCCCAGGG AGGAAA                  56

ATG TGC TGG AGA CCC CTG TGT CGG TTC CTG TGG CTT TGG TCC TAT CTG              104
Met Cys Trp Arg Pro Leu Cys Arg Phe Leu Trp Leu Trp Ser Tyr Leu
 1               5                  10                  15

TCT TAT GTT CAA GCA GTG CCT ATC CAG AAA GTC CAG GAT GAC ACC AAA              152
Ser Tyr Val Gln Ala Val Pro Ile Gln Lys Val Gln Asp Asp Thr Lys
                20                  25                  30

ACC CTC ATC AAG ACC ATT GTC ACC AGG ATC AAT GAC ATT TCA CAC ACG              200
Thr Leu Ile Lys Thr Ile Val Thr Arg Ile Asn Asp Ile Ser His Thr
            35                  40                  45

CAG TCG GTA TCC GCC AAG CAG AGG GTC ACT GGC TTG GAC TTC ATT CCT              248
Gln Ser Val Ser Ala Lys Gln Arg Val Thr Gly Leu Asp Phe Ile Pro
        50                  55                  60

GGG CTT CAC CCC ATT CTG AGT TTG TCC AAG ATG GAC CAG ACT CTG GCA              296
Gly Leu His Pro Ile Leu Ser Leu Ser Lys Met Asp Gln Thr Leu Ala
 65                  70                  75                  80

GTC TAT CAA CAG GTC CTC ACC AGC CTG CCT TCC CAA AAT GTG CTG CAG              344
Val Tyr Gln Gln Val Leu Thr Ser Leu Pro Ser Gln Asn Val Leu Gln
                85                  90                  95

ATA GCC AAT GAC CTG GAG AAT CTC CGA GAC CTC CTC CAT CTG CTG GCC              392
Ile Ala Asn Asp Leu Glu Asn Leu Arg Asp Leu Leu His Leu Leu Ala
               100                 105                 110

TTC TCC AAG AGC TGC TCC CTG CCT CAG ACC AGT GGC CTG CAG AAG CCA              440
Phe Ser Lys Ser Cys Ser Leu Pro Gln Thr Ser Gly Leu Gln Lys Pro
           115                 120                 125

GAG AGC CTG GAT GGC GTC CTG GAA GCC TCA CTC TAC TCC ACA GAG GTG              488
Glu Ser Leu Asp Gly Val Leu Glu Ala Ser Leu Tyr Ser Thr Glu Val
       130                 135                 140

GTG GCT TTG AGC AGG CTG CAG GGC TCT CTG CAG GAC ATT CTT CAA CAG              536
Val Ala Leu Ser Arg Leu Gln Gly Ser Leu Gln Asp Ile Leu Gln Gln
145                 150                 155                 160

TTG GAT GTT AGC CCT GAA TGC TGA AGTTTCAAAG GCCACCAGGC TCCCAAGA               588
Leu Asp Val Ser Pro Glu Cys *
               165

ATCATGTAGA GGGAAGAAAC CTTGGCTTCC AGGGGTCTTC AGGAGAAGAG AGCCATGTGC            648
```

```
ACACATCCAT CATTCATTTC TCTCCCTCCT GTAGACCACC CATCCAAAGG CATGACTCCA      708

CAATGCTTGA CTCAAGTTAT CCACACAACT TCATGAGCAC AAGGAGGGGC CAGCCTGCAG      768

AGGGGACTCT CACCTAGTTC TTCAGCAAGT AGAGATAAGA GCCATCCCAT CCCCTCCATG      828

TCCCACCTGC TCCGGGTACA TGTTCCTCCG TGGGTACACG CTTCGCTGCG GCCCAGGAGA      888

GGTGAGGTAG GGATGGGTAG AGCCTTTGGG CTGTCTCAGA GTCTTTGGGA GCACCGTGAA      948

GGCTGCATCC ACACACAGCT GGAAACTCCC AAGCAGCACA CGATGGAAGC ACTTATTTAT     1008

TTATTCTGCA TTCTATTTTG GATGGATCTG AAGCAAGGCA TCAGCTTTTT CAGGCTTTGG     1068

GGGTCAGCCA GGATGAGGAA GGCTCCTGGG GTGCTGCTTT CAATCCTATT GATGGGTCTG     1128

CCCGAGGCAA ACCTAATTTT TGAGTGACTG GAAGGAAGGT TGGGATCTTC CAAACAAGAG     1188

TCTATGCAGG TAGCGCTCAA GATTGACCTC TGGTGACTGG TTTTGTTTCT ATTGTGACTG     1248

ACTCTATCCA AACACGTTTG CAGCGGCATT GCCGGGAGCA TAGGCTAGGT TATTATCAAA     1308

AGCAGATGAA TTTTGTCAAG TGTAATATGT ATCTATGTGC ACCTGAGGGT AGAGGATGTG     1368

TTAGAGGGAG GGTGAAGGAT CCGGAAGTGT TCTCTGAATT ACATATGTGT GGTAGGCTTT     1428

TCTGAAAGGG TGAGGCATTT TCTTACCTCT GTGGCCACAT AGTGTGGCTT TGTGAAAAGG     1488

ACAAAGGAGT TGACTCTTTC CGGAACATTT GGAGTGTACC AGGCACCCTT GGAGGGGCTA     1548

AAGCTACAGG CCTTTTGTTG GCATATTGCT GAGCTCAGGG AGTGAGGGCC CCACATTTGA     1608

GACAGTGAGC CCCAAGAAAA GGGTCCCTGG TGTAGATCTC CAAGGTTGTC AGGGTTGAG      1668

CTCACAATGC GTTTCTTAAG CAGGTAGACG TTTGCATGCC AATATGTGGT TCTCATCTGA     1728

TTGGTTCATC CAAAGTAGAA CCCTGTCTCC CACCCATTCT GTGGGAGTT TTGTTCCAGT      1788

GGGAATGAGA AATCACTTAG CAGATGGTCC TGAGCCCTGG GCCAGCACTG CTGAGGAAGT     1848

GCCAGGGCCC CAGGCCAGGC TGCCAGAATT GCCCTTCGGG CTGGAGGATG AACAAAGGGG     1908

CTTGGGTTTT TCCATCACCC CTGCACCCTA TGTCACCATC AAACTGGGGG GCAGATCAGT     1968

GAGAGGACAC TTGATGGAAA GCAATACACT TTAAGACTGA GCACAGTTTC GTGCTCAGCT     2028

CTGTCTGGTG CTGTGAGCTA GAGAAGCTCA CCACATACAT ATAAAAATCA GAGGCTCATG     2088

TCCCTGTGGT TAGACCCTAC TCGCGGCGGT GTACTCCACC ACAGCAGCAC CGCACCGCTG     2148

GAAGTACAGT GCTGTCTTCA ACAGGTGTGA AAGAACCTGA GCTGAGGGTG ACAGTGCCCA     2208

GGGGAACCCT GCTTGCAGTC TATTGCATTT ACATACCGCA TTTCAGGGCA CATTAGCATC     2268

CACTCCTATG GTAGCACACT GTTGACAATA GGACAAGGGA TAGGGGTTGA CTATCCCTTA     2328

TCCAAAATGC TTGGGACTAG AAGAGTTTTG GATTTTAGAG TCTTTTCAGG CATAGGTATA     2388

TTTGAGTATA TATAAAATGA GATATCTTGG GGATGGGCC CAAGTATAAA CATGAAGTTC      2448

ATTTATATTT CATAATACCG TATAGACACT GCTTGAAGTG TAGTTTTATA CAGTGTTTTA     2508

AATAACGTTG TATGCATGAA AGACGTTTTT ACAGCATGAA CCTGTCTACT CATGCCAGCA     2568

CTCAAAAACC TTGGGGTTTT GGAGCAGTTT GGATCTTGGG TTTTCTGTTA AGAGATGGTT     2628

AGCTTATACC TAAAACCATA ATGGCAAACA GGCTGCAGGA CCAGACTGGA TCCTCAGCCC     2688

TGAAGTGTGC CCTTCCAGCC AGGTCATACC CTGTGGAGGT GAGCGGGATC AGGTTTTGTG     2748

GTGCTAAGAG AGGAGTTGGA GGTAGATTTT GGAGGATCTG AGGGC                    2793
```

(2) INFORMATION FOR SEQ ID NO: 2:

(i) SEQUENCE CHARACTERISTICS:
    (A) LENGTH: 167 amino acids
    (B) TYPE: amino acid (D) TOPOLOGY: linear (ii) MOLECULE TYPE: protein
          (A) DESCRIPTION: Murine ob polypeptide (xi) SEQUENCE DESCRIPTION: SEQ ID NO: 2:

Met Cys Trp Arg Pro Leu Cys Arg Phe Leu Trp Leu Trp Ser Tyr Leu
 1               5                  10                  15

Ser Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ala Lys Gln Arg Val Thr Gly Leu Asp Phe Ile Pro
     50                  55                  60

Gly Leu His Pro Ile Leu Ser Leu Ser Lys Met Asp Gln Thr Leu Ala
 65                  70                  75                  80

Val Tyr Gln Gln Val Leu Thr Ser Leu Pro Ser Gln Asn Val Leu Gln
                85                  90                  95

Ile Ala Asn Asp Leu Glu Asn Leu Arg Asp Leu Leu His Leu Leu Ala
            100                 105                 110

Phe Ser Lys Ser Cys Ser Leu Pro Gln Thr Ser Gly Leu Gln Lys Pro
        115                 120                 125

Glu Ser Leu Asp Gly Val Leu Glu Ala Ser Leu Tyr Ser Thr Glu Val
    130                 135                 140

Val Ala Leu Ser Arg Leu Gln Gly Ser Leu Gln Asp Ile Leu Gln Gln
145                 150                 155                 160

Leu Asp Val Ser Pro Glu Cys
                165

(2) INFORMATION FOR SEQ ID NO: 3:

(i) SEQUENCE CHARACTERISTICS:
          (A) LENGTH: 700 base pairs
          (B) TYPE: nucleic acid
          (C) STRANDEDNESS: double
          (D) TOPOLOGY: linear (ii) MOLECULE TYPE: cDNA
          (A) DESCRIPTION: Human ob cDNA where N represents any
              nucleotide (iii) HYPOTHETICAL: NO (iv) ANTI-SENSE: NO (vi) ORIGINAL SOURCE:
          (A) ORGANISM: Human (ix) FEATURE:
          (A) NAME/KEY: CDS
          (B) LOCATION: 46..546

(xi) SEQUENCE DESCRIPTION: SEQ ID NO: 3:

NNNGNNGTTG CAAGGCCCAA GAAGCCCANN NTCCTGGGAA GGAAA ATG CAT TGG           54
                                                 Met His Trp
                                                   1

GGA ACC CTG TGC GGA TTC TTG TGG CTT TGG CCC TAT CTT TTC TAT GTC        102
Gly Thr Leu Cys Gly Phe Leu Trp Leu Trp Pro Tyr Leu Phe Tyr Val
        5                  10                  15

CAA GCT GTG CCC ATC CAA AAA GTC CAA GAT GAC ACC AAA ACC CTC ATC        150
Gln Ala Val Pro Ile Gln Lys Val Gln Asp Asp Thr Lys Thr Leu Ile
    20                  25                  30                  35

AAG ACA ATT GTC ACC AGG ATC AAT GAC ATT TCA CAC ACG CAG TCA GTC        198

-continued

```
Lys Thr Ile Val Thr Arg Ile Asn Asp Ile Ser His Thr Gln Ser Val
                 40                  45                  50

TCC TCC AAA CAG AAA GTC ACC GGT TTG GAC TTC ATT CCT GGG CTC CAC         246
Ser Ser Lys Gln Lys Val Thr Gly Leu Asp Phe Ile Pro Gly Leu His
             55                  60                  65

CCC ATC CTG ACC TTA TCC AAG ATG GAC CAG ACA CTG GCA GTC TAC CAA         294
Pro Ile Leu Thr Leu Ser Lys Met Asp Gln Thr Leu Ala Val Tyr Gln
         70                  75                  80

CAG ATC CTC ACC AGT ATG CCT TCC AGA AAC GTG ATC CAA ATA TCC AAC         342
Gln Ile Leu Thr Ser Met Pro Ser Arg Asn Val Ile Gln Ile Ser Asn
     85                  90                  95

GAC CTG GAG AAC CTC CGG GAT CTT CTT CAC GTG CTG GCC TTC TCT AAG         390
Asp Leu Glu Asn Leu Arg Asp Leu Leu His Val Leu Ala Phe Ser Lys
100                 105                 110                 115

AGC TGC CAC TTG CCC TGG GCC AGT GGC CTG GAG ACC TTG GAC AGC CTG         438
Ser Cys His Leu Pro Trp Ala Ser Gly Leu Glu Thr Leu Asp Ser Leu
                120                 125                 130

GGG GGT GTC CTG GAA GCT TCA GGC TAC TCC ACA GAG GTG GTG GCC CTG         486
Gly Gly Val Leu Glu Ala Ser Gly Tyr Ser Thr Glu Val Val Ala Leu
            135                 140                 145

AGC AGG CTG CAG GGG TCT CTG CAG GAC ATG CTG TGG CAG CTG GAC CTC         534
Ser Arg Leu Gln Gly Ser Leu Gln Asp Met Leu Trp Gln Leu Asp Leu
        150                 155                 160

AGC CCT GGG TGC TGAGGCCTT GAAGGTCACT CTTCCTGCAA GGACTNACGT              585
Ser Pro Gly Cys
    165

TAAGGGAAGG AACTCTGGTT TCCAGGTATC TCCAGGATTG AAGAGCATTG CATGGACACC       645

CCTTATCCAG GACTCTGTCA ATTTCCCTGA CTCCTCTAAG CCACTCTTCC AAAGG            700

(2) INFORMATION FOR SEQ ID NO: 4:

(i) SEQUENCE CHARACTERISTICS:
        (A) LENGTH: 167 amino acids
        (B) TYPE: amino acid
        (D) TOPOLOGY: linear (ii) MOLECULE TYPE: protein
        (A) DESCRIPTION: Human ob polypeptide (vi) ORIGINAL SOURCE:

(xi) SEQUENCE DESCRIPTION: SEQ ID NO: 4:

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
             20                  25                  30

Thr Leu Ile Lys Thr Ile Val Thr Arg Ile Asn Asp Ile Ser His Thr
         35                  40                  45

Gln Ser Val Ser Ser Lys Gln Lys Val Thr Gly Leu Asp Phe Ile Pro
     50                  55                  60

Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
             85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
```

```
                  130                 135                 140
Val Ala Leu Ser Arg Leu Gln Gly Ser Leu Gln Asp Met Leu Trp Gln
145                 150                 155                 160

Leu Asp Leu Ser Pro Gly Cys
                165
```

(2) INFORMATION FOR SEQ ID NO: 5:

(i) SEQUENCE CHARACTERISTICS:
        (A) LENGTH: 166 amino acids
        (B) TYPE: amino acid
        (D) TOPOLOGY: linear (ii) MOLECULE TYPE: protein
        (A) DESCRIPTION: Murine ob polypeptide lacking Gln at
            position 49

(vi) ORIGINAL SOURCE:
        (A) ORGANISM: Murine (xi) SEQUENCE DESCRIPTION: SEQ ID NO: 5:

```
Met Cys Trp Arg Pro Leu Cys Arg Phe Leu Trp Leu Trp Ser Tyr Leu
  1                 5                  10                  15

Ser Tyr Val Gln Ala Val Pro Ile Gln Lys Val Gln Asp Asp Thr Lys
                 20                  25                  30

Thr Leu Ile Lys Thr Ile Val Thr Arg Ile Asn Asp Ile Ser His Thr
                 35                  40                  45

Ser Val Ser Ala Lys Gln Arg Val Thr Gly Leu Asp Phe Ile Pro Gly
 50                  55                  60

Leu His Pro Ile Leu Ser Leu Ser Lys Met Asp Gln Thr Leu Ala Val
 65                  70                  75                  80

Tyr Gln Gln Val Leu Thr Ser Leu Pro Ser Gln Asn Val Leu Gln Ile
                 85                  90                  95

Ala Asn Asp Leu Glu Asn Leu Arg Asp Leu Leu His Leu Leu Ala Phe
                100                 105                 110

Ser Lys Ser Cys Ser Leu Pro Gln Thr Ser Gly Leu Gln Lys Pro Glu
                115                 120                 125

Ser Leu Asp Gly Val Leu Glu Ala Ser Leu Tyr Ser Thr Glu Val Val
130                 135                 140

Ala Leu Ser Arg Leu Gln Gly Ser Leu Gln Asp Ile Leu Gln Gln Leu
145                 150                 155                 160

Asp Val Ser Pro Glu Cys
                165
```

(2) INFORMATION FOR SEQ ID NO: 6:

(i) SEQUENCE CHARACTERISTICS:
        (A) LENGTH: 166 amino acids
        (B) TYPE: amino acid
        (D) TOPOLOGY: linear (ii) MOLECULE TYPE: protein
        (A) DESCRIPTION: Human ob polypeptide lacking Gln at
            position 49

(vi) ORIGINAL SOURCE:
        (A) ORGANISM: Human (xi) SEQUENCE DESCRIPTION: SEQ ID NO: 6:

```
Met His Trp Gly Thr Leu Cys Gly Phe Leu Trp Leu Trp Pro Tyr Leu
  1                 5                  10                  15

Phe Tyr Val Gln Ala Val Pro Ile Gln Lys Val Gln Asp Asp Thr Lys
```

```
                    20                  25                  30
Thr Leu Ile Lys Thr Ile Val Thr Arg Ile Asn Asp Ile Ser His Thr
            35                  40                  45
Ser Val Ser Ser Lys Gln Lys Val Thr Gly Leu Asp Phe Ile Pro Gly
50                  55                  60
Leu His Pro Ile Leu Thr Leu Ser Lys Met Asp Gln Thr Leu Ala Val
65                  70                  75                  80
Tyr Gln Gln Ile Leu Thr Ser Met Pro Ser Arg Asn Val Ile Gln Ile
                85                  90                  95
Ser Asn Asp Leu Glu Asn Leu Arg Asp Leu Leu His Val Leu Ala Phe
            100                 105                 110
Ser Lys Ser Cys His Leu Pro Trp Ala Ser Gly Leu Glu Thr Leu Asp
        115                 120                 125
Ser Leu Gly Gly Val Leu Glu Ala Ser Gly Tyr Ser Thr Glu Val Val
    130                 135                 140
Ala Leu Ser Arg Leu Gln Gly Ser Leu Gln Asp Met Leu Trp Gln Leu
145                 150                 155                 160
Asp Leu Ser Pro Gly Cys
            165

(2) INFORMATION FOR SEQ ID NO: 7:

(i) SEQUENCE CHARACTERISTICS:
        (A) LENGTH: 176 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: exon 2G7

(iii) HYPOTHETICAL: NO (iv) ANTI-SENSE: NO (xi) SEQUENCE DESCRIPTION: SEQ ID NO: 7:

GTGCAAGAAG AAGAAGATCC CAGGGCAGGA AAATGTGCTG GAGACCCCTG TGTCGGGTCC      60

NGTGGNTTTG GTCCTATCTG TCTTATGTNC AAGCAGTGCC TATCCAGAAA GTCCAGGATG     120

ACACCAAAAG CCTCATCAAG ACCATTGTCA NCAGGATCAC TGANATTTCA CACACG         176

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: PCR 5' primer for exon 2G7

(iii) HYPOTHETICAL: NO (iv) ANTI-SENSE: NO (xi) SEQUENCE DESCRIPTION: SEQ ID NO: 8:

CCAGGGCAGG AAAATGTG                                                    18

(2) INFORMATION FOR SEQ ID NO: 9:

(i) SEQUENCE CHARACTERISTICS:
        (A) LENGTH: 22 base pairs
        (B) TYPE: nucleic acid
```

(C) STRANDEDNESS: single
        (D) TOPOLOGY: linear (ii) MOLECULE TYPE: DNA (primer)
        (A) DESCRIPTION: PCR 3' primer for exon 2G7

(iii) HYPOTHETICAL: NO (iv) ANTI-SENSE: YES (xi) SEQUENCE DESCRIPTION: SEQ ID NO: 9:

```
CATCCTGGAC TTTCTGGATA GG                                       22
```

(2) INFORMATION FOR SEQ ID NO: 10:

(i) SEQUENCE CHARACTERISTICS:
        (A) LENGTH: 23 amino acids
        (B) TYPE: amino acid
        (D) TOPOLOGY: linear (ii) MOLECULE TYPE: peptide
        (A) DESCRIPTION: putative N-terminal signal peptide (xi) SEQUENCE DESCRIPTION: SEQ ID NO: 10:

```
Met Cys Trp Arg Pro Leu Cys Arg Phe Leu Trp Leu Trp Ser Tyr Leu
1               5                   10                  15

Ser Tyr Val Gln Ala Val Pro
            20
```

(2) INFORMATION FOR SEQ ID NO: 11:

(i) SEQUENCE CHARACTERISTICS:
        (A) LENGTH: 287 base pairs
        (B) TYPE: nucleic acid
        (C) STRANDEDNESS: double
        (D) TOPOLOGY: circular (ii) MOLECULE TYPE: DNA (plasmid)
        (A) DESCRIPTION: pET-15b expression vector (iii) HYPOTHETICAL: NO (iv) ANTI-SENSE: NO (ix) FEATURE:
        (A) NAME/KEY: T7 promoter
        (B) LOCATION: 20..37

(ix) FEATURE:
        (A) NAME/KEY: lac operator
        (B) LOCATION: 39..64

(ix) FEATURE:
        (A) NAME/KEY: CDS
        (B) LOCATION: 108..243

(ix) FEATURE:
        (A) NAME/KEY: His-Tag
        (B) LOCATION: 123..137

(ix) FEATURE:
        (A) NAME/KEY: Thrombin cleavage site
        (B) LOCATION: 184..196

(xi) SEQUENCE DESCRIPTION: SEQ ID NO: 11:

```
AGATCTCGAT CCCGCGAAAT TAATACGACT CACTATAGGG GAATTGTGAG CGGATAACAA    60

TTCCCCTCTA CAAATAATTT TGTTTAACTT TAAGAAGGAG ATATACC ATG GGC AGC     116
                                                    Met Gly Ser
                                                    1

AGC CAT CAT CAT CAT CAT CAC AGC AGC GGC CTG GTG CCG CGC GGC AGC    164
Ser His His His His His His Ser Ser Gly Leu Val Pro Arg Gly Ser
```

```
         5                   10                  15
CAT ATG CTC GAG GAT CCC GCT GCT AAC AAA GCC CGA AAG GAA GCT GAG        212
His Met Leu Glu Asp Pro Ala Ala Asn Lys Ala Arg Lys Glu Ala Glu
 20                  25                  30                  35

TTG GCT GCT GCC ACC GCT GAG CAA TAA CTA G CATAACCCCT TGGGGCCTCT        263
Leu Ala Ala Ala Thr Ala Glu Gln   *
                     40

AAACGGGTCT TGAGGGGTTT TTTG                                             287
```

(2) INFORMATION FOR SEQ ID NO: 12:

(i) SEQUENCE CHARACTERISTICS:
        (A) LENGTH: 43 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Gly Ser Ser His His His His His His Ser Ser Gly Leu Val Pro
 1               5                  10                  15

Arg Gly Ser His Met Leu Glu Asp Pro Ala Ala Asn Lys Ala Arg Lys
             20                  25                  30

Glu Ala Glu Leu Ala Ala Ala Thr Ala Glu Gln
         35                  40
```

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Murine 5' primer (iii) HYPOTHETICAL: NO (iv) ANTI-SENSE: NO (xi) SEQUENCE DESCRIPTION: SEQ ID NO: 13:

```
CTTATGTTCA TATGGTGCCG ATCCAGAAAG TC                                    32
```

(2) INFORMATION FOR SEQ ID NO: 14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Murine 3' primer (iii) HYPOTHETICAL: NO (iv) ANTI-SENSE: Yes (xi) SEQUENCE DESCRIPTION: SEQ ID NO: 14:

```
TCCCTCTACA TATGTCTTGG GAGCCTGGTG GC                                    32
```

(2) INFORMATION FOR SEQ ID NO: 15:

(i) SEQUENCE CHARACTERISTICS:
        (A) LENGTH: 32 base pairs
        (B) TYPE: nucleic acid

```
            (C) STRANDEDNESS: single
            (D) TOPOLOGY: linear (ii) MOLECULE TYPE: DNA (primer)
            (A) DESCRIPTION: Human 5' primer (iii) HYPOTHETICAL: NO (iv) ANTI-SENSE: NO (xi) SEQUENCE DESCRIPTION: SEQ ID NO: 15:

TCTATGTCCA TATGGTGCCG ATCCAAAAAG TC                                32

(2) INFORMATION FOR SEQ ID NO: 16:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (primer)
            (A) DESCRIPTION: Human 3' primer (iii) HYPOTHETICAL: NO (iv) ANTI-SENSE: Yes (xi) SEQUENCE DESCRIPTION: SEQ ID NO: 16:

TTCCTTCCCA TATGGTACTC CTTGCAGGAA GA                                32

(2) INFORMATION FOR SEQ ID NO: 17:

(i) SEQUENCE CHARACTERISTICS:
            (A) LENGTH: 11 base pairs
            (B) TYPE: nucleic acid
            (C) STRANDEDNESS: double
            (D) TOPOLOGY: linear (ii) MOLECULE TYPE: cDNA
            (A) DESCRIPTION: Splice acceptor site in ob (iii) HYPOTHETICAL: NO (iv) ANTI-SENSE: NO (ix) FEATURE:
            (A) NAME/KEY: Splice acceptor site (xi) SEQUENCE DESCRIPTION: SEQ ID NO: 17:

AGCAGTCGGT A                                                       11

(2) INFORMATION FOR SEQ ID NO: 18:

(i) SEQUENCE CHARACTERISTICS:
            (A) LENGTH: 16 amino acids
            (B) TYPE: amino acid
            (D) TOPOLOGY: unknown (ii) MOLECULE TYPE: peptide
            (A) DESCRIPTION: ob peptide fragment (v) FRAGMENT TYPE: internal (vi) ORIGINAL SOURCE:
            (A) ORGANISM: Murine (xi) SEQUENCE DESCRIPTION: SEQ ID NO: 18:

Val Pro Ile Gln Lys Val Gln Asp Asp Thr Lys Thr Leu Ile Lys Thr
 1               5                  10                  15
```

```
(2) INFORMATION FOR SEQ ID NO: 19:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide
        (A) DESCRIPTION: ob peptide fragment (v) FRAGMENT TYPE: internal (vi) ORIGINAL SOURCE:
        (A) ORGANISM: Murine (xi) SEQUENCE DESCRIPTION: SEQ ID NO: 19:

Leu His Pro Ile Leu Ser Leu Ser Lys Met Asp Gln Thr Leu Ala
1               5                   10                  15

(2) INFORMATION FOR SEQ ID NO: 20:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide
        (A) DESCRIPTION: ob peptide fragment (v) FRAGMENT TYPE: internal (vi) ORIGINAL SOURCE:
        (A) ORGANISM: Murine (xi) SEQUENCE DESCRIPTION: SEQ ID NO: 20:

Ser Lys Ser Cys Ser Leu Pro Gln Thr Ser Gly Leu Gln Lys Pro Glu
1               5                   10                  15

Ser Leu Asp (2) INFORMATION FOR SEQ ID NO: 21:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide
        (A) DESCRIPTION: ob peptide fragment (v) FRAGMENT TYPE: Carboxyl terminal (vi) ORIGINAL SOURCE:
        (A) ORGANISM: Murine (xi) SEQUENCE DESCRIPTION: SEQ ID NO: 21:

Ser Arg Leu Gln Gly Ser Leu Gln Asp Ile Leu Gln Gln Leu Asp Val
1               5                   10                  15

Ser Pro Glu Cys
        20

(2) INFORMATION FOR SEQ ID NO: 22:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: portion of the human ob gene including
            noncoding sequence upstream of first exon, coding
```

```
           sequence of first exon, and 5' region of first union (iii) HYPOTHETICAL: NO (iv) ANTI-SENSE: NO (vi) ORIGINAL SOURCE:
        (A) ORGANISM: Human (ix) FEATURE:
        (A) NAME/KEY: CDS
        (B) LOCATION: 38..181

(ix) FEATURE:
        (A) NAME/KEY: 5' region of first intron
        (B) LOCATION: 182..414

(ix) FEATURE:
        (A) NAME/KEY: 5' noncoding sequence of the human ob gene from
            which the HOB 1gF DNA primer was generated
        (B) LOCATION: 11..28

(ix) FEATURE:
        (A) NAME/KEY: intronic sequence of the human ob gene from
            which the HOB 1gR primer was generated
        (B) LOCATION: 241..260

(xi) SEQUENCE DESCRIPTION: SEQ ID NO: 22:

GGTTGCAAGG CCCAAGAAGC CCATCCTGGG AAGGAAA ATG CAT TGG GGA ACC CTG       55
                                        Met His Trp Gly Thr Leu
                                         1               5

TGC GGA TTC TTG TGG CTT TGG CCC TAT CTT TTC TAT GTC CAA GCT GTG      103
Cys Gly Phe Leu Trp Leu Trp Pro Tyr Leu Phe Tyr Val Gln Ala Val
         10                  15                  20

CCC ATC CAA AAA GTC CAA GAT GAC ACC AAA ACC CTC ATC AAG ACA ATT      151
Pro Ile Gln Lys Val Gln Asp Asp Thr Lys Thr Leu Ile Lys Thr Ile
     25                  30                  35

GTC ACC AGG ATC AAT GAC ATT TCA CAC ACG GTAAGGAGAG TATGCGGGGA        201
Val Thr Arg Ile Asn Asp Ile Ser His Thr
         40                  45

CAAAGTAGAA CTGCAGCCAG CCCAGCACTG GCTCCTAGTG GCACTGGACC CAGATAGTCC    261

AAGAAACATT TATTGAACGC CTCCTGAATG CCAGGCACCT ACTGGAAGCT GAGAAGGATT    321

TTGGATAGCA CAGGGCTCCA CTCTTTCTGG TTGTTTCTTN TGGCCCCCTC TGCCTGCTGA    381

GATNCCAGGG GTTAGNGGTT CTTAATTCCT AAA                                 414

(2) INFORMATION FOR SEQ ID NO: 23:

(i) SEQUENCE CHARACTERISTICS:
        (A) LENGTH: 48 amino acids
        (B) TYPE: amino acid
        (D) TOPOLOGY: linear (ii) MOLECULE TYPE: protein
        (A) DESCRIPTION: N-terminal portion of the human ob protein (xi) SEQUENCE DESCRIPTION: SEQ ID NO: 23:

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
                 20                  25                  30

Thr Leu Ile Lys Thr Ile Val Thr Arg Ile Asn Asp Ile Ser His Thr
             35                  40                  45

(2) INFORMATION FOR SEQ ID NO: 24:

(i) SEQUENCE CHARACTERISTICS:
```

```
        (A) LENGTH: 801 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: portion of the human ob gene including
            3' region of first intron, coding sequence of second
            exon, and 3' noncoding sequence (iii) HYPOTHETICAL: NO (iv) ANTI-SENSE: NO (vi) ORIGINAL SOURCE:
        (A) ORGANISM: Human (ix) FEATURE:
        (A) NAME/KEY: CDS
        (B) LOCATION: 291..648

(ix) FEATURE:
        (A) NAME/KEY: 3' of first intron
        (B) LOCATION: 1..290

(ix) FEATURE:
        (A) NAME/KEY: intronic sequence of the human ob gene HOB
            from which the HOB 2gF primer was generated
        (B) LOCATION: 250..269

(ix) FEATURE:
        (A) NAME/KEY: 3' noncoding sequence of the human ob gene
            from which the HOB 2gR DNA primer was generated
        (B) LOCATION: 707..728

(xi) SEQUENCE DESCRIPTION: SEQ ID NO: 24:
```

```
CTGGTTCTTT CAGGAAGAGG CCATGTAAGA GAAAGGAATT GACCTAGGGA AAATTGGCCT      60

GGGAAGTGGA GGGAACGGAT GGTGTGGGAA AAGCAGGAAT CTCGGAGACC AGCTTAGAGG     120

CTTGGCAGTC ACCTGGGTGC AGGANACAAG GGCCTGAGCC AAAGTGGTGA GGGAGGGTGG     180

AAGGAGACAG CCCAGAGAAT GACCCTCCAT GCCCACGGGG AAGGCAGAGG GCTCTGAGAG     240

CGATTCCTCC CACATGCTGA GCACTTGTTC TCCCTCTTCC TCCTNCATAG CAG TCA        296
                                                       Gln Ser
                                                         1

GTC TCC TCC AAA CAG AAA GTC ACC GGT TTG GAC TTC ATT CCT GGG CTC       344
Val Ser Ser Lys Gln Lys Val Thr Gly Leu Asp Phe Ile Pro Gly Leu
          5                  10                  15

CAC CCC ATC CTG ACC TTA TCC AAG ATG GAC CAG ACA CTG GCA GTC TAC       392
His Pro Ile Leu Thr Leu Ser Lys Met Asp Gln Thr Leu Ala Val Tyr
         20                  25                  30

CAA CAG ATC CTC ACC AGT ATG CCT TCC AGA AAC GTG ATC CAA ATA TCC       440
Gln Gln Ile Leu Thr Ser Met Pro Ser Arg Asn Val Ile Gln Ile Ser
 35                  40                  45                  50

AAC GAC CTG GAG AAC CTC CGG GAT CTT CTT CAC GTG CTG GCC TTC TCT       488
Asn Asp Leu Glu Asn Leu Arg Asp Leu Leu His Val Leu Ala Phe Ser
                 55                  60                  65

AAG AGC TGC CAC TTG CCC TGG GCC AGT GGC CTG GAG ACC TTG GAC AGC       536
Lys Ser Cys His Leu Pro Trp Ala Ser Gly Leu Glu Thr Leu Asp Ser
                     70                  75                  80

CTG GGG GGT GTC CTG GAA GCT TCA GGC TAC TCC ACA GAG GTG GTG GCC       584
Leu Gly Gly Val Leu Glu Ala Ser Gly Tyr Ser Thr Glu Val Val Ala
                 85                  90                  95

CTG AGC AGG CTG CAG GGG TCT CTG CAG GAC ATG CTG TGG CAG CTG GAC       632
Leu Ser Arg Leu Gln Gly Ser Leu Gln Asp Met Leu Trp Gln Leu Asp
            100                 105                 110

CTC AGC CCT GGG TGC T GAGGCCTTGA AGGTCACTCT TCCTGCAAGG ACTACGTTAA     688
Leu Ser Pro Gly Cys
```

```
                                                         -continued
115
GGGAAGGAAC TCTGGCTTTC CAGGTATCTC CAGGATTGAA GAGCATTGCA TGGACACCCC       748

TTATCCAGGA CTCTGTCAAT TTCCCTGACT CCTCTAAGCC ACTCTTCCAA AGG             801
```

(2) INFORMATION FOR SEQ ID NO: 25:

(i) SEQUENCE CHARACTERISTICS:
        (A) LENGTH: 119 amino acids
        (B) TYPE: amino acid
        (D) TOPOLOGY: linear (ii) MOLECULE TYPE: protein
        (A) DESCRIPTION: C-terminal portion of the human ob protein
            encoded by second exon (xi) SEQUENCE DESCRIPTION: SEQ ID NO: 25:

```
Gln Ser Val Ser Ser Lys Gln Lys Val Thr Gly Leu Asp Phe Ile Pro
 1               5                  10                  15

Gly Leu His Pro Ile Leu Thr Leu Ser Lys Met Asp Gln Thr Leu Ala
            20                  25                  30

Val Tyr Gln Gln Ile Leu Thr Ser Met Pro Ser Arg Asn Val Ile Gln
        35                  40                  45

Ile Ser Asn Asp Leu Glu Asn Leu Arg Asp Leu Leu His Val Leu Ala
    50                  55                  60

Phe Ser Lys Ser Cys His Leu Pro Trp Ala Ser Gly Leu Glu Thr Leu
65                  70                  75                  80

Asp Ser Leu Gly Gly Val Leu Glu Ala Ser Gly Tyr Ser Thr Glu Val
                85                  90                  95

Val Ala Leu Ser Arg Leu Gln Gly Ser Leu Gln Asp Met Leu Trp Gln
            100                 105                 110

Leu Asp Leu Ser Pro Gly Cys
            115
```

(2) INFORMATION FOR SEQ ID NO: 26:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: internal (vi) ORIGINAL SOURCE:
        (A) ORGANISM: pichia yeast (xi) SEQUENCE DESCRIPTION: SEQ ID NO: 26:

```
Leu Glu Lys Arg Glu Ala Glu Ala
 1               5
```

(2) INFORMATION FOR SEQ ID NO: 27:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (v) FRAGMENT TYPE: internal (vi) ORIGINAL SOURCE:
        (A) ORGANISM: pichia yeast (xi) SEQUENCE DESCRIPTION: SEQ ID NO: 27:

Glu Ala Glu Ala
 1

(2) INFORMATION FOR SEQ ID NO: 28:

(i) SEQUENCE CHARACTERISTICS:
            (A) LENGTH: 4 amino acids
            (B) TYPE: amino acid
            (D) TOPOLOGY: unknown (ii) MOLECULE TYPE: peptide (v) FRAGMENT TYPE: Internal (vi) ORIGINAL SOURCE:
            (A) ORGANISM: pichia yeast (xi) SEQUENCE DESCRIPTION: SEQ ID NO: 28:

Leu Glu Lys Arg
 1

(2) INFORMATION FOR SEQ ID NO: 29:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
            (A) DESCRIPTION: HOB 1gF DNA primer generated from the 5'
                noncoding sequence of the human ob gene (iii) HYPOTHETICAL: NO (iv) ANTI-SENSE: NO (xi) SEQUENCE DESCRIPTION: SEQ ID NO: 29:

CCCAAGAAGC CCATCCTG                                                       18

(2) INFORMATION FOR SEQ ID NO: 30:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (primer)
            (A) DESCRIPTION: HOB 1gR DNA primer generated from the first
                intronic sequence of the human ob gene (iii) HYPOTHETICAL: NO (iv) ANTI-SENSE: YES (xi) SEQUENCE DESCRIPTION: SEQ ID NO: 30:

GACTATCTGG GTCCAGTGCC                                                     20

(2) INFORMATION FOR SEQ ID NO: 31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (primer)
            (A) DESCRIPTION: HOB 2gF DNA primer generated from the first
                intronic sequence of the human ob gene (iii) HYPOTHETICAL: NO (iv) ANTI-SENSE: NO (xi) SEQUENCE DESCRIPTION: SEQ ID NO: 31:

CCACATGCTG AGCACTTGTT                                                        20

(2) INFORMATION FOR SEQ ID NO: 32:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (primer)
            (A) DESCRIPTION: HOB 2gR DNA primer generated from the 3'
                noncoding sequence of the human ob gene (iii) HYPOTHETICAL: NO (iv) ANTI-SENSE: YES (xi) SEQUENCE DESCRIPTION: SEQ ID NO: 32:

CTTCAATCCT GGAGATACCT GG                                                     22

(2) INFORMATION FOR SEQ ID NO: 33:

(i) SEQUENCE CHARACTERISTICS:
            (A) LENGTH: 51 base pairs
            (B) TYPE: nucleic acid
            (C) STRANDEDNESS: double
            (D) TOPOLOGY: circular (ii) MOLECULE TYPE: DNA
            (A) DESCRIPTION: pPIC.9 cloning site (iii) HYPOTHETICAL: NO (iv) ANTI-SENSE: NO (xi) SEQUENCE DESCRIPTION: SEQ ID NO: 33:

CTCGAGAAAA GAGAGGCTGA AGCTTACGTA GAATTCCCTA GGCCGGCCGG G                     51

(2) INFORMATION FOR SEQ ID NO: 34:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (primer)
            (A) DESCRIPTION: PCR 5' primer for amplifying human ob cDNA
                sequence (iii) HYPOTHETICAL: NO (iv) ANTI-SENSE: NO (xi) SEQUENCE DESCRIPTION: SEQ ID NO: 34:

GTATCTCTCG AGAAAAGAGT GCCCATCCAA AAAGTCCAAG                                   40

(2) INFORMATION FOR SEQ ID NO: 35:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (primer)
            (A) DESCRIPTION: PCR 3' primer for amplifying human ob cDNA
                sequence (iii) HYPOTHETICAL: NO (iv) ANTI-SENSE: YES (xi) SEQUENCE DESCRIPTION: SEQ ID NO: 35:

GCGCGAATTC TCAGCACCCA GGGCTGAGGT C                                              31

(2) INFORMATION FOR SEQ ID NO: 36:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (primer)
            (A) DESCRIPTION: PCR 5' primer for amplifying murine ob cDNA
                sequence (iii) HYPOTHETICAL: NO (iv) ANTI-SENSE: NO (xi) SEQUENCE DESCRIPTION: SEQ ID NO: 36:

GTATCTCTCG AGAAAAGAGT GCCTATCCAG AAAGTCCAGG                                     40

(2) INFORMATION FOR SEQ ID NO: 37:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (primer)
            (A) DESCRIPTION: PCR 3' primer for amplifying murine ob cDNA
                sequence (iii) HYPOTHETICAL: NO (iv) ANTI-SENSE: YES (xi) SEQUENCE DESCRIPTION: SEQ ID NO: 37:

GCGCGAATTC TCAGCATTCA GGGCTAACAT C                                              31

(2) INFORMATION FOR SEQ ID NO: 38:

(i) SEQUENCE CHARACTERISTICS:
            (A) LENGTH: 4 amino acids
            (B) TYPE: amino acid
            (D) TOPOLOGY: linear (ii) MOLECULE TYPE: protein
            (A) DESCRIPTION: tetrapeptide at N-terminus of renatured
                murine ob protein after thrombin cleavage (vi) ORIGINAL SOURCE:
            (A) ORGANISM: Murine (xi) SEQUENCE DESCRIPTION: SEQ ID NO: 38:

Gly Ser His Met
  1

(2) INFORMATION FOR SEQ ID NO: 39:

(i) SEQUENCE CHARACTERISTICS:

(A) LENGTH: 19 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS1734

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 39:

CAAGACAAAT GAGATAAGG                                                19

(2) INFORMATION FOR SEQ ID NO: 40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS1734

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 40:

AGAGTTACAG CTTTACAG                                                 18

(2) INFORMATION FOR SEQ ID NO: 41:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS494

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 41:

CTAAACACCT TTCCATTCC                                                19

(2) INFORMATION FOR SEQ ID NO: 42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer sWSS494

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 42:

TTATATTCAC TTTTCCCCTC TC                                              22

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS883

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 43:

TGCAGTAAGC TGTGATTGAG                                                 20

(2) INFORMATION FOR SEQ ID NO: 44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS883

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 44:

GTGCAGCTTT AATTGTGAGC                                                 20

(2) INFORMATION FOR SEQ ID NO: 45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS2359

(iii) HYPOTHETICAL: NO (iv) ANTI-SENSE: NO (vi) ORIGINAL SOURCE:

```
            (A) ORGANISM: Human (xi) SEQUENCE DESCRIPTION: SEQ ID NO: 45:

AGTGTTGTGT TTCTCCTG                                                18

(2) INFORMATION FOR SEQ ID NO: 46:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS2359

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 46:

AAAGGGGATG TGATAAGTG                                               19

(2) INFORMATION FOR SEQ ID NO: 47:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS2336

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 47:

GGTGTTACGT TTAGTTAC                                                18

(2) INFORMATION FOR SEQ ID NO: 48:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS2336

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 48:

GGAATAATGA GAGAAGATTG                                              20
```

(2) INFORMATION FOR SEQ ID NO: 49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS1218

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 49:

GCTCAACTGA CAGAAAAC                                                    18

(2) INFORMATION FOR SEQ ID NO: 50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS1218

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 50:

GACTATGTAA AAGAAATGCC                                                  20

(2) INFORMATION FOR SEQ ID NO: 51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS1402

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 51:

AAAGGGCTTC TAATCTAC                                                    18

(2) INFORMATION FOR SEQ ID NO: 52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
    (ii) MOLECULE TYPE: DNA (primer)
        (A) DESCRIPTION: sequence tagged-site specific PCR primer
            sWSS1402

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 52:

CCTTCCAACT TCTTTGAC                                                   18

(2) INFORMATION FOR SEQ ID NO: 53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS999

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 53:

TAAACCCCCT TTCTGTTC                                                   18

(2) INFORMATION FOR SEQ ID NO: 54:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS999

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 54:

TTGCATAATA GTCACACCC                                                  19

(2) INFORMATION FOR SEQ ID NO: 55:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS1751

(iii) HYPOTHETICAL: NO
```

(iv) ANTI-SENSE: NO (vi) ORIGINAL SOURCE:
            (A) ORGANISM: Human (xi) SEQUENCE DESCRIPTION: SEQ ID NO: 55:

CCAAAATCAG AATTGTCAGA AG                                              22

(2) INFORMATION FOR SEQ ID NO: 56:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS1751

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 56:

AAACCGAAGT TCAGATACAG                                                 20

(2) INFORMATION FOR SEQ ID NO: 57:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS1174

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 57:

AATATCTGAC ATTGGCAC                                                   18

(2) INFORMATION FOR SEQ ID NO: 58:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS1174

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 58:

TTAGACCTGA GAAAAGAG                                                    18

(2) INFORMATION FOR SEQ ID NO: 59:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS2061

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 59:

GTTGCACAAT ACAAAATCC                                                   19

(2) INFORMATION FOR SEQ ID NO: 60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS2061

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 60:

CTTCCATTAG TGTCTTATAG                                                  20

(2) INFORMATION FOR SEQ ID NO: 61:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS2588

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 61:

ATCACTACAC ACCTAATC                                                    18

(2) INFORMATION FOR SEQ ID NO: 62:

(i) SEQUENCE CHARACTERISTICS:
        (A) LENGTH: 18 base pairs (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS2588

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 62:

CCATTCTACA TTTCCACC                                                       18

(2) INFORMATION FOR SEQ ID NO: 63:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS808

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 63:

GGCTGTGTGA GCAAGATCCT AGGA                                                24

(2) INFORMATION FOR SEQ ID NO: 64:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS808

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 64:

TTGCCAGGCA AAGAGGGCTG GAC                                                 23

(2) INFORMATION FOR SEQ ID NO: 65:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: sequence tagged-site specific PCR primer
            sWSS1392

(iii) HYPOTHETICAL: NO (iv) ANTI-SENSE: NO (vi) ORIGINAL SOURCE:
             (A) ORGANISM: Human (xi) SEQUENCE DESCRIPTION: SEQ ID NO: 65:

CTCAGGTATG TCTTTATC                                                          18

(2) INFORMATION FOR SEQ ID NO: 66:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
             (A) DESCRIPTION: sequence tagged-site specific PCR primer
                 sWSS1392

(iii) HYPOTHETICAL: NO (iv) ANTI-SENSE: NO (vi) ORIGINAL SOURCE:
             (A) ORGANISM: Human (xi) SEQUENCE DESCRIPTION: SEQ ID NO: 66:

TGTCTCTGCA TTCTTTTC                                                          18

(2) INFORMATION FOR SEQ ID NO: 67:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
             (A) DESCRIPTION: sequence tagged-site specific PCR primer
                 sWSS1148

(iii) HYPOTHETICAL: NO (iv) ANTI-SENSE: NO (vi) ORIGINAL SOURCE:
             (A) ORGANISM: Human (xi) SEQUENCE DESCRIPTION: SEQ ID NO: 67:

GACACATACA AACACAAG                                                          18

(2) INFORMATION FOR SEQ ID NO: 68:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (primer)
             (A) DESCRIPTION: sequence tagged-site specific PCR primer
                 sWSS1148

(iii) HYPOTHETICAL: NO (iv) ANTI-SENSE: NO (vi) ORIGINAL SOURCE:
             (A) ORGANISM: Human (xi) SEQUENCE DESCRIPTION: SEQ ID NO: 68:

ATTGAGTTGA GTGTAGTAG                                                        19

(2) INFORMATION FOR SEQ ID NO: 69:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS1529

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 69:

CAGGGATTTC TAATTGTC                                                         18

(2) INFORMATION FOR SEQ ID NO: 70:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS1529

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 70:

AAAAGATGGA GGCTTTTG                                                         18

(2) INFORMATION FOR SEQ ID NO: 71:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS2619

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 71:

CGTTAAGGGA AGGAACTCTG G                                                     21

(2) INFORMATION FOR SEQ ID NO: 72:

```
        (i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS2619

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 72:

TGGCTTAGAG GAGTCAGGGA                                                   20

(2) INFORMATION FOR SEQ ID NO: 73:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS404

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 73:

ACCAGGGTCA ATACAAAG                                                     18

(2) INFORMATION FOR SEQ ID NO: 74:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (primer)
            (A) DESCRIPTION: sequence tagged-site specific PCR primer
                sWSS404

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 74:

TAATGTGTCC TTCTTGCC                                                     18

(2) INFORMATION FOR SEQ ID NO: 75:

(i) SEQUENCE CHARACTERISTICS:
            (A) LENGTH: 18 base pairs
            (B) TYPE: nucleic acid
            (C) STRANDEDNESS: single
            (D) TOPOLOGY: linear
```

```
    (ii) MOLECULE TYPE: DNA (primer)
         (A) DESCRIPTION: sequence tagged-site specific PCR primer
             sWSS2367

(iii) HYPOTHETICAL: NO (iv) ANTI-SENSE: NO (vi) ORIGINAL SOURCE:
         (A) ORGANISM: Human (xi) SEQUENCE DESCRIPTION: SEQ ID NO: 75:

CAATCCTGGC TTCATTTG                                                      18

(2) INFORMATION FOR SEQ ID NO: 76:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (primer)
         (A) DESCRIPTION: sequence tagged-site specific PCR primer
             sWSS2367

(iii) HYPOTHETICAL: NO (iv) ANTI-SENSE: NO (vi) ORIGINAL SOURCE:
         (A) ORGANISM: Human (xi) SEQUENCE DESCRIPTION: SEQ ID NO: 76:

AAGGTGGGTA GGATGCTA                                                      18

(2) INFORMATION FOR SEQ ID NO: 77:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (primer)
         (A) DESCRIPTION: Marker UT528

(iii) HYPOTHETICAL: NO (iv) ANTI-SENSE: NO (vi) ORIGINAL SOURCE:
         (A) ORGANISM: Human (xi) SEQUENCE DESCRIPTION: SEQ ID NO: 77:

TGCAGTAAGC TGTGATTGAG                                                    20

(2) INFORMATION FOR SEQ ID NO: 78:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (primer)
         (A) DESCRIPTION: Marker UT528

(iii) HYPOTHETICAL: NO (iv) ANTI-SENSE: NO (vi) ORIGINAL SOURCE:
```

-continued (A) ORGANISM: Human (xi) SEQUENCE DESCRIPTION: SEQ ID NO: 78:

GTGCAGCTTT AATTGTGAGC                                                    20

(2) INFORMATION FOR SEQ ID NO: 79:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (primer)
            (A) DESCRIPTION: Marker AFMa065zg9

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 79:

AGCTTCAAGA CTTTNAGCCT                                                    20

(2) INFORMATION FOR SEQ ID NO: 80:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (primer)
            (A) DESCRIPTION: Marker AFMa065zg9

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 80:

GGTCAGCAGC ACTGTGATT                                                     19

(2) INFORMATION FOR SEQ ID NO: 81:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (primer)
            (A) DESCRIPTION: Marker AFMa125wh1

(iii) HYPOTHETICAL: NO (iv) ANTI-SENSE: NO (vi) ORIGINAL SOURCE:
            (A) ORGANISM: Human (xi) SEQUENCE DESCRIPTION: SEQ ID NO: 81:

TCACCTTGAG ATTCCATCC                                                     19

(2) INFORMATION FOR SEQ ID NO: 82:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Marker AFMa125wh1

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 82:

AACACCGTGG TCTTATCAAA                                           20

(2) INFORMATION FOR SEQ ID NO: 83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Marker AFM309yf10

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 83:

CATCCAAGTT GGCAGTTTTT                                           20

(2) INFORMATION FOR SEQ ID NO: 84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Marker AFM309yf10

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 84:

AGATGCTGAA TTCCCAGACA                                           20

(2) INFORMATION FOR SEQ ID NO: 85:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Marker AFM218xf10

(iii) HYPOTHETICAL: NO
```

```
      (iv) ANTI-SENSE: NO (vi) ORIGINAL SOURCE:
           (A) ORGANISM: Human (xi) SEQUENCE DESCRIPTION: SEQ ID NO: 85:

TGGGCAACAC AGCAAA                                                    16

(2) INFORMATION FOR SEQ ID NO: 86:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (primer)
           (A) DESCRIPTION: Marker AFM218xf10

(iii) HYPOTHETICAL: NO (iv) ANTI-SENSE: NO (vi) ORIGINAL SOURCE:
           (A) ORGANISM: Human (xi) SEQUENCE DESCRIPTION: SEQ ID NO: 86:

TGCAGTTAGT GCCAATGTCA                                                20

(2) INFORMATION FOR SEQ ID NO: 87:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: DNA (primer)
           (A) DESCRIPTION: Marker AFM206xc1

(iii) HYPOTHETICAL: NO (iv) ANTI-SENSE: NO (vi) ORIGINAL SOURCE:
           (A) ORGANISM: Human (xi) SEQUENCE DESCRIPTION: SEQ ID NO: 87:

CCAGGCCATG TGGAAC                                                    16

(2) INFORMATION FOR SEQ ID NO: 88:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (primer)
           (A) DESCRIPTION: Marker AFM206xc1

(iii) HYPOTHETICAL: NO (iv) ANTI-SENSE: NO (vi) ORIGINAL SOURCE:
           (A) ORGANISM: Human (xi) SEQUENCE DESCRIPTION: SEQ ID NO: 88:

AGTTCTTGGC TTGCGTCAGT                                                20
```

```
(2) INFORMATION FOR SEQ ID NO: 89:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Marker AFM199xh12

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 89:

TCTGATTGCT GGCTGC                                                 16

(2) INFORMATION FOR SEQ ID NO: 90:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Marker AFM199xh12

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 90:

GCGCGTGTGT ATGTGAG                                                17

(2) INFORMATION FOR SEQ ID NO: 91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Marker AFMa345wc9

(iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 91:

AGCTCTTGGC AAACTCACAT                                             20

(2) INFORMATION FOR SEQ ID NO: 92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Marker AFMa345wc9
```

(iii) HYPOTHETICAL: NO (iv) ANTI-SENSE: NO (vi) ORIGINAL SOURCE:
             (A) ORGANISM: Human (xi) SEQUENCE DESCRIPTION: SEQ ID NO: 92:

GCCTAAGGGA ATGAGACACA                                                    20

(2) INFORMATION FOR SEQ ID NO: 93:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (primer)
             (A) DESCRIPTION: primer for mouse Pax4 gene (iii) HYPOTHETICAL: NO (iv) ANTI-SENSE: NO (vi) ORIGINAL SOURCE:
             (A) ORGANISM: murine (xi) SEQUENCE DESCRIPTION: SEQ ID NO: 93:

GGGAGCCTTG TCCTGGGTAC AAAG                                               24

(2) INFORMATION FOR SEQ ID NO: 94:

(i) SEQUENCE CHARACTERISTICS:
             (A) LENGTH: 491 base pairs
             (B) TYPE: nucleic acid
             (C) STRANDEDNESS: double
             (D) TOPOLOGY: linear (ii) MOLECULE TYPE: cDNA
             (A) DESCRIPTION: Recombinant murine met ob (iii) HYPOTHETICAL: NO (iv) ANTI-SENSE: NO (vi) ORIGINAL SOURCE:
             (A) ORGANISM: murine (ix) FEATURE:
             (A) NAME/KEY: CDS
             (B) LOCATION: 41..478

(xi) SEQUENCE DESCRIPTION: SEQ ID NO: 94:

TCTAGATTTG AGTTTTAACT TTTAGAAGGA GGAATAACAT ATG GTA CCG ATC CAG         55
                                            Met Val Pro Ile Gln
                                             1               5

AAA GTT CAG GAC GAC ACC AAA ACC TTA ATT AAA ACG ATC GTT ACG CGT        103
Lys Val Gln Asp Asp Thr Lys Thr Leu Ile Lys Thr Ile Val Thr Arg
                 10                  15                  20

ATC AAC GAC ATC AGT CAC ACC CAG TCG GTC TCC GCT AAA CAG CGT GTT        151
Ile Asn Asp Ile Ser His Thr Gln Ser Val Ser Ala Lys Gln Arg Val
             25                  30                  35

ACC GGT CTG GAC TTC ATC CCG GGT CTG CAC CCG ATC CTA AGC TTG TCC        199
Thr Gly Leu Asp Phe Ile Pro Gly Leu His Pro Ile Leu Ser Leu Ser
         40                  45                  50

AAA ATG GAC CAG ACC CTG GCT GTA TAC CAG CAG GTG TTA ACC TCC CTG        247
Lys Met Asp Gln Thr Leu Ala Val Tyr Gln Gln Val Leu Thr Ser Leu
     55                  60                  65

```
CCG TCC CAG AAC GTT CTT CAG ATC GCT AAC GAC CTC GAG AAC CTT CGC     295
Pro Ser Gln Asn Val Leu Gln Ile Ala Asn Asp Leu Glu Asn Leu Arg
70               75                  80                  85

GAC CTG CTG CAC CTG CTG GCA TTC TCC AAA TCC TGC TCC CTG CCG CAG     343
Asp Leu Leu His Leu Leu Ala Phe Ser Lys Ser Cys Ser Leu Pro Gln
                90                  95                  100

ACC TCA GGT CTT CAG AAA CCG GAA TCC CTG GAC GGG GTC CTG GAA GCA     391
Thr Ser Gly Leu Gln Lys Pro Glu Ser Leu Asp Gly Val Leu Glu Ala
            105                 110                 115

TCC CTG TAC AGC ACC GAA GTT GTT GCT CTG TCC CGT CTG CAG GGT TCC     439
Ser Leu Tyr Ser Thr Glu Val Val Ala Leu Ser Arg Leu Gln Gly Ser
        120                 125                 130

CTT CAG GAC ATC CTT CAG CAG CTG GAC GTT TCT CCG GAA TGT TAATGGA     488
Leu Gln Asp Ile Leu Gln Gln Leu Asp Val Ser Pro Glu Cys
    135                 140                 145

TCC                                                                  491
```

(2) INFORMATION FOR SEQ ID NO: 95:

(i) SEQUENCE CHARACTERISTICS:
        (A) LENGTH: 147 amino acids
        (B) TYPE: amino acid
        (D) TOPOLOGY: linear (ii) MOLECULE TYPE: protein
        (A) DESCRIPTION: Recombinant murine met ob protein (xi) SEQUENCE DESCRIPTION: SEQ ID NO: 95:

```
Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ala Lys Gln Arg Val Thr Gly Leu Asp Phe Ile Pro Gly Leu His Pro
        35                  40                  45

Ile Leu Ser Leu Ser Lys Met Asp Gln Thr Leu Ala Val Tyr Gln Gln
    50                  55                  60

Val Leu Thr Ser Leu Pro Ser Gln Asn Val Leu Gln Ile Ala Asn Asp
65                  70                  75                  80

Leu Glu Asn Leu Arg Asp Leu Leu His Leu Leu Ala Phe Ser Lys Ser
                85                  90                  95

Cys Ser Leu Pro Gln Thr Ser Gly Leu Gln Lys Pro Glu Ser Leu Asp
            100                 105                 110

Gly Val Leu Glu Ala Ser Leu Tyr Ser Thr Glu Val Val Ala Leu Ser
        115                 120                 125

Arg Leu Gln Gly Ser Leu Gln Asp Ile Leu Gln Gln Leu Asp Val Ser
    130                 135                 140

Pro Glu Cys
145
```

(2) INFORMATION FOR SEQ ID NO: 96:

(i) SEQUENCE CHARACTERISTICS:
        (A) LENGTH: 454 base pairs
        (B) TYPE: nucleic acid
        (C) STRANDEDNESS: double
        (D) TOPOLOGY: linear (ii) MOLECULE TYPE: DNA
        (A) DESCRIPTION: Recombinant human met ob (iii) HYPOTHETICAL: NO (iv) ANTI-SENSE: NO (vi) ORIGINAL SOURCE:
    (A) ORGANISM: human (ix) FEATURE:
    (A) NAME/KEY: CDS
    (B) LOCATION: 4..444

(xi) SEQUENCE DESCRIPTION: SEQ ID NO: 96:

```
CAT ATG GTA CCG ATC CAG AAA GTT CAG GAC GAC ACC AAA ACC TTA ATT      48
    Met Val Pro Ile Gln Lys Val Gln Asp Asp Thr Lys Thr Leu Ile
     1               5                  10                  15

AAA ACG ATC GTT ACG CGT ATC AAC GAC ATC AGT CAC ACC CAG TCG GTG      96
Lys Thr Ile Val Thr Arg Ile Asn Asp Ile Ser His Thr Gln Ser Val
             20                  25                  30

AGC TCT AAA CAG CGT GTT ACA GGC CTG GAC TTC ATC CCG GGT CTG CAC     144
Ser Ser Lys Gln Arg Val Thr Gly Leu Asp Phe Ile Pro Gly Leu His
         35                  40                  45

CCG ATC CTG ACC TTG TCC AAA ATG GAC CAG ACC CTG GCT GTA TAC CAG     192
Pro Ile Leu Thr Leu Ser Lys Met Asp Gln Thr Leu Ala Val Tyr Gln
     50                  55                  60

CAG ATC TTA ACC TCC ATG CCG TCC CGT AAC GTT CTT CAG ATC TCT AAC     240
Gln Ile Leu Thr Ser Met Pro Ser Arg Asn Val Leu Gln Ile Ser Asn
 65                  70                  75

GAC CTC GAG AAC CTT CGC GAC CTG CTG CAC GTG CTG GCA TTC TCC AAA     288
Asp Leu Glu Asn Leu Arg Asp Leu Leu His Val Leu Ala Phe Ser Lys
 80                  85                  90                  95

TCC TGC CAC CTG CCA TGG GCT TCA GGT CTT GAG ACT CTG GAC TCT CTG     336
Ser Cys His Leu Pro Trp Ala Ser Gly Leu Glu Thr Leu Asp Ser Leu
                100                 105                 110

GGC GGG GTC CTG GAA GCA TCC GGT TAC AGC ACC GAA GTT GTT GCT CTG     384
Gly Gly Val Leu Glu Ala Ser Gly Tyr Ser Thr Glu Val Val Ala Leu
            115                 120                 125

TCC CGT CTG CAG GGT TCC CTT CAG GAC ATG CTT TGG CAG CTG GAC CTG     432
Ser Arg Leu Gln Gly Ser Leu Gln Asp Met Leu Trp Gln Leu Asp Leu
        130                 135                 140

TCT CCG GGT TGT TAATGGATCC                                          454
Ser Pro Gly Cys
    145
```

(2) INFORMATION FOR SEQ ID NO: 97:

(i) SEQUENCE CHARACTERISTICS:
        (A) LENGTH: 147 amino acids
        (B) TYPE: amino acid
        (D) TOPOLOGY: linear (ii) MOLECULE TYPE: protein
        (A) DESCRIPTION: Recombinant human met ob protein (xi) SEQUENCE DESCRIPTION: SEQ ID NO: 97:

```
Met Val Pro Ile Gln Lys Val Gln Asp Asp Thr Lys Thr Leu Ile Lys
 1               5                  10                  15

Thr Ile Val Thr Arg Ile Asn Asp Ile Ser His Thr Gln Ser Val Ser
             20                  25                  30

Ser Lys Gln Arg Val Thr Gly Leu Asp Phe Ile Pro Gly Leu His Pro
         35                  40                  45

Ile Leu Thr Leu Ser Lys Met Asp Gln Thr Leu Ala Val Tyr Gln Gln
     50                  55                  60

Ile Leu Thr Ser Met Pro Ser Arg Asn Val Leu Gln Ile Ser Asn Asp
 65                  70                  75                  80
```

-continued

```
Leu Glu Asn Leu Arg Asp Leu Leu His Val Leu Ala Phe Ser Lys Ser
                 85              90                  95

Cys His Leu Pro Trp Ala Ser Gly Leu Glu Thr Leu Asp Ser Leu Gly
                100             105             110

Gly Val Leu Glu Ala Ser Gly Tyr Ser Thr Glu Val Val Ala Leu Ser
            115             120             125

Arg Leu Gln Gly Ser Leu Gln Asp Met Leu Trp Gln Leu Asp Leu Ser
    130             135             140

Pro Gly Cys
145

(2) INFORMATION FOR SEQ ID NO: 98:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO: 98:

Met Gly Ser Ser His His His His His His Ser Ser Gly Leu Val Pro
 1           5                  10                  15

Arg Gly Ser His Met
             20
```